(12) United States Patent
Orwat et al.

(10) Patent No.: US 9,079,929 B2
(45) Date of Patent: Jul. 14, 2015

(54) SUBSTITUTED TETRAHYDROISOQUINOLINE COMPOUNDS AS FACTOR XIA INHIBITORS

(71) Applicant: BRISTOL-MYERS SQUIBB COMPANY, Princeton, NJ (US)

(72) Inventors: Michael J. Orwat, New Hope, PA (US); Donald J. P. Pinto, Churchville, PA (US); Leon M. Smith, II, Somerset, NJ (US); Shefali Srivastava, Jaipur (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/350,411

(22) PCT Filed: Oct. 12, 2012

(86) PCT No.: PCT/US2012/059932
§ 371 (c)(1),
(2) Date: Apr. 8, 2014

(87) PCT Pub. No.: WO2013/056034
PCT Pub. Date: Apr. 18, 2013

(65) Prior Publication Data
US 2014/0274960 A1 Sep. 18, 2014

Related U.S. Application Data

(60) Provisional application No. 61/547,301, filed on Oct. 14, 2011.

(51) Int. Cl.
| | |
|---|---|
| C07D 217/26 | (2006.01) |
| C07D 401/10 | (2006.01) |
| C07D 401/12 | (2006.01) |
| C07D 401/14 | (2006.01) |
| C07F 9/6524 | (2006.01) |
| C07D 405/14 | (2006.01) |

(52) U.S. Cl.
CPC ............ *C07F 9/6524* (2013.01); *C07D 217/26* (2013.01); *C07D 401/10* (2013.01); *C07D 401/12* (2013.01); *C07D 401/14* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,624,936 A | 4/1997 | deSolms | |
| 5,869,682 A | 2/1999 | deSolms | |

FOREIGN PATENT DOCUMENTS

| | | |
|---|---|---|
| DE | 40 34 829 | 5/1992 |
| EP | 0 525 420 | 5/1999 |
| EP | 1 016 663 | 7/2000 |
| EP | 1 125 925 | 8/2001 |
| FR | 1525186 | 5/1968 |
| FR | 7155 | 2/1970 |
| WO | WO 93/20099 | 10/1993 |
| WO | WO 96/34010 | 10/1996 |
| WO | WO 97/36891 | 10/1997 |
| WO | WO 99/47545 | 9/1999 |
| WO | WO 99/61444 | 12/1999 |
| WO | WO 00/18733 | 4/2000 |
| WO | WO 00/40571 | 7/2000 |
| WO | WO 00/61608 | 10/2000 |
| WO | WO 01/85695 | 11/2001 |
| WO | WO 02/18369 | 3/2002 |
| WO | WO 03/041641 | 5/2003 |
| WO | WO 2004/080971 | 9/2004 |
| WO | WO 2004/094372 | 11/2004 |
| WO | WO 2005/014533 | 2/2005 |
| WO | WO 2005/099709 | 10/2005 |
| WO | WO 2005/123050 | 12/2005 |
| WO | WO 2005/123680 | 12/2005 |
| WO | WO 2006/017295 | 2/2006 |
| WO | WO 2006/076575 | 7/2006 |
| WO | WO 2006/089005 | 8/2006 |
| WO | WO 2007/070816 | 6/2007 |
| WO | WO 2007/070818 | 6/2007 |

(Continued)

OTHER PUBLICATIONS

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

(Continued)

*Primary Examiner* — Zinna Northington Davi
(74) *Attorney, Agent, or Firm* — Hong Liu

(57) ABSTRACT

The present invention provides compounds of Formula (I) or stereoisomers, pharmaceutically acceptable salts thereof, wherein all of the variables are as defined herein. These compounds are inhibitors of factor XIa and/or plasma kallikrein which may be used as medicaments.

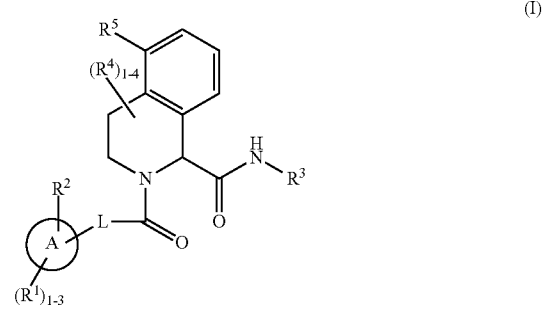

11 Claims, No Drawings

(56) References Cited

FOREIGN PATENT DOCUMENTS

| | | |
|---|---|---|
| WO | WO 2007/070826 | 6/2007 |
| WO | WO 2008/076805 | 6/2008 |
| WO | WO 2008/157162 | 12/2008 |
| WO | WO 2009/114677 | 9/2009 |
| WO | WO 2010/151317 | 12/2010 |
| WO | WO 2011/002520 | 1/2011 |
| WO | WO 2011/017296 | 2/2011 |
| WO | WO 2011/100401 | 8/2011 |
| WO | WO 2011/100402 | 8/2011 |
| WO | WO 2013/009527 | 1/2013 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2013/093484 | 6/2013 |
| WO | WO 2013/111107 | 8/2013 |
| WO | WO 2013/111108 | 8/2013 |
| WO | WO 2013/118805 | 8/2013 |
| WO | WO 2013/167669 | 11/2013 |
| WO | WO 2014/014050 | 1/2014 |
| WO | WO 2014/022766 | 2/2014 |
| WO | WO 2014/022767 | 2/2014 |

OTHER PUBLICATIONS

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kérniai Folyóirat (Hungarian Journal of Chemistry), vol. 116, No. 3, pp. 126-130 (2010).

Wu, Y.-J. et al., "Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

SUBSTITUTED TETRAHYDROISOQUINOLINE COMPOUNDS AS FACTOR XIA INHIBITORS

CONTINUING DATA

This application is a 371 of PCT/US2012/059932 filed Oct. 12, 2012 which claims benefit of 61/547,301 filed Oct. 14, 2011.

FIELD OF THE INVENTION

The present invention provides novel substituted tetrahydroisoquinoline (THQ) compounds, and their analogues thereof, which are inhibitors of factor XIa or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., Arterioscler. Thromb. Vasc. Biol., 27:2507-2513 (2007).) The resulting burst of thrombin converts fibrinogen to fibrin that polymerizes to form the structural framework of a blood clot, and activates platelets, which are a key cellular component of coagulation (Hoffman, M., Blood Reviews, 17:S1-S5 (2003)). Therefore, factor XIa plays a key role in propagating this amplification loop and is thus an attractive target for antithrombotic therapy.

SUMMARY OF THE INVENTION

The present invention provides novel substituted tetrahydroisoquinoline compounds, and their analogues thereof, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two, other agent(s).

These and other features of the invention will be set forth in expanded form as the disclosure continues.

DETAILED DESCRIPTION OF THE INVENTION

I. Compounds of the Invention

In a first aspect, the present invention provides compounds of Formula (I):

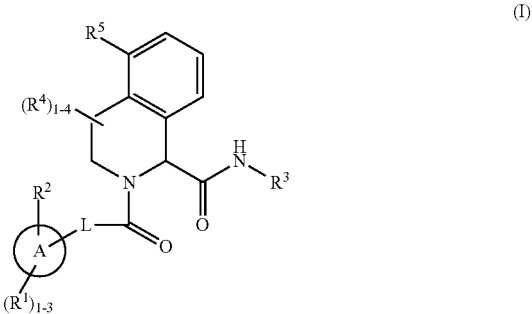

or stereoisomers, tautomers, pharmaceutically acceptable salts, or solvates thereof, wherein:

ring A is $C_{3-6}$ carbocycle;

L is selected from the group consisting of: —$CHR^{10}CHR^{10}$—, —$CR^{10}$=$CR^{10}$—, —C≡C—, —$CHR^{10}NH$—, —$NHCHR^{10}$—, —$SCH_2$—, —$CH_2S$—, —$SO_2CH_2$—, —$CH_2SO_2$—, —$NHCH_2$—, and —$CH_2NH$—;

$R^1$, at each occurrence, is selected from the group consisting of: H, halo, $C_{1-6}$ alkyl, $C_{1-4}$ alkoxy, $C_{1-4}$ alkylthio, OH, SH, $CHF_2$, $CF_3$, $OCF_3$, CN, $NH_2$, $COC_{1-4}$ alkyl, $CO_2(C_{1-4}$ alkyl), —$CH_2CO_2H$, —$CH_2CO_2(C_{1-4}$ alkyl), —$CH_2NH_2$, —$CONH_2$, —$CONH(C_{1-4}$ alkyl), —$NHCO(C_{1-4}$ alkyl), —$NHCO_2(C_{1-4}$ alkyl), —$NHSO_2(C_{1-4}$ alkyl), —$SO_2NH_2$, and —C(=NH)$NH_2$;

$R^2$ is selected from the group consisting of: H, halo, CN, OH, $C_{1-6}$ alkyl, $C_{1-4}$ alkoxy, $C_{1-6}$haloalkyl, $C_{1-6}$haloalkoxy, $CO(C_{1-4}$ alkyl), $CONH_2$, $CO_2H$, $CH_2NH_2$, and a 5- to 7-membered heterocycle comprising carbon atoms and 1-4 heteroatoms selected from N, $NR^c$, O, and $S(O)_p$, wherein said heterocycle is substituted with 0-2 $R^{2a}$;

$R^{2a}$, at each occurrence, is selected from the group consisting of: H, halo, $C_{1-4}$ alkyl, —$CH_2OH$, $C_{1-4}$ alkoxy, OH, $CF_3$, $OCF_3$, CN, $NH_2$, $CO_2H$, $CO_2(C_{1-4}$ alkyl), $CO(C_{1-4}$ alkyl), —CONH$_2$, —CH$_2$OH, —CH$_2$OC$_{1-4}$alkyl, —CH$_2$NH$_2$—, CONH(C$_{1-4}$ alkyl), —CON(C$_{1-4}$ alkyl)$_2$, —SO$_2$(C$_{1-4}$ alkyl), —SO$_2$NH$_2$, —SO$_2$NH(C$_{1-4}$ alkyl), and —SO$_2$N(C$_{1-4}$ alkyl)$_2$;

R$^3$ is selected from the group consisting of: C$_{1-6}$ alkyl substituted with 1-3 R$^{3a}$, —(CH$_2$)$_n$—C$_{3-10}$ carbocycle substituted with 0-3 R$^{3a}$ or —(CH$_2$)$_n$-5-10 membered heterocycle containing carbon atoms and 1-4 heteroatoms selected from the group consisting of N, NR$^7$, O, and S(O)$_p$; wherein said heterocycle is substituted with 0-3 R$^{3a}$;

R$^{3a}$, at each occurrence, is selected from the group consisting of: H, halo, C$_{1-4}$ alkyl, —OH, C$_{1-4}$ alkoxy, —CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO$_2$—C$_{1-4}$ alkylene-O(C$_{1-4}$ alkyl), —CO$_2$—C$_{1-4}$ alkylene-N(C$_{1-4}$ alkyl)$_2$, —CO$_2$—C$_{1-4}$ alkylene-O—C$_{1-4}$ alkylene-N(C$_{1-4}$ alkyl)$_2$, —CO$_2$—C$_{1-4}$ alkylene-O—C$_{1-4}$ alkylene-O(C$_{1-4}$ alkyl), —CONH$_2$, —CONH (C$_{1-6}$ alkyl), —CON(C$_{1-4}$ alkyl)$_2$, —CONH—C$_{1-4}$ alkylene-CO$_2$(C$_{1-4}$ alkyl), —CONHCO$_2$C$_{1-4}$ alkyl, —CONH—C$_{1-4}$ alkylene-NHCO(C$_{1-4}$ alkyl), —CONH—C$_{1-4}$ alkylene-CONH$_2$, —NHCOC$_{1-4}$ alkyl, —NHCO$_2$(C$_{1-4}$ alkyl), R$^c$, —CONHR$^c$, and —CO$_2$R$^c$;

R$^4$, at each occurrence, is selected from the group consisting of: H, halo and C$_{1-4}$ alkyl;

R$^5$, at each occurrence, is selected from the group consisting of: halo, C$_{1-4}$ alkyl substituted with 0-2 R$^e$, C$_{2-4}$ alkenyl substituted with 0-2 R$^e$, C$_{2-4}$ alkynyl substituted with 0-2 R$^b$OH, CN, NH$_2$, —N(C$_{1-4}$ alkyl)$_2$, NO$_2$, C$_{1-4}$ alkoxy, —OCO(C$_{1-4}$ alkyl), —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$ alkyl), —CONH$_2$, —(CH$_2$)$_2$CONH$_2$, —CONR$^9$(C$_{1-4}$ alkyl), —CONR$^9$—C$_{1-4}$ alkylene-O(C$_{1-4}$ alkyl), —CON(C$_{1-4}$ alkyl)$_2$, —CONR$^9$—C$_{1-4}$ alkylene-N(C$_{1-4}$ alkyl)$_2$, —CON(C$_{1-4}$ alkyl)-C$_{1-4}$ alkylene-O(C$_{1-4}$ alkyl), —CONR$^9$—C$_{1-4}$ alkylene-CO$_2$(C$_{1-4}$ alkyl), —NR$^9$COC$_{1-4}$ alkyl, —NR$^9$CO$_2$C$_{1-4}$ alkyl, —NR$^9$CONH(C$_{1-4}$ alkyl), —NR$^9$CONR$^9$—C$_{1-4}$ alkylene-CO$_2$C$_{1-4}$ alkyl, —NR$^9$—C$_{1-4}$ alkylene-N(C$_{1-4}$ alkyl)$_2$, R$^8$, —OR$^8$, —O—C$_{1-4}$ alkylene-R$^8$, —COR$^8$, —CO$_2$R$^8$, —CONR$^9$R$^8$, —NR$^9$COR$^8$, —NR$^9$CO$_2$R$^8$, and —NR$^9$CONR$^9$R$^8$;

R$^7$, at each occurrence, is selected from the group consisting of: H, C$_{1-4}$ alkyl, COC$_{1-4}$ alkyl, CO$_2$(C$_{1-4}$ alkyl), CO$_2$Bn, —CONH—C$_{1-4}$ alkylene-CO$_2$C$_{1-4}$ alkyl, phenyl, benzyl, and —CO$_2$—C$_{1-4}$ alkylene-aryl;

R$^8$, at each occurrence, is selected from the group consisting of: —(CH$_2$)$_n$—C$_{3-10}$ carbocycle and —(CH$_2$)$_n$-5- to 10-membered heterocycle containing carbon atoms and 1-4 heteroatoms selected from the group consisting of: N, NR$^a$, O, and S(O)$_p$; wherein said carbocycle or heterocycle is substituted with 0-3 R$^b$;

R$^9$, at each occurrence, is selected from the group consisting of: H and C$_{1-4}$alkyl;

R$^{10}$, at each occurrence, is selected from the group consisting of: H, halo, OH, and C$_{1-4}$ alkyl;

R$^a$ is selected from the group consisting of: H, C$_{1-4}$ alkyl, —(CH$_2$)—OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$;

R$^b$ is selected from the group consisting of: =O, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N'(C$_{1-4}$ alkyl)$_2$-C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$ is, independently at each occurrence, selected from the group consisting of: —(CH$_2$)$_n$—C$_{3-6}$ cycloalkyl, —(CH$_2$)$_n$- phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$ is selected from the group consisting of: =O, halo, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

n, at each occurrence, is selected from 0, 1, 2, 3, and 4; and p, at each occurrence, is selected from 0, 1, and 2.

In a second aspect, the present invention provides compounds of Formula (II)

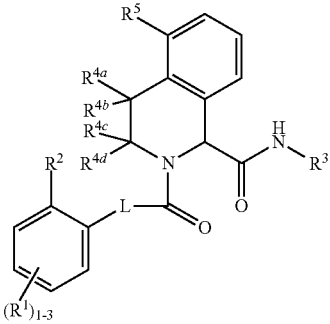

or stereoisomers, tautomers, pharmaceutically acceptable salts thereof, within the scope of the first aspect, wherein:

L is selected from the group consisting of: a bond, —CHR$^{10}$CHR$^{10}$—, —CR$^{10}$=CR$^{10}$—, and —C≡C—;

R$^1$, at each occurrence, is selected from the group consisting of: H, halo, C$_{1-2}$ alkyl, —O(C$_{1-4}$ alkyl), CN, —CH$_2$NH$_2$, and —C(=NH)NH$_2$;

R$^{4a}$, R$^{4b}$, R$^{4c}$, and R$^{4d}$ are independently selected from the group consisting of: H, F, and C$_{1-4}$ alkyl;

R$^5$ is selected from the group consisting of: halo, C$_{1-4}$ alkyl substituted with 0-2 R$^b$, C$_{2-4}$ alkenyl substituted with 0-2 R$^b$, —OH, —CN, —N(C$_{1-4}$ alkyl)$_2$, —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$alkyl), —CON(C$_{1-4}$alkyl)$_2$, —CONR$^9$—C$_{1-4}$alkylene-O(C$_{1-4}$ alkyl), —CONR$^9$—C$_{1-4}$ alkylene-CO$_2$(C$_{1-4}$ alkyl), —NR$^9$COC$_{1-4}$ alkyl, NR$^9$CO$_2$C$_{1-4}$ alkyl, —NR$^9$CONR$^9$—C$_{1-4}$ alkylene-CO$_2$C$_{1-4}$ alkyl, —NHSO$_2$(C$_{1-4}$ alkyl), R$^8$, C$_{2-4}$ alkenylene-R$^8$, —OR$^8$, —COR$^8$, C$_{2-4}$ alkenylene-COR$^8$, —CONR$^9$R$^8$, —NR$^9$COR$^8$, and —NR$^9$CONR$^9$R$^8$.

In a third aspect, the present invention includes compounds of Formula (III):

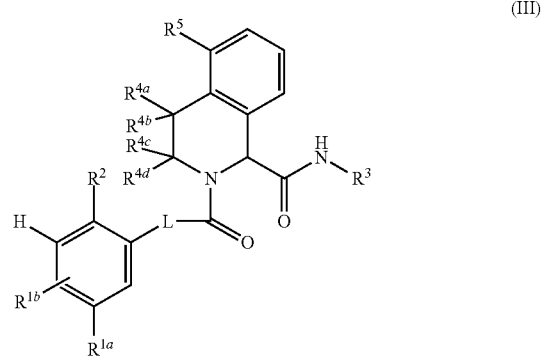

or stereoisomers, tautomers, pharmaceutically acceptable salts, or solvates thereof, within the scope of the second aspect, wherein:

$R^{1a}$ is selected from the group consisting of: H, halo, $C_{1-2}$ alkyl, and methoxy;

$R^{1b}$ is selected from the group consisting of: H and halo;

$R^2$ is selected from the group consisting of: H, F, CN, OH, $C_{1-4}$ alkoxy, —$CHF_2$, —$CF_3$, —$CH_2NH_2$, —$OCHF_2$, —CO($C_{1-4}$ alkyl), —$CONH_2$, —COOH, triazole substituted with $R^{2a}$, and tetrazole substituted with $R^{2a}$;

$R^3$ is selected from the group consisting of: phenyl substituted with 1-2 $R^{3a}$, $C_{3-6}$ cycloalkyl substituted with 1-2 $R^{3a}$, and heterocycle substituted with 1-2 $R^{3a}$; wherein said heterocycle is selected from the group consisting of: piperidinyl, pyridyl, indolyl, and indazolyl;

$R^{3a}$, at each occurrence, is selected from the group consisting of: H, halo, —OH, —O($C_{1-4}$ alkyl), —CN, —$CO_2H$, —$CONH_2$, —$CO_2(C_{1-4}$ alkyl), —$CO_2$—$C_{1-4}$ alkylene-O($C_{1-4}$ alkyl), —$CO_2$—$C_{1-4}$ alkylene-N($C_{1-4}$ alkyl)$_2$, —$CO_2$—$C_{1-4}$ alkylene-O—$C_{1-4}$ alkylene-N($C_{1-4}$ alkyl)$_2$, —$CO_2$—$C_{1-4}$ alkylene-O—$C_{1-4}$ alkylene-O($C_{1-4}$ alkyl), —$NHCO_2$($C_{1-4}$ alkyl), $R^c$, and —$CO_2R^c$;

$R^5$ is selected from the group consisting of: $R^8$, $C_{2-4}$ alkenylene-$R^8$, —$OR^8$, $COR^8$, $C_{2-4}$ alkenylene-$COR^8$, —$CONHR^8$, and $NHCONHR^8$;

$R^8$, at each occurrence, is selected from the group consisting of: —$(CH_2)_n$—$C_{3-6}$ cycloalkyl, —$(CH_2)_n$-phenyl and —$(CH_2)_n$-5- to 10-membered heterocycle containing carbon atoms and 1-4 heteroatoms selected from the group consisting of: N, $NR^a$, O, and $S(O)_p$; wherein said cycloalkyl, phenyl and heterocycle are substituted with 0-3 $R^b$;

$R^a$, at each occurrence, is selected from the group consisting of: H, $C_{1-4}$ alkyl, —$(CH_2)_nOH$, $CO(C_{1-4}$ alkyl), $COCF_3$, $CO_2(C_{1-4}$ alkyl), —CONH—$C_{1-4}$ alkylene-$CO_2(C_{1-4}$ alkyl), $C_{1-4}$ alkylene-$CO_2(C_{1-4}$ alkyl), $R^c$, and $CO_2R^c$;

$R^b$, at each occurrence, is selected from the group consisting of: halo, $C_{1-4}$ alkyl, $C_{1-4}$ alkoxy, $OCF_3$, $NH_2$, $NO_2$, $CO_2(C_{1-4}$ alkyl), $CONH_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-$CO_2(C_{1-4}$ alkyl), —CONH—$C_{1-4}$ alkylene-$N^+(C_{1-4}$ alkyl)$_2$-$C_{1-4}$ alkylene-O—P(O)(OH)$_2$, —$NHCO_2(C_{1-4}$ alkyl), $R^c$, $COR^c$, and $CONHR^c$; and $R^c$, at each occurrence, is selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, O, and $S(O)_p$; wherein each ring moiety is substituted with 0-2 $R^d$.

In a fourth aspect, the present invention includes compounds of Formula (III), or stereoisomers, tautomers, pharmaceutically acceptable salts, or solvates thereof, within the scope of the third aspect, wherein:

$R^{1a}$ is Cl;

$R^{1b}$ is selected from the group consisting of: H and F;

$R^2$ is selected from the group consisting of: H, F, $CF_3$, $COC_{1-4}$ alkyl, and tetrazolyl;

$R^3$ is selected from the group consisting of: phenyl substituted with 1-2 $R^{3a}$, $C_{3-6}$ cycloalkyl substituted with 1-2 $R^{3a}$, and indazolyl substituted with 1-2 $R^{3a}$;

$R^{3a}$, at each occurrence, is selected from the group consisting of: H, halo, —OH, —O($C_{1-4}$ alkyl), —CN, —$CO_2H$, —$CONH_2$, —$CO_2(C_{1-4}$ alkyl), —$CO_2$—$(CH_2)_{1-4}$—O($C_{1-4}$ alkyl), —$CO_2$—$(CH_2)_{1-4}$—N($C_{1-4}$ alkyl)$_2$, —$CO_2$—$(CH_2)_{1-4}$—O—$(CH_2)_{1-4}$—N($C_{1-4}$ alkyl)$_2$, —$CO_2$—$(CH_2)_{1-4}$—O—$(CH_2)_{1-4}$—O($C_{1-4}$ alkyl), —$NHCO_2(C_{1-4}$ alkyl), $R^c$, and —$CO_2R^c$; and $R^8$, at each occurrence, is selected from the group consisting of: phenyl, cyclopropyl, cyclobutyl, cyclopentyl, cyclohexyl, morpholine, thiamorpholine, —$(CH2)_{0-2}$-piperidine, tetrahydroquinoline, piperazine, pyridine, benzodioxolyl, pyrazolyl, and indazolyl.

In a fifth aspect, the present invention includes compounds of Formula (III): or stereoisomers, tautomers, pharmaceutically acceptable salts, or solvates thereof, within the scope of the fourth aspect, wherein:

$R^2$ is selected from the group consisting of: H, F, $CF_3$, C(O)Me, and tetrazolyl;

$R^3$ is selected from the group consisting of: phenyl substituted with 1-2 $R^{3a}$, $C_{3-6}$ cycloalkyl substituted with 1-2 $R^{3a}$, pyridyl substituted with 1-2 $R^{3a}$,

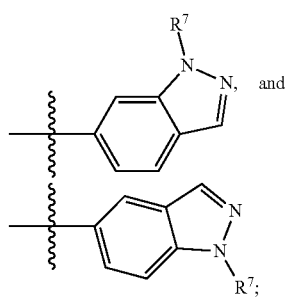

$R^{3a}$, at each occurrence, is selected from the group consisting of: F, —OH, —OMe, —OEt, —CN, —$CO_2H$, —$CONH_2$, —$CO_2Me$, —$CO_2Et$, —$CO_2$(t-butyl), —$CO_2$($CH_2)_2OMe$, —$CO_2(CH_2)_2N(C_{1-4}$ alkyl)$_2$, —$CO_2(CH_2)_2O(CH_2)_2N(C_{1-4}$ alkyl)$_2$, —$CO_2(CH_2)_2O(CH_2)_2OMe$, —$NHCO_2Me$, $R^c$, and —$CO_2R^c$;

$R^5$, at each occurrence, is selected from the group consisting of:

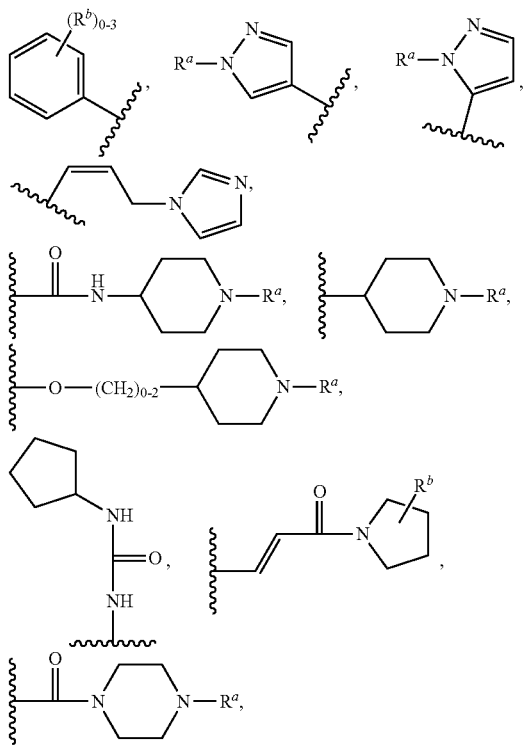

-continued

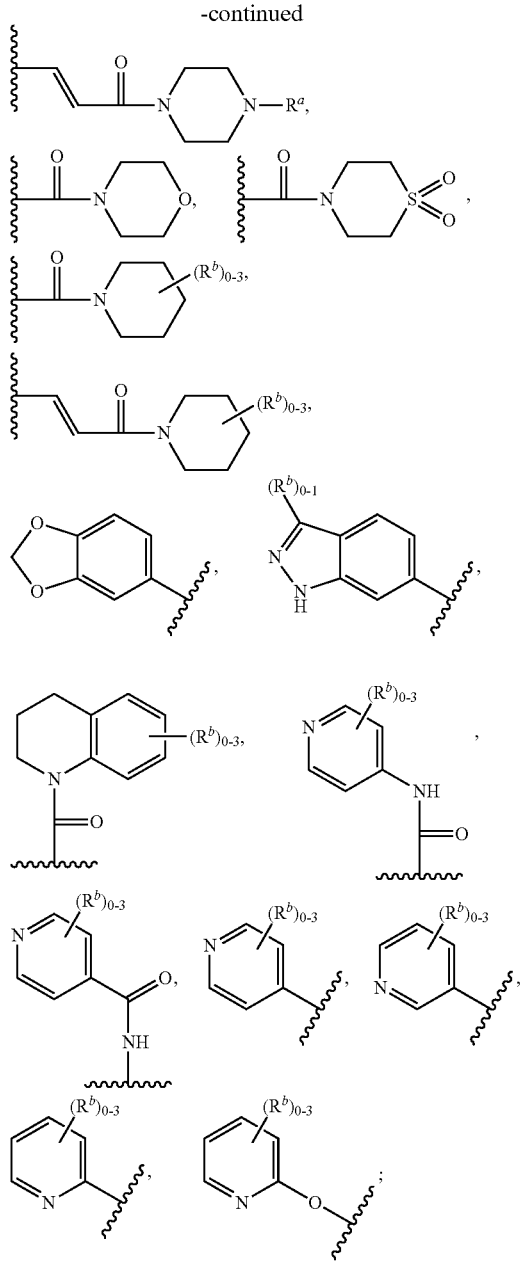

$R^a$ is selected from the group consisting of: H, Me, Et, —(CH$_2$)$_3$OH, COCF$_3$, COMe, CO$_2$Me, CO$_2$Et, CO$_2$(t-butyl), —CONH(CH$_2$)$_2$CO$_2$(C$_{1-4}$ alkyl), R$^c$, and CO$_2$R$^c$;

$R^b$ is, independently at each occurrence, selected from the group consisting of: Me, Et, Cl, OMe, OCF$_3$, NO$_2$, NH$_2$, N(Me)$_2$, CO$_2$Me, CO$_2$Et, CONH$_2$, —CONH(C$_{1-4}$ alkyl), —CON(C$_{1-4}$ alkyl)$_2$, —CONH(CH$_2$)$_{1-2}$O(C$_{1-4}$ alkyl), —CONH(CH$_2$)$_{1-2}$N(C$_{1-4}$ alkyl)$_2$, —CONH(CH$_2$)$_{1-2}$N$^+$(C$_{1-4}$ alkyl)$_2$(CH$_2$)$_{1-2}$—O—P(O)(OH)$_2$, —NHCO$_2$(C$_{1-4}$ alkyl), —R$^c$, COR$^c$, CONHR$^c$; and $R^c$ is, independently at each occurrence, selected from the group consisting of: —(CH$_2$)$_n$—C$_{3-6}$ cycloalkyl, —(CH$_2$)$_n$-phenyl, and —(CH$_2$)$_{0-2}$-morpholine, methylpiperazine, pyrrolidine optionally substituted with =O, and pyrazole.

In a sixth aspect, the present invention includes compounds of Formula (IV):

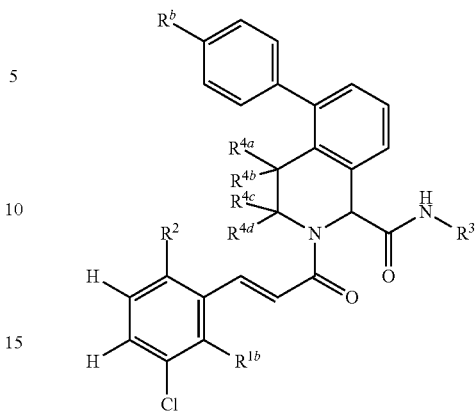

or stereoisomers, tautomers, pharmaceutically acceptable salts, or solvates thereof, within the scope of the fifth aspect, wherein:

$R^{1b}$ is H and F;

$R^2$ is independently selected from the group consisting of: H, F, CF$_3$, C(O)Me, and tetrazole;

$R^3$ is independently selected from the group consisting of: phenyl substituted with 1-2 R$^{3a}$, cyclohexyl substituted with 1-3 R$^{3a}$,

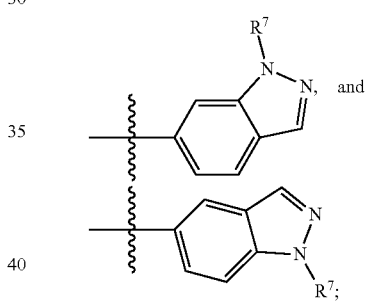

and $R^{3a}$ is, independently at each occurrence, selected from the group consisting of: F and —CO$_2$H;

$R^7$ is selected from the group consisting of: H and C$_{1-4}$ alkyl;

$R^b$ is, independently at each occurrence, selected from the group consisting of: Cl, OMe, OCF$_3$, NO$_2$, CONH$_2$, —CONHMe, —CONHEt, —CON(Me)$_2$, —CON(Et)$_2$, —CONH(CH$_2$)$_{1-2}$O(C$_{1-4}$ alkyl), —CONH(CH$_2$)$_{1-2}$N(C$_{1-4}$ alkyl)$_2$, —CONH(CH$_2$)$_{1-2}$N$^+$(C$_{1-4}$ alkyl)$_2$(CH$_2$)$_{1-2}$—O—P(O)(OH)$_2$, NHCO$_2$Me, NHCO$_2$Et, and COR$^c$; and $R^c$ is, independently at each occurrence, selected from the group consisting of: —(CH$_2$)$_n$—C$_{3-6}$ cycloalkyl, —(CH$_2$)$_n$-phenyl, and —(CH$_2$)$_{0-2}$-morpholine, methylpiperazine, pyrrolidine optionally substituted with =O, and pyrazole.

In a seventh aspect, the present invention includes compounds of Formula (II): or stereoisomers, tautomers, pharmaceutically acceptable salts thereof, within the scope of the second aspect, wherein:

$R^2$ is selected from the group consisting of: H, F, CF$_3$, C(O)Me, and tetrazolyl;

$R^3$ is selected from the group consisting of: phenyl substituted with 1-2 R$^{3a}$ and pyridyl substituted with 1-2 R$^{3a}$;

$R^5$ is selected from the group consisting of: halo, C$_{1-4}$ alkyl substituted with 0-2 R$^b$, C$_{2-4}$ alkenyl substituted with 0-2 R$^b$, —OH, —N(C$_{1-4}$ alkyl)$_2$, —O—C$_{1-4}$ alkylene-O(C$_{1-4}$ alkyl), —O—C$_{1-4}$ alkylene-N(C$_{1-4}$ alkyl)$_2$, and —NHSO$_2$(C$_{1-4}$ alkyl);

R$^{3a}$, at each occurrence, is selected from the group consisting of: F and —CO$_2$H;

R$^b$, at each occurrence, is selected from the group consisting of: CONH$_2$, CO$_2$(C$_{1-4}$ alkyl), R$^c$, and COR$^c$;

R$^c$, at each occurrence, is selected from the group consisting of:
imidazole, methylpiperazine, pyrrolidine substituted with 0-2 R$^d$, and piperidine substituted with 0-2 R$^d$; and R$^d$, at each occurrence, is selected from the group consisting of: NH$_2$ and pyrrolidine.

In an eighth aspect, the present invention includes compounds of Formula (V),

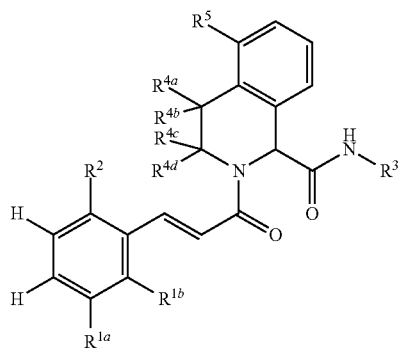

(V)

or stereoisomers, tautomers, pharmaceutically acceptable salts, or solvates thereof, within the scope of the second aspect, wherein:

R$^{1b}$ is selected from the group consisting of: H and F;

R$^3$ is selected from the group consisting of: phenyl substituted with 1-2 R$^{3a}$,

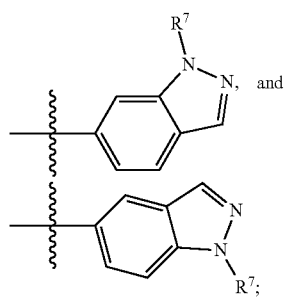

R$^{3a}$, at each occurrence, is selected from the group consisting of: H, halo, CN, CO$_2$H, —CO$_2$(C$_{1-4}$ alkyl), —CO$_2$(CH$_2$)$_{1-2}$O(C$_{1-4}$ alkyl), —CO$_2$(CH$_2$)$_{1-2}$CON(C$_{1-4}$ alkyl)$_2$, —CONH$_2$, —CONH(C$_{1-4}$ alkyl), —NHCO$_2$(C$_{1-4}$ alkyl), —CO$_2$(C$_{3-6}$ cycloalkyl), —CO$_2$(CH$_2$)$_{1-2}$Ph, and —CO$_2$(CH$_2$)$_{1-2}$triazole.

R$^{4a}$, R$^{4b}$, R$^{4c}$, and R$^{4d}$ are independently selected from the group consisting of: H and methyl;

R$^5$ is selected from the group consisting of: halo, C$_{1-4}$ alkyl substituted with 0-2 R$^b$, C$_{2-4}$ alkenyl substituted with 0-2 R$^b$, —OH, —CN, —N(C$_{1-4}$ alkyl)$_2$, —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$ alkyl), —CONR$^9$(C$_{1-4}$ alkyl)$_2$, —CONR$^9$—C$_{1-4}$ alkylene-O(C$_{1-4}$ alkyl), —CONR$^9$—C$_{1-4}$ alkylene-N(C$_{1-4}$ alkyl)$_2$, —CON(C$_{1-4}$ alkyl)$_2$, —CONR$^9$—C$_{1-4}$ alkylene-CO$_2$(C$_{1-4}$ alkyl), —NR$^9$COC$_{1-4}$ alkyl, NR$^9$CO$_2$C$_{1-4}$ alkyl, —NR$^9$CONR$^9$—C$_{1-4}$ alkylene-CO$_2$C$_{1-4}$ alkyl, —NR$^9$SO$_2$(C$_{1-4}$ alkyl), R$^8$, C$_{2-4}$ alkenylene-R$^8$, —OR$^8$, —COR$^8$, —CO$_2$R$^8$, C$_{2-4}$ alkenylene-COR$^8$, —CONR$^9$R$^8$, —NR$^9$COR$^8$, and —NR$^9$CONR$^9$R$^8$;

R$^7$, at each occurrence, is selected from the group consisting of: H and methyl;

R$^8$, at each occurrence, is selected from the group consisting of: C$_{3-6}$ cycloalkyl, phenyl and 5- to 10-membered heterocycle containing carbon atoms and 1-4 heteroatoms selected from the group consisting of: N, NR$^a$, O, and S(O)$_p$; wherein said cycloalkyl, phenyl and heterocycle are substituted with 0-3 R$^b$;

R$^a$, at each occurrence, is selected from the group consisting of: H, C$_{1-4}$ alkyl, —(CH$_2$)—OH, CO(C$_{1-4}$ alkyl), COCF$_3$, CO$_2$(C$_{1-4}$ alkyl), —CONH—C$_{1-4}$ alkylene-CO$_2$(C$_{1-4}$ alkyl), R$^c$, and CO$_2$R$^c$;

R$^b$, at each occurrence, is selected from the group consisting of: halo, C$_{1-4}$ alkoxy, OCF$_3$, NH$_2$, NO$_2$, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-CO$_2$(C$_{1-4}$ alkyl), —CONH—C$_{1-4}$ alkylene-N$^+$(C$_{1-4}$ alkyl)$_2$-C$_{1-4}$ alkylene-O—P(O)(OH)$_2$, —NHCO$_2$(C$_{1-4}$ alkyl), R$^c$, COR$^c$, and CONHR$^c$;

R$^c$, at each occurrence, is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NR$^c$, O, and S; wherein each ring moiety is substituted with 0-2 R$^d$; and R$^d$, at each occurrence, is selected from the group consisting of: =O, N(C$_{1-4}$ alkyl)$_2$, heterocycle containing carbon atoms and 1-4 heteroatoms selected from the group consisting of: N, NH, N(C$_{1-4}$ alkyl), O, and S.

In a ninth aspect, the present invention includes compounds of Formula (V): or stereoisomers, tautomers, pharmaceutically acceptable salts, or solvates thereof, within the scope of the eighth aspect, wherein:

R$^5$ is selected from the group consisting of: C$_{1-4}$ alkyl substituted with 0-2 R$^b$, C$_{2-4}$ alkenyl substituted with 0-2 R$^b$, —N(Me)$_2$, —O(CH$_2$)$_2$N(Me)$_2$, O(CH$_2$)$_2$OMe, CONH(CH$_2$)$_2$N(Me)$_2$, —NHSO$_2$Me,

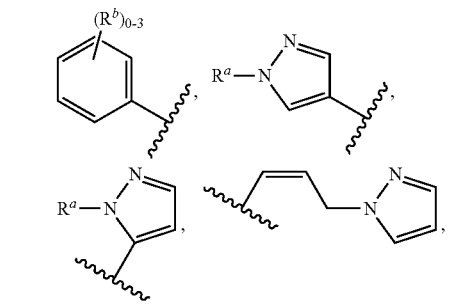

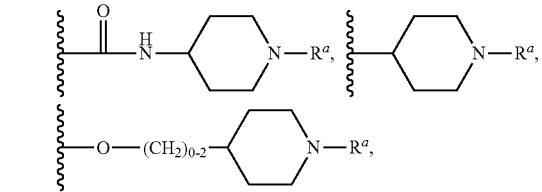

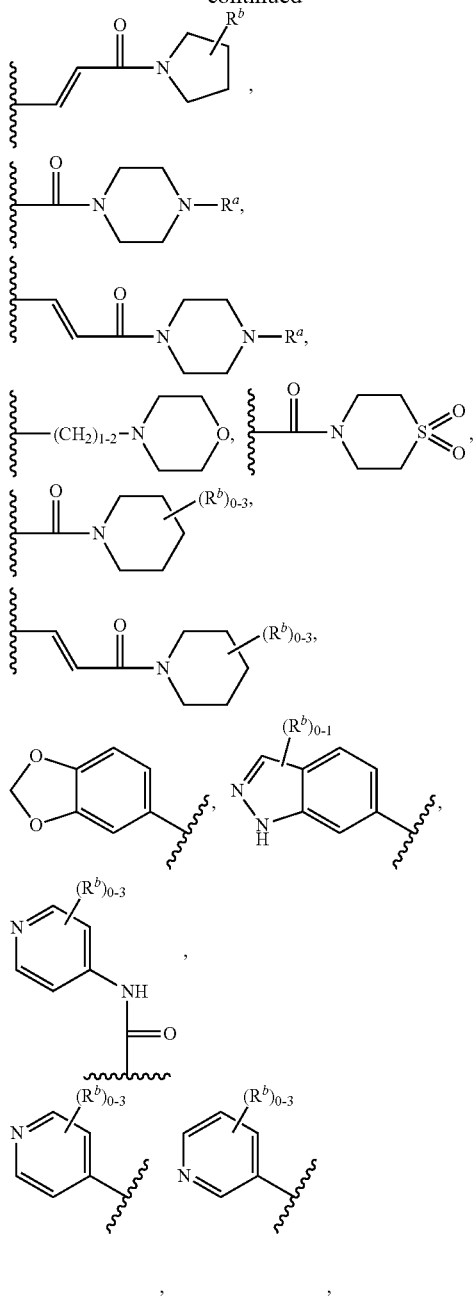

wherein said ring moieties are substituted with 0-3 $R^b$;

$R^{3a}$, at each occurrence, is selected from the group consisting of: F, CN, $CO_2H$, $CO_2Me$, $CO_2Et$, $CO_2$(i-Bu), and $NHCO_2Me$;

$R^a$, at each occurrence, is selected from the group consisting of: H, methyl, —$(CH_2)_{0-3}OH$, COMe, $COCF_3$, $CO_2Me$, $R^c$, and $CO_2R^c$;

$R^b$, at each occurrence, is selected from the group consisting of: HCl, OMe, $OCF_3$, $NO_2$, $NH_2$, —$N(Me)_2$, —$CO_2Me$, —$CO_2Et$, $CONH_2$, —CONHMe, —CONHEt, —CON$(Me)_2$, —$CONH(CH_2)_2OMe$, —$CONH(CH_2)_2N(Me)_2$, —$CONH(CH_2)_2N^+(Me)_2CH_2$—$OP(O)(OH)_2$, —$NHCO_2Et$, —$NHCO_2Me$, $R^c$, $COR^c$, and $CONHR^c$;

$R^c$, at each occurrence, is selected from the group consisting of: —$(CH_2)_{0-1}$phenyl, pyrrolidine substituted with 0-2 $R^d$, pyrazole, imidazole, —$(CH_2)_{0-2}$morpholine, piperidine substituted with 0-2 $R^d$, methylpiperidine, and methylpiperazine; and $R^d$, at each occurrence, is selected from the group consisting of: =O, pyrrolidine, and $N(Me)_2$.

In another embodiment, ring A is phenyl.

In another aspect, ring A is

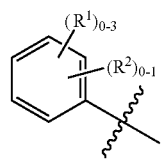

wherein $R^1$ is, independently at each occurrence, selected from the group consisting of: halogen, $C_{1-4}$ alkyl, OH, $C_{1-4}$ alkoxy, $CO(C_{1-4}$ alkyl), CN, $CH_2F$, $CHF_2$, $OCHF_2$, and —$CH_2NHCO_2(C_{1-4}$ alkyl); $R^2$ is a 5- to 7-membered heterocycle comprising carbon atoms and 1-4 heteroatoms selected from N, $NR^c$, O, and $S(O)_p$, wherein said heterocycle is substituted with 0-2 $R^{2a}$.

In another aspect, ring A is

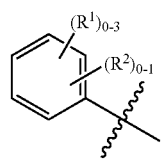

is independently selected from the group consisting of:

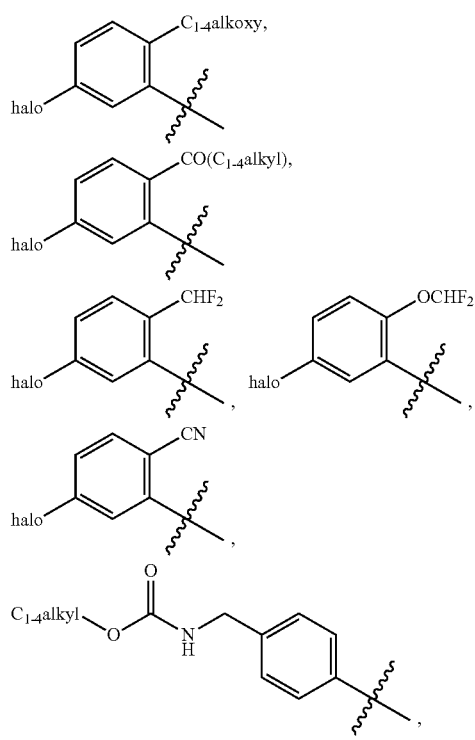

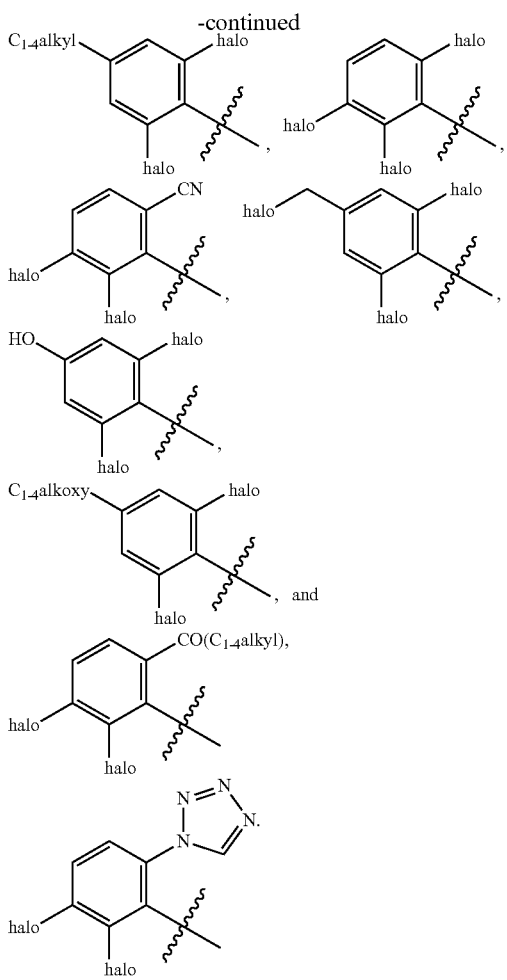

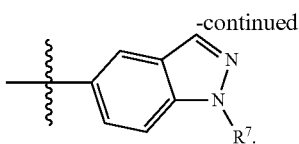

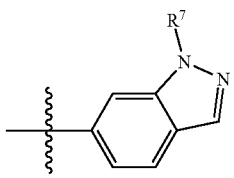

In another embodiment, L is independently selected from the group consisting of: a bond, —CH$_2$CH$_2$—, —CH=CH—, —C(Me)=CH—, —C≡C—, and —CH$_2$NH—.

In another embodiment, L is independently selected from the group consisting of: a bond, —CH$_2$CH$_2$—, —CH=CH—, and —C(Me)=CH.

In another embodiment, L is independently selected from the group consisting of: a bond, —CH$_2$CH$_2$— and —CH=CH—.

In another embodiment, L is —CH=CH—.

In another embodiment, R$^5$ is substituted phenyl.

In another embodiment, R$^3$ is C$_{1-4}$ alkyl substituted with R$^{3a}$.

In another embodiment, R$^3$ is phenyl substituted with R$^{3a}$.

In another embodiment, R$^3$ is cyclohexyl substituted with R$^{3a}$.

In another embodiment, R$^3$ is a heterocycle substituted with R$^{3a}$ and selected from:

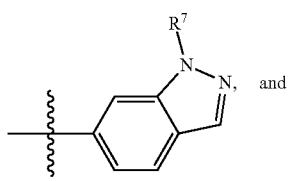

substituted with R$^{3a}$.

In another aspect, the present invention provides a compound selected from the exemplified examples or a stereoisomer, a tautomer, a pharmaceutically acceptable salt, or a solvate thereof In another aspect, the present invention provides a compound selected from any subset list of compounds within the scope of the exemplified examples or a stereoisomer, a tautomer, a pharmaceutically acceptable salt, or a solvate thereof In another embodiment, the compounds of the present invention have Factor XIa Ki values ≤10 μM.

In another embodiment, the compounds of the present invention have Factor XIa Ki values ≤1 μM.

In another embodiment, the compounds of the present invention have Factor XIa Ki values ≤0.5 μM.

In another embodiment, the compounds of the present invention have Factor XIa Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor XIa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R," and "S" are used as described herein for indicating atom configuration(s) relative to a core molecule and are intended to be used as defined in the literature (IUPAC Recommendations 1996, Pure and Applied Chemistry, 68, 2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Ed.), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl"

or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, King, F. D., ed. The Royal Society of Chemistry, Cambridge, UK (1994); Testa, B. et al., *Hydrolysis in*

*Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc or BOC tert-butyloxycarbonyl
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz Carbobenzyloxy
DCM or CH$_2$Cl$_2$ Dichloromethane
CH$_3$CN or ACN Acetonitrile
CDCl$_3$ deutero-chloroform
CHCl$_3$ Chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA Diethylamine
Dess-Martin 1,1,1-tris(acetyloxy)-1,1-dihydro-1,2-beniziodoxol-3-(1H)-one
DIC or DIPCDI Diisopropylcarbodiimide
DIEA, DIPEA diisopropylethylamine (Hunig's base)
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA Triethylamine
EtOAc ethyl acetate
Et$_2$O diethyl ether
EtOH Ethanol
GMF glass microfiber filter
Grubbs (II) (1,3-bis(2,4,6-trimethylphenyl)-2-imidazolidinylidene)dichloro(phenylmethylene) (triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA Isopropanol
PS Polystyrene
SEM-Cl 2-(trimethysilyl)ethoxymethyl chloride
$SiO_2$ silica oxide
$SnCl_2$ tin(II) chloride
TBAI tetra-n-butylammonium iodide
TFA trifluoroacetic acid
THF tetrahydrofuran
$TMSCHN_2$ trimethylsilyldiazomethane
T3P propane phosphonic acid anhydride
TRIS tris(hydroxymethyl)aminomethane The compounds of the present invention can be prepared in a number of ways known to one skilled in the art of organic synthesis. The compounds of the present invention can be synthesized using the methods described below, together with synthetic methods known in the art of synthetic organic chemistry, or by variations thereof as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 3rd Ed., Wiley-Interscience (1999)).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders which include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis, for example, alterations of the vessel wall, changes in the flow of blood, and alterations in the composition of the vascular compartment. These risk factors are collectively known as Virchow's triad. (*Hemostasis and Thrombosis, Basic Principles and Clinical Practice,* 5th Ed., p. 853, Colman, R. W. et al., eds., Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy) are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood,* 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood,* 108:192-199 (2006)). Contact activation is a surface mediated process responsible in part for the regulation of thrombosis and inflammation, and is mediated, at least in part, by fibrinolytic, complement, kininogen/kinin, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.,* 202:271-281 (2005); Kleinschmitz et al., *J. Exp. Med.,* 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.,* 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.,* 101:329-354 (2001)). Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.,* 87:774-777 (2002); Wang et al., *J. Thromb. Haemost.,* 3:695-702 (2005)). Also, factor XI deficiency rescues the perinatal lethal phenotype of complete protein C deficiency (Chan et al., *Amer. J. Pathology,* 158:469-479 (2001)). Furthermore, baboon cross-reactive, function blocking antibodies to human factor XI protect against baboon arterial—venous shunt thrombosis (Gruber et al., *Blood,* 102:953-955 (2003)). Evidence for an antithrombotic effect of small molecule inhibitors of factor XIa is also disclosed in published U.S. Patent Application No. 2004/0180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience,* 6:201-207 (2001); Gailani, D. et al., *Blood Coagulation and Fibrinolysis,* 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either Cl inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.,* 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.,* 15:1107-1113 (1995)). In another study, Factor XI levels above the 90th percentile in patients were associated with a 2.2-fold increased risk for venous thrombosis (Meijers, J. C. M. et al., *N. Engl. J. Med.,* 342:696-701 (2000)).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Ed., pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility, (i) factors that are ideal for use as a parenteral agent such as solubility profile and pharmacokinetics.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, Vol. 3 (Suppl. 1):P1228 (2005); Schumacher, W. A. et al., *European Journal of Pharmacology*, pp. 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.,* 334(11):677-681 (1996); Blom, J. W. et al., *JAMA,* 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery,* 88:913-930 (2001).)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX®) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)_n)))$; and $K_i=IC_{50}/(1+S/K_m)$ for a competitive inhibitor where:

$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 50 or 100 percent, respectively. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Ill.) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 µM (10000 nM) was observed. Table 1 below lists Factor XIa Ki values measured for the following examples.

TABLE 1

| Example No. | Factor XIa Ki (nM) |
|---|---|
| 1 | 38.69 |
| 3 | 21.28 |
| 9 | <5.00 |
| 14 | 579.80 |
| 16 | 332.20 |
| 24 | 169.6 |
| 29 | 552.60 |
| 30 | <5.00 |
| 34 | 21.43 |
| 47 | <5.00 |
| 50 | 3372.00 |
| 61 | 341.90 |
| 65 | 49.16 |
| 66 | 533.90 |
| 78 | <5.00 |
| 80 | 20.12 |
| 89 | <5.00 |
| 93 | 950.90 |
| 98 | 132.20 |
| 108 | <5.00 |
| 120 | 291.10 |
| 132 | <5.00 |
| 146 | 24.81 |
| 150 | 36.97 |
| 152 | 100.00 |
| 160 | 3530.00 |
| 173 | <5.00 |
| 188 | 3862.00 |
| 191 | <5.00 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Ed. (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXR beta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example 52366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., Heterocycles, 16(1): 35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates a few approaches to the synthesis of compounds of Formula (I). Amide 1c can be prepared by amide coupling of commercially available or readily accessible acid 1a and readily accessible aniline 1b using methods commonly used in the literature, such as T3P/base, HOAt/EDC/base and/or $POCl_3$, pyridine. Deprotection of the protecting group $PG_1$ using appropriate conditions known to those in the art of organic synthesis, followed by coupling with acid 1e can yield compounds of formula 1g. Alternatively, coupling of amine 1d with acid 1e followed by deprotection can give acid 1f. The coupling of acid 1f with amine 1b under standard peptide coupling procedures can yield compounds of formula 1g. Appropriate functionalization of intermediates used in this invention to prepare compounds of formula 1g can be achieved through the Suzuki, Buchwald, Ullman or Mitsunobu reactions or simple reactions known to those in the art.

Scheme 1:

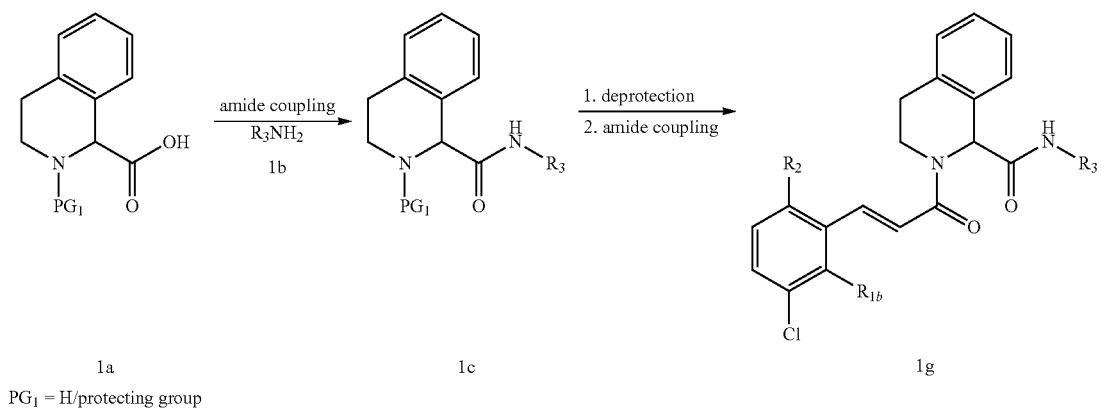

$PG_1$ = H/protecting group

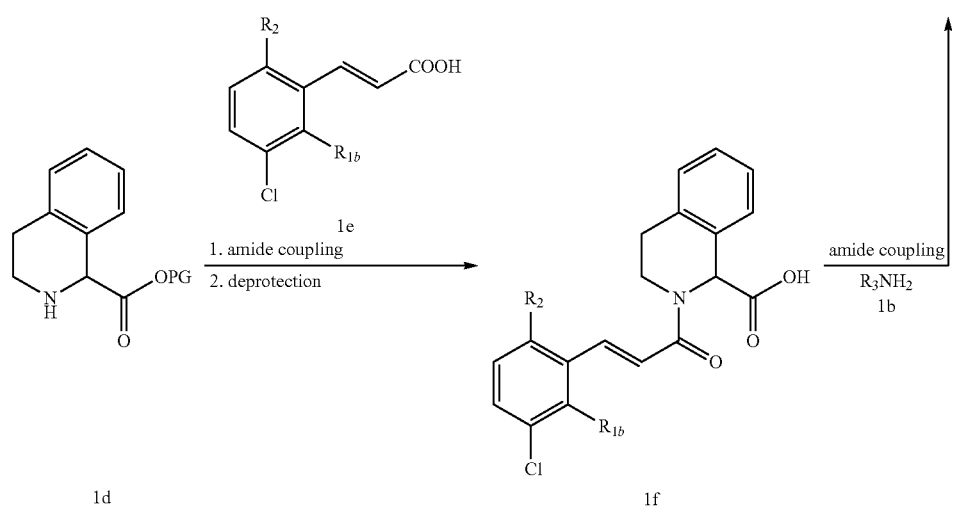

Scheme 2 describes an alternative method to access compounds of this invention. Reaction of acid 1e, isocyanide 2a, and imine 2b can give Ugi product 2d (Schuster, I. et al., Letters in Organic Chemistry, 4(2):102-108 (2007)). Selective oxidation of tetrahydroisoquinoline 2c using known methods such as $MnO_2$ (Aoyama, T. et al., Synlett, 1:35-36 (1998)) can yield imine 2b, which can then be used via the three component Ugi coupling procedures described above. The Ugi coupling procedures can be used extensively with other imino derived intermediates contained in this invention. Further manipulations of the Ugi derived products can afford compounds of this invention.

synthesized from ketone 3k by the Beckmann rearrangement. Reduction of 3l can afford intermediates such as 3c (Vernier, J. et al., WO 2008024398 (2008)). In Method E, the dihydroisoquinoline carbaldehyde (3m) was converted to 3c under basic conditions (Martin, S. et al., WO 2006134143 (2006)). In Method F, dihydroisoquinolinethione was converted to 3c treating the thione 3o with bromopropene followed by treatment with perchloric acid and sodium borohydride (Mohinder, B, et al., Indian Journal of Chemistry, Section B: Organic Chemistry Including Medicinal Chemistry, 18B (4); 312-15 (1979)).

Scheme 2:

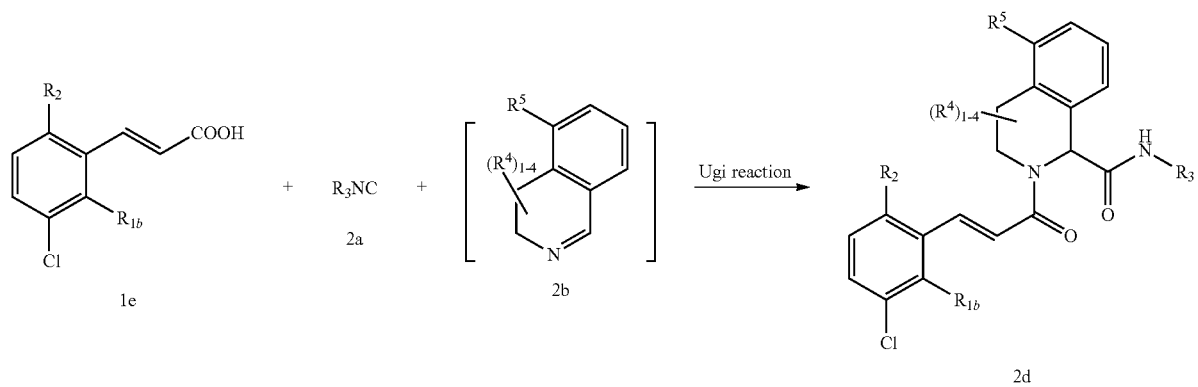

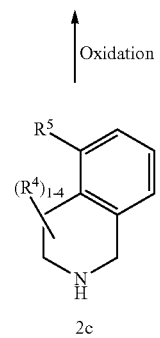

Scheme 3 describes methods for preparing the tetrahydroisoquinoline intermediate 3c and 3e. Method A uses Bischler-Napieralski cyclization to access compounds such as intermediate 3c (Al-Hiari, Y. M. et al., Journal of Heterocyclic Chemistry, 42(4): 647-659 (2005)) or 3e (Zalan, Z. et al., Tetrahedron, 62(12): 2883-2891 (2006)). Method B uses the Friedel-Crafts alkylation reaction to access compounds such as intermediate 3c (Topsom, R. D. et al., Journal of the Chemical Society [Section] D: Chemical Communications, 15:799 (1971)). Alternatively, as described in Method C, cyclization of intermediate 3h and 3-aminopropanol (3i) can afford 3j. Reduction with $NaBH_4$, followed by PCC oxidation gave β-amino aldehyde, which can be converted to 3c under basic conditions (Umetsu, K.; Asao, N., Tetrahedron Letters, 49(17): 2722-2725 (2008)). In Method D, lactam 3l can be Scheme 3:

A)

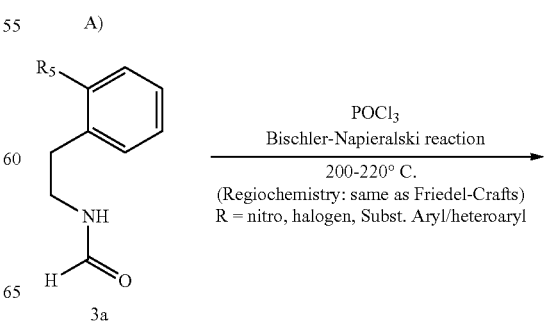

-continued
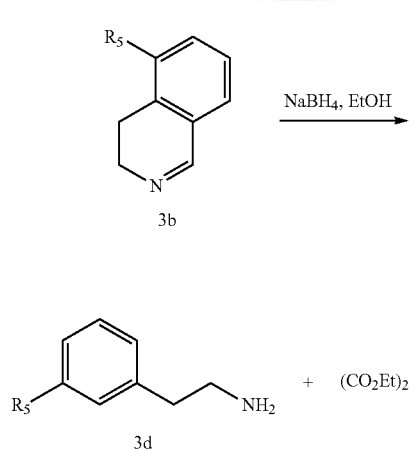
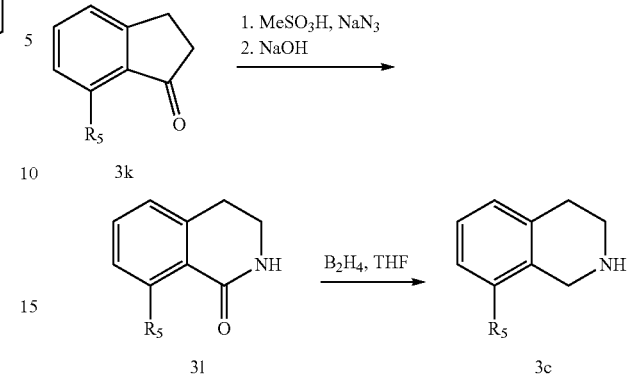
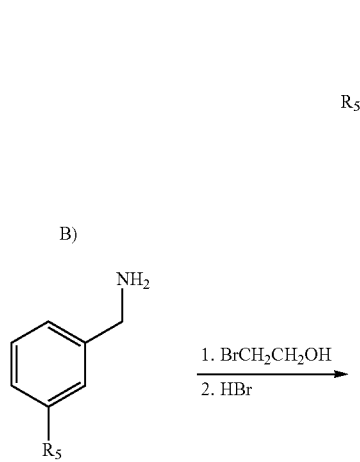
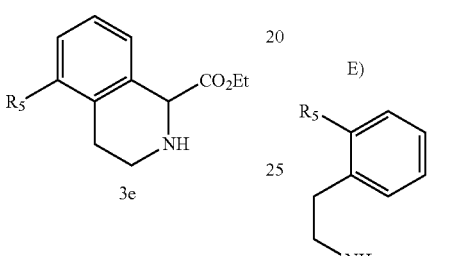
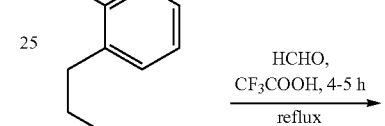
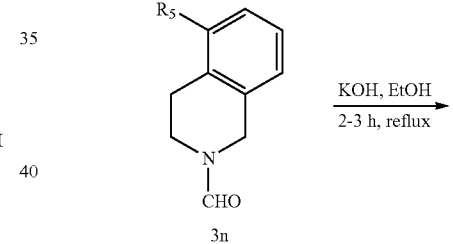
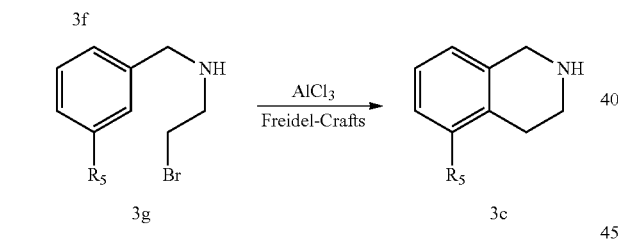
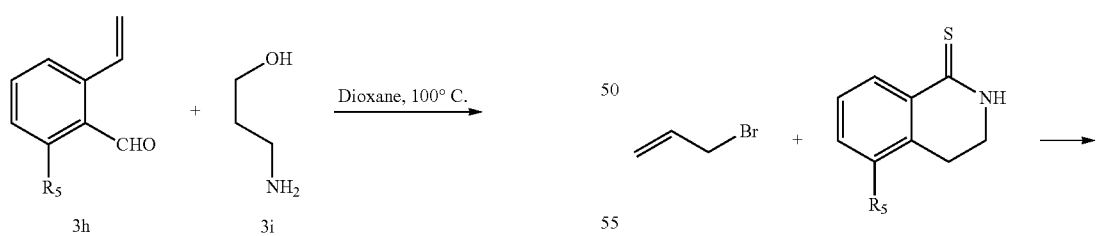
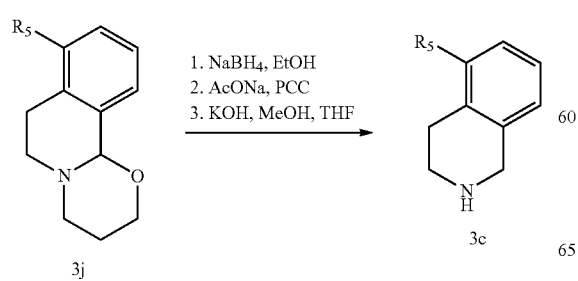
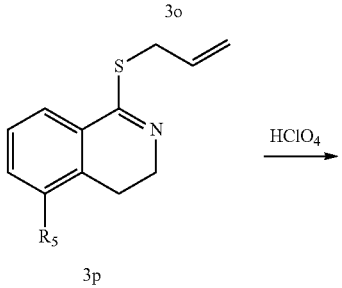

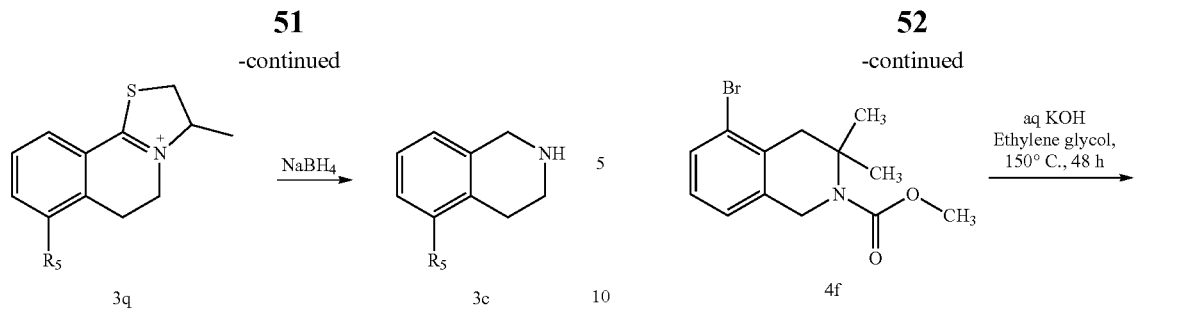

Preparation of substituted THQ analogs is shown in Scheme 4. Bromide 4a can be converted to nitrile 4b under lithiation conditions. Hydrolysis under basic conditions should lead to acid 4c, which can be converted to carbamate 4e via Curtius rearrangement. Formation of the THQ intermediate 4f can then be accomplished by treatment with paraformaldehyde in a mixture of acetic and sulfuric acid (Bigge, C. F. et al, Bioorganic & Medicinal Chemistry Letters, 3(1): 39-42 (1993)). Deprotection of carbamate 4f followed by protection with Boc$_2$O should afford intermediate 4h, which can be subjected to the Suzuki cross coupling reaction with an appropriate boronate or boronic acid or the Stille coupling procedures known to those in the art.

Scheme 4:

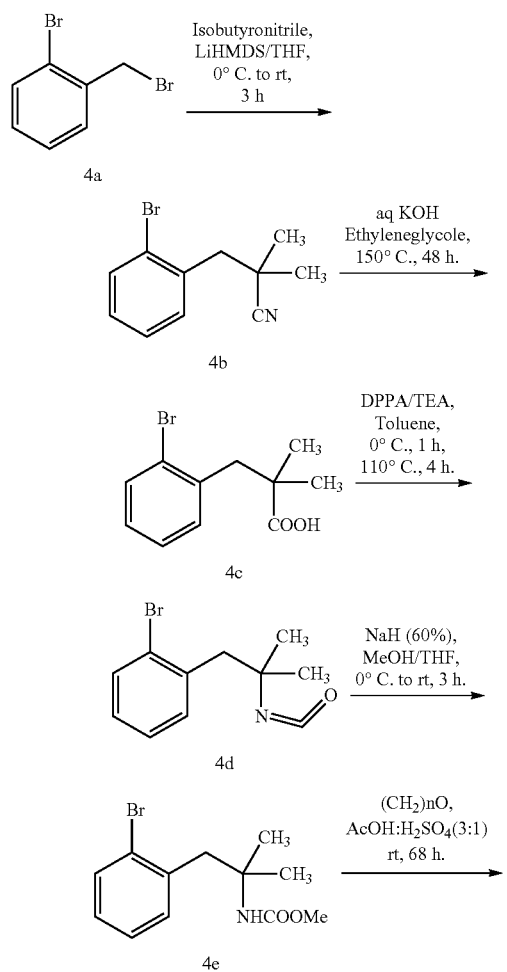

Scheme 5 describes functionalization on intermediates 3c through coupling reactions, such as Suzuki, Buchwald, Ullman or Mitsunobu reactions or substitution reactions when halogen and hydroxyl groups are present on the aromatic ring. Esters or amides 5h can be synthesized from commercially available esters 5f or can be obtained via standard reactions involving organometallic reactions of the halogen with $CO_2$. Reduction of isoquinoline 5d or 5i using literature conditions, such as $H_2$/PtO$_2$ (Schlittler, E.; Muller, J. Helv. Chim. Acta., 31:914-924 (1948)), Na/NH$_3$ (The Birch reduction of aromatic compounds. Rabideau, P. W. et al., Organic Reactions, 42 (1992)) can yield tetrahydroisoquinolines. Sulfonamide 5l can be accessed through readily available sulfonyl chloride 5i. Sulfones 5k can be prepared through coupling with alkyl halides using conditions such as Zn mediated coupling reactions (Sun, X. et al., Synthetic Communications, 28(10): 1785-1791 (1998)). Alternatively the sulfones can be readily accessed via the oxidation of the thioalkyl derivatives with MCPBA. It should be noted that the same sequence of reactions can easily be adopted for other THQ like compounds where the phenyl is replaced with either a 5 and or 6-membered heterocyclic ring. In these cases appropriate steps known to those in the art of organic synthesis can be taken to prepare intermediate compounds of this invention Scheme 5:

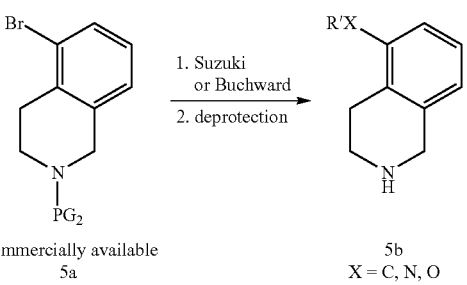

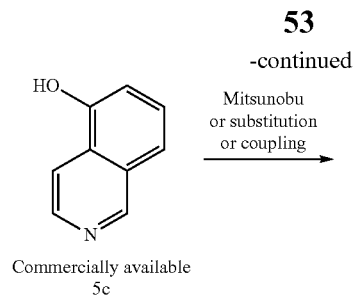

Commercially available
5c

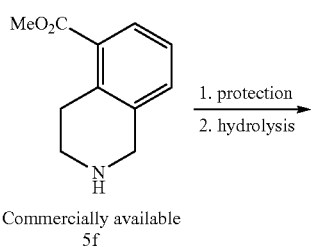

Commercially available
5f

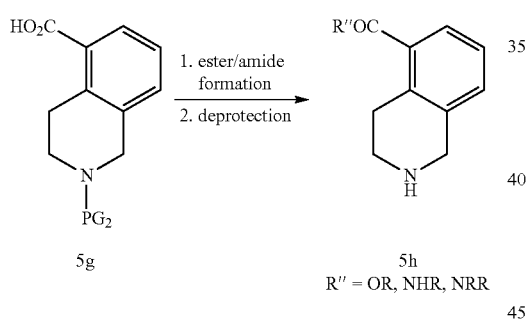

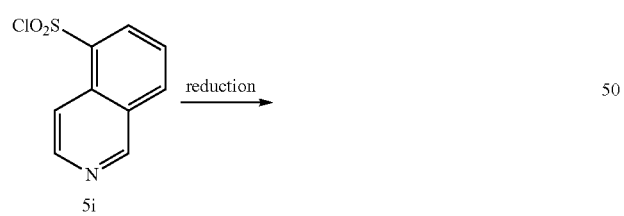

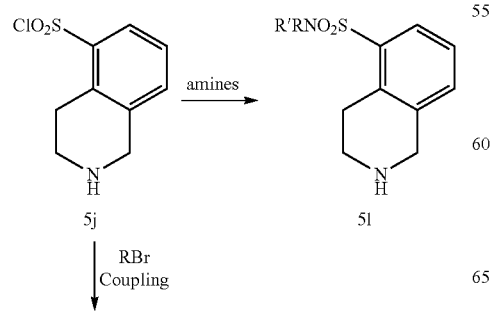

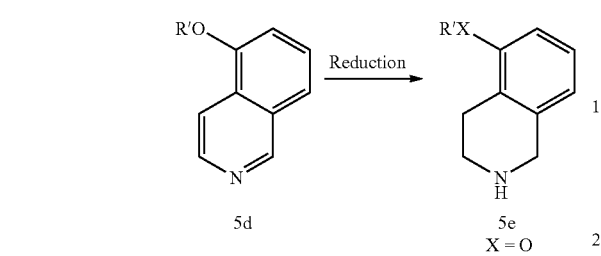

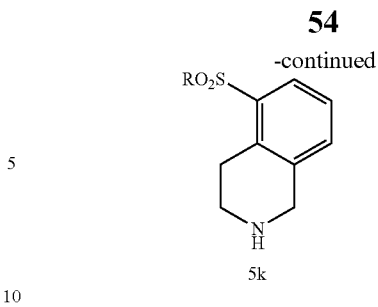

Purification of intermediates and final products was carried out via either normal or reverse phase chromatography. Normal phase chromatography was carried out using prepacked $SiO_2$ cartridges eluting with either gradients of hexanes and EtOAc or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm).

Unless otherwise stated, analysis of final products was carried out by reverse phase analytical HPLC.

Method A: A majority of analytical HPLC runs were: SunFire (4.6×150 mm) (15 min gradient—95:5 $H_2O$/ACN- to 95:5 ACN/$H_2O$-0.05% TFA).

Method B: A minority of analytical HPLC runs were: Zorbax (4.6×75 mm) (8 min gradient—10:90 MeOH/$H_2O$ to 90:10 MeOH/$H_2O$, 0.2% $H_3PO_4$)

A majority of mass spectra runs were run using Phenomenex Luna C18 (2×30 mm) (2 min gradient 90% $H_2O$/10% MeOH/0.1% TFA to 90% MeOH/10% $H_2O$/0.1% TFA)

Intermediate 1

(E)-2,5-Dioxopyrrolidin-1-yl 3-(5-chloro-2-(1H-tetrazol-1-yl)phenyl)acrylate

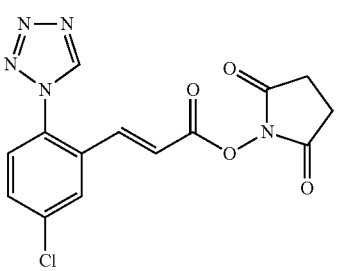 [SMILES: O=C(/C=C/c1cc(Cl)ccc1-n1cnnn1)ON1C(=O)CCC1=O]

The synthesis was described as Intermediate 1 in PCT International Application, WO 2009/114677 published Sep. 17, 2009.

Intermediate 2

(E)-3-(5-chloro-2-tetrazol-1-yl-phenyl)-acrylic acid

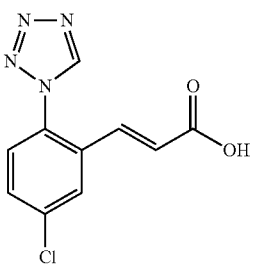 [SMILES: O=C(O)/C=C/c1cc(Cl)ccc1-n1cnnn1]

The synthesis was described as Intermediate 1B in PCT International Application, WO 2009/114677 published Sep. 17, 2009.

Intermediate 3

(E)-3-(3-Chloro-2-fluoro-6-tetrazol-1-yl-phenyl)-acrylic acid 2,5-dioxopyrrolidin-1-yl ester

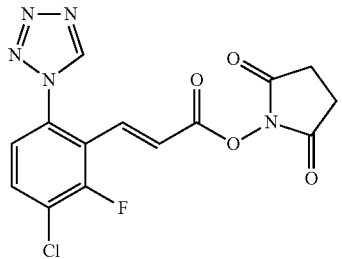 [SMILES: O=C(/C=C/c1c(-n2cnnn2)ccc(Cl)c1F)ON1C(=O)CCC1=O]

Intermediate 3A: (E)-3-(3-chloro-2-fluoro-6-(1H-tetrazol-1-yl)phenyl)acrylic acid: The synthesis of Intermediate 3A was described as Intermediate 7 in PCT International Application, WO 2009/114677 published Sep. 17, 2009.

Intermediate 3: To a slightly turbid mixture of Intermediate 3A (1.0 g, 3.72 mmol) in THF (18.70 mL) and DMF (1.870 mL) was added 1-hydroxypyrrolidine-2,5-dione (0.471 g, 4.09 mmol) and DIC (0.638 mL, 4.09 mmol). The reaction was stirred at rt and a white precipitate formed overtime. The solid was collected by suction filtration and washed with MeOH and H$_2$O. The solid was then, dried under vacuum to give Intermediate 3 (0.98 g, 72%), as a white solid. $^1$H NMR (500 MHz, DMSO-d$_6$) δ 9.92 (s, 1H), 8.06 (t, J=8.12 Hz, 1H), 7.72 (d, J=8.80 Hz, 1H), 7.36 (d, J=16.23 Hz, 1H), 6.81 (d, J=16.51 Hz, 1H), 2.84 (s, 4H) ppm. MS (ESI) m/z: 366.2 (M+H)$^+$.

Intermediate 4

(E)-3-(2-acetyl-5-chlorophenyl)acrylic acid

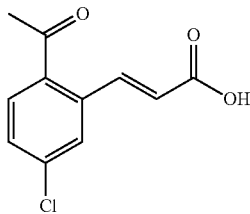

Intermediate 4A: (E)-tert-butyl 3-(2-acetyl-5-chlorophenyl)acrylate: To a degassed solution of 1-(2-bromo-4-chlorophenyl)ethanone (1.0 g, 4.28 mmol), tributylamine (2.041 mL, 8.57 mmol), and tert-butyl acrylate (1.255 mL, 8.57 mmol) in DMF (10 mL) was added palladium on carbon (0.456 g, 0.428 mmol) and Pd(OAc)$_2$ (0.096 g, 0.428 mmol). The reaction mixture was warmed to 100° C. After 16 h, the reaction was cooled to rt. The reaction was filtered and the solid was rinsed with DMF. The filtrate was diluted with EtOAc, washed with H$_2$O (2×), brine, dried over Na$_2$SO$_4$, filtered and concentrated. Purification by normal phase chromatography afforded Intermediate 4A (0.760 g, 63%), as a brown oil. MS (ESI) m/z: 225.0 (M-C4H8+H)$^+$. Intermediate 4: A solution of Intermediate 4A (0.048 g, 0.171 mmol) in 50% TFA/DCM (2 mL) was stirred at rt. After 1 h, the reaction was concentrated to give Intermediate 4 (0.038 g, 100% yield) as a yellow solid. The material was carried onto the next step without further purification. MS (ESI) m/z: 225.1 (M+H)$^+$.

Intermediate 5

(E)-3-(5-chloro-4-fluoro-2-(1H-tetrazol-1-yl)phenyl)acrylic acid

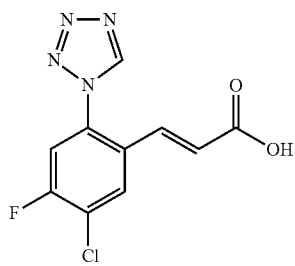 [SMILES: O=C(O)/C=C/c1cc(Cl)c(F)cc1-n1cnnn1]

Intermediate 5A: 4-chloro-5-fluoro-2-iodoaniline: To 4-chloro-3-fluoroaniline (25 g, 0.17 mmol) in 250 mL of H$_2$O was added NaHCO$_3$ (21.6 g, 0.25 mmol). After cooling to 0° C., iodine (43.5 g, 0.17 mmol) was added. After 18 h at rt, an additional 10.8 g of iodine was added and the reaction was stirred overnight. The reaction was extracted with DCM (4×250 mL), the combined organics were washed with sodium thiosulfate solution (2×250 mL) and brine (2×250 mL) and dried (Na$_2$SO$_4$). Purification by silica gel chromatography gave 47 g of Intermediate 5A. MS (ESI) m/z: 145.2 (M+H)$^+$.

Intermediate 5B: 1-(4-chloro-5-fluoro-2-iodophenyl)-1H-tetrazole: To Intermediate 5A (47 g, 17.3 mmol) in AcOH (470 mL) was added NaN$_3$ (33.76 g, 51.9 mmol) and trimethyl orthoformate (56.8 mL, 51.9 mmol). After 30 h, the reaction was poured into ice water, then solid was filtered-off and washed with petroleum ether to afford 49 g of Intermediate 5B. MS (ESI) m/z: 324.8 (M+H)$^+$.

Intermediate 5C: (E)-methyl 3-(5-chloro-4-fluoro-2-(1H-tetrazol-1-yl)phenyl)acrylate: A solution of Intermediate 5B (100 g, 324.4 mmol) in ACN (1000 mL) was degassed with N$_2$. TEA (64 mL) and methyl acrylate (60 mL) were added and the reaction was further degassed. Pd(OAc)$_2$ (8 g, 11.8 mmol) was added and the reaction was heated to 85° C. for 18 h. The reaction was concentrated and the residue was diluted with H$_2$O. The aqueous layer was extracted with EtOAc and the combined organics were washed with brine. Purification by silica gel chromatography gave 25 g of Intermediate 5C. MS (ESI) m/z: 283.0 (M+H)$^+$.

Intermediate 5: (E)-3-(5-chloro-4-fluoro-2-(1H-tetrazol-1-yl)phenyl)acrylic acid: To Intermediate 5C (5 g, 17.7 mmol) in MeOH (50 mL) and THF (25 mL) was added 10% NaOH solution (25 mL). After 2 h, the reaction was concentrated and the residue was diluted with H$_2$O. The pH was adjusted to 2 to 3 with 1.5 N HCl and the resultant solid was filtered and washed with petroleum ether to afford 2 g of Intermediate 5. MS (ESI) m/z: 269.0 (M+H)$^+$.

Intermediate 6 tert-Butyl 4-isocyanobenzoate

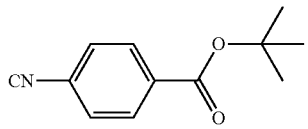

Intermediate 6A: tert-Butyl 4-formamidobenzoate: Combined tert-butyl 4-aminobenzoate (15.3 g, 79 mmol), DMAP (1.935 g, 15.84 mmol), N-methylmorpholine (15.67 mL, 143 mmol) in DCM (120 mL) and, after cooling to 0° C., slowly added formic acid (9.11 mL, 238 mmol). After stirring 18 h, the reaction was concentrated and then partitioned with 1N HCl (100 mL) and EtOAc (200 mL). The aqueous layer was extracted with EtOAc (100 mL). The combined organic layers were washed with brine (50 mL) and dried (MgSO$_4$). A thick yellow syrup (16 g) was collected and was carried onto the next step.

Intermediate 6: To Intermediate 6A in THF (300 mL) was added TEA (33 mL, 238 mmol) and then after cooling to 0° C., POCl$_3$ (7.3 mL, 79 mmol) was slowly added and the reaction was stirred at rt. After 24 h, the reaction was partitioned with EtOAc (200 mL) and dilute aqueous NaHCO$_3$ (100 mL). The aqueous layer was extracted with EtOAc (100 mL). The combined organic layers were washed with brine (50 mL) and dried (MgSO$_4$). Purification by normal phase chromatography afforded 10.4 g (65%) of intermediate 6 as a green solid. $^1$H NMR (400 MHz, CDCl$_3$) δ 8.02 (d, J=8.59 Hz, 2H), 7.41 (d, J=8.34 Hz, 2H), 1.60 (s, 9H) ppm.

Intermediate 7

4-Isocyanobenzonitrile

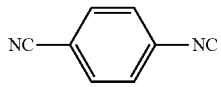

Intermediate 7 was prepared in a similar manner as Intermediate 6 from 4-isocyanoaniline. $^1$H NMR (400 MHz, CDCl$_3$) δ 7.68-7.84 (m, 2H) 7.51 (d, J=8.34 Hz, 2H) ppm.

Intermediate 8 tert-Butyl 6-isocyano-1H-indazole-1-carboxylate

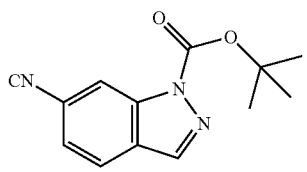

Intermediate 8 was prepared in a similar manner as Intermediate 6 from tert-butyl 6-amino-1H-indazole-1-carboxylate. 1H NMR (400 MHz, CDCl$_3$) δ 8.28 (1H, s), 8.20 (1H, s), 7.76 (1H, d, J=8.34 Hz), 7.28-7.40 (1H, m), 1.74 (9H, s) ppm. MS (ESI) m/z: 144 (M+H-tboc)+.

Intermediate 9

Ethyl 4-isocyanobenzoate

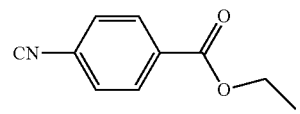

Intermediate 9 was prepared in a similar manner as Intermediate 6. $^1$H NMR (400 MHz, CDCl$_3$) δ 1.40 (t, J=7.20 Hz, 3H) 4.40 (q, J=7.24 Hz, 2H) 7.44 (d, J=8.59 Hz, 2H) 8.00-8.17 (m, 2H) ppm. MS (ESI) m/z: 176 (M+H)$^+$.

Intermediate 10

Methyl 4-isocyanophenylcarbamate

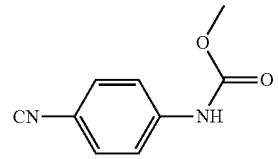

Intermediate 10A: 1-Boc-methyl 4-aminophenylcarbamate: To tert-butyl 4-aminophenylcarbamate (2.1 g, 10.08 mmol) in a separatory funnel with DCM (75 mL) and saturated aqueous NaHCO$_3$ (25 mL) was added methyl chloroformate (0.937 mL, 12.10 mmol). After shaking for 10 min a thick pink gel formed. The solid was filtered off and dried. The aqueous layer was extracted with DCM (50 mL) and dried (MgSO$_4$). All solids collected were combined to afford 2.6 g of Intermediate 10A. $^1$H NMR (400 MHz, MeOD) δ 7.32 (4H, s), 3.73 (3H, s), 1.53 (9H, s) ppm.

Intermediate 10B: methyl 4-aminophenylcarbamate: Intermediate 10A (2.6 g, 9.77 mmol) was deprotected with 30% TFA in DCM (40 mL). After 2 h, the reaction was concentrated and the residue was partitioned with EtOAc (75 mL) and saturated NaHCO$_3$ (50 mL). The organic layer was washed with brine (20 mL) and dried (MgSO$_4$). Crude Intermediate 10B was carried onto the next step. $^1$H NMR (400 MHz, DMSO-d$_6$) δ 9.86 (1H, s), 7.56 (2H, d, J=8.84 Hz), 7.28 (2H, d, J=8.84 Hz), 6.90 (2H, s), 3.68 (3H, s) ppm.

Intermediate 10C: Methyl 4-formamidophenylcarbamate: Crude Intermediate 10B was heated to reflux in ethyl formate for several days. The solvent was removed and the residue was purified by silica gel chromatography to afford 2.9 g of Intermediate 10C as a brown oil. MS (ESI) m/z: 195.0 (M+H)$^+$.

Intermediate 10 was made in a similar manner as Intermediate 6 to afford 0.31 g (17.8%) of a tan solid. $^1$H NMR (400 MHz, CDCl$_3$) δ 7.45 (2H, d, J=8.8 Hz), 7.33-7.41 (2H, m), 6.73 (1H, br.s.), 3.82 (3H, s) ppm.

Intermediate 11

Benzyl 6-isocyano-1H-indazole-1-carboxylate

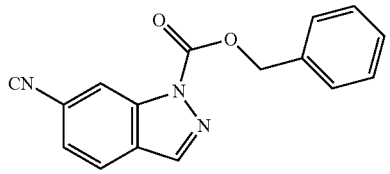

Intermediate 11 was made in a similar manner as Intermediate 6 and Intermediate 8 starting from benzyl 6-amino-1H-indazole-1-carboxylate. $^1$H NMR (400 MHz, CDCl$_3$) δ 8.31 (1H, s), 8.21 (1H, s), 7.76 (1H, d, J=8.34 Hz), 7.54 (2H, d, J=6.82 Hz), 7.30-7.47 (4H, m), 5.56 (2H, s) ppm. MS (ESI) m/z: 234 (M+H—CO$_2$)+.

Intermediate 12

(E)-3-(6-acetyl-3-chloro-2-fluorophenyl)acrylic acid

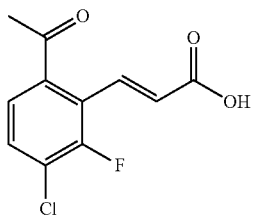 [SMILES: CC(=O)c1ccc(Cl)c(F)c1/C=C/C(=O)O]

Intermediate 12A: 2-bromo-4-chloro-3-fluorobenzoic acid: To a cooled (−78° C.) solution of DIEA (4.9 mL, 48 mmol) in THF was added drop wise n-BuLi (132 mL, 2.3 eq, 2.5 M solution). The mixture was stirred at −30° C. for 30 min. Again the reaction mixture was cooled to −78° C., and a solution of 4-chloro-3-fluorobenzoic acid (25 g, 143 mmol) in THF was added over 1 h. The reaction was stirred at −78° C. overnight. The next day a solution of 1,2-dibromo-1,1,2,2-tetrachloroethane (87 g, 267 mmol) in THF was added and the reaction was stirred at −78° C. for further 2 h and then rt for 4 h. The reaction mixture was quenched with H$_2$O, organic layer was separated and aqueous layer washed with Et$_2$O. Aqueous layer acidified with 1.5N HCl and extracted in EtOAc (2×200 mL), dried over anhydrous Na$_2$SO$_4$, filtered and concentrated to afford Intermediate 12A (30 g, 83.3% yield). MS (ESI) m/z: 252.6 (M−H)+.

Intermediate 12B: Diethyl 2-((2-bromo-4-chloro-3-fluorophenyl)(hydroxy)methylene) malonate: To a suspension of Intermediate 12A (14.6 g, 57 mmol) in DCM (200 mL) was added thionyl chloride (6.6 mL, 88 mmol). The mixture was stirred at reflux for 3 h. Solvent was removed and the residue was dried in vacuum to give the acid chloride as a light brown solid. To a cooled (0° C.) suspension of sodium hydride (3.66 g (60%), 91.5 mmol) in THF was added a solution of diethyl malonate (0.612 g, 3.82 mmol) in THF (5 mL). After 10 min, a solution of the acid chloride (16.4 g, 60 mmol) in THF (160 mL) was added slowly. Following the addition, the reaction was warmed to rt. After 30 min, the solvent was removed and the residue was treated with cold (0° C.) 1.2 M HCl (150 mL). The mixture was extracted with EtOAc (3×250 mL). The combined organic layers were washed with brine, dried over Na$_2$SO$_4$, filtered and concentrated to give Intermediate 12B (20 g, 87% yield) as a solid. MS (ESI) m/z: 395/397 (M+H)$^+$.

Intermediate 12C: 1-(2-Bromo-4-chloro-3-fluorophenyl) ethanone: A solution of Intermediate 12B (18.6 g, 47 mmol) in acetic acid (200 mL), H$_2$O (150 mL) and H$_2$SO$_4$ (2.0 mL) was stirred at 110° C. for 4 h. Most of the solvent was removed and the residue was diluted with EtOAc (400 mL), washed with H$_2$O (5×20 mL), saturated NaHCO$_3$, 1N NaOH, and brine. The solvent was removed to give Intermediate 12C (10 g, 84%) as a low melting solid. $^1$H NMR (400 MHz, DMSO-d$_6$) δ: 7.42 (q, J=6.8, 6.4 Hz, 1H), 7.24 (q, J=6.4, 5.2 Hz, 1H), 2.5 (s, 3H) ppm.

Intermediate 12D: (E)-tert-Butyl 3-(6-acetyl-3-chloro-2-fluorophenyl)acrylate: To a mixture of Intermediate 12C (50 g, 198 mmol), tert-butyl acrylate (50.9 g, 397 mmol) and TEA (55 mL, 397 mmol) in DMF (500 mL) was added Pd(OAc)$_2$ (8.9 g, 39.7 mmol). The resulting mixture was stirred at 90° C. overnight. The reaction was cooled to rt, filtered, and the filtrate was concentrated. Purification by column chromatography gave Intermediate 12D (30 g, 50.8%) as a light yellow solid. MS (ESI) m/z: 242.7 (M+H)$^+$.

Intermediate 12: A solution of Intermediate 12D (25 g, 84 mmol) in DCM (330 mL) and TFA (330 mL) was stirred at rt. After 1.5 h, the solvent was concentrated to give Intermediate 12 (19.5 g, 97.0% yield) as a white solid. $^1$H NMR (400 MHz, DMSO-d$_6$) δ: 12.69 (bs, 1H), 7.80-7.76 (m, 2H), 7.62 (d, J=12.1 Hz, 1H), 6.30 (dd, J=2.4, 2.0 Hz, 1H), 2.6 (s, 3H) ppm. MS (ESI) m/z: 241 (M−H)+.

Intermediate 13

(E)-3-(3-Chloro-6-cyano-2-fluorophenyl)acrylic acid

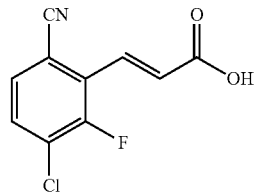 [SMILES: N#Cc1ccc(Cl)c(F)c1/C=C/C(=O)O]

Intermediate 13: 2-Bromo-4-chloro-3-fluorobenzamide: To a solution of 2-bromo-4-chloro-3-fluorobenzoic acid (20 g, 0.078 mol) in DCM (200 mL) was added thionyl chloride (14.7 g, 0.125 mol) followed by DMF (29.5 g, 0.5 moles) and the reaction was heated to reflux for 4h. The reaction was cooled to 0° C. and NH$_3$ gas was bubbled in until the pH was basic. After 30 min., the reaction mixture was quenched with H$_2$O and extracted with DCM, the combined organics were washed with H$_2$O, brine, dried over Na$_2$SO$_4$, filtered and concentrated. Crude product was suspended in petroleum ether and filtered to afford 16.5 g of Intermediate 13A. MS (ESI) m/z: 250-254.0 (M+H)$^+$.

Intermediate 13B: 2-Bromo-4-chloro-3-fluorobenzonitrile: To Intermediate 13A (10 g, 39 mmol) was added POCl$_3$ (100 mL) and NaOH (5 g, 87 mmol) and the reaction was heated to 110° C. for 2 h. The reaction mixture was concentrated and the residue was quenched with ice water. Extracted with EtOAc and the combined organics were washed with 10% NaHCO$_3$, brine, dried over Na$_2$SO$_4$, filtered and concentrated to afford 8.5 g of 13B. MS (ESI) m/z: 232.9-234.9 (M+H)$^+$.

Intermediate 13C: (E)-Methyl 3-(3-chloro-6-cyano-2-fluorophenyl)acrylate: Combined Intermediate 13B (7 g, 29.9 mmol), tetrabutylammonium bromide (9.6 g, 29.9 mmol), NaHCO$_3$ (6.2 g, 74.8 mmol), methyl acrylate (5.2 g, 59.8 mmol) and Pd(OAc)$_2$ in DMF (50 mL). After 18 h, the reaction was heated to 90° C. for 4h. The reaction was cooled to rt and filtered through Celite. Purification by normal phase chromatography afforded 3.5 g of Intermediate 13C. MS (ESI) m/z: 257 (M+H$_2$O)+.

Intermediate 13: To Intermediate 13C (0.5 g, 2.0 mmol) in THF (15 mL) and MeOH (5 mL) was added 1N LiOH (5 mL, 5 mmol). After 2h, the volatile solvents were removed and the aqueous layer was extracted with EtOAc. The aqueous layer was acidified and extracted with EtOAc and the combined organics were washed with H$_2$O, brine, dried over Na$_2$SO$_4$, filtered and concentrated to afford 0.3 g of Intermediate 13. MS (ESI) m/z: 224-226.2 (M+H)$^+$.

Intermediate 14

(E)-3-(5-Chloro-2-(difluoromethyl)phenyl)acrylic acid

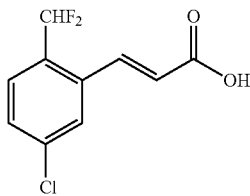 [SMILES: O=C(O)/C=C/c1cc(Cl)ccc1C(F)F]

Intermediate 14A: 2-Bromo-4-chloro-1-(difluoromethyl)benzene: To a solution of 2-bromo-4-chlorobenzaldehyde (1 g, 4.56 mmol) in DCM (15 mL) was added DAST (0.903 mL, 6.83 mmol) at 0° C. The reaction was allowed to warm to rt and stirred overnight. The reaction mixture was diluted with EtOAc, washed with saturated NaHCO$_3$ and brine. The organic phase was dried over MgSO$_4$, filtered and concentrated to give Intermediate 14A (0.88 g, 80% yield) as a clear oil. MS (ESI) m/z: 261.2 (M+Na)+.

Intermediate 14B: (E)-tert-Butyl 3-(5-chloro-2-(difluoromethyl)phenyl) acrylate: To a solution of Intermediate 14A (0.88 g, 3.64 mmol) in DMF (10 mL) was added tert-butyl acrylate (1.401 g, 10.93 mmol), TEA (1.270 mL, 9.11 mmol) and Pd(OAc)$_2$ (0.082 g, 0.364 mmol). The reaction was warmed to 90° C. After 5 h, the reaction was cooled to rt and then filtered to remove the solid. The filtrate was diluted with EtOAc, washed with 1M HCl, saturated NaHCO$_3$ and brine. The organic phase was dried over MgSO$_4$, filtered and concentrated. Purification by normal phase chromatography gave Intermediate 14B (232 mg, 22% yield) as a tan oil. MS (ESI) m/z: 233.1 (M-tBu)+.

Intermediate 14: To a solution of Intermediate 14B (232 mg, 0.804 mmol) in DCM (2.0 mL) was added TFA (2.0 mL, 26.0 mmol). The reaction was stirred under argon at rt. After 1 h, the solvent was removed and residue was dried to give Intermediate 14 (191 mg, 100%) as tan solid. $^1$H NMR (400 MHz, MeOD) δ 7.99 (dt, J=15.8, 1.5 Hz, 1H), 7.83 (s, 1H), 7.60 (d, J=8.3 Hz, 1H), 7.55-7.48 (m, 1H), 7.01 (t, J=54.6 Hz, 1H), 6.51 (d, J=15.8 Hz, 1H). 19F NMR (376 MHz, MEOD) δ -111.67 (s, 2F) ppm. MS (ESI) m/z: 233.1 (M+H)$^+$.

Intermediate 15

(E)-3-(5-Chloro-2-(difluoromethoxy)phenyl)acrylic acid

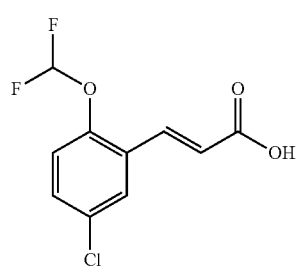 [SMILES: O=C(O)/C=C/c1cc(Cl)ccc1OC(F)F]

Intermediate 15A (E)-tert-Butyl 3-(5-chloro-2-(difluoromethoxy)phenyl) acrylate: To a solution of potassium tert-butoxide (0.407 g, 3.63 mmol) in THF (10 mL) were added tert-butyl 2-(dimethoxyphosphoryl)acetate (0.528 mL, 2.66 mmol) and 5-chloro-2-(difluoromethoxy)benzaldehyde (0.50 g, 2.420 mmol) at 0° C. After 4 hrs, NH$_4$Cl solution was added and the reaction mixture was diluted with EtOAc, washed with sat'd NH$_4$Cl solution, sat'd NaHCO$_3$ and brine. The organic phase was dried over Na$_2$SO$_4$, filtered and concentrated. The crude product was purified by normal phase chromatography. Intermediate 15A was obtained as a white solid 550 mg (74%). MS (ESI) m/z: 327.0 (M+Na)+.19F NMR (376 MHz, CDCl$_3$) δ: -81.11 (1° F., s) ppm.

Intermediate 15: To a solution of (E)-tert-butyl 3-(5-chloro-2-(difluoromethoxy)phenyl)acrylate (458 mg, 1.503 mmol) in DCM (4.0 mL) was added TFA (2.0 mL, 26.0 mmol). After 1 h, the solvent was removed to give Intermediate 15 as a white solid. MS (ESI) m/z: 249.0 (M+H)$^+$.

Intermediate 16

(E)-3-(3-chloro-2-fluoro-6-(trifluoromethyl)phenyl)acrylic acid

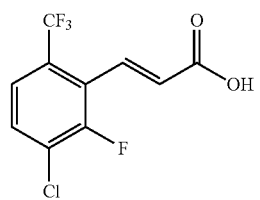 [SMILES: O=C(O)/C=C/c1c(C(F)(F)F)ccc(Cl)c1F]

Intermediate 16 was made in a similar manner as Intermediate 15 substituting 3-chloro-2-fluoro-6-(trifluoromethyl)benzaldehyde for 5-chloro-2-(difluoromethoxy)benzaldehyde followed by TFA deprotection. MS (ESI) m/z: 292 (M+Na)$^+$. $^1$H NMR (400 MHz, CDCl$_3$) δ 7.87 (1H, dd, J=16.17, 2.02 Hz), 7.49-7.62 (2H, m), 6.67 (1H, dd, J=16.30, 1.39 Hz) ppm.

Intermediate 17

1-cyclopentyl-3-(3,4-dihydroisoquinolin-5-yl)urea

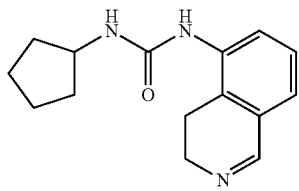 [SMILES: O=C(Nc1cccc2c1CCN=C2)NC1CCCC1]

Intermediate 17A: 1-Cyclopentyl-3-(isoquinolin-5-yl) urea: To isoquinolin-5-amine (0.23 g, 1.595 mmol) in DCM (5 mL) was added DIEA (0.557 mL, 3.19 mmol) and isocyanatocyclopentane (0.180 mL, 1.595 mmol). After 24 h, the reaction was quenched with H$_2$O (15 mL) and extracted with EtOAc (3×30 mL). The combined organic layers were washed with brine (10 mL) and dried (MgSO$_4$). An impure yellow solid was collected and was carried onto the next step. MS (ESI) m/z: 256 (M+H)$^+$.

Intermediate 17B: 1-Cyclopentyl-3-(1,2,3,4-tetrahydroisoquinolin-5-yl)urea: Intermediate 17A was hydrogenated at 55 psi in EtOH (25 mL) in the presence of PtO$_2$ (30 mg). After 24 h, the reaction was filtered through Celite and filtrate concentrated to give 0.389 g of 17B as a white oily solid. MS (ESI) m/z: 260.1 (M+H)$^+$.

Intermediate 17: Intermediate 17B was oxidized with MnO$_2$ (2.496 g, 28.7 mmol) in DCM (20 mL). After 24h, the reaction was filtered through Celite and concentrated to 0.34 g (83.0%) of brown solid. MS (ESI) m/z: 258.1 (M+H)$^+$.

Intermediate 18

5-Bromo-3,3-dimethyl-1,2,3,4-tetrahydroisoquinoline

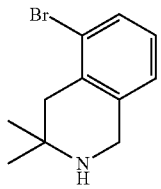

Intermediate 18A: 3-(2-Bromophenyl)-2,2-dimethylpropanenitrile: To a solution of isobutyronitrile (3.58 g, 52 mmol) in dry THF (30 mL) was added LiHMDS (1.0 M in THF) (80 mL, 80 mmol) at 0° C., stirred for 20 min., and to this solution was added 1-bromo-2-(bromomethyl)benzene (10 g, 40 mmol) in dry THF (70 mL). After 3 h at rt, the reaction mixture was quenched with saturated NH$_4$Cl solution, extracted with EtOAc (2×), the combined organics were washed with H$_2$O, brine, dried over Na$_2$SO$_4$, filtered and concentrated to give 9.5 g (99%) of 18A as red wine liquid. $^1$H NMR (400 MHz, CDCl$_3$) δ 7.57-7.60 (2H, m), 7.30-7.34 (1H, m), 7.12-7.17 (1H, m), 3.08 (2H, s), 1.4 (6H, s) ppm.

Intermediate 18B: 3-(2-Bromophenyl)-2,2-dimethylpropanoic acid: To a solution of 18A (19 g, 79.83 mmol) in ethylene glycol (100 mL) was added potassium hydroxide pellets (20 g, 359.24 mmol) and the reaction was heated at 150° C. for 48 h. The reaction mixture was cooled, diluted with H$_2$O and the aqueous layer was washed with EtOAc (2×). The aqueous layer was acidified with 1.5 N HCl, extracted with EtOAc (2×), the combined organics were washed with H$_2$O, brine, dried over Na$_2$SO$_4$, filtered and concentrated. The crude was purified by silica gel column chromatography to give 18.0 g, (87.8%) of 18B as a white solid. MS (ESI) m/z: 257 (M+H)$^+$.

Intermediate 18C: 1-Bromo-2-(2-isocyanato-2-methylpropyl)benzene: To a solution of 18B (9.0 g, 35.0 mmol) in toluene (80 mL) at 0° C., was added TEA (4.7 mL, 33.2 mmol) and, slowly, diphenylphosphoryl azide (9.17 g, 33.2 mmol). After 45 min. at 0° C., the reaction was heated to reflux for 4 h. The reaction mixture was cooled to rt, quenched with H$_2$O, extracted with EtOAc (2×), the combined organics were washed with saturated NaHCO$_3$ solution, H$_2$O, brine, dried over Na$_2$SO$_4$, filtered and concentrated to give 8.0 g of 18C as colorless liquid. $^1$H NMR (400 MHz, CDCl$_3$) δ: 7.37-7.59 (2H, m), 7.30 (1H, m), 7.14 (1H, m), 3.03 (2H, s), 1.41 (6H, s) ppm.

Intermediate 18D: Methyl 1-(2-bromophenyl)-2-methylpropan-2-ylcarbamate: To a stirred solution of 18C (8.0 g, 31.5 mmol) in dry THF (80 mL) at 0° C., was added MeOH (5.0 mL, 157.5 mmol) and, slowly, NaH (60% in oil) (3.8 g, 94.5 mmol). After 3 h at rt, the reaction was quenched with ice cold H$_2$O and extracted with EtOAc twice. The combined organics were washed with H$_2$O, brine, dried over Na$_2$SO$_4$, filtered and concentrated to give 18D (8.5 g, 94.5%) as white solid. MS (ESI) m/z: 286.0 (M+H)$^+$.

Intermediate 18E: Methyl 5-bromo-3,3-dimethyl-3,4-dihydroisoquinoline-2(1H)-carboxylate: To a solution of 18D (5.0 g, 17.5 mmol) in AcOH/H$_2$SO$_4$ (3:1; 15+5 mL) at 0° C. was, slowly, added paraformaldehyde (0.524 g, 17.5 mmol). After 48 h at rt, the reaction mixture was quenched with H$_2$O, extracted with EtOAc (2×), the combined organics were washed with saturated NaHCO$_3$ solution, H$_2$O, brine, dried over Na$_2$SO$_4$, filtered and concentrated to give 4.6 g of 18E as a brown liquid. MS (ESI) m/z: 300.0 (M+H)$^+$.

Intermediate 18: 5-Bromo-3,3-dimethyl-1,2,3,4-tetrahydroisoquinoline: To a solution of 18E (4.6 g) in ethylene glycol (50 mL) was added 50% aqueous KOH solution (23 mL) and the reaction was heated at 150° C. for 3 days. The reaction mixture was cooled, diluted with H$_2$O, extracted with EtOAc twice. The combined organics were extracted with 1.5 N HCl solution, the aqueous layer was basified with 10% NaOH solution, extracted with EtOAc twice, the combined organics were washed with H$_2$O, brine, dried over Na$_2$SO$_4$, filtered and concentrated to give Intermediate 18 (1.5 g, 39.4%) as a brown liquid. MS (ESI) m/z: 242.2 (M+H)$^+$.

Intermediate 19

N-phenyl-3,4-dihydroisoquinoline-6-carboxamide

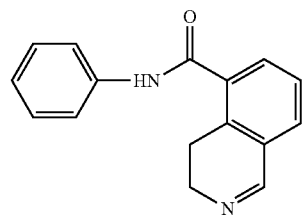 [SMILES: O=C(Nc1ccccc1)c1cccc2c1CCN=C2]

Intermediate 19A: tert-Butyl 6-(phenylcarbamoyl)-3,4-dihydroisoquinoline-2(1H)-carboxylate: To 2-(tert-butoxycarbonyl)-1,2,3,4-tetrahydroisoquinoline-6-carboxylic acid (0.2 g, 0.721 mmol) and aniline (0.066 mL, 0.721 mmol) and TEA (0.251 mL, 1.803 mmol) in EtOAc (5 mL) was added a 50% solution of T3P in DMF (0.408 mL, 1.442 mmol). After 24 h, the reaction was partitioned with dilute HCl (10 mL) and EtOAc (20 mL). The organic layer was washed with brine (10 mL) and dried (MgSO$_4$). Purification by silica gel chromatography afforded 0.238 g of Intermediate 19A. MS (ESI) m/z: 352.9 (M+H)$^+$.

Intermediate 19B: N-phenyl-1,2,3,4-tetrahydroisoquinoline-6-carboxamide: Intermediate 19A (0.23 g 0.65 mmol) was deprotected in 30% TFA/DCM (15 mL). After 24h, the reaction was concentrated. The residue was partitioned with saturated NaHCO$_3$ (15 mL) and EtOAc (50 mL). The organic layer was washed with brine (10 mL) and dried (MgSO$_4$). Collected 0.114 g of Intermediate 19B as a thick yellow oil. MS (ESI) m/z: 252.9 (M+H)$^+$.

Intermediate 19: To Intermediate 19B (0.114 g, 0.45 mmol) in DCM (15 mL) was added MnO$_2$ (0.71 g, 8.17 mmol). After 24h, the reaction was filtered through celite and concentrated to 0.113 g (62.6%) of a yellow oil. MS (ESI) m/z: 250.9 (M+H)$^+$.

Intermediate 20

3,4-dihydroisoquinoline-5-carbonitrile

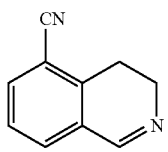 [SMILES: N#Cc1cccc2c1CCN=C2]

1,2,3,4-tetrahydroisoquinoline-5-carbonitrile (0.338 g, 2.137 mmol) was oxidized with MnO$_2$ (2.79 g, 32.0 mmol) in DCM (30 mL) over night. Filtered through Celite® and concentrated to yield 0.313 g (94%) of desired product as a pale yellow solid. $^1$H NMR (400 MHz, CDCl$_3$) δ 8.36 (1H, t, J=2.3 Hz), 7.67 (1H, dd, J=7.7, 1.4 Hz), 7.47-7.54 (1H, m), 7.43 (1H, d, J=7.8 Hz), 3.88 (2H, td, J=7.8, 2.3 Hz), 2.95-3.04 (2H, m) ppm. MS (ESI) m/z: 157 (M+H)$^+$ Intermediate 21 methyl 3,4-dihydroisoquinoline-5-carboxylate

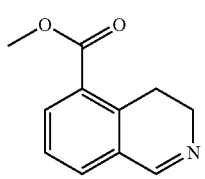

Intermediate 21 is prepared the same way as Intermediate 20. $^1$H NMR (400 MHz, CDCl$_3$) δ 8.35 (1H, t, J=2.0 Hz), 7.98 (1H, dd, J=7.8, 1.5 Hz), 7.41-7.47 (1H, m), 7.36 (1H, t, J=7.6 Hz), 3.91 (3H, s), 3.76 (2H, td, J=7.8, 2.1 Hz), 3.09-3.22 (2H, m) ppm. MS (ESI) m/z: 190 (M+H)$^+$ Example 1

(E)-4-(2-(3-(5-chloro-2-(1H-tetrazol-1-yl)phenyl)acryloyl)-5-cyano-1,2,3,4-tetrahydroisoquinoline-1-carboxamido)benzoic acid

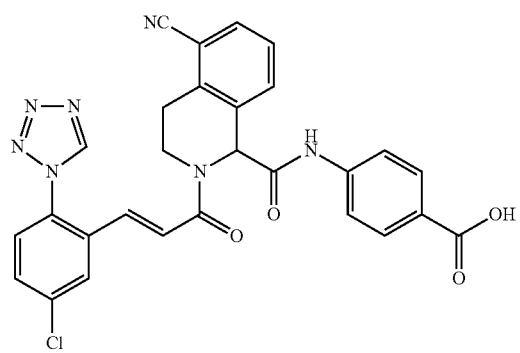 [SMILES: N#Cc1cccc2c1CCN(C(=O)/C=C/c1cc(Cl)ccc1-n1cnnn1)C2C(=O)Nc1ccc(C(=O)O)cc1]

Intermediate 20 (0.05 g, 0.320 mmol), Intermediate 6 (0.065 g, 0.320 mmol) and Intermediate 2 (0.080 g, 0.320 mmol) were heated in EtOH (3 mL) to reflux for 24 h. The reaction mixture cooled to rt and was concentrated, followed by treatment with TFA/DCM to give the desired product as a white solid (0.0065 g, 3.6%). $^1$H NMR (400 MHz, DMSO-d$_6$) δ 12.65 (1H, br.s.), 10.79 (1H, s), 9.79 (1H, s), 8.38 (1H, d, J=1.8 Hz), 7.78-7.90 (3H, m), 7.66-7.76 (5H, m), 7.53 (1H, d, J=15.4 Hz), 7.43 (1H, t, J=7.8 Hz), 6.91 (1H, d, J=15.2 Hz), 5.87 (1H, s), 4.20-4.35 (1H, m), 4.01-4.12 (1H, m), 3.03-3.13 (1H, m), 2.82-3.00 (1H, m) ppm. MS (ESI) m/z: 553.8 (M+H)$^+$. Analytical HPLC: RT=8.51 min.

Example 2

(E)-4-(2-(3-(5-chloro-2-(1H-tetrazol-1-yl)phenyl)acryloyl)-5-(methoxycarbonyl)-1,2,3,4-tetrahydroisoquinoline-1-carboxamido)benzoic acid

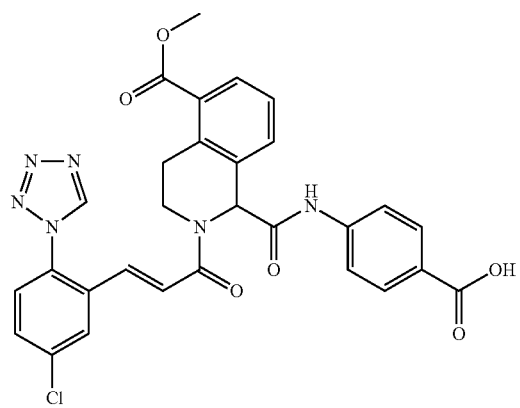 [SMILES: COC(=O)c1cccc2c1CCN(C(=O)/C=C/c1cc(Cl)ccc1-n1cnnn1)C2C(=O)Nc1ccc(C(=O)O)cc1]

Intermediate 21 (0.450 g, 1.797 mmol), Intermediate 6 (0.365 g, 1.797 mmol) and Intermediate 2 (0.34 g, 1.797 mmol) were heated in EtOH (3 mL) to reflux for 24 h. The reaction mixture cooled to rt and was concentrated, followed by treatment with TFA/DCM to give the desired product as a white solid (0.0065 g, 3.6%). $^1$H NMR (400 MHz, MeOD) δ 9.54 (1H, s), 8.21 (1H, d, J=2.27 Hz), 7.96 (2H, d, J=8.59 Hz), 7.89 (1H, d, J=7.83 Hz), 7.68-7.77 (1H, m), 7.60-7.68 (3H, m), 7.55-7.60 (1H, m), 7.33-7.45 (2H, m), 7.17-7.29 (1H, d, J=15.4 Hz), 5.91 (1H, s), 4.31 (1H, ddd, J=12.38, 5.43, 5.18 Hz), 3.93 (3H, s), 3.81 (1H, ddd, J=12.63, 8.97, 4.17 Hz), 3.56-3.68 (1H, m), 3.44-3.57 (1H, m) ppm. MS (ESI) m/z: 586.9 (M+H)$^+$. Analytical HPLC: RT=8.52 min.

Example 3

(E)-4-(2-(3-(5-Chloro-2-(1H-tetrazol-1-yl)phenyl) acryloyl)-5-(2-methoxyethylcarbamoyl)-1,2,3,4-tetrahydroisoquinoline-1-carboxamido)benzoic acid

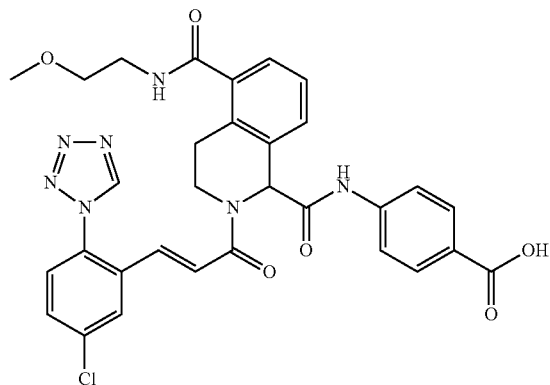 [SMILES: COCCNC(=O)c1cccc2c1CCN(C(=O)/C=C/c1cc(Cl)ccc1-n1cnnn1)C2C(=O)Nc1ccc(C(=O)O)cc1]

3A: (E)-1-(4-(tert-Butoxycarbonyl)phenylcarbamoyl)-2-(3-(5-chloro-2-(1H-tetrazol-1-yl)phenyl)acryloyl)-1,2,3,4-tetrahydroisoquinoline-5-carboxylic acid: To the tert-butyl ester from Example 2 (0.63 g, 0.980 mmol) in 1:1 THF/H$_2$O (20 mL) was added LiOH (0.164 g, 3.92 mmol). Quenched the reaction after 3 h and obtained 0.6 g mixture of acid and starting ester. The mixture was hydrolized again and after 3 h, adjusted pH to 5 with dilute HCl and extracted with EtOAc (2×20 mL). The organic layer was washed with brine (10 mL) and dried (MgSO$_4$) to afford 0.22 g of 3A. MS (ESI) m/z: 629.0 (M+H)$^+$.

3B: (E)-tert-Butyl 4-(2-(3-(5-chloro-2-(1H-tetrazol-1-yl) phenyl)acryloyl)-5-(2-methoxyethylcarbamoyl)-1,2,3,4-tetrahydroisoquinoline-1-carboxamido)benzoate: To 3A (46 mg, 0.073 mmol), 2-methoxyethanamine (5.49 mg, 0.073 mmol), BOP (32.3 mg, 0.073 mmol) in DMF (1 mL) was added DIEA (12.77 μL, 0.073 mmol). After 24 h, the reaction was quenched with H$_2$O (10 mL) and extracted with EtOAc (3×20 mL). The combined organic layers were washed with brine (10 mL) and dried (MgSO$_4$). MS (ESI) m/z: 686.0 (M+H)$^+$.

Example 3: 3B was treated with 30% TFA/DCM (10 mL). After 1 h, the reaction was concentrated, purified by reverse phase HPLC, and freeze-dried to afford 4.8 mg (10.4%) of white solid. $^1$H NMR (400 MHz, DMSO-d$_6$) δ 12.63 (1H, br.s.), 10.69 (1H, s), 9.79 (1H, s), 8.28-8.39 (2H, m), 7.76-7.87 (2H, m), 7.55-7.74 (5H, m), 7.49 (1H, d, J=15.16 Hz), 7.17-7.32 (2H, m), 6.90 (1H, d, J=15.41 Hz), 5.78 (1H, s), 4.18-4.30 (1H, m), 3.67-3.81 (1H, m), 3.32-3.44 (4H, m), 3.21 (3H, s), 2.94-3.11 (2H, m) ppm. MS (ESI) m/z: 629.9 (M+H)$^+$. Analytical HPLC: RT=7.02 min.

The following compounds in Table 2 were made in a similar manner as Example 3 using the appropriate amine instead of 2-methoxyethanamine.

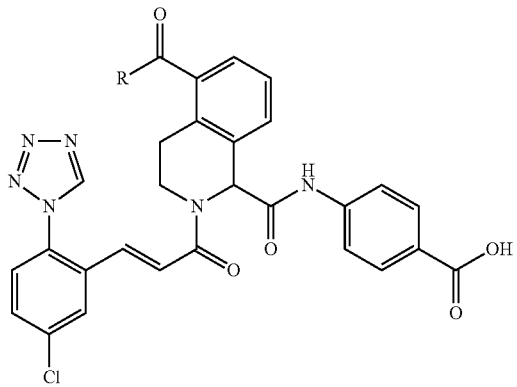

TABLE 2

| Example # | R | M + H | RT |
|---|---|---|---|
| 4 | 2-methoxy-N-methylethanamine | 643.9 | 7.48 |
| 5 | Morpholine | 642.3 | 7.25 |
| 6 | Piperidine | 640.4 | 8.25 |
| 7 | Dimethylamine | 600.3 | 7.09 |

Example 8

(E)-4-(2-(3-(5-chloro-2-(1H-tetrazol-1-yl)phenyl) acryloyl)-5-(6-methyl-1,2,3,4-tetrahydroquinoline-1-carbonyl)-1,2,3,4-tetrahydroisoquinoline-1-carboxamido)benzoic acid

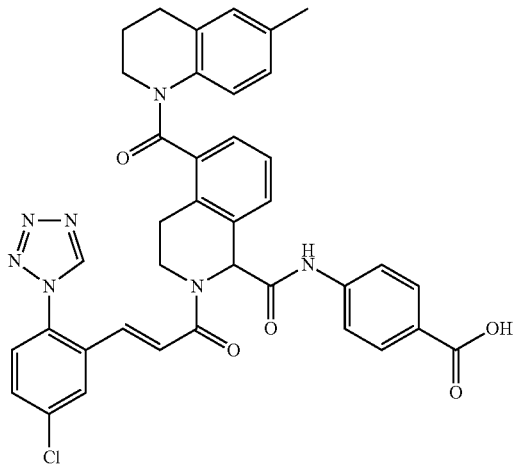 [SMILES: Cc1ccc2c(c1)CCCN2C(=O)c1cccc2c1CCN(C(=O)/C=C/c1cc(Cl)ccc1-n1cnnn1)C2C(=O)Nc1ccc(C(=O)O)cc1]

8A: tert-Butyl 5-(6-methyl-1,2,3,4-tetrahydroquinoline-1-carbonyl)-3,4-dihydroisoquinoline-2(1H)-carboxylate: To 2-(tert-butoxycarbonyl)-1,2,3,4-tetrahydroisoquinoline-5-carboxylic acid (0.28 g, 1.010 mmol), 6-methyl-1,2,3,4-tetrahydroquinoline (0.149 g, 1.010 mmol), DIEA (0.441 mL, 2.52 mmol) in EtOAc (4 mL) was added 50% T3P in EtOAc (0.428 mL, 1.515 mmol). After 24 h, the reaction was quenched with H$_2$O (10 mL) and extracted with EtOAc (3×20 mL). The combined organic layers were washed with brine (10 mL) and dried (MgSO$_4$). Purification by normal phase chromatography afforded 0.33 g (80%) of 8A as a clear yellow oil. MS (ESI) m/z: 350.9 (M+H-tbutyl)+

8B: (6-Methyl-3,4-dihydroquinolin-1(2H)-yl)(1,2,3,4-tetrahydroisoquinolin-5-yl)methanone: To 8A (0.33 g, 0.812 mmol) was added 30% TFA/DCM (10 mL). After 3 h, the reaction was concentrated and quenched with saturated NaHCO$_3$ (20 mL) and extracted with EtOAc (3×40 mL). The combined organic layers were washed with brine (10 mL) and dried (MgSO$_4$) to afford 0.164 g of 8B. MS (ESI) m/z: 307.0 (M+H)$^+$ 8C: (3,4-Dihydroisoquinolin-5-yl)(6-methyl-3,4-dihydroquinolin-1(2H)-yl)methanone: 8B was oxidized with MnO$_2$ to afford 8C. MS (ESI) m/z: 305.0 (M+H)$^+$ Example 8: Example 8 was prepared by heating intermediate 8C and intermediates 2 and 6 in EtOH to refluxing temperatures for 24h. The reaction mixture cooled to rt and was concentrated, followed by treatment with TFA/DCM to give the desired product as a yellow solid (9.2 mg, 4.6%). $^1$H NMR (400 MHz, DMSO-d$_6$) δ 12.53-12.78 (1H, m), 10.67 (1H, br.s.), 9.75-9.82 (1H, m), 8.32 (1H, d, J=2.02 Hz), 7.74-7.92 (2H, m), 7.53-7.72 (5H, m), 7.38-7.48 (1H, m), 7.20 (2H, br.s.), 6.79-6.98 (2H, m), 5.73 (1H, br.s.), 4.20 (1H, br.s.), 2.82-3.89 (6H, m), 2.69 (3H, br.s.), 2.02-2.17 (3H, m), 1.85 (2H, br.s.) ppm. MS (ESI) m/z: 701.9 (M+H)$^+$. Analytical HPLC: RT=9.40 min.

Example 9

(E)-4-(2-(3-(3-chloro-2-fluoro-6-(1H-tetrazol-1-yl)phenyl)acryloyl)-5-(methylsulfonamido)-1,2,3,4-tetrahydroisoquinoline-1-carboxamido)benzoic acid Example 9: Example 9 was prepared in a similar manner as Example 1, substituting Intermediate 3A for Intermediate 2 in the Ugi reaction followed by TFA deprotection. $^1$H NMR (400 MHz, DMSO-d$_6$) δ 12.72 (1H, br.s.), 10.78 (1H, s), 9.86 (1H, s), 9.26 (1H, s), 7.93-7.98 (3H, m), 7.64-7.70 (3H, m), 7.56 (1H, d, J=6.60 Hz), 7.22-7.33 (2H, m), 7.11 (1H, d, J=15.96 Hz), 6.93-6.98 (1H, m), 5.83 (1H, s), 4.07-4.16 (1H, m), 3.56-3.66 (1H, m), 3.06-3.12 (2H, m), 2.96-3.00 (3H, m) ppm. MS (ESI) m/z: 640.4 (M+H)$^+$. Analytical HPLC: RT=8.67 min.

The following Examples in Table 3 were made by the Ugi reaction using the corresponding imine intermediate that was made in a similar manner as Intermediate 19, using the appropriate amine, and as shown in Example 8. The acids, Intermediates 2 or 3A and the isonitriles, Intermediates 6, 8, 10 or commercially available 1-fluoro-4-isocyanobenzene were used as required. Final deprotection of the t-butyl esters or carbamates with TFA/DCM were carried out as described previously.

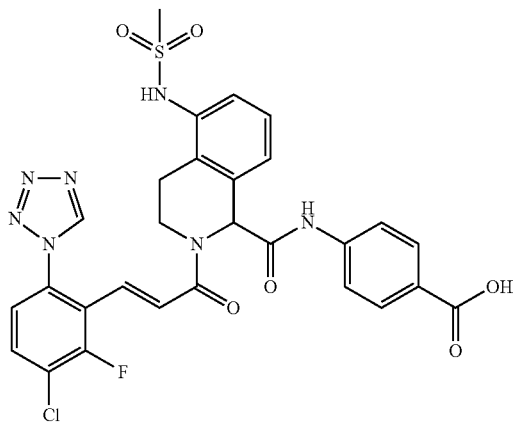 [SMILES: CS(=O)(=O)Nc1cccc2c1CCN(C(=O)/C=C/c1c(-n3cnnn3)ccc(Cl)c1F)C2C(=O)Nc1ccc(C(=O)O)cc1]

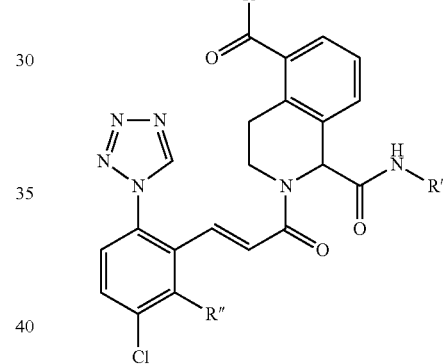

TABLE 3

| Example # | R | R' | R" | M + H | RT |
|---|---|---|---|---|---|
| 10 | (3-piperidinyl ethyl ester) | -4-PhCOOH | H | 711.9 | 8.46 |
| 11 | (3-piperidinyl ethyl ester) | -4-PhCOOH | H | 712.0 | 8.52 |
| 12 | (3-piperidinyl ethyl ester) | -4-PhCOOH | F | 730.4 | 8.50 |

TABLE 3-continued

| Example # | R | R' | R" | M + H | RT |
|---|---|---|---|---|---|
| 13 | ethyl 4-(amino)butanoate (ethyl ester of 4-aminobutyric acid, attached via NH) | -4-PhCOOH | H | 686.0 | 7.81 |
| 14 | ethyl 4-(amino)butanoate | -4-Ph—F | H | 660.0 | 8.92 |
| 15 | (3S)-N-phenyl-piperidine-3-carboxamide (attached via piperidine N) | -4-PhNHCOOCH$_3$ | H | 788.1 | 8.75 |
| 16 | ethyl piperidine-3-carboxylate (attached via piperidine N) | -4-PhNHCOOCH$_3$ | H | 741.1 | 8.78 |
| 17 | ethyl 3-(amino)propanoate (attached via NH) | -4-PhNHCOOCH$_3$ | H | 785.1 | 8.23 |
| 18 | methyl 4-(amino)nicotinate (attached via NH) | -4-PhCOOH | F | 725.1 | 6.29 |
| 19 | Piperazine | -6-indazole | F | 655.2 | 5.28 |
| 20 | ethyl piperidin-4-ylcarbamate (attached via piperidine N) | -6-indazole | F | 741.3 | 7.51 |
| 21 | ethyl piperidin-4-ylcarbamate (attached via piperidine N) | -4-PhCOOH | F | 745.2 | 7.54 |
| 22 | 4-aminopyridine | -6-indazole | F | 663.1 | 5.36 |
| 23 | 4-aminopyridine | -4-PhCOOH | F | 667.1 | 5.28 |
| 24 | tert-butyl piperazine-1-carboxylate | -4-PhCOOtBu | F | 815.2 | 10.8 |
| 25 | Piperazine | -4-PhCOOH | F | 659.0 | 4.82 |
| 26 | 1-methylpiperidin-4-amine | -4-PhCOOH | F | 687.4 | 5.25 |

TABLE 3-continued

| Example # | R | R' | R" | M + H | RT |
|---|---|---|---|---|---|
| 27 | 4-aminopiperidine | -4-PhCOOH | F | 673.1 | 5.18 |
| 28 | 1-methylpiperidin-4-amine | -6-indazole | F | 683.2 | 5.28 |

The following Examples in Table 4 were made in a similar manner as Example in Table 3 and then late stage intermediates were separated by chiral HPLC and then deprotected.

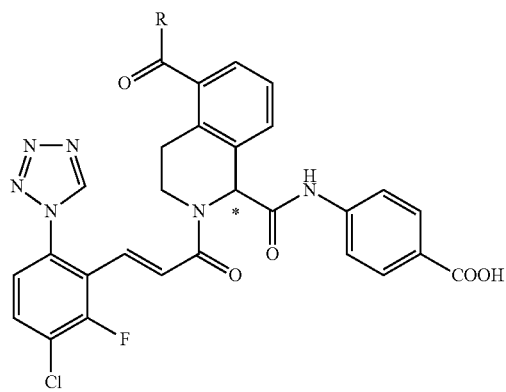

TABLE 4

| Example # | Stereochemistry | R | M + H | RT |
|---|---|---|---|---|
| 29 | R-enantiomer[a] | 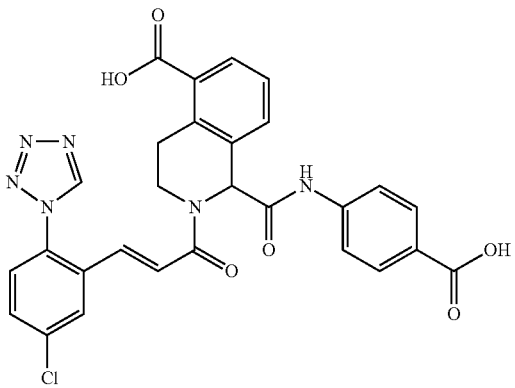 | 659.1 | 5.13 |
| 30 | S-enantiomer[a] |  | 659.1 | 5.12 |
| 31 | Racemic |  | 708.4 | 8.86 |
| 32 | Racemic |  | 727.4 | 4.60* |

[a]Chiracel OD 25° Cm x 4.6 mm column and (1:1 EtOH/MeOH-0.1% DEA) at 1 mL/min.
*Method B Example 33

(E)-1-(4-Carboxyphenylcarbamoyl)-2-(3-(5-chloro-2-(1H-tetrazol-1-yl)phenyl)acryloyl)-1,2,3,4-tetrahydroisoquinoline-5-carboxylic acid

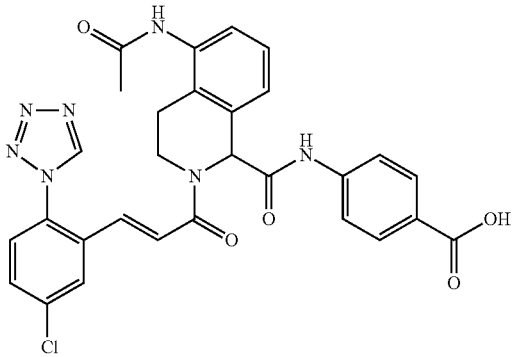 [SMILES: CC(=O)Nc1cccc2c1CCN(C(=O)/C=C/c1cc(Cl)ccc1-n1cnnn1)C2C(=O)Nc1ccc(C(=O)O)cc1]

Example 33: 3A (80 mg, 0.127 mmol) was deprotected with 30% TFA in DCM (5 mL). Purified by reverse phase HPLC to afford 8.5 mg (11%) of Example 33. $^1$H NMR (400 MHz, DMSO-d$_6$) δ 12.94 (1H, br.s.), 12.68 (1H, br.s.), 10.70 (1H, s), 9.79 (1H, s), 8.36 (1H, d, J=2.02 Hz), 7.77-7.84 (2H, m), 7.56-7.73 (6H, m), 7.49 (1H, d, J=15.41 Hz), 7.30 (1H, t, J=7.71 Hz), 6.90 (1H, d, J=15.16 Hz), 5.80 (1H, s), 4.20-4.31 (1H, m), 3.67-3.88 (1H, m), 3.35-3.52 (1H, m), 2.44-2.51 (1H, m) ppm. MS (ESI) m/z: 572.8 (M+H)$^+$. Analytical HPLC: RT=7.38 min.

Example 34

(E)-4-(5-Acetamido-2-(3-(5-chloro-2-(1H-tetrazol-1-yl)phenyl) acryloyl)-1,2,3,4-tetrahydro isoquinoline-1-carboxamido)benzoic acid Example 34 was prepared by the Ugi reaction as in Example 1 starting from commercially available N-(1,2,3,4- tetrahydroisoquinolin-5-yl)acetamide and Intermediates 2 and 6 followed by TFA deprotection. 1H NMR (400 MHz, DMSO-d$_6$) δ 12.62 (1H, br.s.), 10.71 (1H, s), 9.79 (1H, s), 9.47 (1H, s), 8.36 (1H, d, J=2.27 Hz), 7.74-7.84 (2H, m), 7.57-7.73 (3H, m), 7.49 (1H, d, J=15.41 Hz), 7.38 (1H, d, J=7.33 Hz), 7.21-7.26 (1H, m), 7.13-7.18 (1H, m), 6.90 (1H, d, J=15.41 Hz), 5.76 (1H, s), 4.14-4.32 (1H, m), 3.74-3.88 (1H, m), 2.85-2.98 (1H, m), 2.73-2.85 (1H, m), 2.01 (3H, s), 1.17 (1H, br.s.) ppm. MS (ESI) m/z: 586 (M+H)$^+$. Analytical HPLC: RT=6.85 min.

Example 35

(E)-4-(2-(3-(5-Chloro-2-(1H-tetrazol-1-yl)phenyl) acryloyl)-5-(methoxycarbonylamino)-1,2,3,4-tetrahydroisoquinoline-1-carboxamido)benzoic acid

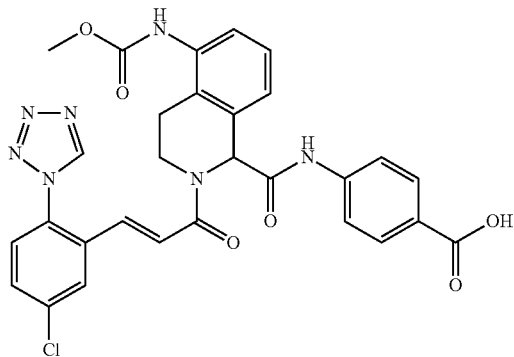

35A: Methyl 1,2,3,4-tetrahydroisoquinolin-5-ylcarbamate: To a separatory funnel was added tert-butyl 5-amino-3,4-dihydroisoquinoline-2(1H)-carboxylate (0.2 g, 0.805 mmol) in DCM (15 mL) and 1N NaOH (5 mL), then methyl chloroformate (0.062 mL, 0.805 mmol). The reaction was shaken 5 min and the layers were separated. The organic layer was washed with brine and dried (MgSO$_4$). MS (ESI) m/z: 251 (M+H-tbutyl)+. The compound was heated in 10 mL H$_2$O to 150° C. in a microwave for 35 min. Removal of the H$_2$O afforded 0.163 g of 35A as a yellow solid. MS (ESI) m/z: 207 (M+H)$^+$ 35B: Methyl 3,4-dihydroisoquinolin-5-ylcarbamate: To 35A in DCM (15 mL) was added MnO$_2$ (1 g, 11.50 mmol) and after 24 h, the reaction was filtered through Celite® to afford 35B as a 0.1 g brown solid. MS (ESI) m/z: 205 (M+H)$^+$ Example 35 was made in a similar manner as Example 8 using Intermediate 6 and substituting 35B for 6-methyl-1,2,3,4-tetrahydroisoquinoline followed by TFA deprotection. $^1$H NMR (400 MHz, MeOD) δ 10.42 (1H, s), 9.54 (1H, s), 8.84 (1H, br.s.), 8.21 (1H, d, J=2.02 Hz), 7.91-8.05 (2H, m), 7.55-7.78 (3H, m), 7.40 (2H, t, J=8.46 Hz), 7.27-7.36 (1H, d, J=15.4 Hz), 7.15-7.26 (1H, m), 5.87 (1H, s), 4.25-4.34 (1H, m), 3.79-3.92 (1H, m), 3.77 (3H, s), 3.09-3.20 (1H, m), 2.93-3.07 (1H, m) ppm. MS (ESI) m/z: 602 (M+H)$^+$. Analytical HPLC: RT=7.56 min.

The following compounds in Table 5 were made in a similar manner as Example 35 using the appropriate acid chloride or isocyanate, followed by TFA deprotection, MnO2 oxidation, Ugi reaction with Intermediate 2 and Intermediate 6, and t-butyl hydrolysis by TFA/DCM.

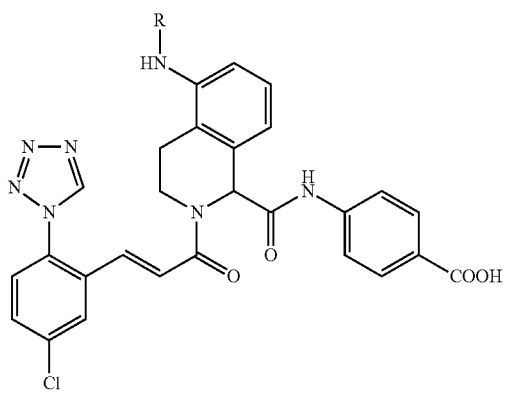

TABLE 5

| Example # | R | M + H | RT |
|---|---|---|---|
| 36 | ethyl propanoate-NHC(O)- group | 687.0 | 7.51 |
| 37 | 4-pyridyl-C(O)- group | 649.1 | 5.76 |
| 38 | cyclopentyl-NHC(O)- group | 655.1 | 8.14 |

Example 39

(E)-4-(2-(3-(5-Chloro-2-(1H-tetrazol-1-yl)phenyl) acryloyl)-5-(4-(meth-oxycarbonylamino)phenyl)-1,2,3,4-tetrahydroisoquinoline-1-carboxamido)benzoic acid

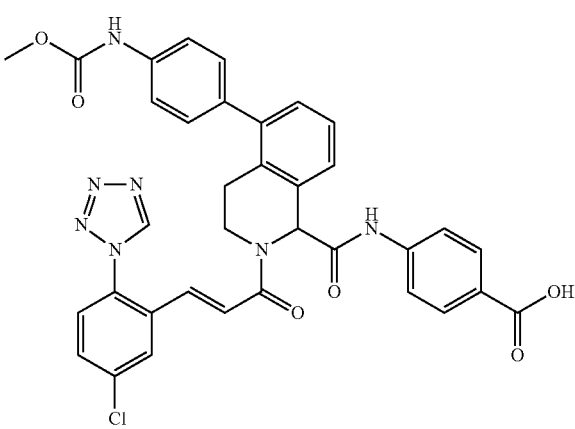 [SMILES: COC(=O)Nc1ccc(-c2cccc3c2CCN(C(=O)/C=C/c2cc(Cl)ccc2-n2cnnn2)C3C(=O)Nc2ccc(C(=O)O)cc2)cc1]

Example 39: tert-Butyl 5-bromo-3,4-dihydroisoquinoline-2(1H)-carboxylate (0.20 g, 0.64 mmol), 4-(methoxycarbonylamino)phenylboronic acid (0.125 g, 0.641 mmol), potassium phosphate tribasic (0.476 g, 2.24 mmol) and tricyclohexylphosphine (0.018 g, 0.064 mmol) were placed in a pressure vial containing toluene (10 mL) and H$_2$O (1.0 mL) which had been degassed with argon for 15 minutes. Pd(OAc)$_2$ (7.19 mg, 0.032 mmol) was added, the vial was sealed, and heated at 100° C. for 12 h. After cooling to rt, the reaction mixture was diluted with EtOAc (50 mL), and filtered through a plug of celite. The filtrate was washed with H$_2$O (50 mL). The aqueous phase was extracted with EtOAc (3×25 mL). Combined organic extract was washed with brine, dried (Na$_2$SO$_4$), filtered, and concentrated. Purification by silica gel chromatography gave tert-butyl 5-(4-(methoxycarbonylamino)phenyl)-3,4-dihydroisoquinoline-2(1H)-carboxylate as a colorless oil (75 mg, 31%). This material was treated with 50% TFA/DCM for 48 h and then concentrated. The resulting oil was dissolved in EtOAc and neutralized with saturated NaHCO$_3$. The organic layer was washed with H$_2$O, brine, dried over Na$_2$SO$_4$, filtered, and concentrated. The residue was oxidized as in Example 8B and then carried onto an Ugi reaction with Intermediate 2 and Intermediate 6 in a similar manner as Example 8 followed by TFA deprotection. Purification by reverse phase HPLC and freeze-drying afforded Example 39 (8 mg, 1.75%) as a white solid. $^1$H NMR (500 MHz, DMSO-d$_6$) δ 12.70 (1H, br.s.), 10.81 (1H, s), 9.86 (1H, s), 9.76 (1H, s), 8.38 (1H, d, J=2.21 Hz), 7.88 (2H, d, J=8.83 Hz), 7.68-7.79 (4H, m), 7.63 (1H, d, J=7.57 Hz), 7.49-7.58 (3H, m), 7.33 (1H, t, J=7.72 Hz), 7.26-7.31 (2H, m), 7.22 (1H, d, J=7.57 Hz), 6.96 (1H, d, J=15.45 Hz), 5.88 (1H, s), 4.22-4.30 (1H, m), 3.72-3.80 (1H, m), 3.03-3.12 (1H, m), 2.86-2.94 (1H, m) ppm. MS (ESI) m/z: 678.0 (M+H)$^+$. Analytical HPLC: RT=6.76 min.

Example 40

(E)-4-(2-(3-(5-Chloro-2-(1H-tetrazol-1-yl)phenyl)acryloyl)-5-(dimethylamino)-1,2,3,4-tetrahydroisoquinoline-1-carboxamido)benzoic acid, TFA salt

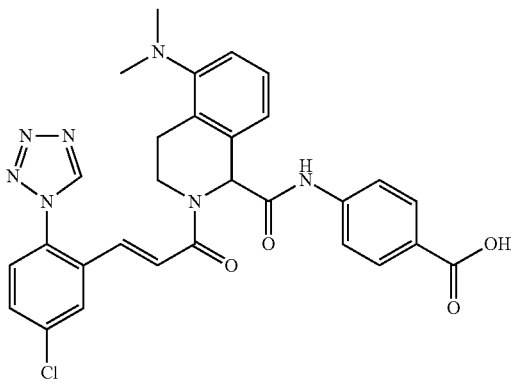 [SMILES: CN(C)c1cccc2c1CCN(C(=O)/C=C/c1cc(Cl)ccc1-n1cnnn1)C2C(=O)Nc1ccc(C(=O)O)cc1]

40A: tert-Butyl 5-(dimethylamino)-3,4-dihydroisoquinoline-2(1H)-carboxylate: To tert-butyl 5-amino-3,4-dihydroisoquinoline-2(1H)-carboxylate (0.26 g, 1.047 mmol) in THF (5 mL), cooled to 0° C., was added NaH (0.105 g, 2.62 mmol). After 15 min, added iodomethane (0.196 mL, 3.14 mmol). After 24 h, additional NaH and iodomethane were added and the reaction was heated to reflux for 4 h. The reaction was quenched with H$_2$O (15 mL) and extracted with EtOAc (3×30 mL). The combined organic layers were washed with brine (10 mL) and dried (MgSO$_4$). Purification by silica gel chromatography afforded 40A as 0.213 g of a yellow oil. MS (ESI) m/z: 277.1 (M+H)$^+$.

40B: N,N-dimethyl-3,4-dihydroisoquinolin-5-amine: 40A (0.213 g, 0.77 mmol) was deprotected and oxidized with MnO$_2$ as in Example 8 to afford 101 mg of 40B. MS (ESI) m/z: 175.1 (M+H)$^+$.

Example 40: 40B was carried onto an Ugi reaction with Intermediate 2 and Intermediate 6 in a similar manner as Example 8 followed by TFA deprotection and purification by reverse phase HPLC. $^1$H NMR (400 MHz, MeOD) δ 9.54 (1H, s), 8.19 (1H, d, J=2.02 Hz), 7.96 (2H, d, J=8.59 Hz), 7.51-7.71 (6H, m), 7.47 (1H, t, J=7.83 Hz), 7.28-7.37 (1H, d, J=15.4 Hz), 7.18-7.27 (1H, d, J=15.4 Hz), 5.92 (1H, s), 4.32-4.46 (1H, m), 3.84 (1H, ddd, J=12.51, 8.97, 4.04 Hz), 3.35-3.40 (1H, m), 3.18-3.24 (1H, m), 3.16 (6H, s) ppm. MS (ESI) m/z: 572.2 (M+H)$^+$. Analytical HPLC: RT=5.39 min.

Example 41

(E)-4-(2-(3-(3-chloro-2-fluoro-6-(1H-tetrazol-1-yl)phenyl)acryloyl)-5-(pyridin-4-yl)-1,2,3,4-tetrahydroisoquinoline-1-carboxamido)benzoic acid, TFA Salt

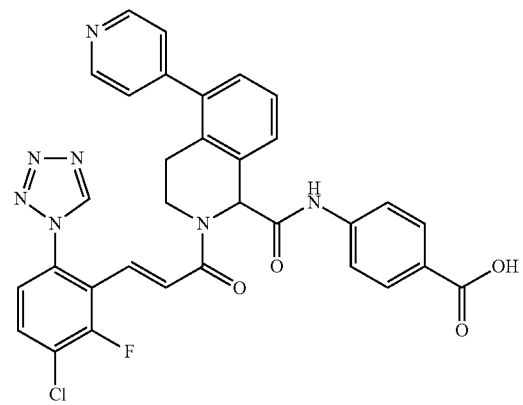 [SMILES: O=C(O)c1ccc(NC(=O)C2c3cccc(-c4ccncc4)c3CCN2C(=O)/C=C/c2c(-n3cnnn3)ccc(Cl)c2F)cc1]

41A: tert-Butyl 5-(pyridin-4-yl)-3,4-dihydroisoquinoline-2(1H)-carboxylate: To tert-butyl 5-bromo-3,4-dihydroisoquinoline-2(1H)-carboxylate (0.989 g, 3.17 mmol), 4-(tributylstannyl)pyridine (1.75 g, 4.75 mmol), LiCl (1.343 g, 31.7 mmol) in toluene (15 mL) was added dichlorobis(triphenylphosphine) palladium (II) (0.222 g, 0.317 mmol) and the reaction was heated to 110° C. After 72 h, the reaction was partitioned with 10% aq. KF (20 mL) and ethyl acetate (50 mL). The aqueous layer was extracted with ethyl acetate (2×50 mL). The combined organic layers were washed with brine (15 mL) and dried (MgSO$_4$). Purification by silica gel chromatography afforded 41A as 0.63 g of a clear oil (64%). $^1$H NMR (400 MHz, CHLOROFORM-d) δ 8.66 (2H, d, J=6.06 Hz), 7.23-7.33 (3H, m), 7.17-7.21 (1H, m), 7.13 (1H, d, J=7.58 Hz), 4.65 (2H, s), 3.55 (2H, br. s.), 2.72 (2H, t, J=5.68 Hz), 1.50 (9H, s) ppm.

41B: 5-(Pyridin-4-yl)-1,2,3,4-tetrahydroisoquinoline: To 41A (0.14 g, 0.451 mmol) was added 10 mL water and 4N HCl in dioxane (0.025 mL, 0.100 mmol). The reaction was heated to 150° C. in a microwave for 35 min, then freeze-dried to afford 41B as 90 mgs of a brown solid. MS (ESI) m/z: 211.1 (M+H)$^+$.

41C: 5-(Pyridin-4-yl)-3,4-dihydroisoquinoline: 41B (90 mgs, 0.42 mmol) was oxidized as in Intermediate 17 to afford 75 mgs (80%) of 41C as a yellow oil. MS (ESI) m/z: 209.1 (M+H)$^+$.

Example 41: Example 41 was prepared in a similar manner as Example 1 using Intermediate 3A, Intermediate 6 and Intermediate 41C followed by deprotection to afford 2.1 mgs (1.7%) of a white solid. $^1$H NMR (400 MHz, MeOD) δ 9.41-9.65 (1H, m), 8.90 (2H, d, J=6.57 Hz), 8.05 (2H, d, J=6.57 Hz), 7.98 (2H, d, J=8.84 Hz), 7.79 (2H, dd, J=16.67, 8.84 Hz), 7.68 (2H, dd, J=8.84, 1.52 Hz), 7.39-7.59 (3H, m), 7.18 (1H, d, J=15.92 Hz), 6.98 (1H, d, J=15.92 Hz), 5.95 (1H, s), 4.06-4.18 (1H, m), 3.48-3.63 (1H, m), 3.35-3.43 (1H, m), 2.86-3.01 (1H, m) ppm. MS (ESI) m/z: 624.0 (M+H)$^+$. Analytical HPLC; RT=6.18 min.

Example 42

(E)-benzyl 6-(2-(3-(3-chloro-2-fluoro-6-(1H-tetrazol-1-yl)phenyl)acryloyl)-5-(pyridin-4-yl)-1,2,3,4-tetrahydroisoquinoline-1-carboxamido)-1H-indazole-1-carboxylate, TFA Salt

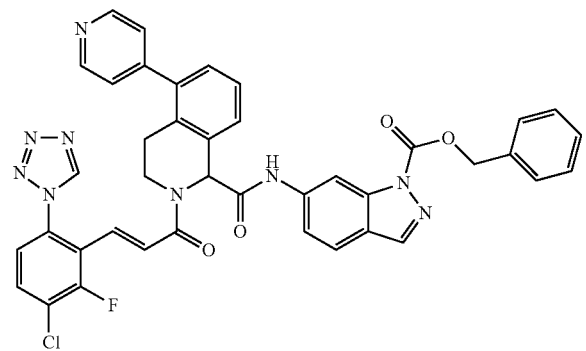 [SMILES: O=C(Nc1ccc2cnn(C(=O)OCc3ccccc3)c2c1)C1c2cccc(-c3ccncc3)c2CCN1C(=O)/C=C/c1c(-n2cnnn2)ccc(Cl)c1F]

Example 42: Example 42 was made in a similar manner as Example 41 substituting Intermediate 11 for Intermediate 41C to afford 38 mg (21%) of a white solid. $^1$H NMR (400 MHz, MeOD) δ 9.55 (1H, s), 8.91 (2H, d, J=6.57 Hz), 8.64 (1H, s), 8.22 (1H, s), 8.10 (2H, d, J=6.57 Hz), 7.71-7.87 (3H, m), 7.54 (3H, d, J=7.58 Hz), 7.49 (3H, t, J=7.45 Hz), 7.33-7.42 (3H, m), 7.19 (1H, d, J=15.92 Hz), 7.00 (1H, d, J=15.92 Hz), 5.99 (1H, s), 5.53 (2H, s), 4.14 (1H, d, J=11.87 Hz), 3.53-3.62 (1H, m), 3.37 (1H, br. s.), 2.96 (1H, dd, J=15.54, 4.42 Hz) ppm. MS (ESI) m/z: 754.2 (M+H)$^+$. Analytical HPLC; RT=6.87 min.

Example 43

(E)-4-(2-(3-(3-chloro-2-fluoro-6-(1H-tetrazol-1-yl)phenyl)acryloyl)-5-(4-(ethylcarbamoyl)phenyl)-1,2,3,4-tetrahydroisoquinoline-1-carboxamido)benzoic acid

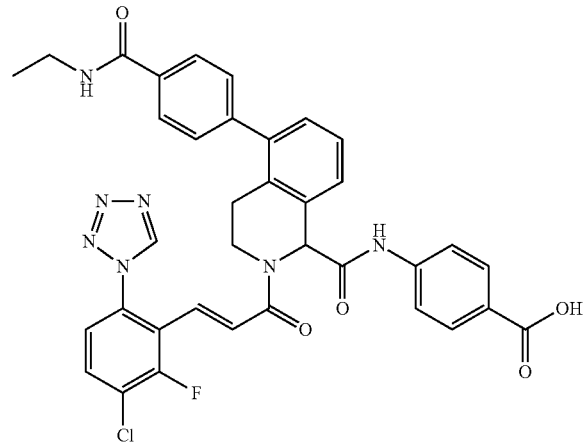 [SMILES: CCNC(=O)c1ccc(-c2cccc3c2CCN(C(=O)/C=C/c2c(-n4cnnn4)ccc(Cl)c2F)C3C(=O)Nc2ccc(C(=O)O)cc2)cc1]

Example 43 (30 mg, 6.8%) was made in a similar manner as Example 39 using 4-(ethylcarbamoyl)-phenylboronic acid. $^1$H NMR (400 MHz, DMSO-d$_6$) δ 10.84 (1H, s), 9.86 (1H, s), 8.54 (1H, t, J=5.50 Hz), 7.85-7.99 (5H, m), 7.62-7.77 (4H, m), 7.35-7.48 (3H, m), 7.22-7.30 (1H, m), 7.03-7.12 (1H, m), 6.89-7.00 (1H, m), 5.88 (1H, s), 4.02-4.13 (1H, m), 3.49-3.61 (1H, m), 3.26-3.37 (2H, m), 3.03-3.19 (1H, m), 2.78-2.91 (1H, m), 1.14 (3H, t, J=7.15 Hz) ppm. MS (ESI) m/z: 694.1 (M+H)$^+$. Analytical HPLC: RT=8.37 min.

Example 44

(E)-4-(5-(benzo[d][1,3]dioxol-5-yl)-2-(3-(3-chloro-2-fluoro-6-(1H-tetrazol-1-yl)phenyl)acryloyl)-1,2,3,4-tetrahydroisoquinoline-1-carboxamido)-benzoic acid

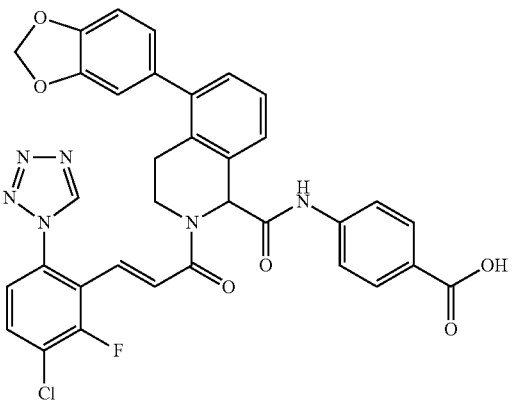 [SMILES: O=C(O)c1ccc(NC(=O)C2c3cccc(-c4ccc5c(c4)OCO5)c3CCN2C(=O)/C=C/c2c(-n3cnnn3)ccc(Cl)c2F)cc1]

Example 44 (26 mg, 6.1%) was made in a similar manner as Example 39 using 3,4-methylenedioxyphenylboronic acid. $^1$H NMR (400 MHz, DMSO-d$_6$) δ 10.79 (1H, s), 9.85 (1H, s), 7.84-7.98 (3H, m), 7.60-7.73 (4H, m), 7.32 (1H, t, J=7.58 Hz), 7.20 (1H, d, J=7.33 Hz), 6.90-7.10 (4H, m), 6.75-6.82 (1H, m), 6.07 (2H, s), 5.87 (1H, s), 3.97-4.10 (1H, m), 3.44-3.64 (1H, m), 3.01-3.15 (1H, m), 2.78-2.90 (1H, m) ppm. MS (ESI) m/z: 667.0 (M+H)$^+$. Analytical HPLC: RT=9.99 min.

Example 45

(E)-methyl 4-(2-(3-(3-chloro-2-fluoro-6-(1H-tetrazol-1-yl)phenyl)acryloyl)-1-(4-fluorophenyl carbamoyl)-1,2,3,4-tetrahydroisoquinolin-5-yl)phenylcarbamate

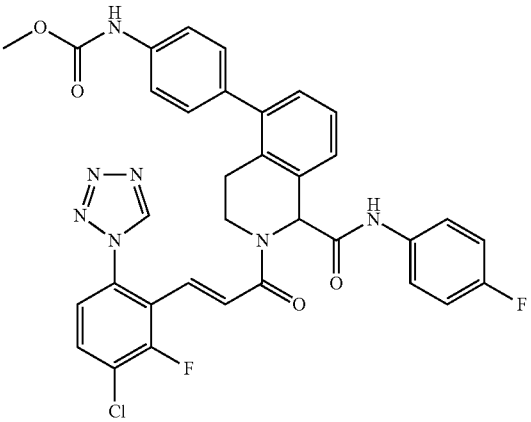 [SMILES: COC(=O)Nc1ccc(-c2cccc3c2CCN(C(=O)/C=C/c2c(-n4cnnn4)ccc(Cl)c2F)C3C(=O)Nc2ccc(F)cc2)cc1]

Example 45 (84 mg, 22%) was made in a similar manner as Example 39 using commercially available 1-fluoro-4-isocyanobenzene. $^1$H NMR (400 MHz, DMSO-d$_6$) δ 10.57 (1H, s), 9.87 (1H, s), 9.79 (1H, s), 7.96 (1H, t, J=8.24 Hz), 7.52-7.70 (6H, m), 7.06-7.38 (7H, m), 6.91-7.00 (1H, m), 5.84 (1H, s), 4.01-4.09 (1H, m), 3.70 (3H, s), 3.50-3.61 (1H, m), 3.01-3.13 (1H, m), 2.86 (1H, ddd) ppm. MS (ESI) m/z: 670.1 (M+H)$^+$. Analytical HPLC: RT=10.46 min.

Example 46

(E)-4-(2-(3-(3-chloro-2-fluoro-6-(1H-tetrazol-1-yl) phenyl)acryloyl)-5-(4-(trifluoromethoxy)phenyl)-1, 2,3,4-tetrahydroisoquinoline-1-carboxamido)benzoic acid

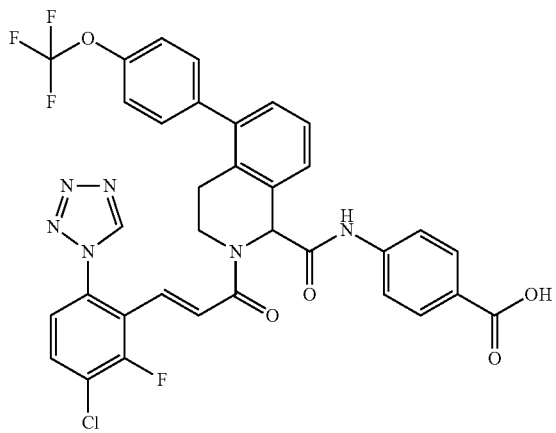 [SMILES: O=C(O)c1ccc(NC(=O)C2c3cccc(-c4ccc(OC(F)(F)F)cc4)c3CCN2C(=O)/C=C/c2c(-n3cnnn3)ccc(Cl)c2F)cc1]

Example 46 (36 mg, 8%) was made in a similar manner as Example 39 using 4-(trifluoromethoxy)phenylboronic acid. $^1$H NMR (500 MHz, DMSO-d$_6$) δ 12.72 (1H, br.s.), 10.83 (1H, s), 9.86 (1H, s), 7.86-7.98 (3H, m), 7.61-7.74 (4H, m), 7.43-7.52 (4H, m), 7.37 (1H, t, J=7.70 Hz), 7.26 (1H, d, J=7.15 Hz), 7.04-7.12 (1H, m), 6.92-7.00 (1H, m), 5.90 (1H, s), 4.00-4.10 (1H, m), 3.52-3.63 (1H, m), 3.02-3.13 (1H, m), 2.81 (1H, ddd, J=15.82, 4.68, 4.54 Hz) ppm. MS (ESI) m/z: 707.1 (M+H)$^+$. Analytical HPLC: RT=11.43 min.

Example 47

(E)-4-(2-(3-(3-chloro-2-fluoro-6-(1H-tetrazol-1-yl) phenyl)acryloyl)-5-(2-chloro-4-methoxyphenyl)-1,2, 3,4-tetrahydroisoquinoline-1-carboxamido)benzoic acid

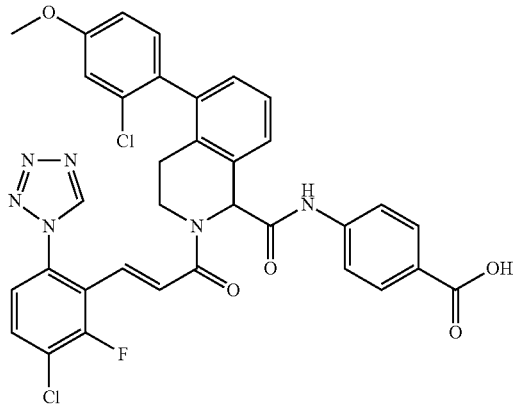 [SMILES: COc1ccc(-c2cccc3c2CCN(C(=O)/C=C/c2c(-n4cnnn4)ccc(Cl)c2F)C3C(=O)Nc2ccc(C(=O)O)cc2)c(Cl)c1]

Example 47 (72 mg, 14.7%) was made in a similar manner as Example 39 using 2-chloro-4-methoxyphenylboronic acid. $^1$H NMR (500 MHz, DMSO-d$_6$) δ 12.72 (1H, br.s.), 10.84 (1H, d, J=2.48 Hz), 9.85 (1H, d, J=1.65 Hz), 7.87-8.01 (3H, m), 7.61-7.78 (4H, m), 6.86-7.43 (7H, m), 5.88 (1H, d, J=4.40 Hz), 3.99-4.11 (1H, m), 3.75-3.90 (4H, m), 3.51-3.65 (1H, m), 2.84-3.03 (1H, m) ppm. MS (ESI) m/z: 687.0 (M+H)$^+$. Analytical HPLC: RT=10.67 min.

Example 48

(E)-4-(2-(3-(3-chloro-2-fluoro-6-(1H-tetrazol-1-yl) phenyl)acryloyl)-5-(4-(2-methoxyethylcarbamoyl) phenyl)-1,2,3,4-tetrahydroisoquinoline-1-carboxamido)benzoic acid

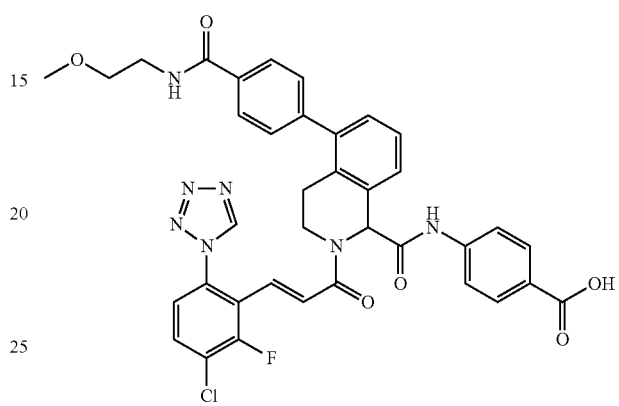

Example 48 (37 mg, 7.6%) was made in a similar manner as Example 39 using 4-(2-methoxyethylcarbamoyl)phenylboronic acid. $^1$H NMR (400 MHz, DMSO-d$_6$) δ 10.84 (1H, s), 9.86 (1H, s), 8.57-8.68 (1H, m), 7.92-7.97 (3H, m), 7.88 (2H, d, J=8.79 Hz), 7.63-7.75 (4H, m), 7.45 (2H, d, J=8.24 Hz), 7.38 (1H, t, J=7.70 Hz), 7.27 (1H, d, J=6.60 Hz), 7.04-7.14 (1H, m), 6.91-6.99 (1H, m), 5.88 (1H, s), 3.97-4.12 (1H, m), 3.40-3.61 (5H, m), 3.28 (3H, s), 3.00-3.17 (1H, m), 2.74-2.87 (1H, m) ppm. MS (ESI) m/z: 724.1 (M+H)$^+$. Analytical HPLC: RT=8.07 min.

Example 49

(E)-4-(2-(3-(3-Chloro-2-fluoro-6-(1H-tetrazol-1-yl) phenyl)acryloyl)-5-(4-(morpholine-4-carbonyl)phenyl)-1,2,3,4-tetrahydroisoquinoline-1-carboxamido) benzoic acid

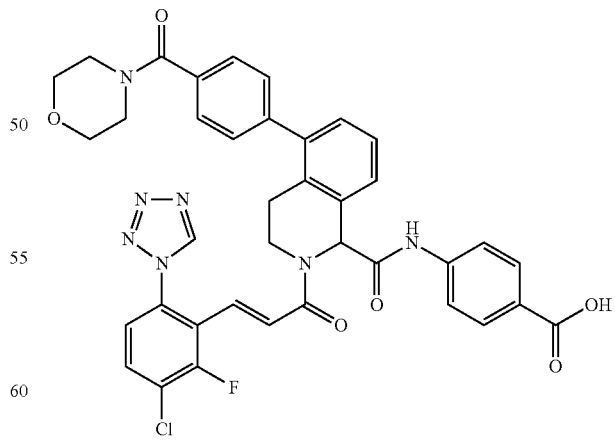

Example 49 (36 mg, 7.3%) was made in a similar manner as Example 39 using 4-(morpholine-4-carbonyl)phenylboronic acid. $^1$H NMR (500 MHz, MeOD) δ 10.51 (1H, s), 9.56 (1H, s), 7.81 (1H, t, J=8.12 Hz), 7.68-7.73 (2H, m), 7.63 (1H, d, J=7.70 Hz), 7.57-7.60 (2H, m), 7.50 (3H, d, J=8.25 Hz), 7.41 (1H, t, J=7.70 Hz), 7.33 (1H, d, J=6.60 Hz), 7.14-7.20 (1H, m), 7.01-7.07 (1H, m), 5.92 (1H, s), 4.11 (1H, dt, J=11.83, 4.95 Hz), 3.46-3.90 (9H, m), 3.23-3.32 (1H, m), 2.89-2.99 (1H, m) ppm. MS (ESI) m/z: 736.1 (M+H)⁺. Analytical HPLC: RT=8.09 min.

Example 50

(R,E)-Methyl 4-(2-(3-(3-chloro-2-fluoro-6-(1H-tetrazol-1-yl)phenyl)acryloyl)-1-(4-fluorophenyl carbamoyl)-1,2,3,4-tetrahydroisoquinolin-5-yl)phenylcarbamate

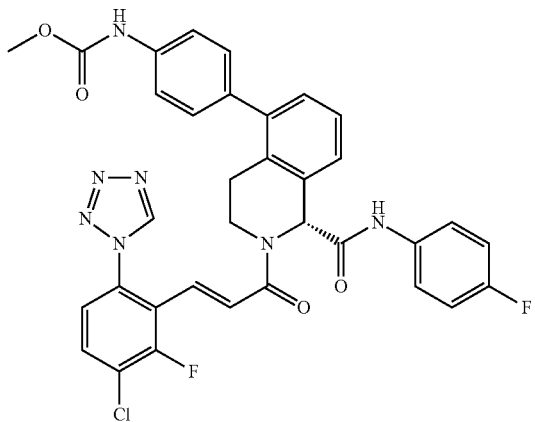 [SMILES: COC(=O)Nc1ccc(-c2cccc3c2CCN(C(=O)/C=C/c2c(-n4cnnn4)ccc(Cl)c2F)[C@H]3C(=O)Nc2ccc(F)cc2)cc1]

Example 50 was obtained by chiral resolution of Example 45. The starting material (60 mg) was dissolved in 60 mL MeOH with 2% pyridine (1 mg/mL). This solution was loaded onto a Chiralcel (OD-H, 250×30 mm ID, 5 μm) and purified using a mobile phase consisting of 60/40 $CO_2$/MeOH:EtOH (3:1) with a flow rate of 70 mL/min, 100 bar backpressure. Example 50 was designated as peak 1 (>99.0% ee). ¹H NMR (500 MHz, DMSO-$d_6$) δ 10.54 (1H, s), 9.86 (1H, s), 9.76 (1H, s), 7.95 (1H, t, J=8.12 Hz), 7.65 (1H, d, J=8.53 Hz), 7.58-7.63 (3H, m), 7.55 (1H, d, J=8.53 Hz), 7.33 (1H, t, J=7.70 Hz), 7.27 (2H, d, J=8.53 Hz), 7.21 (1H, d, J=7.70 Hz), 7.13 (2H, t, J=8.94 Hz), 7.05-7.10 (1H, m), 6.93-6.98 (1H, m), 6.51 (1H, s), 5.83 (1H, s), 4.01-4.08 (1H, m), 3.69 (3H, s), 3.51-3.62 (1H, m), 3.05 (1H, dd, J=8.94, 5.36 Hz), 2.77-2.89 (1H, m) ppm. MS (ESI) m/z: 670.1 (M+H)⁺. Analytical HPLC: RT=10.48 min.

Example 51

(S,E)-Methyl 4-(2-(3-(3-chloro-2-fluoro-6-(1H-tetrazol-1-yl)phenyl)acryloyl)-1-(4-fluorophenyl carbamoyl)-1,2,3,4-tetrahydroisoquinolin-5-yl)phenylcarbamate

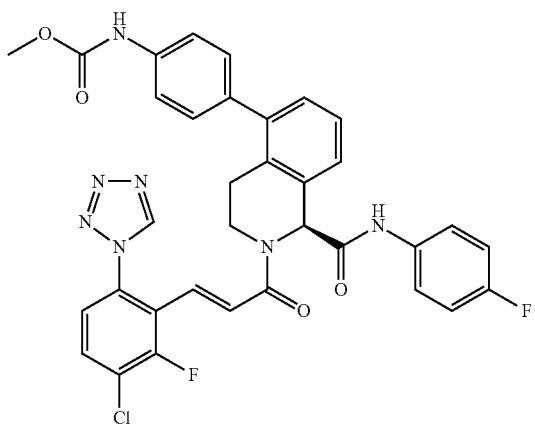 [SMILES: COC(=O)Nc1ccc(-c2cccc3c2CCN(C(=O)/C=C/c2c(-n4cnnn4)ccc(Cl)c2F)[C@@H]3C(=O)Nc2ccc(F)cc2)cc1]

Example 51 was obtained by chiral resolution of Example 45. The starting material (60 mg) was dissolved in 60 mL MeOH with 2% pyridine (1 mg/mL). This solution was loaded onto a Chiralcel (OD-H, 250×30 mm ID, 5 μm) and purified using a mobile phase consisting of 60/40 $CO_2$/MeOH:EtOH (3:1) with a flow rate of 70 mL/min, 100 bar backpressure. Example 51 was designated as peak 2 (>99.0% ee). ¹H NMR (500 MHz, DMSO-$d_6$) δ 10.53 (1H, s), 9.85 (1H, s), 9.75 (1H, s), 7.94 (1H, t, J=8.12 Hz), 7.65 (1H, d, J=8.80 Hz), 7.58-7.63 (3H, m), 7.54 (2H, d, J=8.25 Hz), 7.32 (1H, t, J=7.70 Hz), 7.26 (2H, d, J=8.53 Hz), 7.20 (1H, d, J=7.43 Hz), 7.04-7.15 (3H, m), 6.91-6.97 (1H, m), 6.50 (1H, s), 5.83 (1H, s), 3.97-4.09 (1H, m), 3.69 (3H, s), 3.49-3.59 (1H, m), 3.01-3.11 (1H, m), 2.78-2.89 (1H, m) ppm. MS (ESI) m/z: 670.1 (M+H)⁺. Analytical HPLC: RT=10.41 min.

Example 52

(E)-4-(2-(3-(3-Chloro-2-fluoro-6-(1H-tetrazol-1-yl)phenyl)acryloyl)-5-(4-(2-morpholinoethyl carbamoyl)phenyl)-1,2,3,4-tetrahydroisoquinoline-1-carboxamido)benzoic acid, TFA salt

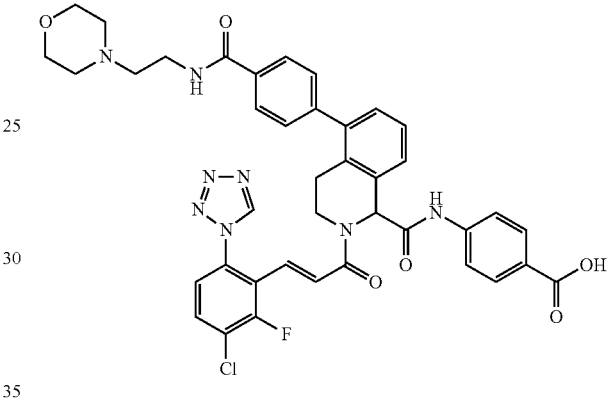

Example 52 (21 mg, 3.7%) was made in a similar manner as Example 39 using [4-(4'-(2'-Aminoethyl)morpholine-1-carbonyl)phenyl]boronic acid. ¹H NMR (400 MHz, DMSO-$d_6$) δ 12.76 (1H, br.s.), 10.85 (1H, s), 9.87 (1H, s), 8.75-8.89 (1H, m), 7.84-8.02 (5H, m), 7.63-7.75 (4H, m), 7.50 (2H, d, J=8.25 Hz), 7.39 (1H, t, J=7.70 Hz), 7.27 (1H, d, J=7.70 Hz), 6.86-7.10 (2H, m), 5.89 (1H, s), 3.93-4.11 (3H, m), 3.27-3.76 (9H, m), 3.06-3.22 (3H, m) ppm. MS (ESI) m/z: 779.2 (M+H)⁺. Analytical HPLC: RT=6.80 min.

Example 53

(E)-4-(2-(3-(3-Chloro-2-fluoro-6-(1H-tetrazol-1-yl)phenyl)acryloyl)-5-(4-(4-methylpiperazine-1-carbonyl)phenyl)-1,2,3,4-tetrahydroisoquinoline-1-carboxamido)benzoic acid, TFA salt

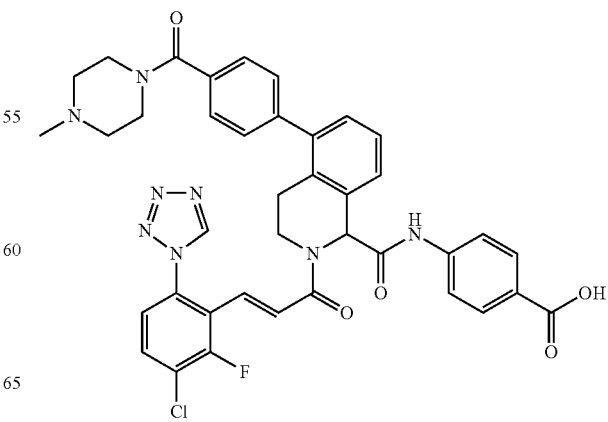

Example 53: tert-Butyl 5-bromo-3,4-dihydroisoquinoline-2(1H)-carboxylate (0.20 g, 0.64 mmol), (4-methyl-piperazine-1-yl)-[4-(4,4,5,5-tetramethyl-1,3,2-dioxaborolan-2-yl)-phenyl]-methanone (0.23 g, 0.71 mmol), and 2.0 M K$_2$CO$_3$ (3 mL) were added to dioxane (5 mL)/EtOH (1 mL) and degassed with N$_2$. Tetrakis(triphenyl-phosphine)palladium (0) (0.037 g, 0.032 mmol) was added and the mixture irradiated in microwave at 130° C. for 15 min. The reaction mixture was diluted with H$_2$O and extracted with EtOAc (3×20 mL). The combined organic layer was washed with saturated NaHCO$_3$ solution, brine, dried over Na$_2$SO$_4$, filtered, and concentrated. Purification by silica gel chromatography gave a beige oil. The Boc-group was removed by treatment with 50% TFA/DCM for 3 h. The reaction mixture was concentrated, dissolved in EtOAc (50 mL), and neutralized with saturated NaHCO$_3$ solution. The organic layer was washed with H$_2$O, brine, dried over Na$_2$SO$_4$, filtered, and concentrated to give the free based amine. The residue was oxidized as in Example 8C and the product was combined with Intermediate 3A (0.172 g, 0.641 mmol) and Intermediate 6 (0.156 g, 0.77 mmol) in an Ugi reaction as in Example 8. Purification by reverse phase chromatography gave Example 53 (35 mg, 6%) as a white solid. $^1$H NMR (400 MHz, DMSO-d$_6$) δ 12.75 (1H, br.s.), 10.87 (1H, s), 9.88 (1H, s), 7.87-8.00 (3H, m), 7.64-7.75 (4H, m), 7.55-7.60 (2H, m), 7.48 (2H, d, J=7.70 Hz), 7.40 (1H, t, J=7.70 Hz), 7.28 (1H, d, J=7.70 Hz), 6.86-7.10 (2H, m), 5.90 (1H, s), 3.98-4.13 (1H, m), 3.31-3.62 (7H, m), 3.04-3.21 (3H, m), 2.79-2.92 (4H, m) ppm. MS (ESI) m/z: 749.2 (M+H)$^+$. Analytical HPLC: RT=5.63 min.

The following Examples in Table 6 were prepared according to methods analogous to that described for Example 53 substituting the appropriate commercially available boronic acid or boronate in the Suzuki reaction step and Intermediate 6, 7, 8, 9, 10 or 11 or commercially available isonitrile in the Ugi reaction. Representative chiral compounds were obtained by chiral resolution of the appropriate late stage intermediate followed by deprotection and purification.

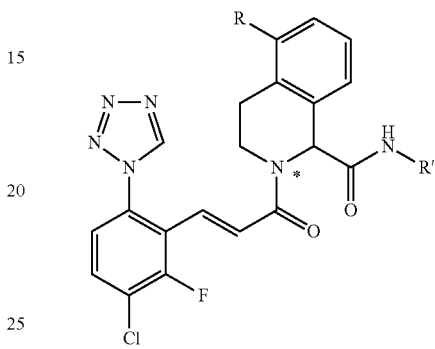

TABLE 6

| Example # | Stereochemistry | R | R' | (M + H)$^+$ | RT |
|---|---|---|---|---|---|
| 54 | racemic | 4-(aminocarbonyl)phenyl (—NH—C(O)—C$_6$H$_4$—) | 4-PhCO$_2$H | 680.2 | 7.86 |
| 55 | racemic | 4-(aminocarbonyl)phenyl | trans-4-hydroxycyclohexyl | 658.5 | 6.98 |
| 56 | racemic | 4-(aminocarbonyl)phenyl | cyclohexyl | 642.5 | 9.45 |
| 57 | racemic | 4-(aminocarbonyl)phenyl | tert-butyl | 616.2 | 8.86 |
| 58 | racemic | 4-(aminocarbonyl)phenyl | isopropyl | 602.3 | 8.23 |
| 59 | racemic | 4-(aminocarbonyl)phenyl | n-propyl | 588.3 | 7.46 |
| 60 | racemic | 4-(aminocarbonyl)phenyl | isobutyl | 616.4 | 9.22 |
| 61 | racemic | 4-(aminocarbonyl)phenyl | —CH$_2$C(O)OCH$_3$ | 632.2 | 7.42 |

TABLE 6-continued

| Example # | Stereochemistry | R | R' | (M + H)+ | RT |
|---|---|---|---|---|---|
| 62 | racemic | 4-(methylcarbamoyl)phenyl | isopropyl-CH(wedge)- | 630.4 | 9.61 |
| 63 | racemic | 4-(methylcarbamoyl)phenyl | isopropyl-CH(dash)- | 630.4 | 9.61 |
| 64 | racemic | 4-(methylcarbamoyl)phenyl | sec-butyl (wedge) | 616.4 | 9.14 |
| 65 | racemic | 4-(methylcarbamoyl)phenyl | sec-butyl (dash) | 616.4 | 9.15 |
| 66 | racemic | 4-(methylcarbamoyl)phenyl | (1-methylimidazol-2-yl)methyl | 656.2 | 5.09 |
| 67 | racemic | 4-carbamoylphenyl | 4-PhCO$_2$H | 666.2 | 7.42 |
| 68 | R enantiomer[a] | 4-carbamoylphenyl | 4-PhCO$_2$H | 666.2 | 7.48 |
| 69 | S enantiomer[a] | 4-carbamoylphenyl | 4-PhCO$_2$H | 666.2 | 7.42 |
| 70 | racemic | 4-(dimethylcarbamoyl)phenyl | 4-PhCO$_2$H | 694.2 | 8.23 |
| 71 | R enantiomer[b] | 4-(dimethylcarbamoyl)phenyl | 4-PhCO$_2$H | 694.2 | 8.20 |
| 72 | S enantiomer[b] | 4-(dimethylcarbamoyl)phenyl | 4-PhCO$_2$H | 694.2 | 8.26 |
| 73 | racemic | 4-((2-(dimethylamino)ethyl)carbamoyl)phenyl | 4-PhCO$_2$H | 737.2 | 5.67 |

TABLE 6-continued
| Example # | Stereochemistry | R | R' | (M + H)+ | RT |
|---|---|---|---|---|---|
| 74 | R enantiomer[c] | 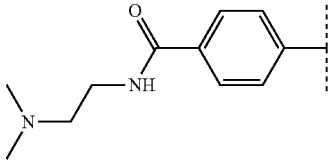 | 4-PhCO$_2$H | 737.2 | 5.60 |
| 75 | S enantiomer[c] | 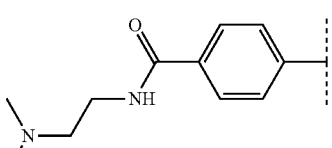 | 4-PhCO$_2$H | 737.2 | 5.60 |
| 76 | racemic | 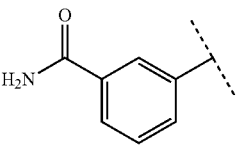 | 4-PhCO$_2$H | 666.2 | 7.65 |
| 77 | racemic | 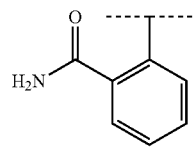 | 4-PhCO$_2$H | 666.2 | 7.77 |
| 78 | racemic | 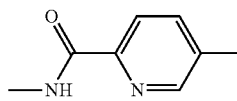 | 4-PhCO$_2$H | 681 | 7.96 |
| 79 | racemic | 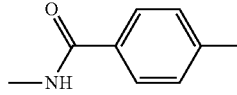 | 6-indazolyl | 676.2 | 7.86 |
| 80 | R enantiomer[d] | 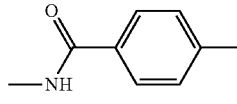 | 6-indazolyl | 676.2 | 7.83 |
| 81 | S enantiomer[d] | 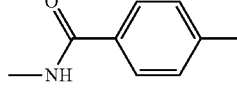 | 6-indazolyl | 676.2 | 7.83 |
| 82 | racemic | 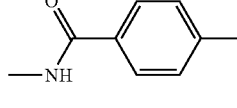 | 4-PhF | 654.0 | 9.36 |
| 83 | racemic | 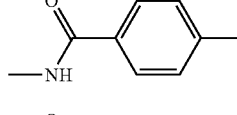 | 4-PhCN | 661.0 | 9.00 |
| 84 | racemic | 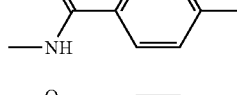 | 4-PhNHCO$_2$Me | 709.0 | 8.41 |
| 85 | racemic | 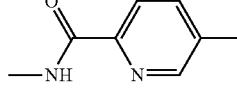 | 4-PhCN | 662.0 | 9.11 |

TABLE 6-continued

| Example # | Stereochemistry | R | R' | (M + H)+ | RT |
|---|---|---|---|---|---|
| 86 | racemic | 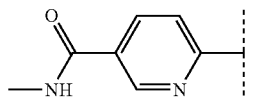 | 4-PhCN | 662.0 | 7.82 |
| 87 | racemic | 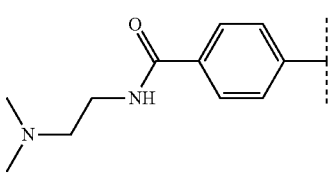 | 4-PhCO$_2$tBu | 793.0 | 8.25 |
| 88 | R enantiomer[e] | 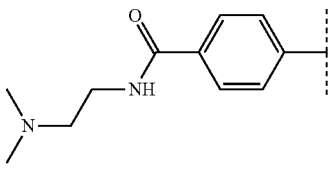 | 4-PhCO$_2$tBu | 793.0 | 8.37 |
| 89 | S enantiomer[e] | 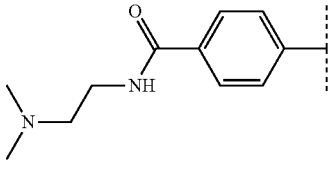 | 4-PhCO$_2$tBu | 793.0 | 8.37 |
| 90 | S enantiomer | 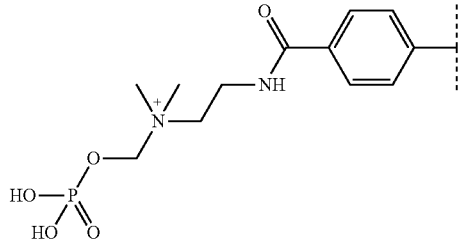 | 4-PhCO$_2$H | 847.3 | 6.55 |
| 91 | racemic | 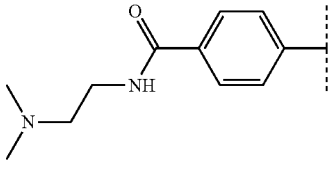 | 4-PhF | 711.0 | 7.02 |
| 92 | racemic | 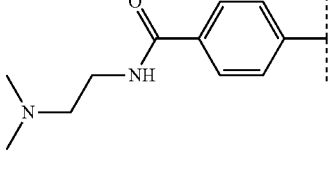 | 4-PhNHCO$_2$Me | 766.0 | 6.48 |

[a]Chiralcel OJ-H SFC, 150 × 30 mm, 5 μm, using 45% to 60% IPA/CO$_2$ at 80 mL/min, 100 bar, 35° C.

[b]Chiralcel OJ-H SFC, 150 × 30 mm, 5 μm, using 40% to 55% IPA/CO$_2$ at 80 mL/min, 100 bar, 35° C.

[c]Chiralpak AD-H SFC, 150 × 20 mm, 5 μm, using 45% to 60% IPA/CO$_2$ at 80 mL/min, 100 bar, 35° C.

[d]Chiralcel OJ-H SFC, 150 × 30 mm, 5 μm, using 40% (1:1:1 MeOH/EtOH/IPA)/60% CO$_2$ at 70 mL/min, 100 bar, 35° C.

[e]Chiralcel AD-H SFC, 150 × 210 mm, 5 μm, using 40% IPA/60% CO$_2$ at 70 mL/min, 100 bar, 35° C.

Example 93

(R,E)-2-(dimethylamino)ethyl 4-(2-(3-(3-chloro-2-fluoro-6-(1H-tetrazol-1-yl)phenyl)acryloyl)-5-(4-((2-(dimethylamino)ethyl)carbamoyl)phenyl)-1,2,3,4-tetrahydroisoquinoline-1-carboxamido)benzoate; bis-TFA salt

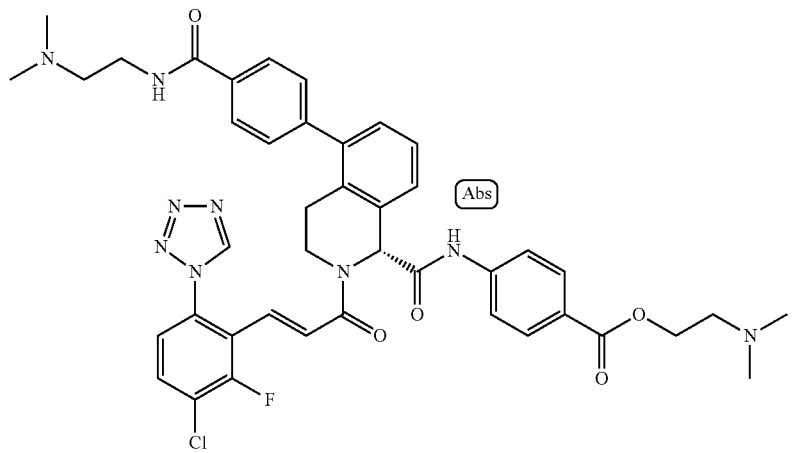

Example 93 (R,E)-4-(2-(3-(3-chloro-2-fluoro-6-(1H-tetrazol-1-yl)phenyl)acryloyl)-5-(4-((2-(dimethylamino)ethyl)carbamoyl)phenyl)-1,2,3,4-tetrahydroisoquinoline-1-carboxamido)benzoic acid (0.025 g, 0.034 mmol) and DMEA (0.10 mL, 0.994 mmol) in pyridine (0.5 mL) was treated dropwise at −20° C. with POCl$_3$ (3.16 µl, 0.034 mmol). The reaction mixture was allowed to come to rt. Purification was done by reverse phase HPLC and isolated the desired product.

$^1$H NMR (400 MHz, MeOD) δ 9.55 (s, 1H), 8.05 (d, J=8.8 Hz, 2H), 7.99 (d, J=8.8 Hz, 2H), 7.82-7.76 (m, 1H), 7.75-7.71 (m, 2H), 7.61 (d, J=7.1 Hz, 1H), 7.52-7.46 (m, 3H), 7.42-7.37 (m, 1H), 7.33-7.29 (m, 1H), 7.17-7.11 (m, 1H), 7.05-6.99 (m, 1H), 5.87 (s, 1H), 4.69-4.64 (m, 2H), 4.08 (dt, J=11.8, 4.5 Hz, 1H), 3.81 (t, J=5.8 Hz, 2H), 3.61 (dt, J=4.7, 2.6 Hz, 2H), 3.53-3.47 (m, 1H), 3.43 (t, J=5.8 Hz, 2H), 3.28-3.22 (m, 1H), 3.05-3.00 (m, 12H), 2.93-2.85 (m, 1H) ppm.

MS (ESI) m/z: 808.4 (M+H)$^+$. Analytical HPLC: RT=5.07 min.

The following Examples in Table 7 were prepared according to methods analogous to that described for Example 93 substituting the appropriate commercially available intermediates. Representative chiral compounds were obtained by chiral resolution of the appropriate late stage intermediate followed by deprotection and purification.

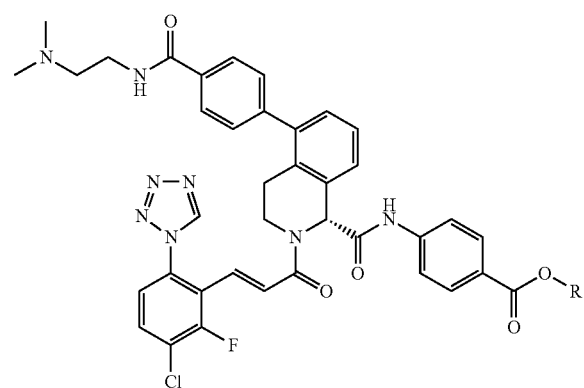

TABLE 7

| Example # | R | (M + H)$^+$ | RT |
|---|---|---|---|
| 94 | ~O~ | 795.3 | 6.82 |
| 95 | Me$_2$N-CH$_2$CH$_2$-O-CH$_2$CH$_2$- | 852.0 | 1.59** |
| 96 | MeO-CH$_2$CH$_2$-O-CH$_2$CH$_2$- | 839.3 | 7.49 |
| 97 | 3-pyridylmethyl | 828.3 | 6.15 |
| 98 | 2-pyridylmethyl | 828.3 | 6.50 |
| 99 | 1,2,4-triazol-1-yl-ethyl | 832.3 | 6.89 |

**LCMS RT

Example 100

(E)-4-(2-(3-(3-chloro-2-fluoro-6-(1H-tetrazol-1-yl)phenyl)acryloyl)-5-(piperidin-4-ylmethoxy)-1,2,3,4-tetrahydroisoquinoline-1-carboxamido)benzoic acid, TFA salt

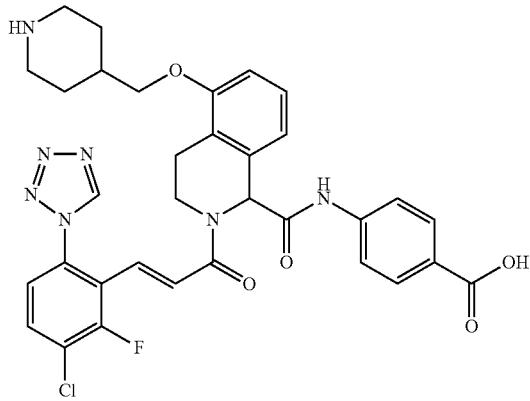 [SMILES: O=C(O)c1ccc(NC(=O)C2c3cccc(OCC4CCNCC4)c3CCN2C(=O)/C=C/c2c(-n3cnnn3)ccc(Cl)c2F)cc1]

Example 100: Diethyl azodicarboxylate (40% in toluene; 0.390 g, 0.896 mmol) was added to a solution of isoquinolin-5-ol (0.100 g, 0.689 mmol), tert-butyl 4-(hydroxymethyl)piperidine-1-carboxylate (0.148 g, 0.689 mmol), and triphenyl phosphine (0.235 g, 0.896 mmol) in THF (15 mL) under $N_2$. After 20 h, the reaction mixture was partitioned between EtOAc and $H_2O$. The $H_2O$ layer was washed with additional EtOAc (2×15 mL). The combined organic layer was washed with saturated $NaHCO_3$ solution, brine, dried over $Na_2SO_4$, filtered, and concentrated. Purification by silica gel chromatography gave a yellow oil. This material was reduced and then oxidized as described in Example 8 to afford an imine. The imine, Intermediate 3A (0.185 g, 0.689 mmol), and Intermediate 6 (0.140 g, 0.689 mmol) were combined in an Ugi reaction as described in Example 18 and then, deprotected with TFA. Purification by reverse phase HPLC gave Example 100 (45 mg, 7.8%) as a white solid. $^1H$ NMR (400 MHz, DMSO-$d_6$) δ 12.77 (1H, br.s.), 10.84 (1H, s), 9.88 (1H, s), 8.50-8.67 (1H, m), 8.19-8.40 (1H, m), 7.85-8.00 (3H, m), 7.62-7.73 (3H, m), 7.17-7.27 (2H, m), 6.85-7.11 (3H, m), 5.83 (1H, s), 4.03-4.15 (1H, m), 3.81-3.96 (2H, m), 3.72 (1H, dt, J=12.09, 6.05 Hz), 3.34 (2H, d, J=12.09 Hz), 2.83-3.03 (4H, m), 2.04-2.17 (1H, m), 1.86-1.99 (2H, m), 1.39-1.62 (2H, m) ppm. MS (ESI) m/z: 660.2 (M+H)$^+$. Analytical HPLC: RT=5.54 min.

Example 101

(E)-4-(2-(3-(3-chloro-2-fluoro-6-(1H-tetrazol-1-yl)phenyl)acryloyl)-5-(2-methoxyethoxy)-1,2,3,4-tetrahydroisoquinoline-1-carboxamido)benzoic acid

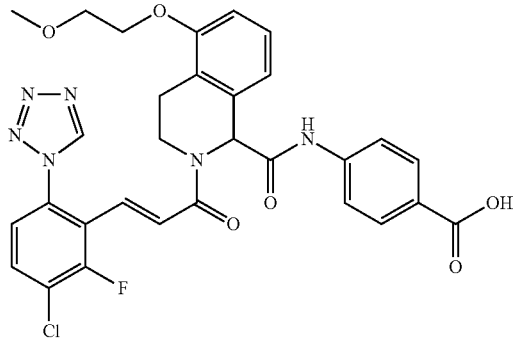 [SMILES: COCCOc1cccc2c1CCN(C(=O)/C=C/c1c(-n3cnnn3)ccc(Cl)c1F)C2C(=O)Nc1ccc(C(=O)O)cc1]

101A: 5-(2-Methoxyethoxy)isoquinoline: Cesium carbonate (2.25 g, 6.89 mmol) was added to a solution of 5-hydroxyisoquinoline (0.500 g, 3.44 mmol) and 2-methoxyethylmethanesulfonate (1.06 g, 6.89 mmol) in ACN (15 mL) and heated at 70° C. overnight. The reaction mixture was diluted with DCM (100 mL) and washed with $H_2O$. The aqueous layer was extracted with additional DCM (25 mL). The combined organic layer was washed with brine, dried over $Na_2SO_4$, filtered, and concentrated. The crude product was purified by silica gel chromatography to give a brown oil (633 mg, 90%). MS (ESI) m/z: 204.1 (M+H)$^+$.

101B: 5-(2-Methoxyethoxy)-3,4-dihydroisoquinoline: 101A was reduced and then oxidized as described in previous Examples. MS (ESI) m/z: 206.1 (M+H)$^+$.

Example 101: 101B (0.170 g, 0.828 mmol), Intermediate 3A (0.222 g, 0.828 mmol), and Intermediate 6 (0.252 g, 1.242 mmol) were subjected to an Ugi reaction as described in Example 1 followed by TFA deprotection and purification by reverse phase HPLC to give Example 101 (33 mg, 6.4%) as a white solid. $^1H$ NMR (500 MHz, DMSO-$d_6$) δ 12.72 (1H, br.s.), 10.80 (1H, s), 9.87 (1H, s), 7.96 (1H, t, J=8.12 Hz), 7.85-7.91 (2H, m), 7.64-7.71 (3H, m), 7.17-7.23 (2H, m), 7.08-7.14 (1H, m), 6.90-6.99 (2H, m), 5.82 (1H, s), 4.05-4.14 (3H, m), 3.67-3.75 (3H, m), 3.35 (3H, s), 2.84-2.99 (2H, m) ppm. MS (ESI) m/z: 621.1 (M+H)$^+$. Analytical HPLC: RT=8.74 min.

Example 102

(E)-4-(5-(1-(Benzyloxycarbonyl)piperidin-4-yl)-2-(3-(3-chloro-2-fluoro-6-(1H-tetrazol-1-yl)phenyl)acryloyl)-1,2,3,4-tetrahydroisoquinoline-1-carboxamido)benzoic acid

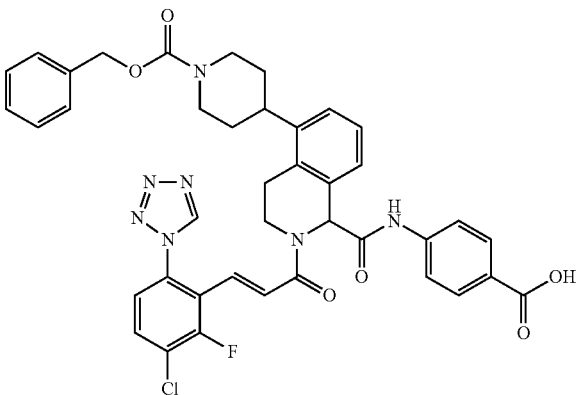 [SMILES: O=C(O)c1ccc(NC(=O)C2c3cccc(C4CCN(C(=O)OCc5ccccc5)CC4)c3CCN2C(=O)/C=C/c2c(-n3cnnn3)ccc(Cl)c2F)cc1]

102A: tert-Butyl 5-(1-(benzyloxycarbonyl)piperidin-4-yl)-3,4-dihydro isoquinoline-2(1H)-carboxylate: To Intermediate 41A (0.160 g, 0.515 mmol) in THF (6 mL), cooled to 0° C., was added Superhydride® (1.546 mL, 1.546 mmol). After 1.5 h, an additional 1 mL of hydride was added and the reaction was stirred at rt for 2h. MS (ESI) m/z: 315.1 (M+H)$^+$. The reaction was concentrated and the residue was partitioned in DCM/saturated $NaHCO_3$ in a separatory funnel with benzyl chloroformate (0.074 mL, 0.515 mmol). After shaking for 10 min. the layers were separated and the organic layer was washed with brine and dried ($MgSO_4$). Purification by silica gel chromatography afforded 0.164 g (71%) of 102A as a clear oil. MS (ESI) m/z: 393.1 (M+H-tbutyl)$^+$.

102B: Benzyl 4-(1,2,3,4-tetrahydroisoquinolin-5-yl)piperidine-1-carboxylate: 102A (0.164 g, 0.364 mmol) in $H_2O$ (10 mL)/ACN (4 mL) and 4N HCl (0.018 mL, 0.073 mmol) in dioxane was heated in a microwave at 150° C. in microwave for 35 min. Concentrated partially and freeze-dried to afford 0.12 g of 102B as a tan solid. MS (ESI) m/z: 351 (M+H)$^+$ 102C: Benzyl 4-(3,4-dihydroisoquinolin-5-yl)piperidine-1-carboxylate: 102C (0.12 g, 0.342 mmol) was oxidized as in Intermediate 17 to afford 82 mgs of 102C as a yellow oil. MS (ESI) m/z: 349.1 (M+H)$^+$ Example 102 was prepared in a similar manner as Example 1 using Intermediate 102C, Intermediate 6 and Intermediate 3A. $^1$H NMR (400 MHz, MeOD) δ 10.40 (1H, s), 9.55 (1H, s), 7.96 (2H, d, J=8.59 Hz), 7.75-7.87 (1H, m), 7.60-7.72 (2H, m), 7.45-7.54 (2H, m), 7.31-7.45 (5H, m), 7.26 (1H, t, J=7.58 Hz), 7.11-7.20 (2H, m), 6.99-7.10 (1H, d, J=15.9 Hz), 5.82 (1H, s), 5.66 (1H, br.s.), 5.20 (2H, s), 4.05-4.28 (4H, m), 3.76 (2H, br.s.), 3.47-3.61 (1H, m), 3.16-3.26 (1H, m), 2.91-3.03 (1H, m), 2.24-2.55 (2H, m) ppm. MS (ESI) m/z: 762.2 (M+H)$^+$. Analytical HPLC: RT=10.48 min.

Example 103

(E)-4-(5-Bromo-2-(3-(5-chloro-2-(1H-tetrazol-1-yl) phenyl)acryloyl)-4,4-dimethyl-1,2,3,4-tetrahydroisoquinoline-1-carboxamido)benzoic acid

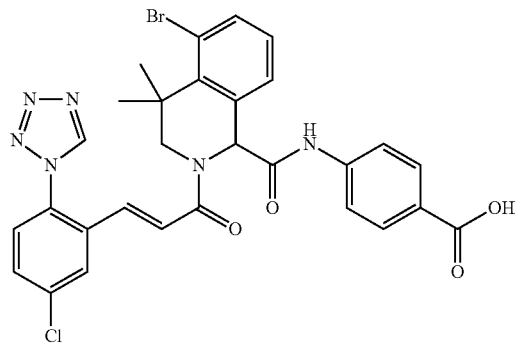 [SMILES: CC1(C)CN(C(=O)/C=C/c2cc(Cl)ccc2-n2cnnn2)C(C(=O)Nc2ccc(C(=O)O)cc2)c2cccc(Br)c21]

103A: 2-(2-Bromophenyl)-2-methylpropan-1-amine: To a solution of 2-(2-bromophenyl)-2-methylpropanenitrile (4.0 g, 17.8 mmol), in dry THF (40 mL) was added borane-dimethyl sulfide (5.08 mL, 53.5 mmol) at 0° C. and the reaction mixture was slowly brought to rt, stirred for 1 h and then, heated to reflux for 18 h. The solvent was removed and quenched with MeOH, and heated to reflux for 18 h. The reaction was concentrated and the residue was dissolved in EtOAc, washed with H$_2$O, brine, dried (Na$_2$SO$_4$), filtered and concentrated to give 4.0 g of 103A as a white solid. MS (ESI) m/z: 230.2 (M+H)$^+$.

103B: Methyl 2-(2-bromophenyl)-2-methylpropylcarbamate: To a solution of 103A (3.5 g, 15.3 mmol) in dry THF (30 mL) at 0° C., was added TEA (3.25 mL, 23.0 mmol), followed by drop-wise addition of methyl chloroformate (1.74 g, 18.4 mmol). The reaction mixture was allowed to stir at rt for 1 h. The reaction mixture was diluted with H$_2$O, extracted with EtOAc (2×), the combined organics were washed with saturated NaHCO$_3$ solution, brine, dried (Na$_2$SO$_4$), filtered and concentrated to give 3.5 g of 103B as colorless a solid. MS (ESI) m/z: 286.0 (M+H)$^+$.

103C: 5-Bromo-4,4-dimethyl-3,4-dihydroisoquinoline-1 (2H)-one: To 103B (3.5 g, 12.23 mmol) was added polyphosphoric acid (2.45 g, 7.0 vol.) and the reaction was heated at 150° C. for 1 h. The reaction mixture was diluted with H$_2$O, extracted with EtOAc (2×), the combined organics were washed with saturated NaHCO$_3$ solution, brine, dried (Na$_2$SO$_4$), filtered and concentrated. The crude product was purified by silica gel chromatography to give 103C (1.0 g, 31.9%) as a brown solid. MS (ESI) m/z: 256.0 (M+H)$^+$.

103D: 5-Bromo-4,4-dimethyl-1,2,3,4-tetrahydroisoquinoline: To a solution of 103C (1.0 g, 3.93 mmol) in dry THF (10 mL) at 0° C., was added borane-dimethyl sulfide complex (1.12 mL, 11.81 mmol), the reaction mixture was slowly brought to rt, stirred for 1 h and then heated to reflux for 18 h. The solvent was removed and the residue was quenched with MeOH and heated to reflux for 18 h. The solvent was removed and the residue was dissolved in EtOAc, washed with H$_2$O, brine, dried (Na$_2$SO$_4$), filtered and concentrated to give 0.8 g of 103D as a white solid. The material was carried onto the next step without further purification. MS (ESI) m/z: 240.0 (M+H)$^+$.

103E: 5-Bromo-4,4-dimethyl-3,4-dihydroisoquinoline: To the stirred solution of 103D (0.5 g, 2.08 mmol) in dry DCM (5 mL) was added MnO$_2$ (5.0 g, 10 vol). Reaction mixture stirred at rt. After 18 h, the reaction was filtered through celite and concentrated to afford 0.4 g of 103E as yellow oil. MS (ESI) m/z: 238.0 (M+H)$^+$.

Example 103 was prepared by the Ugi reaction as in Example 8 starting from 103E and Intermediates 2 and 6 followed by TFA deprotection to afford 8.6 mg as a white solid. $^1$H NMR (400 MHz, DMSO-d$_6$) δ 10.92 (1H, s), 9.88 (1H, s), 8.46 (1H, d, J=2.0 Hz), 7.92 (2H, d, J=8.8 Hz), 7.78 (4H, m), 7.59 (2H, t, J=7.2 Hz), 7.49 (1H, d, J=7.6 Hz), 7.19 (1H, q), 7.09 (1H, d, J=14.8 Hz), 6.01 (1H, s), 4.20 (1H, d, J=14.4 Hz), 4.09 (1H, d, J=13.6 Hz), 1.70 (3H, s), 1.45 (3H, s) ppm. MS (ESI) m/z: 635.0 (M+H)$^+$. Analytical HPLC: RT=18.74 min.

Example 104

(E)-2-(3-(3-Chloro-2-fluoro-6-(1H-tetrazol-1-yl) phenyl)acryloyl)-N-(1H-indazol-6-yl)-5-(2-(piperidin-4-yl)ethoxy)-1,2,3,4-tetrahydroisoquinoline-1-carboxamide, TFA salt

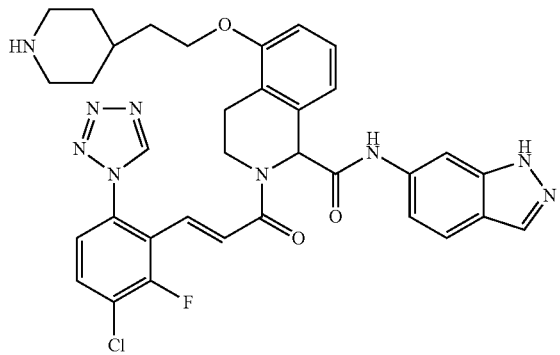 [SMILES: O=C(Nc1ccc2cn[nH]c2c1)C1c2cccc(OCCC3CCNCC3)c2CCN1C(=O)/C=C/c1c(-n2cnnn2)ccc(Cl)c1F]

104A: tert-Butyl 4-(2-(3,4-dihydroisoquinolin-5-yloxy) ethyl)piperidine-1-carboxylate: Sodium iodide (0.052 g, 0.34 mmol) was added to a solution of 5-hydroxyisoquinoline (0.500 g, 3.44 mmol), tert-butyl 4-(2-bromoethyl)piperidine-1-carboxylate (1.107 g, 3.79 mmol), and Cs$_2$CO$_3$ (2.245 g, 6.89 mmol) in DMF (10 mL). The mixture was heated at 90° C. for 14 h and then, the reaction mixture was diluted with DCM (100 mL) and washed with H$_2$O. The aqueous layer was extracted with additional DCM (25 mL). The combined organic layer was washed with brine, dried over Na$_2$SO$_4$, filtered, and concentrated. Purification by silica gel chromatography afforded a brown oil (633 mg, 90%). This material was reduced and then, oxidized as described in Example 8 to afford 104A. MS (ESI) m/z: 359.1 (M+H)$^+$.

Example 104: 104A (0.150 g, 0.418 mmol), Intermediate 3A (0.112 g, 0.418 mmol) and Intermediate 8 (0.102 g, 0.418 mmol), were combined in an Ugi reaction as described in Example 8 followed by TFA deprotection. Purification by reverse phase HPLC gave Example 104 (40 mg, 11.6%) as a white solid after lyophilization. $^1$H NMR (400 MHz, DMSO-d$_6$) δ 10.63 (1H, s), 9.87 (1H, s), 7.92-8.04 (3H, m), 7.58-7.74

(2H, m), 7.14-7.24 (3H, m), 6.87-7.13 (3H, m), 5.87 (1H, s), 3.98-4.16 (3H, m), 3.70-3.82 (1H, m), 3.28 (2H, d, J=11.87 Hz), 2.78-3.00 (4H, m), 1.66-1.97 (5H, m), 1.28-1.46 (2H, m) ppm. MS (ESI) m/z: 670.2 (M+H)+. Analytical HPLC: RT=5.71 min

Example 105

4-(2-((1r,4r)-4-(aminomethyl)cyclohexanecarbonyl)-5-bromo-4,4-dimethyl-1,2,3,4-tetrahydro isoquinoline-1-carboxamido)benzoic acid

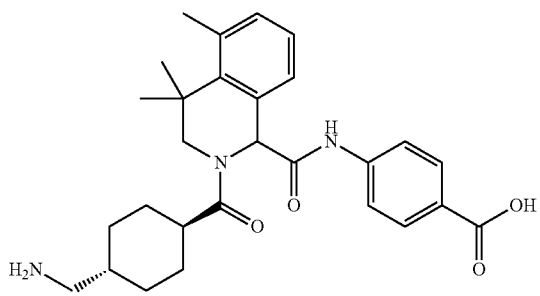 [SMILES: Cc1cccc2c1C(C)(C)CN(C(=O)[C@H]1CC[C@H](CN)CC1)C2C(=O)Nc1ccc(C(=O)O)cc1]

Example 105 was prepared by the Ugi reaction as in Example 103 starting with appropriate intermediates followed by TFA deprotection to afford 15 mg as a white solid. $^1$H NMR (400 MHz, DMSO-$d_6$) δ 12.77 (1H, s), 10.86 (1H, s), 7.95 (2H, t, J=8.8 Hz), 7.73 (5H, m), 7.58 (1H, d, J=7.6 Hz), 7.51 (1H, d, J=7.7 Hz), 7.17 (1H, t, J=7.8 Hz), 5.87 (1H, s), 4.03 (1H, d, J=13.7 Hz), 3.79 (1H, d, J=13.8 Hz), 2.84 (1H, d, J=11.8 Hz), 2.68 (2H, t, J=2.6 Hz), 1.81 (3H, d, J=11.2 Hz), 1.74 (1H, d, J=12.8 Hz), 1.65 (3H, s), 1.54 (2H, t, J=10.5 Hz), 1.45 (3H, s), 1.10 (2H, m). MS (ESI) m/z: 556 (M+H)+. Analytical HPLC: RT=8.91 min.

Example 106

(E)-4-(2-(3-(3-Chloro-2-fluoro-6-(1H-tetrazol-1-yl)phenyl)acryloyl)-5-(2-(piperidin-4-yl)ethoxy)-1,2,3,4-tetrahydroisoquinoline-1-carboxamido)benzoic acid, TFA salt

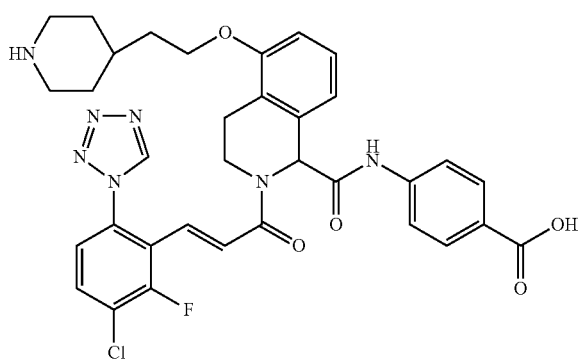 [SMILES: O=C(O)c1ccc(NC(=O)C2c3cccc(OCCC4CCNCC4)c3CCN2C(=O)/C=C/c2c(-n3cnnn3)ccc(Cl)c2F)cc1]

Example 106 (35 mg, 10.6%) was made in a similar manner as Example 104 substituting Intermediate 6 instead of Intermediate 8 in the Ugi reaction step. $^1$H NMR: (400 MHz, MeOD) δ 10.47 (1H, s), 9.56 (1H, s), 7.95 (2H, d, J=8.79 Hz), 7.79 (1H, t, J=8.24 Hz), 7.64 (2H, d, J=8.24 Hz), 7.48 (1H, d, J=8.79 Hz), 7.22 (1H, t, J=7.97 Hz), 7.15 (1H, d, J=15.94 Hz), 7.09 (1H, d, J=7.70 Hz), 6.88-6.98 (2H, m), 5.83 (1H, s), 4.01-4.19 (3H, m), 3.60-3.74 (1H, m), 3.38-3.45 (2H, m), 2.86-3.11 (4H, m), 1.91-2.15 (3H, m), 1.78-1.91 (2H, m), 1.41-1.60 (2H, m) ppm. MS (ESI) m/z: 674.2 (M+H)+. Analytical HPLC: RT=5.78 min.

Example 107

(E)-2-(3-(3-Chloro-2-fluoro-6-(1H-tetrazol-1-yl)phenyl)acryloyl)-N-(4-fluorophenyl)-5-(2-(piperidin-4-yl)ethoxy)-1,2,3,4-tetrahydroisoquinoline-1-carboxamide, TFA salt

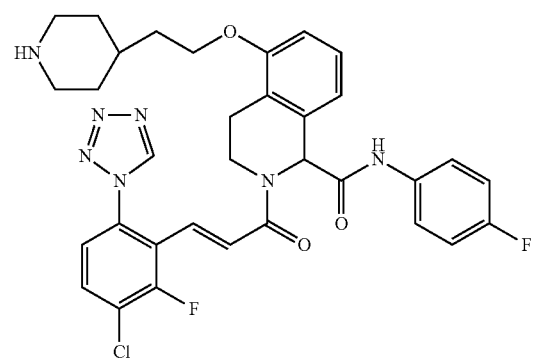 [SMILES: O=C(Nc1ccc(F)cc1)C1c2cccc(OCCC3CCNCC3)c2CCN1C(=O)/C=C/c1c(-n2cnnn2)ccc(Cl)c1F]

Example 107 (6 mg, 1.9%) was made in a similar manner as Example 104 substituting commercially available 1-fluoro-4-isocyanobenzene instead of Intermediate 8 in the Ugi reaction step. $^1$H NMR (500 MHz, DMSO-$d_6$) δ 10.56 (1H, s), 9.87 (1H, s), 7.97 (1H, t, J=8.12 Hz), 7.65-7.69 (1H, m), 7.56-7.61 (2H, m), 7.19-7.24 (1H, m), 7.10-7.18 (3H, m), 7.02-7.09 (1H, m), 6.88-7.00 (2H, m), 5.80 (1H, s), 3.99-4.13 (3H, m), 3.71-3.79 (1H, m), 3.28 (2H, d, J=12.38 Hz), 2.78-2.98 (4H, m), 1.78-1.93 (3H, m), 1.74 (2H, d, J=5.23 Hz), 1.31-1.42 (2H, m) ppm. MS (ESI) m/z: 648.2 (M+H)+. Analytical HPLC: RT=6.64 min.

Example 108

Racemate (E)-4-(2-(3-(3-Chloro-2-fluoro-6-(1H-tetrazol-1-yl)phenyl)acryloyl)-5-(piperidin-4-yloxy)-1,2,3,4-tetrahydroisoquinoline-1-carboxamido)benzoic acid, TFA salt

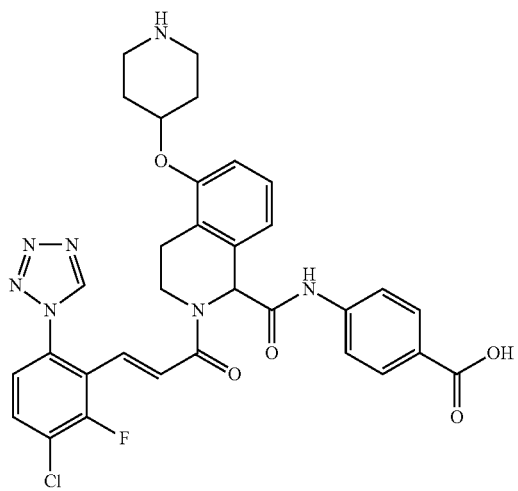 [SMILES: O=C(O)c1ccc(NC(=O)C2c3cccc(OC4CCNCC4)c3CCN2C(=O)/C=C/c2c(-n3cnnn3)ccc(Cl)c2F)cc1]

Example 108 (24 mg, 13.9%) was made in a similar manner as Example 104 substituting commercially available tert-butyl 4-(tosyloxy)piperidine-1-carboxylate for tert-butyl 4-(2-bromoethyl)piperidine-1-carboxylate in the alkylation reaction step and Intermediate 6 instead of Intermediate 8 in the Ugi reaction step. $^1$H NMR (400 MHz, DMSO-$d_6$) δ 12.76 (1H, br.s.), 10.85 (1H, s), 9.88 (1H, s), 7.84-8.01 (3H, m), 7.62-7.72 (3H, m), 7.16-7.29 (2H, m), 6.93-7.13 (3H, m), 5.83 (1H, s), 4.68 (1H, d, J=3.30 Hz), 4.04-4.15 (1H, m), 3.68-3.79 (1H, m), 3.18-3.30 (2H, m), 3.13 (2H, br.s.), 2.83-3.02 (2H, m), 2.01-2.15 (2H, m), 1.78-1.92 (2H, m) ppm. MS (ESI) m/z: 646.1 (M+H)$^+$. Analytical HPLC: RT=5.40 min.

Example 109

(E)-tert-Butyl 4-(2-(3-(3-chloro-2-fluoro-6-(1H-tetrazol-1-yl)phenyl)acryloyl)-5-(piperidin-4-yloxy)-1,2,3,4-tetrahydroisoquinoline-1-carboxamido)benzoate, TFA salt

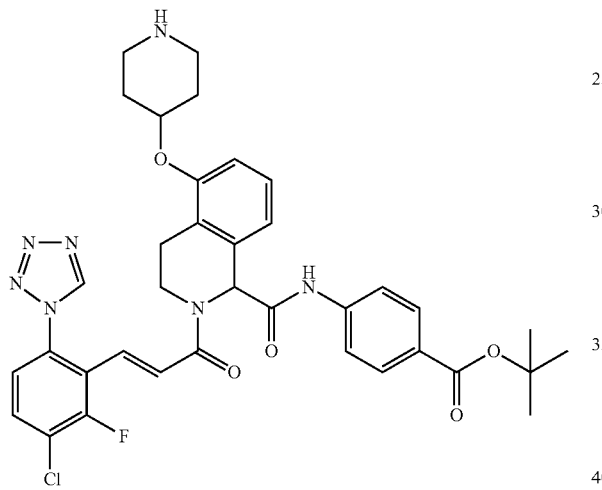

Example 109 (11 mg, 6%) was made as an intermediate in the preparation of Example 108. $^1$H NMR (400 MHz, DMSO-$d_6$) δ 10.86 (1H, s), 9.88 (1H, s), 7.93-8.01 (1H, m), 7.80-7.90 (2H, m), 7.61-7.73 (3H, m), 7.18-7.27 (2H, m), 7.05-7.12 (1H, m), 6.90-7.04 (2H, m), 5.83 (1H, s), 4.62-4.72 (1H, m), 4.03-4.16 (1H, m), 3.68-3.81 (1H, m), 3.18-3.30 (2H, m), 3.05-3.17 (2H, m), 2.83-3.01 (2H, m), 2.02-2.15 (2H, m), 1.78-1.94 (2H, m), 1.52 (9H, s) ppm. MS (ESI) m/z: 702.2 (M+H)$^+$. Analytical HPLC: RT=7.43 min.

The following Examples in Table 8 were prepared according to methods analogous to that described for Example 53 substituting 4-(methylcarbomoyl)phenylboronic acid or N-(2-(dimethylamino)ethyl)-4-(4,4,5,5-tetramethyl-1,3,2-dioxaborolan-2-yl)benzamide in the Suzuki reaction step and Intermediate 2, 4, 5, 12, 13, 14, 15, 16 or commercially available cinnamic acid and previously described isonitriles in the Ugi reaction. Representative chiral compounds were obtained by chiral resolution of the appropriate advanced intermediate followed by deprotection and purification.

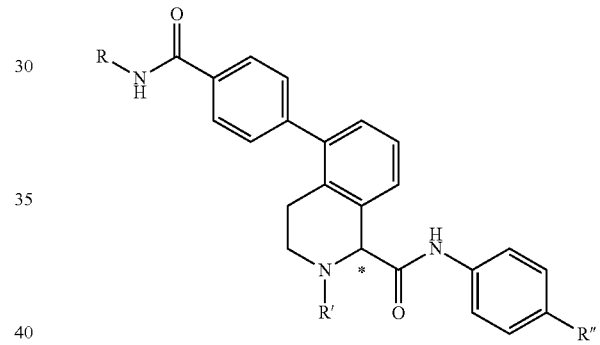

TABLE 8

| Example # | Stereochemistry | R | R' | R" | (M + H)$^+$ | RT |
|---|---|---|---|---|---|---|
| 110 | Racemic | —CH$_3$ | ![structure] | CO$_2$H | 662.2 | 7.75 |
| 111 | Racemic | —CH$_3$ | ![structure] | CO$_2$H | 654.2 | 8.30 |

TABLE 8-continued
| Example # | Stereochemistry | R | R' | R" | (M + H)+ | RT |
|---|---|---|---|---|---|---|
| 112 | Racemic | —CH₃ | 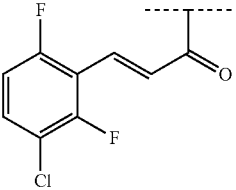 | CO₂H | 630.2 | 8.89 |
| 113 | Racemic | —CH₃ | 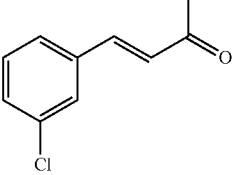 | CO₂H | 594.1 | 8.76 |
| 114 | Racemic | —CH₂CH₂N(CH₃)₂ | 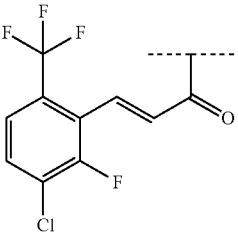 | CO₂H | 737.5 | 6.83 |
| 115 | Racemic | —CH₂CH₂N(CH₃)₂ | 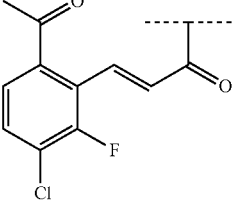 | CO₂Et | 739.0 | 6.68 |
| 116 | R-Enantiomer[a] | —CH₂CH₂N(CH₃)₂ | 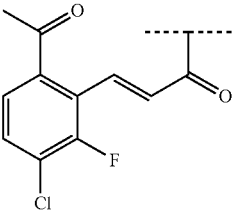 | CO₂Et | 739.3 | 7.01 |
| 117 | S-Enantiomer[a] | —CH₂CH₂N(CH₃)₂ | 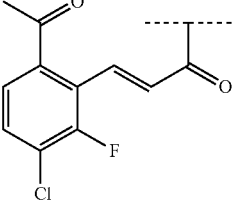 | CO₂Et | 739.3 | 7.01 |
| 118 | Racemic | —CH₂CH₂N(CH₃)₂ | 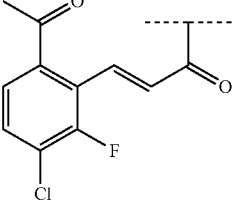 | CN | 692.5 | 6.17 |

TABLE 8-continued

| Example # | Stereochemistry | R | R' | R" | (M + H)+ | RT |
|---|---|---|---|---|---|---|
| 119 | Racemic | —H | (3-acetyl-6-chloro-2-fluorophenyl vinyl ketone) | CO₂H | 640 | 7.62 |
| 120 | R-Enantiomer[b] | —H | (3-acetyl-6-chloro-2-fluorophenyl vinyl ketone) | CO₂H | 640.3 | 7.82 |
| 121 | S-Enantiomer[b] | —H | (3-acetyl-6-chloro-2-fluorophenyl vinyl ketone) | CO₂H | 640.3 | 7.82 |
| 122 | Racemic | —CH₂CH₂N(CH₃)₂ | (2-(1H-tetrazol-1-yl)-5-chlorophenyl vinyl ketone) | CO₂H | 719.0 | 5.08 |

[a]Chiralcel OJ-H SFC, 250 × 21 mm ID, 5 μm, using 30% (4:1) IPA-MeOH-0.1% Formic Acid-0.1% DEA/70% CO₂ at 60 mL/min, 150 bar BP, 35° C.

[b]Chiralcel OJ-H SFC, 250 × 21 mm ID, 5 μm, using 30%-40% EtOH-0.1% DEA/70%-60% CO₂ at 65 mL/min, 100 bar BP, 35° C.

Example 123

(E)-4-(2-(3-(3-Chloro-2-fluoro-6-(1H-tetrazol-1-yl)phenyl)acryloyl)-4,4-dimethyl-5-(4-nitrophenyl)-1,2,3,4-tetrahydroisoquinoline-1-carboxamido)benzoic acid

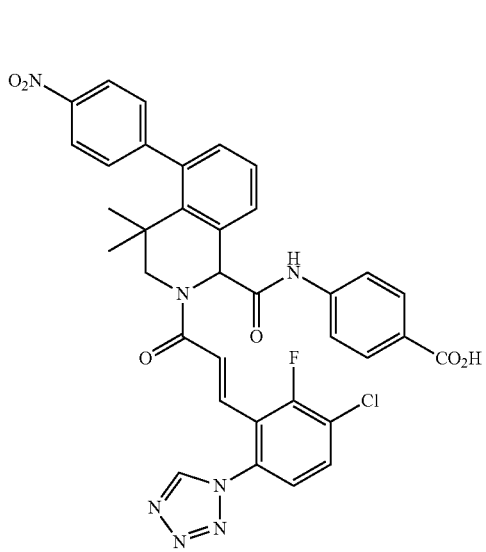 [SMILES: CC1(C)CN(C(=O)/C=C/c2c(-n3cnnn3)ccc(Cl)c2F)C(C(=O)Nc2ccc(C(=O)O)cc2)c2cccc(-c3ccc([N+](=O)[O-])cc3)c21]

123A: tert-Butyl 4,4-dimethyl-5-(4-nitrophenyl)-3,4-dihydroisoquinoline-2(1H)-carboxylate: To tert-butyl 5-bromo-4,4-dimethyl-3,4-dihydroisoquinoline-2(1H)-carboxylate (180 mg, 0.5 mmol) in dioxane (1.8 mL) and EtOH (0.36 mL) was added 2M solution of $Na_2CO_3$ (280 mg, 2.6 mmol), 4-nitrophenyl boronic acid (330 mg, 2.0 mmol). The reaction mixture was degassed, then tetrakistriphenylphosphine palladium (0) (121 mg, 0.1 mmol) was added and the reaction was heated overnight at 90° C. The reaction mixture was poured into $H_2O$ and filtered through celite. The filtrate was extracted with EtOAc twice, then the combined organic layers were washed with $H_2O$, brine, dried ($Na_2SO_4$), filtered and concentrated. The crude was purified by silica gel chromatography to afford 0.120 g of 123A. MS (ESI) m/z: 383 $(M+H)^+$.

123B: 4,4-Dimethyl-5-(4-nitrophenyl)-1,2,3,4-tetrahydroisoquinoline: To a solution of 123A (0.12 g, 0.3 mmol) in DCM (2 mL), HCl in dioxane (1 mL) was added at 0° C. drop-wise. After 24 h, the reaction was concentrated and washed with petroleum ether to afford 0.090 g of 123B as a white solid. MS (ESI) m/z: 283 $(M+H)^+$.

123C: 4,4-Dimethyl-5-(4-nitrophenyl)-3,4-dihydroisoquinoline: To a solution of 123B (0.05 g, 0.1 mmol) in DCM (2 mL) was added $MnO_2$ (800 mg, 1.8 mmol). After 18 h, the reaction mixture was filtered through celite and the filtrate was washed with $H_2O$, brine, dried ($Na_2SO_4$), concentrated to get 50 mg of 123C. The crude was taken to next step without further purification. MS (ESI) m/z: 281 $(M+H)^+$.

Example 123 was prepared by the Ugi reaction as in Example 8 starting from 123C and Intermediates 3A and 6 followed by TFA deprotection to afford 0.05 g of the desired product as a white solid. $^1$H NMR (400 MHz, DMSO-$d_6$) δ 12.73 (1H, s), 11.03 (1H, s), 9.85 (1H, s), 8.30 (2H, d, J=8.0 Hz), 7.91-7.97 (3H, m), 7.76 (2H, d, J=8.0 Hz), 7.57-7.67 (4H, m), 7.33 (1H, t, J=6.0 Hz), 7.05-7.10 (2H, m), 6.96 (1H, d, J=8.0 Hz), 5.94 (1H, s), 3.83 (1H, d, J=12 Hz), 3.53 (1H, d, J=12 Hz), 1.06 (3H, s), 1.0 (3H, s) ppm. MS (ESI) m/z: 696.2 $(M+H)^+$. Analytical HPLC: RT=18.9 min

Example 124

(E)-4-(5-(4-Carbamoylphenyl)-2-(3-(3-chloro-2-fluoro-6-(1H-tetrazol-1-yl)phenyl)acryloyl)-4,4-dimethyl-1,2,3,4-tetrahydroisoquinoline-1-carboxamido)benzoic acid

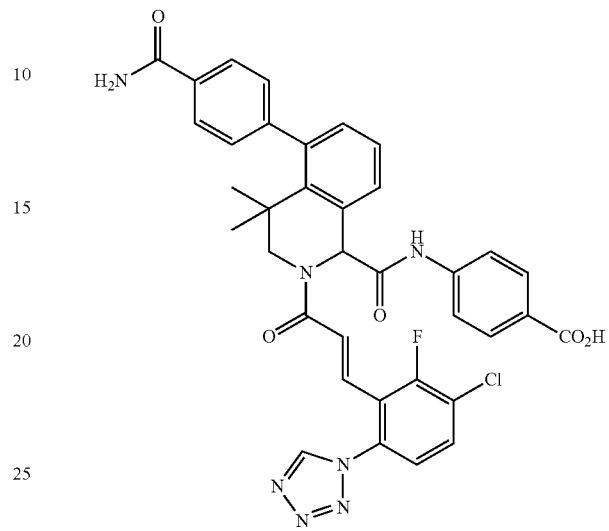

Example 124 was prepared in a similar manner as Example 123 substituting 4-carbamoylphenylboronic acid for 4-nitrophenylboronic acid. $^1$H NMR (400 MHz, DMSO-$d_6$) δ 11.01 (1H, s), 9.86 (1H, s), 8.05 (1H, bs), 7.91-7.97 (5H, m), 7.70 (2H, d, J=8.0 Hz), 7.63-7.66 (3H, m), 7.53-7.60 (3H, m), 7.37-7.41 (3H, m), 7.28 (1H, t, J=7.6 Hz), 7.21 (1H, s), 7.05-7.10 (3H, m), 6.95 (2H, bs), 5.93 (1H, s), 4.49 (1H, d, J=4.0 Hz), 3.82 (1H, d, J=13.2 Hz), 3.51 (1H, d, J=13.6 Hz), 1.51 (3H, s), 1.06 (3H, s), 0.98 (3H, s). MS (ESI) m/z: 694.2 $(M+H)^+$. Analytical HPLC: RT=14.3 min.

Example 125

(E)-4-(2-(3-(3-Chloro-2-fluoro-6-(1H-tetrazol-1-yl)phenyl)acryloyl)-4,4-dimethyl-5-(4-(methyl carbamoyl)phenyl)-1,2,3,4-tetrahydroisoquinoline-1-carboxamido)benzoic acid

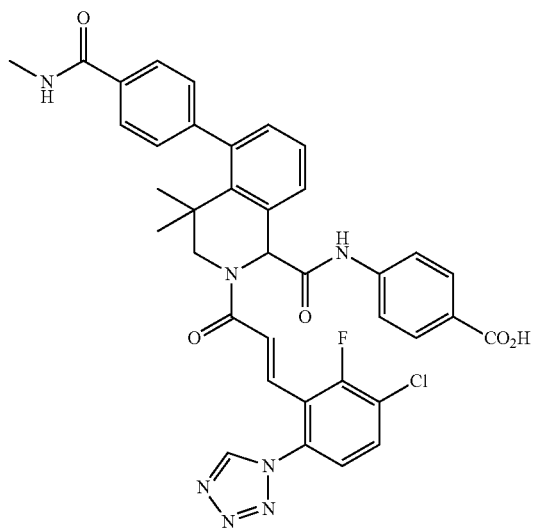 [SMILES: CNC(=O)c1ccc(-c2cccc3c2C(C)(C)CN(C(=O)/C=C/c2c(-n4cnnn4)ccc(Cl)c2F)C3C(=O)Nc2ccc(C(=O)O)cc2)cc1]

Example 125 was prepared in a similar manner as Example 123 substituting 4-(methylcarbamoyl)phenylboronic acid for 4-nitrophenylboronic acid. $^1$H NMR (400 MHz, DMSO-$d_6$) δ 10.87 (1H, s), 9.85 (1H, s), 8.51 (1H, m), 7.87-7.96 (5H, m), 7.63-7.67 (3H, m), 7.54 (1H, d, J=8.0 Hz), 7.39 (2H, d, J=4.0 Hz), 7.28 (1H, t, J=8.0 Hz), 6.92-7.10 (3H, m), 5.94 (1H, s), 3.84 (1H, d, J=16 Hz), 3.50 (1H, d, J=16 Hz), 2.83 (3H, s), 1.06 (3H, s), 0.95 (3H, s). MS (ESI) m/z: 708 (M+H)$^+$. Analytical HPLC: RT=14.7 min.

Example 126

(E)-4-(2-(3-(3-chloro-2-fluoro-6-(1H-tetrazol-1-yl) phenyl)acryloyl)-3,3-dimethyl-5-(4-(methyl carbamoyl)phenyl)-1,2,3,4-tetrahydroisoquinoline-1-carboxamido)benzoic acid

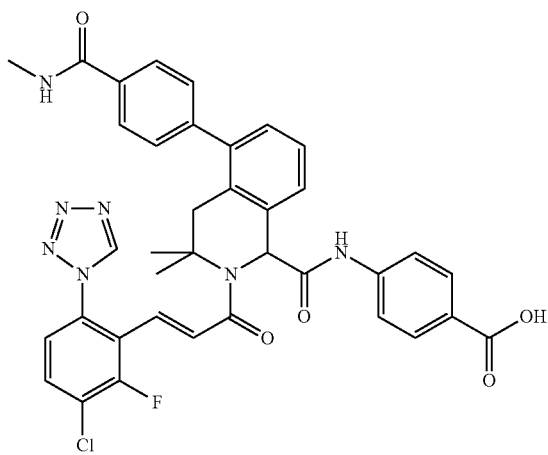 [SMILES: CNC(=O)c1ccc(-c2cccc3c2CC(C)(C)N(C(=O)/C=C/c2c(-n4cnnn4)ccc(Cl)c2F)C3C(=O)Nc2ccc(C(=O)O)cc2)cc1]

126A: 3-(2-Bromophenyl)-2,2-dimethylpropanenitrile: To a solution of isobutyronitrile (3.58 g, 52 mmol) in dry THF (30 mL) was added LiHMDS (1.0 M in THF) (80 mL, 80 mmol) at 0° C., stirred for 20 min., and to this solution was added 1-bromo-2-(bromomethyl)benzene (10 g, 40 mmol) in dry THF (70 mL). After 3 h at rt, the reaction mixture was quenched with saturated NH$_4$Cl solution, extracted with EtOAc (2×), the combined organics were washed with H$_2$O, brine, dried over Na$_2$SO$_4$, filtered and concentrated to give 9.5 g (99%) of 126A as red wine liquid. $^1$H NMR (400 MHz, CDCl$_3$) δ 7.57-7.60 (2H, m), 7.30-7.34 (1H, m), 7.12-7.17 (1H, m), 3.08 (2H, s), 1.4 (6H, s) ppm.

126B: 3-(2-Bromophenyl)-2,2-dimethylpropanoic acid: To a solution of 126A (19 g, 79.83 mmol) in ethylene glycol (100 mL) was added potassium hydroxide pellets (20 g, 359.24 mmol) and the reaction was heated at 150° C. for 48 h. The reaction mixture was cooled, diluted with H$_2$O and the aqueous layer was washed with EtOAc (2×). The aqueous layer was acidified with 1.5 N HCl, extracted with EtOAc (2×), the combined organics were washed with H$_2$O, brine, dried over Na$_2$SO$_4$, filtered and concentrated. The crude was purified by silica gel column chromatography to give 18.0 g, (87.8%) of 126B as a white solid. MS (ESI) m/z: 257 (M+H)$^+$.

126C: 1-Bromo-2-(2-isocyanato-2-methylpropyl)benzene: To a solution of 126B (9.0 g, 35.0 mmol) in toluene (80 mL) at 0° C., was added TEA (4.7 mL, 33.2 mmol) and, slowly, diphenylphosphoryl azide (9.17 g, 33.2 mmol). After 45 min. at 0° C., the reaction was heated to reflux for 4 h. The reaction mixture was cooled to rt, quenched with H$_2$O, extracted with EtOAc (2×), the combined organics were washed with saturated NaHCO$_3$ solution, H$_2$O, brine, dried over Na$_2$SO$_4$, filtered and concentrated to give 8.0 g of 126C as colorless liquid. $^1$H NMR (400 MHz, CDCl$_3$) δ 7.37-7.59 (2H, m), 7.30 (1H, m), 7.14 (1H, m), 3.03 (2H, s), 1.41 (6H, s) ppm.

126D: Methyl 1-(2-bromophenyl)-2-methylpropan-2-yl-carbamate: To a stirred solution of 126C (8.0 g, 31.5 mmol) in dry THF (80 mL) at 0° C., was added MeOH (5.0 mL, 157.5 mmol) and, slowly, NaH (60% in oil) (3.8 g, 94.5 mmol). After 3 h at rt, the reaction was quenched with ice cold H$_2$O and extracted with EtOAc twice. The combined organics were washed with H$_2$O, brine, dried over Na$_2$SO$_4$, filtered and concentrated to give 126D (8.5 g, 94.5%) as white solid. MS (ESI) m/z: 286.0 (M+H)$^+$.

126E: Methyl 5-bromo-3,3-dimethyl-3,4-dihydroisoquinoline-2(1H)-carboxylate: To a solution of 126D (5.0 g, 17.5 mmol) in AcOH/H$_2$SO$_4$ (3:1; 15+5 mL) at 0° C. was slowly added paraformaldehyde (0.524 g, 17.5 mmol). After 48 h at rt, the reaction mixture was quenched with H$_2$O, extracted with EtOAc (2×), the combined organics were washed with saturated NaHCO$_3$ solution, H$_2$O, brine, dried over Na$_2$SO$_4$, filtered and concentrated to give 4.6 g of 126E as a brown liquid. MS (ESI) m/z: 300.0 (M+H)$^+$.

126F: 5-Bromo-3,3-dimethyl-1,2,3,4-tetrahydroisoquinoline: To a solution of 126E (4.6 g) in ethylene glycol (50 mL) was added 50% aqueous KOH solution (23 mL) and the reaction was heated at 150° C. for 3 days. The reaction mixture was cooled, diluted with H$_2$O, extracted with EtOAc twice. The combined organics were extracted with 1.5 N HCl solution, the aqueous layer was basified with 10% NaOH solution, extracted with EtOAc twice, the combined organics were washed with H$_2$O, brine, dried over Na$_2$SO$_4$, filtered and concentrated to give 126F (1.5 g, 39.4%) as a brown liquid. MS (ESI) m/z: 242.2 (M+H)$^+$.

126G: tert-Butyl 5-bromo-3,3-dimethyl-3,4-dihydroisoquinoline-2(1H)-carboxylate: To a solution of 126F (3.0 g, 12.5 mmol) in dry THF (30 mL) at 0° C. was added TEA (4.42 mL, 31.25 mmol) followed by drop-wise addition of Boc$_2$O (3.5 g, 16.25 mmol). After 18 h at rt, the reaction mixture was diluted with H$_2$O, extracted with EtOAc (2×), the combined organics were washed with brine, dried over Na$_2$SO$_4$, filtered and concentrated. The crude was purified by silica gel column chromatography to give 126G (3.2 g, 75.3%) as a white solid. MS (ESI) m/z: 342 (M+H)$^+$.

Example 126: 126G subjected to a Suzuki reaction, deprotected and oxidized to form the imine which was used to prepare Example 126 in a similar manner as Example 126. $^1$H NMR (400 MHz, DMSO-$d_6$) δ 12.8 (1H, s), 10.53 (1H, bs), 9.86 (1H, s), 8.49-8.51 (1H, q), 7.83-7.96 (6H, m), 7.64-7.71 (3H, m), 7.30-7.42 (4H, m), 7.12 (1H, d, J=15.6 Hz), 6.87 (1H, bs), 5.90 (1H, bs), 3.60 (2H, bs), 2.80 (3H, d, J=4.4 Hz), 1.68 (3H, s), 1.07 (3H, s) ppm. MS ESI m/z: 708.0 (M+H)$^+$. Analytical HPLC: RT=9.11 min.

The following Examples in Table 9 were prepared according to methods analogous to that described for Example 53 substituting N-(2-(dimethylamino)ethyl)-4-(4,4,5,5-tetramethyl-1,3,2-dioxaborolan-2-yl)benzamide in the Suzuki reaction step and Intermediate 5, as well as, Intermediate 6, Intermediate 7, Intermediate 11 or commercially available isonitrile in the Ugi reaction. Representative chiral compounds were obtained by chiral resolution of the appropriate late stage intermediate followed by purification.

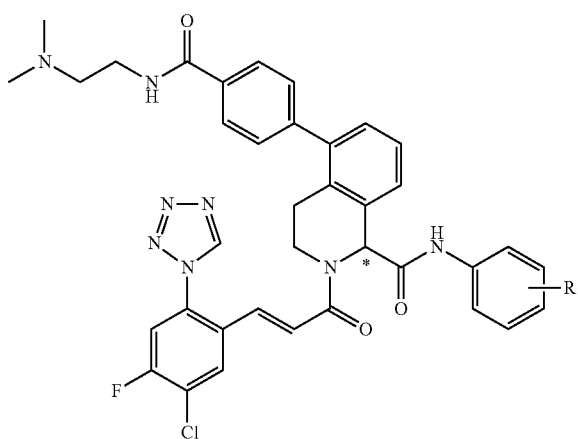

TABLE 9

| Example # | Stereochemistry | R | M + H | RT |
|---|---|---|---|---|
| 127 | Senantiomer[a] | 4-COOH | 737.2 | 5.79 |
| 128 | Racemic | 4-CN | 718.1 | 6.21 |
| 129 | Racemic | 4-F | 711.2 | 6.60 |
| 130 | Racemic | 4-NHCOOMe | 766.1 | 6.06 |

[a]Chiralpak AD-H SFC, 250 × 21 mm ID, 5 µm, using 55% 4:1 Isopropanol-MeOH-0.1% Formic Acid-0.1% DEA at 60 mL/min, 140 Bar, 40° C.

Example 131

(E)-N-(4-carbamoylphenyl)-2-(3-(3-chloro-2-fluoro-6-(1H-tetrazol-1-yl)phenyl)acryloyl)-5-(pyridin-2-yloxy)-1,2,3,4-tetrahydroisoquinoline-1-carboxamide

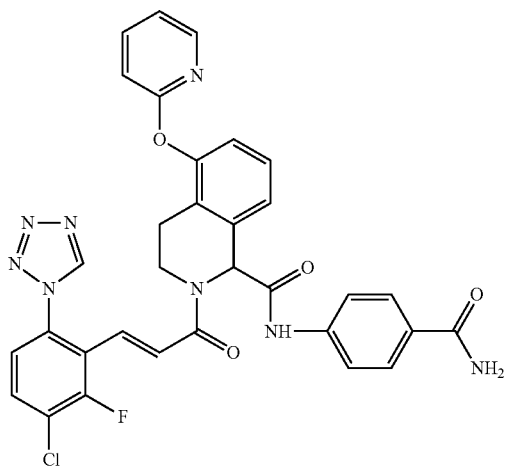 [SMILES: NC(=O)c1ccc(NC(=O)C2c3cccc(Oc4ccccn4)c3CCN2C(=O)/C=C/c2c(-n3cnnn3)ccc(Cl)c2F)cc1]

131A: 2-tert-Butyl 1-methyl 5-(pyridin-2-yloxy)-3,4-dihydroisoquinoline-1,2(1H)-dicarboxylate: To 2-tert-butyl 1-methyl 5-bromo-3,4-dihydroisoquinoline-1,2(1H)-dicarboxylate (0.173 g, 0.467 mmol) was added 1,10-phenanthroline (8.42 mg, 0.047 mmol), pyridin-2-ol (0.071 g, 0.748 mmol), $K_2CO_3$ (0.161 g, 1.168 and DMSO (2.5 mL). The mixture was degassed and copper (1) iodide (0.018 g, 0.093 mmol) was added and the reaction was heated to 130° C. The reaction was cooled and partitioned with $H_2O$ (10 mL)/dilute $NH_4OH$ and EtOAc (20 mL). The organic layer was washed with brine (10 mL) and dried ($MgSO_4$). Purified by silica gel chromatography and only recovered 10 mg 131A. MS (ESI) m/z: 385 (M+H)⁺.

131B: tert-Butyl 1-(4-carbamoylphenylcarbamoyl)-5-(pyridin-2-yloxy)-3,4-dihydroisoquinoline-2(1H)-carboxylate: To 131A (35 mg, 0.091 mmol) in THF (2 mL)/$H_2O$ (2 mL) was added LiOH (19.10 mg, 0.455 mmol). After 3 h, the reaction was concentrated and partitioned with dilute HCl (10 mL) and EtOAc (30 mL). The organic layer was washed with brine (10 mL) and dried ($MgSO_4$). The crude acid was dissolved in DMF (1 mL) and 4-aminobenzamide (12.40 mg, 0.091 mmol), BOP (40 mg, 0.091 mmol) and DIEA (48 µL, 0.273 mmol) were added. After 24 h, the reaction was partitioned with dilute HCl (10 mL) and EtOAc (30 mL). The organic layer was washed with brine (10 mL) and dried ($MgSO_4$) to afford 34 mgs of 131B as clear oil. MS (ESI) m/z: 489.0 (M+H)⁺.

Example 131

Crude 131B (44 mg, 0.090 mmol) was deprotected with 30% TFA/DCM (2 mL). After 24 h, the reaction was concentrated and combined with Intermediate 3 (32.9 mg, 0.090 mmol) and DIEA (47.2 µL, 0.270 mmol) in DMF (2 mL). After 24 h, the reaction was purified by reverse phase HPLC and after freeze-drying 6.3 mg of Example 131 as a white solid was collected. ¹H NMR (400 MHz, MeOD) δ 10.34-10.47 (1H, m), 9.51 (1H, s), 8.12 (1H, d, J=1.77 Hz), 7.80-7.93 (2H, m), 7.72-7.80 (1H, m), 7.66 (2H, dd, J=8.72, 1.39 Hz), 7.40-7.50 (2H, m), 7.35 (1H, d, J=7.83 Hz), 6.82-7.21 (6H, m), 5.92 (1H, s), 3.99-4.13 (1H, m), 3.66-3.76 (1H, m), 2.98-3.09 (1H, m), 2.79-2.92 (1H, m) ppm. MS (ESI) m/z: 639 (M+H)⁺. Analytical HPLC: RT=8.18 min.

Example 132

(E)-4-(2-(3-(3-chloro-2-fluoro-6-(1H-tetrazol-1-yl)phenyl)acryloyl)-5-(2-(dimethylamino)ethoxy)-1,2,3,4-tetrahydroisoquinoline-1-carboxamido)benzoic acid, TFA salt

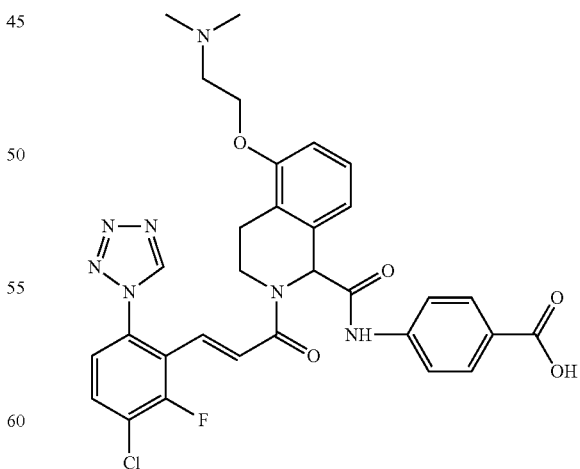

132A: To a suspension of isoquinolin-5-ol (1.50 g, 10.33 mmol), 2-(dimethylamino)EtOH (1.105 g, 12.40 mmol), and Triphenylphosphine, polymer-supported (3 mmol/gram; 2% divinylbenzene) (4.0 g, 15.31 mmol) in THF (25 mL) at 0° C.

was added Di-tert-Butylazodicarboxylate (2.86 g, 12.40 mmol). The mixture was allowed to warm to rt and stirred overnight. The reaction mixture was filtered and concentrated. Carried forward as is because product is too polar to purify.

132B: The residue was dissolved in EtOH (50 mL), PtO$_2$ (0.023 g, 0.103 mmol) added, and stirred under a hydrogen atmosphere (55 psi) overnight. The reaction mixture was filtered through a plug of celite and filtrate concentrated. MnO$_2$ (16.17 g, 186 mmol) was added to a stirring solution of the amine dissolved in DCM (50 mL). The excess MnO$_2$ was filtered through a plug of celite and the filtrate concentrated. A major impurity observed by LC/MS. Nevertheless, the crude product was carried forward as is. MS (ESI) m/z: 219.2 (M+H)$^+$.

132C: tert-butyl 4-isocyanobenzoate (0.144 g, 0.708 mmol) in EtOH (1 mL) was added to a microwave vial containing 132B (0.309 g, 0.708 mmol) and (Z)-3-(3-chloro-2-fluoro-6-(1H-tetrazol-1-yl)phenyl)acrylic acid (0.190 g, 0.708 mmol) in EtOH (3 mL) and stirred at 60° C. overnight. The reaction mixture was concentrated and then treated with 50% TFA/DCM. After 3h, the reaction mixture was concentrated and purified by reverse phase chromatography. $^1$H NMR (500 MHz, DMSO-d$_6$) δ 10.83 (1H, s), 9.85-9.92 (1H, m), 7.83-8.05 (3H, m), 7.63-7.73 (3H, m), 7.23-7.33 (2H, m), 6.89-7.10 (2H, m), 5.85 (1H, s), 4.30-4.38 (2H, m), 4.04-4.14 (1H, m), 3.66-3.76 (1H, m), 3.53-3.64 (2H, m), 2.87-3.01 (7H, m) ppm. MS (ESI) m/z: 634.3 (M+H)$^+$. Analytical HPLC: RT=5.64 min.

Example 133

Racemate (E)-4-(2-(3-(5-Chloro-2-(1H-tetrazol-1-yl)phenyl) acryloyl)-5-(2-(1-(methoxycarbonyl)piperidin-4-yl) ethoxy)-1,2,3,4-tetrahydroisoquinoline-1-carboxamido)benzoic acid

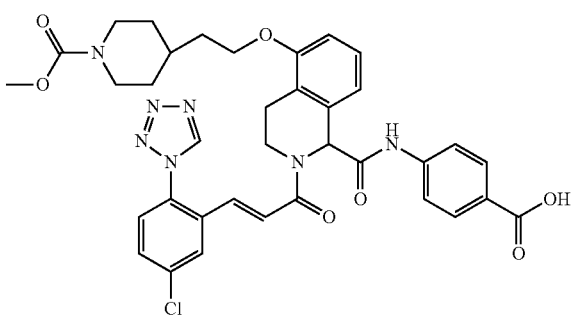 [SMILES: COC(=O)N1CCC(CCOc2cccc3c2CCN(C(=O)/C=C/c2cc(Cl)ccc2-n2cnnn2)C3C(=O)Nc2ccc(C(=O)O)cc2)CC1]

133A: 5-(2-(Piperidin-4-yl)ethoxy)isoquinoline: To tert-butyl 4-(2-hydroxyethyl)piperidine-1-carboxylate (2.3 g, 10.0 mmol) and TEA (2.79 mL, 20.0 mmol) in DCM (25 mL) was added methanesulfonyl chloride (0.93 mL, 12.0 mmol) dropwise at 0° C. After 18h, the reaction was diluted with DCM, washed with H$_2$O and brine, dried over MgSO$_4$, concentrated to afford crude mesylate as amber oil. The mesylate, isoquinolin-5-ol (1.45 g, 10.0 mmol), and Cs$_2$CO$_3$ (6.5 g, 20.0 mmol) were added to DMF (30 mL) and heated at 90° C. for 18 h. The reaction mixture was cooled to rt and inorganics filtered off. The filtrate was diluted with EtOAc (150 mL), washed with H$_2$O (2×), then brine (2×), separated, dried over Na$_2$SO$_4$, filtered, and concentrated. Purification by silica gel chromatography afforded a brown oil that was treated with 50% TFA/DCM for 2h. After concentration, the oil was dissolved in EtOAc and neutralized with saturated NaHCO$_3$ solution. The organic layer was separated. The aqueous layer was extracted with additional EtOAc (2×). The combined organic extract was dried over Na$_2$SO$_4$, filtered, and concentrated to afford 133A. MS (ESI) m/z: 257.0 (M+H)$^+$.

133B: Methyl 4-(2-(3,4-dihydroisoquinolin-5-yloxy) ethyl)piperidine-1-carboxylate: Methyl carbonochloridate (0.184 g, 1.95 mmol) was added to a solution of 133A (0.500 g, 1.95 mmol) and DIEA (0.34 mL, 1.95 mmol) in DCM (30 mL) at 0° C. for 2 h. The reaction mixture was diluted further with DCM (30 mL), washed with H$_2$O, brine, dried over Na$_2$SO$_4$, filtered, and concentrated. The crude product was purified by silica gel chromatography to give brown oil. This material was reduced and then oxidized as described in Example 8 to afford 133B.

Example 133: 133B (0.150 g, 0.47 mmol), Intermediate 3A (0.119 g, 0.47 mmol) and Intermediate 6 (0.096 g, 0.47 mmol) were combined in an Ugi reaction as described in Example 8 followed by TFA deprotection. Purification by reverse phase HPLC gave Example 133 (67 mg, 18.8%) as a light yellow solid after lyophilization. $^1$H NMR (500 MHz, DMSO-d$_6$) δ 12.71 (1H, br.s.), 10.80 (1H, s), 9.86 (1H, s), 8.44 (1H, d, J=2.20 Hz), 7.87 (2H, d, J=8.80 Hz), 7.75-7.78 (1H, m), 7.70-7.74 (1H, m), 7.68 (2H, d, J=8.80 Hz), 7.58 (2H, d, J=15.13 Hz), 7.14-7.23 (2H, m), 6.90-6.99 (2H, m), 5.82 (1H, s), 4.18-4.31 (1H, m), 3.89-4.10 (5H, m), 3.58 (3H, s), 2.67-3.02 (4H, m), 1.67-1.78 (5H, m), 1.03-1.17 (2H, m) ppm. MS (ESI) m/z: 714.0 (M+H)$^+$. Analytical HPLC: RT=9.73 min.

Example 134

Racemate (E)-4-(2-(3-(6-Acetyl-3-chloro-2-fluorophenyl)acryloyl)-5-(2-(1-(methoxycarbonyl)piperidin-4-yl) ethoxy)-1,2,3,4-tetrahydroisoquinoline-1-carboxamido)benzoic acid, TFA salt

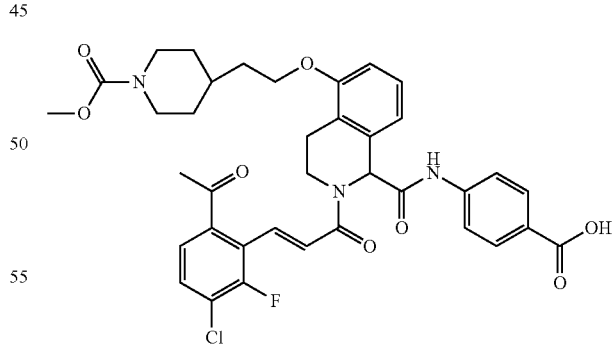

Example 134 (36 mg, 10.2%) was made in a similar manner as Example 133 substituting Intermediate 12 instead of Intermediate 3A in the Ugi reaction step. $^1$H NMR (500 MHz, DMSO-d$_6$) δ ppm 12.72 (1H, br.s.), 10.87 (1H, s), 7.87-7.92 (2H, m), 7.71-7.78 (4H, m), 7.56 (1H, d, J=15.96 Hz), 7.20-7.24 (2H, m), 7.09-7.15 (1H, m), 6.90-6.96 (1H, m), 5.89 (1H, s), 4.13-4.22 (1H, m), 4.04 (2H, t, J=5.36 Hz), 3.92-3.99 (2H, m), 3.81-3.91 (1H, m), 3.58 (3H, s), 2.69-3.01 (4H, m), 2.59

(3H, s), 1.67-1.77 (5H, m), 1.03-1.16 (2H, m) ppm. MS (ESI) m/z: 706.0 (M+H)+. Analytical HPLC: RT=10.48 min.

Example 135

(E)-4-(5-(4-Carbamoylphenyl)-2-(3-(3-chloro-2-fluoro-6-(1H-tetrazol-1-yl)phenyl)acryloyl)-3,3-dimethyl-1,2,3,4-tetrahydroisoquinoline-1-carboxamido)benzoic acid

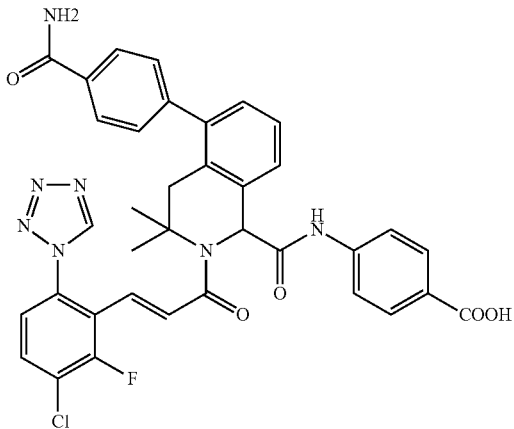 [SMILES: CC1(C)Cc2c(-c3ccc(C(N)=O)cc3)cccc2C(C(=O)Nc2ccc(C(=O)O)cc2)N1C(=O)/C=C/c1c(-n2cnnn2)ccc(Cl)c1F]

Example 135 was prepared in a similar manner as Example 126 substituting 4-carbamoylphenylboronic acid for 4-(methylcarbamoyl)phenylboronic acid. $^1$H NMR (400 MHz, DMSO-$d_6$) δ 12.80 (1H, s), 10.59 (1H, s), 9.86 (1H, s), 8.09 (1H, s), 7.83-7.97 (7H, m), 7.64-7.71 (3H, m), 7.38-7.43 (4H, m), 7.31 (1H, d, J=7.2 Hz), 7.10 (1H, t, J=15.0 Hz), 5.84 (1H, bs), 1.68 (3H, s), 1.07 (3H, s) ppm. MS (ESI) m/z: 694.2 (M+H)+. Analytical HPLC: RT=10.18 min.

Example 136

(E)-4-(5-(1-Acetylpiperidin-4-yl)-2-(3-(3-chloro-2-fluoro-6-(1H-tetrazol-1-yl)phenyl)acryloyl)-1,2,3,4-tetrahydroisoquinoline-1-carboxamido)benzoic acid

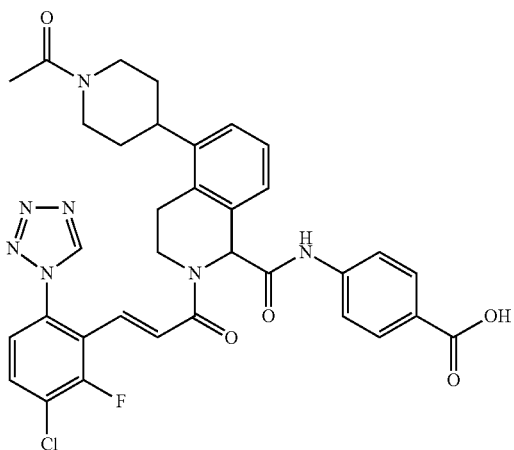 [SMILES: CC(=O)N1CCC(c2cccc3c2CCN(C(=O)/C=C/c2c(-n4cnnn4)ccc(Cl)c2F)C3C(=O)Nc2ccc(C(=O)O)cc2)CC1]

136A: Methyl 2-bromophenethylcarbamate: Methyl chloroformate (1.93 mL, 25 mmol) was added to a stirring solution of 2-(2-bromophenyl)ethanamine (5.0 g, 25 mmol) and pyridine (3.03 mL, 37.5 mmol) in DCM (75 mL) at 0° C. After 1 h, the reaction was quenched with 1.0M HCl solution. The organic phase was washed with additional 1.0 M HCl solution (2×75 mL), $H_2O$, brine, dried over $Na_2SO_4$, filtered, and concentrated. MS (ESI) m/z: 258.0 (M+H)+.

136B: 5-Bromo-2-(methoxycarbonyl)-1,2,3,4-tetrahydroisoquinoline-1-carboxylic acid: Glyoxylic acid (2.035 g, 27.5 mmol) was added to a solution of 136A in AcOH/$H_2SO_4$ (40 mL; 3:1) at 0° C. The reaction mixture was allowed to come to rt and after 20 min., the mixture was poured into ice $H_2O$ and extracted with DCM (3×100 mL). The DCM layer was washed with 2 N NaOH and discarded. The NaOH layer was cooled to 0° C., acidified with 1.0 N HCl aqueous solution, and extracted DCM (2×100 mL) and separately with EtOAc (50 mL). Each organic layer was washed with brine, dried over $MgSO_4$, and combined to give clear, viscous oil (3.4 g). MS (ESI) m/z: 314.0 (M+H)+.

136C: 5-Bromo-2-(tert-butoxycarbonyl)-1,2,3,4-tetrahydroisoquinoline-1-carboxylic acid: NaOH (5.0 M) (4.14 mL, 20.69 mmol) was added to 136B (1.0 g, 3.2 mmol) in dioxane/EtOH (9:1; 10 mL) and irradiated in microwave at 150° C. for 30 min. To the cooled reaction mixture was added di-tert-butyl dicarbonate (1.0 g, 4.8 mmol) in dioxane (3.0 mL) followed by 1.0 N NaOH (3.0 mL). After 2 h, the reaction was diluted with $H_2O$ and extracted with EtOAc (2×25 mL). The aqueous layer was made acidic with 1.0 N HCl solution and extracted with EtOAc (3×25 mL). The combined organic layers were washed with $H_2O$, brine, dried over $Na_2SO_4$, filtered, and concentrated to give a tan solid. MS (ESI) m/z: 356.0 (M+H)+.

136D: 2-tert-Butyl 1-methyl 5-bromo-3,4-dihydroisoquinoline-1,2(1H)-dicarboxylate: To intermediate 136C (2.29 g, 6.43 mmol) in MeOH (25 mL) was slowly added thionyl chloride (0.938 mL, 12.86 mmol). The reaction was heated to 50° C. Additional thionyl chloride was added to cooled reaction to complete the esterification and heating was continued. MS (ESI) m/z: 270-271.9 (M+H)+. The reaction was concentrated and dioxane (100 mL), $NaHCO_3$ (2.70 g, 32.1 mmol), and di-t-butyldicarbonate (1.493 mL, 6.43 mmol) were added. After 24 h, additional reagents were added to complete the reaction. The dioxane was removed and the residue was extracted with EtOAc (3×60 mL). The combined organic layers were washed with brine (20 mL) and dried ($MgSO_4$). Purification by normal phase chromatography afforded 1.57 g (66%) of 136D as a clear oil. MS (ESI) m/z: 393.8 (M+Na)+.

136E: 2-tert-Butyl 1-methyl 5-(pyridin-4-yl)-3,4-dihydroisoquinoline-1,2(1H)-dicarboxylate: To 136D (0.69 g, 1.864 mmol), 4-(tributylstannyl)pyridine (1.029 g, 2.80 mmol), LiCl (0.790 g, 18.64 mmol) was added toluene (10 mL) and the mixture was degassed with $N_2$. Dichlorobis(triphenyl phosphine)palladium(II) (0.131 g, 0.186 mmol) was added and the reaction was heated to 100° C. for 24 h. The reaction was partitioned with 10% KF (20 mL) and EtOAc (30 mL). The organic layer was washed with brine (10 mL) and dried ($MgSO_4$). Purification by normal phase chromatography afforded 0.37 g (53.9%) pale yellow oil. MS (ESI) m/z: 369.0 (M+H)+.

136F: 2-tert-Butyl 1-methyl 5-(piperidin-4-yl)-3,4-dihydroisoquinoline-1,2(1H)-dicarboxylate: To 136E (0.37 g, 1.004 mmol) in EtOH (20 mL) was added $PtO_2$ (40 mg) and the reaction was hydrogenated at 55 psi for 24 h. The reaction was proceeding slowly, so 0.08 mL AcOH was added and the hydrogenation was continued for 24 h. The reaction was filtered and concentrated to afford 0.5 g of 136F as dark oil. MS(ESI) m/z: 375.0 (M+H)+.

136G: 5-(1-Acetylpiperidin-4-yl)-2-(tert-butoxycarbonyl)-1,2,3,4-tetrahydroisoquinoline-1-carboxylic acid: To 136F (0.079 g, 0.211 mmol) was added THF (4 mL), DIEA (0.037 ml, 0.211 mmol), and Ac$_2$O (0.020 ml, 0.211 mmol). After 24h, the reaction was concentrated, the residue was dissolved in 1:1 THF/H$_2$O (5 mL) and LiOH (0.044 g, 1.055 mmol) was added. After 3h, the reaction was acidified with 1N HCl, extracted with EtOAc, and the organic layer was washed with brine and dried (MgSO$_4$) to afford 40 mg of 136G. MS (ESI) m/z: 403.2 (M+H)$^+$.

136H: tert-Butyl 5-(1-acetylpiperidin-4-yl)-1-(4-(tert-butoxycarbonyl)phenyl carbamoyl)-3,4-dihydroisoquinoline-2(1H)-carboxylate: To crude 136G (40 mg, 0.099 mmol) and tert-butyl 4-aminobenzoate (19.20 mg, 0.099 mmol) in DCM (3 mL) and pyridine (0.3 mL), cooled to 0° C., was added POCl$_3$ (9.26 µl, 0.099 mmol). After 3 h, the reaction was poured into saturated NaHCO$_3$ (25 mL) and extracted with EtOAc (3×25 mL), and dried with (MgSO$_4$) to afford 50 mg crude product which was carried onto the next step. MS (ESI) m/z: 578.3 (M+H)$^+$.

Example 136

To 136H (50 mg, 0.087 mmol) was added 3 mL of 30% TFA in DCM. After 1 h, the reaction was concentrated and 1.5 mL DMF, DIEA (76 µl, 0.433 mmol), and Intermediate 3 (31.7 mg, 0.087 mmol) were added. After 24 h, the reaction was purified by reverse phase HPLC to afford 3.8 mg (6.3%) of Example 136. $^1$H NMR (400 MHz, MeOD) δ 9.56 (1H, s), 7.96 (2H, d, J=8.59 Hz), 7.73-7.88 (1H, m), 7.54-7.73 (2H, m), 7.50 (1H, dd, J=8.59, 1.52 Hz), 7.41 (1H, dd, J=6.32, 2.53 Hz), 7.20-7.32 (2H, m), 7.11-7.22 (1H, d, J=15.9 Hz), 7.01-7.10 (1H, m), 5.84 (1H, d, J=2.53 Hz), 4.70 (1H, br.s.), 4.15-4.24 (1H, m), 4.06 (1H, d, J=1.52 Hz), 3.59-3.72 (1H, m), 3.32-3.38 (1H, m), 3.27 (1H, td, J=10.17, 4.93 Hz), 3.08-3.22 (2H, m), 2.79 (1H, d, J=4.55 Hz), 2.18 (3H, s), 1.76-1.94 (2H, m), 1.54-1.80 (2H, m) ppm. MS (ESI) m/z: 672.3 (M+H)$^+$. Analytical HPLC: RT=7.56 min.

Example 137

Racemate (E)-4-(2-(3-(6-acetyl-3-chloro-2-fluorophenyl)acryloyl)-5-(4-(2-(dimethylamino)ethylcarbamoyl)phenyl)-1,2,3,4-tetrahydroisoquinoline-1-carboxamido)benzoic acid, TFA salt

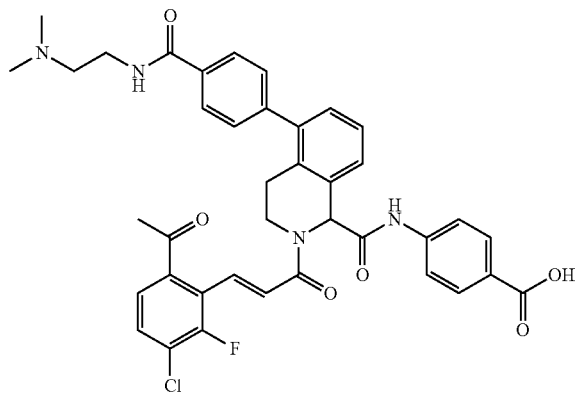

137A: tert-Butyl 5-bromo-1-(4-(tert-butoxycarbonyl)phenylcarbamoyl)-3,4-dihydroisoquinoline-2(1H)-carboxylate: 136C (0.63 g, 1.77 mmol) and tert-butyl 4-aminobenzoate (0.41 g, 2.12 mmol) were dissolved in pyridine (20 mL) at −15° C. POCl$_3$ (0.17 mL, 1.77 mmol) was added drop-wise and after 2 h, the reaction was quenched with 1.0 M HCl solution. The mixture was extracted with EtOAc (3×). The combined organic extract was washed with 1.0 M HCl solution, H$_2$O, brine, dried over Na$_2$SO$_4$, filtered, and concentrated. Purification by silica gel chromatography gave 137A as an off white solid (517 mg, 55%). MS (ESI) m/z: 532.9 (M+H)$^+$.

137B: 4-(5-(4-(2-(Dimethylamino)ethylcarbamoyl)phenyl)-1,2,3,4-tetrahydroisoquinoline-1-carboxamido)benzoic acid, TFA salt: To a microwave vial charged with 2.0 M K$_2$CO$_3$ (5 mL) and dioxane (10 mL)/EtOH (2 mL) were added 4-(2-(dimethylamino)ethylcarbamoyl)phenylboronic acid, HCl salt (0.26 g, 0.94 mmol) and 137A (0.50 g, 0.47 mmol). The mixture was degassed N$_2$ before adding tetrakis(triphenylphosphine)palladium (0) (0.027 g, 0.024 mmol) and irradiated in microwave at 130° C. for 20 min. The reaction mixture was partitioned between EtOAc and H$_2$O. The H$_2$O layer was extracted again with EtOAc. The combined organic layer was washed with saturated NaHCO$_3$ solution, brine, dried over Na$_2$SO$_4$, filtered, and concentrated. The crude material was treated with 50% TFA for 2 h, concentrated, and purified by reverse phase HPLC to afford 137B.

137C: (E)-2,5-dioxopyrrolidin-1-yl 3-(6-acetyl-3-chloro-2-fluorophenyl)acrylate: To a mixture of Intermediate 12 (1.0 g, 4.12 mmol) and 1-hydroxypyrrolidine-2,5-dione (0.498 g, 4.33 mmol) in THF was added DIC (0.674 mL, 4.33 mmol). After 24 h, the white solids were collected by filtration, washed with EtOAc, dried, and used directly in next step. MS (ESI) m/z: 339.9 (M+H)$^+$.

Example 137: DIEA (0.087 mL, 0.500 mmol) was added to a solution of 137B (0.100 g, 0.167 mmol) and 137C (0.057 g, 0.167 mmol) in DMF (5 mL) and heated at 50° C. for 18 h. Purification by reverse phase prep HPLC gave the desired product (21 mg, 15%) as a white solid after lyophilization. $^1$H NMR (500 MHz, DMSO-d$_6$) δ 10.91 (1H, s), 8.75 (1H, t, J=5.50 Hz), 7.97 (2H, d, J=8.53 Hz), 7.91 (2H, d, J=8.80 Hz), 7.74-7.80 (5H, m), 7.58 (1H, d, J=15.68 Hz), 7.51 (2H, d, J=8.25 Hz), 7.41 (1H, t, J=7.70 Hz), 7.28 (1H, d, J=7.70 Hz), 7.03-7.09 (1H, m), 5.98 (1H, s), 4.13-4.22 (1H, m), 3.59-3.71 (3H, m), 3.30 (2H, q, J=5.78 Hz), 3.11-3.21 (1H, m), 2.80-2.91 (8H, m), 2.59 (3H, s) ppm. MS (ESI) m/z: 711.0 (M+H)$^+$. Analytical HPLC: RT=6.14 min.

Example 138

(E)-2-(3-(6-acetyl-3-chloro-2-fluorophenyl)acryloyl)-N-(4-cyanophenyl)-5-(piperidin-4-yloxy)-1,2,3,4-tetrahydroisoquinoline-1-carboxamide, TFA salt

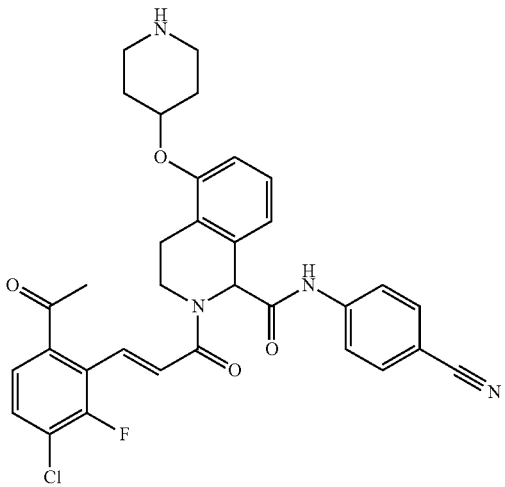 [SMILES: CC(=O)c1ccc(Cl)c(F)c1/C=C/C(=O)N1CCc2c(OC3CCNCC3)cccc2C1C(=O)Nc1ccc(C#N)cc1]

Example 138 (17.5 mg, 14.2%) was made in a similar manner as Example 108 substituting Intermediate 12 instead of Intermediate 3A, as well as, Intermediate 7 in the place of Intermediate 6 in the Ugi reaction step. $^1$H NMR (400 MHz, DMSO-$d_6$) δ 11.02 (1H, s), 8.31-8.61 (2H, m), 7.69-7.89 (5H, m), 7.44-7.62 (1H, m), 6.88-7.31 (4H, m), 5.89 (1H, s), 4.60-4.75 (1H, m), 4.10-4.25 (1H, m), 3.79-3.93 (1H, m), 3.17-3.32 (2H, m), 3.07-3.17 (2H, m), 2.70-3.03 (2H, m), 2.59 (3H, s), 2.02-2.17 (1H, m), 1.77-1.92 (2H, m) ppm. MS (ESI) m/z: 601.0 (M+H)$^+$. Analytical HPLC: RT=10.48 min (method B).

Example 139

Racemate (E)-4-(2-(3-(6-acetyl-3-chloro-2-fluorophenyl)acryloyl)-5-(piperidin-4-yloxy)-1,2,3,4-tetrahydroisoquinoline-1-carboxamido)benzoic acid, TFA salt

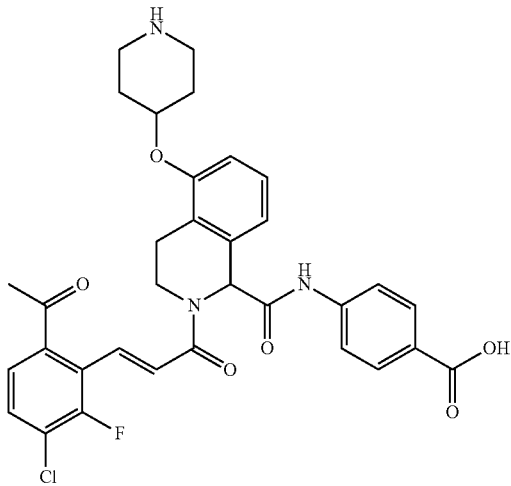 [SMILES: CC(=O)c1ccc(Cl)c(F)c1/C=C/C(=O)N1CCc2c(OC3CCNCC3)cccc2C1C(=O)Nc1ccc(C(=O)O)cc1]

Example 139 (21 mg, 4.49%) was made in a similar manner as Example 108 substituting Intermediate 12 instead of Intermediate 3A in the Ugi reaction step. $^1$H NMR (400 MHz, DMSO-$d_6$) δ 12.78 (1H, br.s.), 10.91 (1H, s), 7.89 (2H, d, J=8.79 Hz), 7.63-7.81 (4H, m), 7.55 (1H, d, J=15.94 Hz), 7.19-7.29 (2H, m), 7.08-7.16 (1H, m), 7.01 (1H, d, J=6.60 Hz), 5.90 (1H, s), 4.63-4.76 (1H, m), 4.13-4.24 (1H, m), 3.82-3.93 (1H, m), 3.17-3.30 (2H, m), 3.04-3.16 (2H, m), 2.86-3.04 (2H, m), 2.59 (3H, s), 2.00-2.17 (2H, m), 1.80-1.92 (2H, m) ppm. MS (ESI) m/z: 619.9 (M+H)$^+$. Analytical HPLC: RT=5.34 min (method B).

Example 140

4-(5-((E)-3-amino-3-oxoprop-1-enyl)-2-((E)-3-(3-chloro-2-fluoro-6-(1H-tetrazol-1-yl)phenyl)acryloyl)-1,2,3,4-tetrahydroisoquinoline-1-carboxamido)benzoic acid

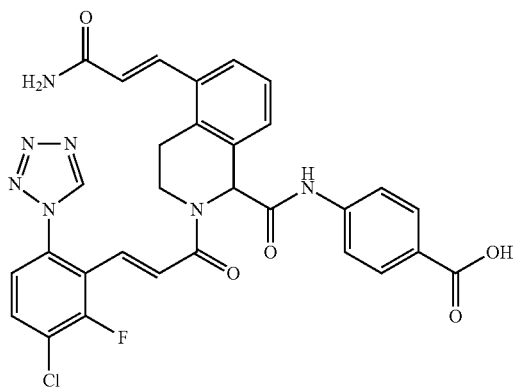 [SMILES: NC(=O)/C=C/c1cccc2c1CCN(C(=O)/C=C/c1c(-n3cnnn3)ccc(Cl)c1F)C2C(=O)Nc1ccc(C(=O)O)cc1]

140A: (E)-tert-Butyl 5-(3-amino-3-oxoprop-1-enyl)-1-(4-(tert-butoxycarbonyl)-phenylcarbamoyl)-3,4-dihydroisoquinoline-2(1H)-carboxylate: 139A (0.200 g, 0.38 mmol) and trans-dichlorobis(tri-o-tolylphosphine)-palladium(II) (0.030 g, 0.038 mmol) were dissolved in (trifluoromethyl)benzene (8 mL) and then acrylamide (0.037 g, 0.53 mmol) followed by TEA (0.16 mL, 1.13 mmol) were added. The reaction was irradiated in microwave at 150° C. for 20 minutes. The reaction mixture was dissolved in EtOAc and washed with saturated NaHCO$_3$ solution followed by brine. The organic layer was dried over Na$_2$SO$_4$, filtered, and concentrated to give a yellow solid. MS (ESI) m/z: 522.4 (M+H)$^+$.

Example 140: 140A (0.090 g, 0.155 mmol) was treated with 50% TFA/DCM for 2.5 h. The reaction mixture was concentrated and the crude amine purified by reverse phase prep HPLC. DIEA (0.25 ml, 1.41 mmol) was added to a solution of the amine TFA salt and Intermediate 3 (0.172 g, 0.470 mmol) in DMF (8 mL). The mixture was heated at 50° C. overnight. Purification by reverse phase prep HPLC afforded the desired product as a white solid. $^1$H NMR (500 MHz, DMSO-$d_6$) δ 10.81 (1H, s), 9.88 (1H, s), 7.93-8.02 (1H, m), 7.88 (2H, d, J=8.80 Hz), 7.57-7.75 (6H, m), 7.52 (1H, d, J=7.98 Hz), 7.33 (1H, t, J=7.84 Hz), 7.14 (2H, d, J=15.68 Hz), 6.94-7.00 (1H, m), 6.51 (1H, d, J=15.68 Hz), 5.85 (1H, s), 4.11-4.22 (1H, m), 3.71 (1H, ddd, J=12.52, 8.12, 4.68 Hz), 3.02-3.22 (2H, m) ppm. MS (ESI) m/z: 616.4 (M+H)$^+$. Analytical HPLC: RT=6.81 min.

The following Examples in Table 10 were prepared according to methods analogous to that described for Example 140. Representative chiral compounds were obtained by chiral resolution of the appropriate late stage intermediate followed by purification.

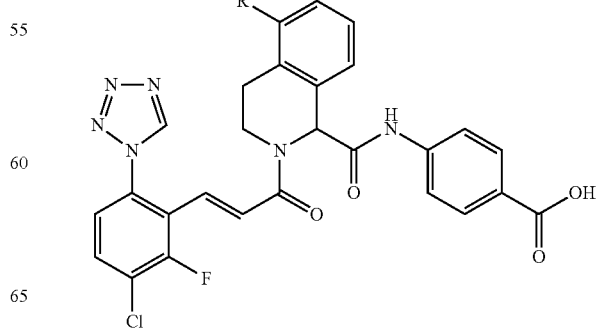

TABLE 10

| Example # | Stereochemistry | R | M+H | RT |
|---|---|---|---|---|
| 141 | Racemic | (ethyl (E)-but-2-enoate group) | 667.5* | 11.44 |
| 142 | Racemic | (N-imidazolyl allyl group) | 653.5 | 8.90 |
| 143 | Racemic | ((E)-1-(4-methylpiperazin-1-yl)but-2-en-1-one group) | 699.5 | 4.89** |
| 144 | Diastereomer | ((E)-1-(3-(dimethylamino)pyrrolidin-1-yl)but-2-en-1-one group) | 713.5 | 5.75 |
| 145 | Racemic | ((E)-1-(4-(pyrrolidin-1-yl)piperidin-1-yl)but-2-en-1-one group) | 753.5 | 5.95 |

*(M+Na)
**Method B

Example 146

(E)-4-(2-(3-(6-acetyl-3-chloro-2-fluorophenyl)acryloyl)-5-hydroxy-1,2,3,4-tetrahydroisoquinoline-1-carboxamido)benzoic acid

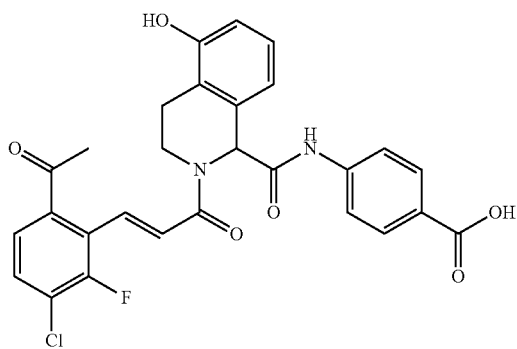 [SMILES: CC(=O)c1ccc(Cl)c(F)c1/C=C/C(=O)N1CCc2c(O)cccc2C1C(=O)Nc1ccc(C(=O)O)cc1]

146A: 5-(tert-Butyldimethylsilyloxy)isoquinoline: To a solution of isoquinolin-5-ol (10.0 g, 68.9 mmol) in DMF (50 mL) were added imidazole (4.92 g, 72.3 mmol) and tert-butyldimethyl chlorosilane (11.42 g, 76 mmol). After 18 h, the reaction mixture was poured into $H_2O$ (250 mL). This solution was extracted with EtOAc (3×100 mL). The combined organic layer was washed with brine, dried over $Na_2SO_4$, and then concentrated. The residue was purified by silica gel chromatography to give 146A (14.35, 80%) as an oil. MS (ESI) m/z: 260.0 (M+H)$^+$.

146B: 5-(tert-Butyldimethylsilyloxy)-3,4-dihydroisoquinoline: 146A (14.30 g, 1 mmol) was reduced and then oxidized as described in Example 8 to afford 146B.

146C: (E)-tert-Butyl 4-(2-(3-(6-acetyl-3-chloro-2-fluorophenyl)acryloyl)-5-(tert-butyldimethylsilyloxy)-1,2,3,4-tetrahydroisoquinoline-1-carboxamido)benzoate: 146B (1.0 g, 3.83 mmol), Intermediate 3A (0.928 g, 3.83 mmol) and Intermediate 6 (0.777 g, 3.83 mmol) were combined in an Ugi reaction as described in Example 8 to afford 146C (1.23 g, 43.2% yield) as an off-white solid. $^1H$ NMR (400 MHz, DMSO-$d_6$) δ 10.86 (1H, s), 7.84-7.89 (2H, m), 7.70-7.79 (5H, m), 7.50-7.67 (2H, m), 7.25 (1H, d, J=7.83 Hz), 7.04-7.20 (2H, m), 5.89 (1H, s), 4.12-4.23 (1H, m), 3.82-3.92 (1H, m), 2.82-3.04 (2H, m), 2.58 (3H, s), 1.53 (9H, s), 0.99 (9H, s), 0.17-0.27 (6H, m) ppm. MS (ESI) m/z: 707.0 (M+H)$^+$.

Example 146: Tetrabutylammonium fluoride (1.0M in THF) (0.160 ml, 0.16 mmol) was added to 146C (0.10 g, 0.141 mmol) in THF (2.36 ml). After 1.5 h, the reaction was quenched with $H_2O$ (10 mL). The aqueous mixture was extracted with DCM (30 mL) and 4/1 DCM/iPrOH (2×20 mL). The combined organic extracts were dried over $Na_2SO_4$, filtered, and concentrated. The residue was treated 50% TFA/DCM. After 2 h, the reaction mixture was concentrated and purified by reverse phase prep HPLC to give the desired product (9 mg, 11%) as a white solid. $^1H$ NMR (400 MHz, DMSO-$d_6$) δ 12.75 (1H, br.s.), 10.85 (1H, s), 9.64 (1H, s), 7.89 (2H, d, J=8.79 Hz), 7.69-7.79 (4H, m), 7.55 (1H, d, J=15.94 Hz), 7.03-7.17 (3H, m), 6.72-6.78 (1H, m), 5.84 (1H, s), 4.14-4.24 (1H, m), 3.75-3.86 (1H, m), 2.83-2.99 (1H, m), 2.60 (3H, s) ppm. MS (ESI) m/z: 536.8 (M+H)$^+$. Analytical HPLC: RT=6.18 min (Method B).

Example 147

(E)-4-(2-(3-(3-Chloro-2-fluoro-6-(1H-tetrazol-1-yl)phenyl)acryloyl)-3,3-dimethyl-5-(piperidin-4-yloxy)-1,2,3,4-tetrahydroisoquinoline-1-carboxamido)benzoic acid, TFA salt

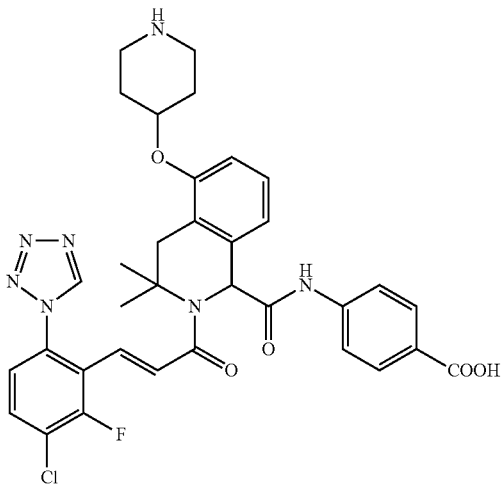 [SMILES: CC1(C)Cc2c(OC3CCNCC3)cccc2C(C(=O)Nc2ccc(C(=O)O)cc2)N1C(=O)/C=C/c1c(-n2cnnn2)ccc(Cl)c1F]

147A: Benzyl 5-bromo-3,3-dimethyl-3,4-dihydroisoquinoline-2(1H)-carboxylate: To 126F (900 mg, 3.75 mmol) in dry THF (9 mL), at 0° C., was added 10% aqueous sodium hydroxide (5.4 mL) followed by drop-wise addition of benzyl chloroformate (0.6 mL, 4.12 mmol). After 48 h, the reaction was quenched with ice cold H$_2$O, extracted with EtOAc (2×), the combined organics were washed with H$_2$O, brine, dried over Na$_2$SO$_4$ and concentrated. Purification by silica gel column chromatography afforded give 147A (0.6 g, 42.8%) as a white liquid. MS (ESI) m/z: 347.0 (M+H)$^+$.

147B: Benzyl 3,3-dimethyl-5-(4,4,5,5-tetramethyl-1,3,2-dioxaborolan-2-yl)-3,4-dihydroisoquinoline-2(1H)-carboxylate: To a solution of 147A (600 mg, 1.60 mmol) in DMSO (4.2 mL, 7.0 vol) was added potassium acetate (471 mg, 4.81 mmol), bis(pinacolato)diborane (1.01 mg, 4.01 mmol), and, after degassing with N$_2$ for 10 minutes, PdCl$_2$(dppf) (13 mg, 0.016 mmol) was added. After 18 h at 85° C., the reaction was cooled to rt, diluted with H$_2$O, extracted with EtOAc twice, the combined organics were washed with saturated NaHCO$_3$ solution, brine, dried over Na$_2$SO$_4$, filtered and concentrated. The crude was purified by silica gel column chromatography to give 147B (900 mg) as colorless semi-solid. MS (ESI) m/z: 422.2 (M+H)$^+$.

147C: Benzyl 5-hydroxy-3,3-dimethyl-3,4-dihydroisoquinoline-2(1H)-carboxylate: To 147B (900 mg, 2.137 mmol) in THF (4.5 mL)/H$_2$O (4.5 mL) was added sodium perborate (986 mg, 6.41 mmol). After 4 h at 50° C., the reaction was cooled to rt, diluted with saturated NH$_4$Cl solution, extracted with EtOAc twice, the combined organics were washed with saturated NaHCO$_3$ solution, brine, dried over Na$_2$SO$_4$, filtered and concentrated. The crude was purified by silica gel column chromatography to give 275 mg of 147C as a colorless liquid. MS (ESI) m/z: 312.2 (M+H)$^+$.

147D: Benzyl 5-(1-(tert-butoxycarbonyl)piperidin-4-yloxy)-3,3-dimethyl-3,4-dihydroisoquinoline-2(1H)-carboxylate: To 147C (200 mg, 0.643 mmol) in DMF (2.0 mL) was added tert-butyl-4-(methylsulfonyloxy)piperidine-1-carboxylate (215 mg, 0.771 mmol) and Cs$_2$CO$_3$ (417 mg, 1.28 mmol). After 18 h at 85° C., the reaction was cooled to rt, diluted with H$_2$O, extracted with EtOAc twice, the combined organics were washed with saturated NaHCO$_3$ solution, brine, dried over Na$_2$SO$_4$, filtered and concentrated. The crude was purified by silica gel column chromatography to give 147D (180 mg) as white solid. MS (ESI) m/z: 495.2 (M+H)$^+$.

147E: tert-Butyl 4-(3,3-dimethyl-1,2,3,4-tetrahydroisoquinolin-5-yloxy)piperidine-1-carboxylate: To 147D (180 mg) in MeOH (1.5 mL) was added 10% Pd/C (36 mg, 20 vol) and the reaction was hydrogenated at 14 psi for 3 h. The reaction was filtered through celite and washed twice with MeOH. The combined organics were evaporated to give 110 mg of 147E as white solid. MS (ESI) m/z: 361.2 (M+H)$^+$.

147F: tert-Butyl 4-(3,3-dimethyl-3,4-dihydroisoquinolin-5-yloxy)piperidine-1-carboxylate: 147E (100 mg, 0.27 mmol) was oxidized in a similar manner as 8B to afford 70 mg of 147F as a brown liquid. MS (ESI) m/z: 359.2 (M+H)$^+$.

Example 147 (9.0 mg) was prepared in an Ugi reaction in a similar manner as Example 8 using 147F, Intermediate 3A, and Intermediate 6 followed by HCl deprotection and HPLC purification. $^1$H NMR (400 MHz, DMSO-d$_6$) δ 12.8 (1H, s), 10.49 (1H, s), 9.86 (1H, s), 8.30 (1H, bs), 8.43 (1H, bs), 7.88-8.0 (3H, m), 7.65 (3H, d, J=8.7 Hz), 7.41 (1H, d, J=8.0 Hz), 7.27 (1H, t, J=8.0 Hz), 7.06-7.12 (2H, m), 6.85 (1H, bs), 5.77 (1H, s), 4.67 (1H, q), 2.98-3.50 (6H, m), 2.0-2.1 (2H, m), 1.70-1.85 (5H, m), 1.18 (3H, s) ppm. MS (ESI) m/z: 674.3 (M+H)$^+$. Analytical HPLC: RT=7.63 min.

Example 148

(S,E)-4-(2-(3-(6-acetyl-3-chloro-2-fluorophenyl)acryloyl)-5-(4-(2-(dimethylamino)ethylcarbamoyl)phenyl)-1,2,3,4-tetrahydroisoquinoline-1-carboxamido)benzoic acid, TFA salt

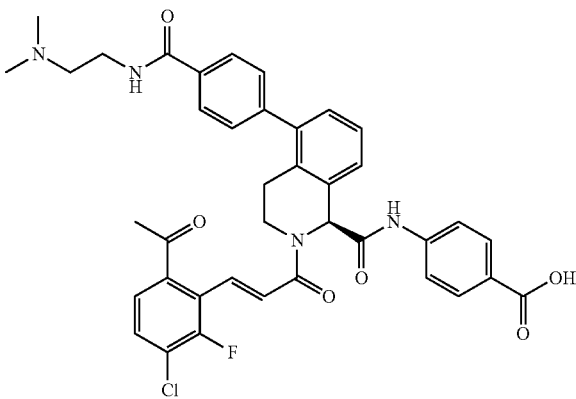 [SMILES: CC(=O)c1ccc(Cl)c(F)c1/C=C/C(=O)N1CCc2c(-c3ccc(C(=O)NCCN(C)C)cc3)cccc2[C@H]1C(=O)Nc1ccc(C(=O)O)cc1]

Example 148 was obtained by chiral resolution of Example 137 using Chiralcel OJ-H SFC, 250×21 mm ID, 5 μm, using step gradient of 30%-40% EtOH-0.1% DEA/70%-60% CO$_2$ at 65 mL/min, 100 bar BP, 35° C. $^1$H NMR (500 MHz, DMSO-d$_6$) δ 10.83 (1H, s), 8.68 (1H, t, J=5.64 Hz), 7.89 (2H, d, J=8.25 Hz), 7.81-7.86 (2H, m), 7.65-7.72 (5H, m), 7.50 (1H, d, J=15.96 Hz), 7.43 (2H, d, J=8.25 Hz), 7.33 (1H, t, J=7.70 Hz), 7.20 (1H, d, J=7.70 Hz), 6.99 (1H, dd, J=15.96, 1.38 Hz), 5.90 (1H, s), 4.10 (1H, ddd, J=11.97, 5.09, 4.95 Hz), 3.49-3.61 (3H, m), 3.22 (2H, q, J=5.96 Hz), 3.04-3.14 (1H, m), 2.74-2.84 (7H, m), 2.51 (3H, s) ppm. MS (ESI) m/z: 711.3 (M+H)$^+$. Analytical HPLC: RT=5.79 min.

Example 149

(E)-4-(2-(3-(3-chloro-2-fluoro-6-(1H-tetrazol-1-yl)phenyl)acryloyl)-5-(1-methylpiperidin-4-yl)-1,2,3,4-tetrahydroisoquinoline-1-carboxamido)benzoic acid, TFA salt

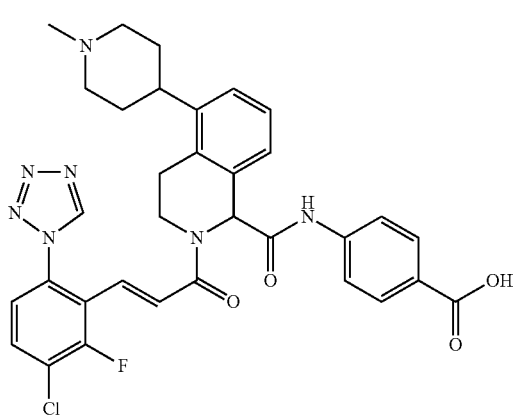 [SMILES: CN1CCC(c2cccc3c2CCN(C(=O)/C=C/c2c(-n4cnnn4)ccc(Cl)c2F)C3C(=O)Nc2ccc(C(=O)O)cc2)CC1]

149A: 2-tert-Butyl 1-methyl 5-(1-methylpiperidin-4-yl)-3,4-dihydroisoquinoline-1,2(1H)-dicarboxylate: To 136F (0.28 g, 0.748 mmol) in EtOH (20 mL) was added paraformaldehyde (0.067 g, 2.243 mmol) and 10% Pd/C (30 mg) and the reaction was hydrogenated at 55 psi for 72 h. The reaction was filtered and concentrated to afford 0.25 g (86%) of 149A as a dark oil. MS(ESI) m/z: 389.0 (M+H)$^+$.

149B: Lithium 2-(tert-butoxycarbonyl)-5-(1-methylpiperidin-4-yl)-1,2,3,4-tetrahydroisoquinoline-1-carboxylate: To 149A (0.25 g, 0.557 mmol) in 2:1 THF/H$_2$O (15 mL) was added LiOH—H$_2$O (0.035 g, 0.836 mmol). After 24 h, the reaction was concentrated and freeze-dried to afford 0.266 g of 149B salt as a white solid. MS(ESI) m/z: 375.0 (M+H)$^+$.

149C: 1-(4-(tert-Butoxycarbonyl)phenyl) 2-tert-butyl 5-(1-methylpiperidin-4-yl)-3,4-dihydroisoquinoline-1,2(1H)-dicarboxylate: To 149B (0.2 g, 0.526 mmol) and tert-butyl 4-aminobenzoate (0.102 g, 0.526 mmol) in DCM (5 mL) and pyridine (0.128 ml, 1.577 mmol), cooled in ice bath, was added POCl$_3$ (0.049 ml, 0.526 mmol). After 24 h, the reaction was partitioned with H$_2$O (20 mL) and DCM (50 mL), separated and organic layer was washed with brine and dried with MgSO$_4$. Purification by normal phase chromatography afforded 24 mg (8.3%) of 149C as a yellow oil. MS(ESI) m/z: 550.1 (M+H)$^+$.

Example 149: 149C (24 mg, 0.044 mmol) was deprotected in 30% TFA/DCM (3 mL) for 2 h, MS (ESI) m/z: 393.9 (M+H)$^+$. The reaction was concentrated and combined with Intermediate 3 (15.97 mg, 0.044 mmol) and DIEA (38.1 μL, 0.218 mmol) in DMF (1 mL). After 72 h, the reaction was diluted with MeOH, filtered and purified by reverse phase HPLC to afford 8.9 mgs of Example 149 as a white solid. $^1$H NMR (400 MHz, MeOD) δ 9.56 (1H, s), 7.96 (2H, d, J=8.84 Hz), 7.81 (1H, t, J=8.21 Hz), 7.59-7.70 (2H, m), 7.41-7.57 (2H, m), 7.25-7.36 (2H, m), 7.18 (1H, d, J=15.92 Hz), 6.97 (1H, d, J=15.92 Hz), 5.86 (1H, s), 4.09-4.24 (1H, m), 3.53-3.77 (3H, m), 3.17-3.31 (4H, m), 3.02-3.15 (1H, m), 2.96 (3H, s), 1.83-2.24 (4H, m) ppm. MS (ESI) m/z: 644.3 (M+H)$^+$. Analytical HPLC: RT=5.13 min.

Example 150

(R,E)-4-(2-(3-(6-Acetyl-3-chloro-2-fluorophenyl)acryloyl)-5-(4-(2-(dimethylamino)ethylcarbamoyl)phenyl)-1,2,3,4-tetrahydroisoquinoline-1-carboxamido)benzoic acid, TFA salt Example 150 was obtained by chiral resolution of Example 137 using Chiralcel OJ-H SFC, 250×21 mm ID, 5 μm, using step gradient of 30%-40% EtOH-0.1% DEA/70%-60% CO$_2$ at 65 mL/min, 100 bar BP, 35° C. $^1$H NMR (500 MHz, DMSO-d$_6$) δ 10.91 (1H, s), 8.77 (1H, t, J=5.64 Hz), 7.97 (1H, d, J=8.25 Hz), 7.91 (2H, d, J=8.80 Hz), 7.73-7.80 (5H, m), 7.58 (1H, d, J=15.68 Hz), 7.51 (2H, d, J=8.25 Hz), 7.41 (1H, t, J=7.70 Hz), 7.28 (1H, d, J=7.43 Hz), 7.03-7.09 (1H, m), 5.98 (1H, s), 4.13-4.23 (1H, m), 3.60-3.69 (3H, m), 3.29 (2H, q, J=5.69 Hz), 3.16 (1H, td, J=10.25, 4.54 Hz), 2.81-2.91 (7H, m), 2.59 (3H, s) ppm. MS (ESI) m/z: 711.3 (M+H)$^+$. Analytical HPLC: RT=5.83 min.

Example 151

(E)-ethyl 4-(2-(3-(3-chloro-2-fluoro-6-(1H-tetrazol-1-yl)phenyl)acryloyl)-3,3-dimethyl-5-(2-(piperidin-4-yl)ethoxy)-1,2,3,4-tetrahydroisoquinoline-1-carboxamido)benzoate, TFA salt Example 151 was made in a similar manner as Example 147. MS (ESI) m/z: 730.2 (M+H)$^+$. Analytical HPLC RT=14.93 mins

Example 152

(E)-ethyl 4-(2-(3-(3-chloro-2-fluoro-6-(1H-tetrazol-1-yl)phenyl)acryloyl)-3,3-dimethyl-5-(2-(1-methyl piperidin-4-yl)ethoxy)-1,2,3,4-tetrahydroisoquinoline-1-carboxamido)benzoate, TFA salt

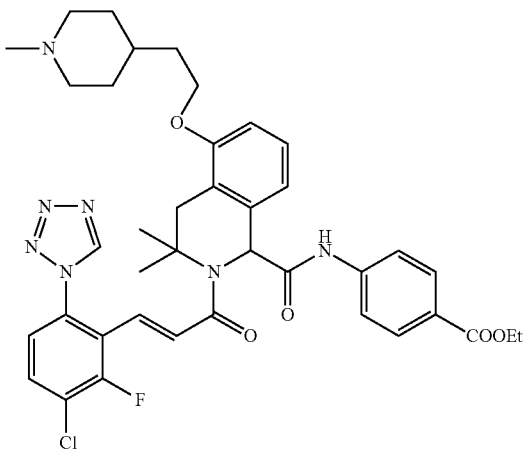 [SMILES: CCOC(=O)c1ccc(NC(=O)C2c3cccc(OCCC4CCN(C)CC4)c3CC(C)(C)N2C(=O)/C=C/c2c(-n3cnnn3)ccc(Cl)c2F)cc1]

Example 152 was made in a similar manner as Example 147. $^1$H NMR (400 MHz, DMSO-$d_6$) δ 10.54 (1H, s), 9.86 (1H, s), 9.00 (1H, bs), 7.90-7.97 (3H, m), 7.64-7.69 (3H, m), 7.37 (1H, d, J=7.6 Hz), 7.24 (1H, dd, J=8.0, 16 Hz), 7.09-7.14 (1H, m), 6.96-7.01 (2H, m), 5.77 (1H, bs), 4.28 (2H, dd, J=7.2, 14.4 Hz), 4.04 (2H, bs), 3.0-3.38 (3H, m), 2.85-2.92 (3H, m), 2.75 (3H, d, J=4.8 Hz), 1.85-1.95 (2H, m), 1.80 (3H, s), 1.71 (3H, bs), 1.31 (5H, t, J=7.2 Hz), 1.17 (3H, s). MS ESI m/z: 744.2 (M+H)$^+$. Analytical HPLC: RT=15.21 min

Example 153

(E)-4-(2-(3-(5-chloro-2-(1H-tetrazol-1-yl)phenyl)acryloyl)-3,3-dimethyl-5-(2-(piperidin-4-yl)ethoxy)-1,2,3,4-tetrahydroisoquinoline-1-carboxamido)benzoic acid, TFA salt

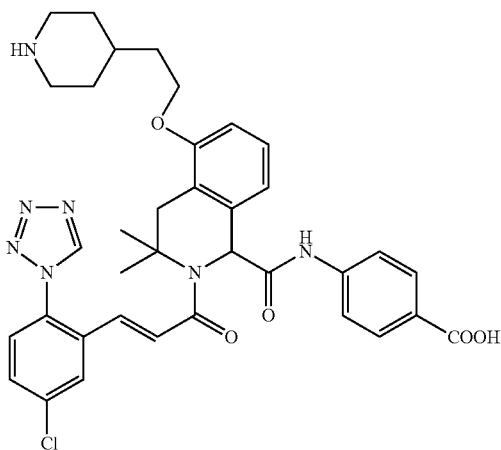 [SMILES: CC1(C)Cc2c(OCCC3CCNCC3)cccc2C(C(=O)Nc2ccc(C(=O)O)cc2)N1C(=O)/C=C/c1cc(Cl)ccc1-n1cnnn1]

Example 153 was made in a similar manner as Example 147 using tert-butyl 4-(2-(methylsulfonyloxy)ethyl)piperidine-1-carboxylate. $^1$H NMR (400 MHz, DMSO-$d_6$) δ 12.8 (1H, s), 10.49 (1H, s), 9.84 (1H, s), 8.40 (1H, s), 8.13 (2H, bs), 7.89 (2H, d, J=8.0 Hz), 7.66-7.78 (4H, m), 6.88-7.35 (5H, m), 5.84 (1H, s), 4.05 (2H, t, J=6.0 Hz), 3.0-3.37 (3H, m), 2.80-2.95 (3H, m), 1.71-1.90 (8H, m), 1.33-1.36 (2H, m), 1.18 (3H, s) ppm. MS (ESI) m/z: 684.3 (M+H)$^+$. Analytical HPLC: RT=8.0 min.

Example 154

(R,E)-4-(2-(3-(3-chloro-2-fluoro-6-(1H-tetrazol-1-yl)phenyl)acryloyl)-3,3-dimethyl-5-(2-(piperidin-4-yl)ethoxy)-1,2,3,4-tetrahydroisoquinoline-1-carboxamido)benzoic acid, bis-TFA salt

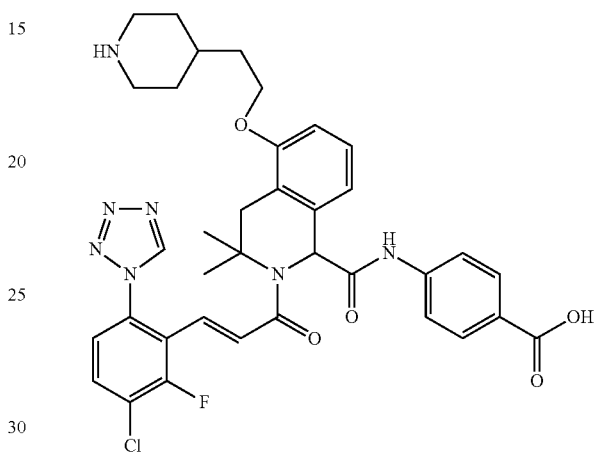

Example 154 was made in a similar manner as Example 147. $^1$H NMR (400 MHz, DMSO-$d_6$) δ 12.73 (1H, s), 10.48 (1H, s), 9.85 (1H, s), 8.43 (1H, bs), 8.12 (1H, bs), 7.87-7.96 (3H, m), 7.64 (3H, d, J=8.8 Hz), 7.36 (1H, d, J=7.6 Hz), 7.23 (1H, t, J=7.6 Hz), 7.08-7.13 (1H, d, J=15.2 Hz), 6.98 (1H, d, J=8.4 Hz), 6.83 (1H, bs), 5.75 (1H, bs), 4.03 (2H, t, J=6.0), 3.14-3.36 (3H, m), 2.83-2.95 (3H, m), 1.70-1.87 (8H, m), 1.28-1.38 (2H, m), 1.16 (3H, s). MS ESI m/z: 702.2 (M+H)$^+$. Analytical HPLC: RT=6.96 min.

Example 155

(S,E)-4-(2-(3-(3-chloro-2-fluoro-6-(1H-tetrazol-1-yl)phenyl)acryloyl)-3,3-dimethyl-5-(2-(piperidin-4-yl)ethoxy)-1,2,3,4-tetrahydroisoquinoline-1-carboxamido)benzoic acid, bis-TFA salt

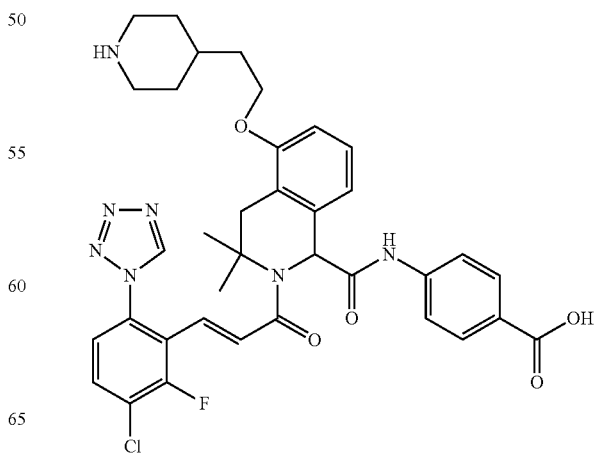

Example 155 was made in a similar manner as Example 147. $^1$H NMR (400 MHz, DMSO-$d_6$) δ 12.73 (1H, s), 10.48 (1H, s), 9.85 (1H, s), 8.41 (1H, bs), 8.13 (1H, bs), 7.87-7.96 (3H, m), 7.64 (3H, d, J=8.0 Hz), 7.36 (1H, d, J=7.6 Hz), 7.24 (1H, t, J=8.0 Hz), 7.11 (1H, d, J=15.6 Hz), 6.98 (1H, d, J=7.6 Hz), 6.85 (1H, bs), 4.03 (2H, t, J=6.0), 3.14-3.35 (3H, m), 2.83-2.95 (3H, m), 1.70-1.85 (8H, m), 1.32-1.38 (2H, m), 1.16 (3H, s). MS ESI m/z: 702.2 (M+H)$^+$. Analytical HPLC: RT=6.96 min.

Example 156

(E)-Methyl 6-(2-(3-(3-chloro-2-fluoro-6-(1H-tetrazol-1-yl)phenyl)-acryloyl)-5-(4-(2-(dimethylamino)ethylcarbamoyl)phenyl)-1,2,3,4-tetrahydroiso-quinoline-1-carboxamido)nicotinate, bis-TFA salt

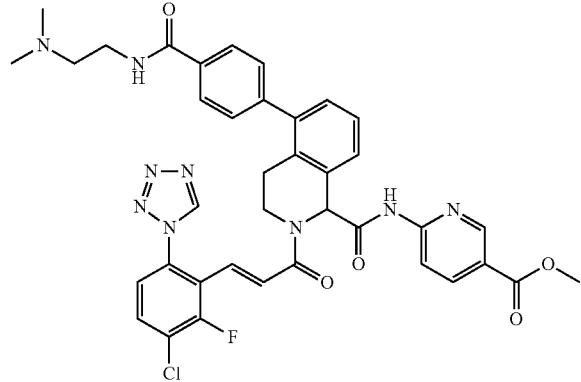

Example 156 (50 mg, 11%) was made in a similar manner as Example 137 substituting methyl 6-aminonicotinate instead of ethyl 4-aminobenzoate. $^1$H NMR (500 MHz, DMSO-$d_6$) δ 11.47 (1H, s), 9.85 (1H, s), 8.88 (1H, d, J=2.20 Hz), 8.75 (1H, t, J=5.78 Hz), 8.25 (1H, dd, J=8.80, 2.48 Hz), 8.06 (1H, d, J=8.53 Hz), 7.92-7.98 (3H, m), 7.83 (1H, d, J=7.43 Hz), 7.64-7.68 (1H, m), 7.49 (2H, d, J=8.25 Hz), 7.39 (1H, t, J=7.70 Hz), 7.26-7.28 (1H, m), 6.94-7.03 (2H, m), 6.03 (1H, s), 3.99-4.07 (1H, m), 3.85 (3H, s), 3.64 (2H, q, J=5.78 Hz), 3.40-3.48 (1H, m), 3.29 (2H, q, J=5.78 Hz), 3.15 (1H, ddd, J=15.34, 10.38, 4.54 Hz), 2.87 (3H, s), 2.86 (3H, s), 2.79 (1H, dt) ppm. MS (ESI) m/z: 752.3 (M+H)$^+$. Analytical HPLC: RT=6.67 min.

Example 157

(E)-ethyl 4-(2-(3-(3-chloro-2-fluoro-6-(1H-tetrazol-1-yl)phenyl)-acryloyl)-5-(4-(2-(dimethylamino)ethylcarbamoyl)phenyl)-1,2,3,4-tetrahydroiso-quinoline-1-carboxamido)benzoate, TFA salt

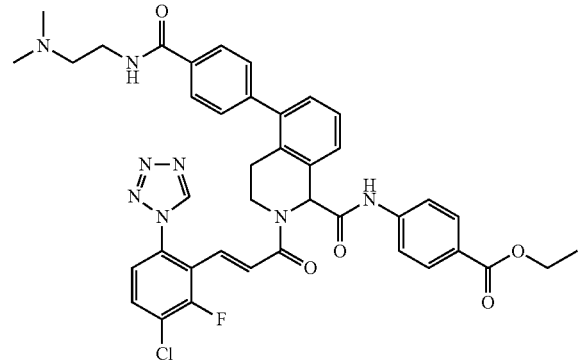 [SMILES: CCOC(=O)c1ccc(NC(=O)C2c3cccc(-c4ccc(C(=O)NCCN(C)C)cc4)c3CCN2C(=O)/C=C/c2c(-n3cnnn3)ccc(Cl)c2F)cc1]

157A: tert-Butyl 5-(4-(2-(dimethylamino)ethylcarbamoyl)phenyl)-1-(4-(ethoxycarbonyl)phenylcarbamoyl)-3,4-dihydroisoquinoline-2(1H)-carboxylate: POCl$_3$ (0.086 g, 0.56 mmol) was added dropwise to a solution of 136C (0.200 g, 0.56 mmol) and ethyl 4-aminobenzoate (0.093 g, 0.561 mmol) in pyridine (5 mL) at −15° C. After 3 h, the reaction mixture was quenched with 1.0 N HCl solution. The mixture was extracted with EtOAc (50 mL), washed with 1.0 N HCl solution (3×30 mL), H$_2$O, brine, dried over MgSO$_4$, filtered, and concentrated. To the above product (0.153 g, 0.561 mmol), potassium phosphate, tribasic (0.477 g, 2.246 mmol), and PdCl$_2$(dppf)-CH$_2$Cl$_2$ Adduct (0.046 g, 0.056 mmol) were added and degassed DMSO (3.74 ml) was added. The reaction mixture was heated to 90° C. for 18 h. After cooling to rt, the dark solution was partitioned between H$_2$O and DCM and the layers separated. The aqueous layer was extracted with DCM. The combined organic layers were washed with H$_2$O, brine, dried over MgSO$_4$, filtered and concentrated. Purification by silica gel chromatography gave 157A (0.12 g, 35%) as an off-white foam. MS (ESI) m/z: 615.4 (M+H)$^+$.

Example 157: 157A (0.12 g, 0.195 mmol) was treated with 50% TFA/DCM. After 2 h, the reaction mixture was concentrated to dryness. In a separate flask, 1-chloro-N,N,2-trimethylprop-1-en-1-amine (0.030 g, 0.22 mmol) was added to a stirring suspension of Intermediate 3A (0.060 g, 0.224 mmol) in DCM/THF (1:1, 7.0 mL). After stirring for 2 h, to the crude TFA amine salt was added DCM (3.0 mL) and pyridine (0.079 ml, 0.98 mmol). After 24 h, the reaction mixture was concentrated and the residue was suspended in H$_2$O, the pH adjusted to 5 with 1.0 N HCl solution, extracted with DCM/IPA (4/1), dried over MgSO$_4$, filtered, and concentrated. Purification by reverse phase prep HPLC gave Example 157 (15 mg, 8%) as a white solid after lyophilization. $^1$H NMR (500 MHz, DMSO-$d_6$) δ 10.87 (1H, s), 9.86 (1H, s), 8.75 (1H, t, J=5.64 Hz), 7.88-7.99 (3H, m), 7.70-7.76 (3H, m), 7.66 (1H, dd, J=8.67, 1.24 Hz), 7.50 (1H, d, J=8.25 Hz), 7.39 (1H, t, J=7.70 Hz), 7.27 (1H, d, J=6.60 Hz), 6.95-7.06 (2H, m), 5.89 (1H, s), 4.28 (2H, q, J=7.06 Hz), 4.01-4.08 (1H, m), 3.64 (2H, q, J=5.78 Hz), 3.46-3.55 (1H, m), 3.29 (2H, q, J=5.69 Hz), 3.13 (1H, ddd, J=15.34, 9.97, 4.95 Hz), 2.88 (3H, s), 2.87 (3H, s), 2.76-2.84 (1H, m), 1.31 (3H, t, J=7.02 Hz) ppm. MS (ESI) m/z: 765.3 (M+H)$^+$. Analytical HPLC: RT=7.16 min.

Example 158

(E)-4-(2-(3-(3-chloro-2-fluoro-6-(1H-tetrazol-1-yl)phenyl)acryloyl)-5-(1-(2,2,2-trifluoroacetyl) piperidin-4-yl)-1,2,3,4-tetrahydroisoquinoline-1-carboxamido)benzoic acid

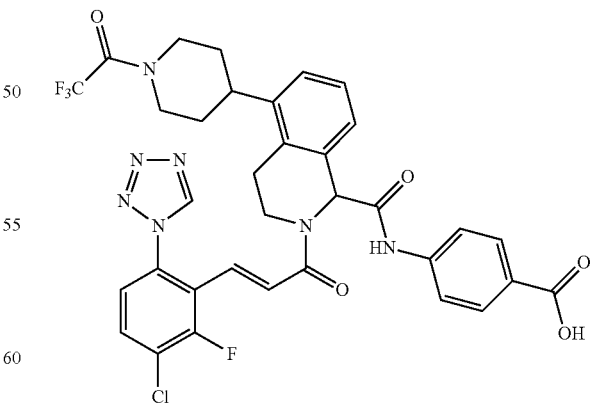

Example 158 was prepared in a similar manner as Example 136 using trifluoroacetic anhydride in place of acetic anhydride. $^1$H NMR (400 MHz, MeOD) δ 10.36 (1H, br.s.), 9.54 (1H, s), 7.94 (2H, d, J=8.59 Hz), 7.71-7.84 (1H, m), 7.63 (2H, d, J=8.59 Hz), 7.44-7.53 (1H, m), 7.39 (1H, br.s.), 7.21-7.34

(1H, m), 7.10-7.21 (1H, m), 7.04 (1H, d), 5.82 (1H, s), 4.66 (1H, br.s.), 4.16 (2H, br.s.), 3.56-3.73 (1H, m), 3.36-3.50 (2H, m), 2.94-3.20 (2H, m), 1.93 (2H, br.s.), 1.57-1.81 (3H, m) ppm. MS (ESI) m/z: 725.9 (M+H)+. Analytical HPLC: RT=9.57 min.

Example 159

(S,E)-ethyl 4-(2-(3-(3-chloro-2-fluoro-6-(1H-tetrazol-1-yl)phenyl)acryloyl)-5-(4-(2-(dimethylamino)ethylcarbamoyl)phenyl)-1,2,3,4-tetrahydroisoquinoline-1-carboxamido)benzoate, TFA salt

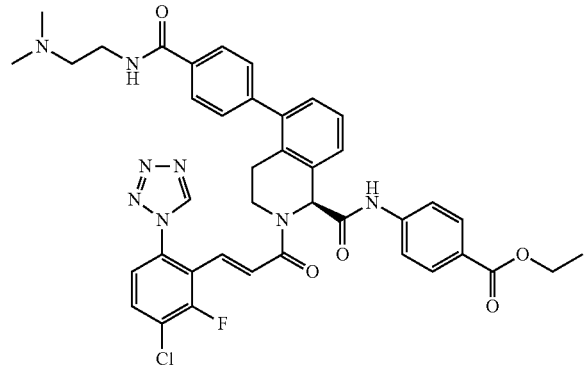 [SMILES: CCOC(=O)c1ccc(NC(=O)[C@@H]2c3cccc(-c4ccc(C(=O)NCCN(C)C)cc4)c3CCN2C(=O)/C=C/c2c(-n3cnnn3)ccc(Cl)c2F)cc1]

Example 159 was obtained by Chiral HPLC resolution of Example 157 performed using a Chiralpak (AD-H, 250×21 mm ID, 5 μm) column and a mobile phase consisting of 45% (1:1 EtOH-IPAl-0.1% DEA)/55% $CO_2$ with a flow rate of 60 mL/min, 100 bar BP, 35° C. $^1$H NMR (500 MHz, DMSO-d$_6$) δ 10.88 (1H, s), 9.87 (1H, s), 8.76 (1H, t, J=5.50 Hz), 7.89-8.01 (5H, m), 7.64-7.78 (4H, m), 7.51 (1H, d, J=8.25 Hz), 7.40 (1H, t, J=7.70 Hz), 7.28 (1H, d, J=6.60 Hz), 6.95-7.06 (2H, m), 5.89 (1H, s), 4.23-4.35 (2H, m), 4.05 (1H, ddd, J=11.90, 5.02, 4.81 Hz), 3.65 (2H, q, J=5.87 Hz), 3.46-3.57 (1H, m), 3.25-3.34 (1H, m), 3.08-3.19 (1H, m), 2.76-2.94 (7H, m), 1.32 (3H, t, J=7.15 Hz) ppm. MS (ESI) m/z: 765.4 (M+H)+. Analytical HPLC: RT=6.68 min.

Example 160

(R,E)-ethyl 4-(2-(3-(3-chloro-2-fluoro-6-(1H-tetrazol-1-yl)phenyl)-acryloyl)-5-(2-(piperidin-4-yl)ethoxy)-1,2,3,4-tetrahydroisoquinoline-1-carboxamido)benzoate, TFA salt

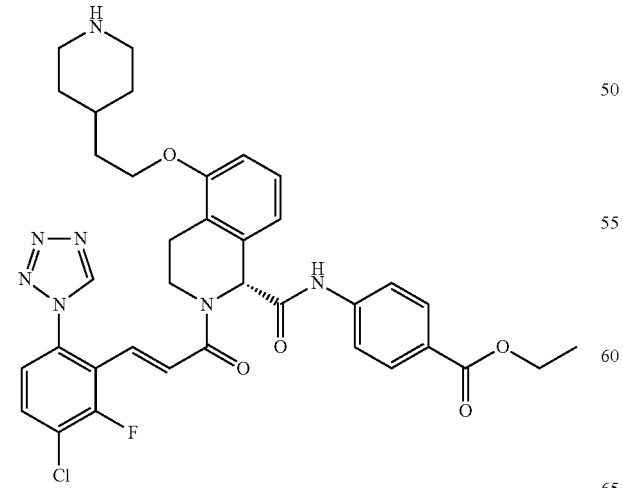

Example 160: The racemate (169 mg, 12%) of Example 160 was made in a similar manner as Example 104 substituting Intermediate 9 instead of Intermediate 8 in the Ugi reaction step. Chiral resolution was accomplished by Chiral prep. HPLC using a Chiralcel (OD-H, 250×30 mm ID, 5 μm) column and a mobile phase consisting of 50/50/0.1, $CO_2$/(1:1, EtOH/ACN)/DEA with a flow rate of 70 mL/min and 150 bar backpressure. Example 160 was obtained as the first eluting enantiomer of the separation of Examples 160 and 161. $^1$H NMR (400 MHz, DMSO-d$_6$) δ 10.87 (1H, s), 9.88 (1H, s), 7.84-8.00 (3H, m), 7.63-7.73 (3H, m), 7.04-7.25 (3H, m), 6.89-7.00 (2H, m), 5.81 (1H, s), 4.27 (2H, q, J=6.96 Hz), 3.98-4.13 (3H, m), 3.65-3.78 (1H, m), 3.28 (2H, d, J=12.09 Hz), 2.77-3.00 (4H, m), 1.58-2.01 (5H, m), 1.22-1.46 (5H, m) ppm. MS (ESI) m/z: 702.3 (M+H)+. Analytical HPLC: RT=6.81 min.

Example 161

(S,E)-Ethyl 4-(2-(3-(3-chloro-2-fluoro-6-(1H-tetrazol-1-yl)phenyl)-acryloyl)-5-(2-(piperidin-4-yl)ethoxy)-1,2,3,4-tetrahydroisoquinoline-1-carboxamido)benzoate, TFA salt

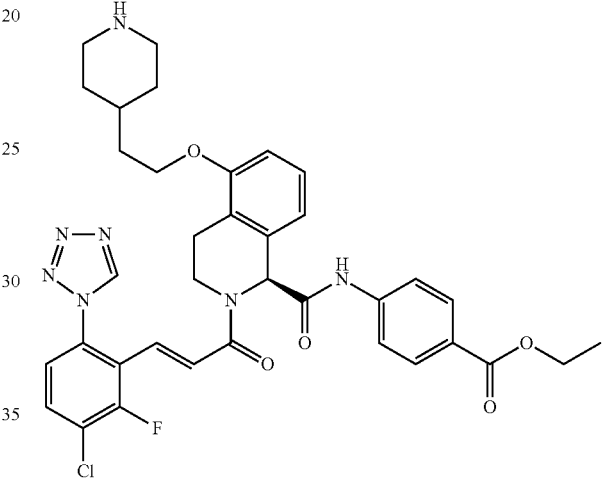

Example 161 was obtained as the second eluting enantiomer while separating Example 160. 1H NMR (400 MHz, DMSO-d$_6$) δ 10.87 (1H, s), 9.88 (1H, s), 7.86-8.02 (3H, m), 7.60-7.78 (3H, m), 7.14-7.26 (2H, m), 7.03-7.12 (1H, m), 6.87-7.00 (2H, m), 5.81 (1H, s), 4.27 (2H, q, J=6.96 Hz), 3.96-4.14 (3H, m), 3.62-3.79 (1H, m), 3.28 (2H, d, J=12.09 Hz), 2.80-2.99 (4H, m), 1.64-1.96 (5H, m), 1.21-1.44 (5H, m) ppm. MS (ESI) m/z: 702.3 (M+H)+. Analytical HPLC: RT=6.82 min.

Example 162

(S,E)-Methyl 6-(2-(3-(3-chloro-2-fluoro-6-(1H-tetrazol-1-yl)phenyl)acryloyl)-5-(4-(2-(dimethylamino)ethylcarbamoyl)phenyl)-1,2,3,4-tetrahydroisoquinoline-1-carboxamido)nicotinate

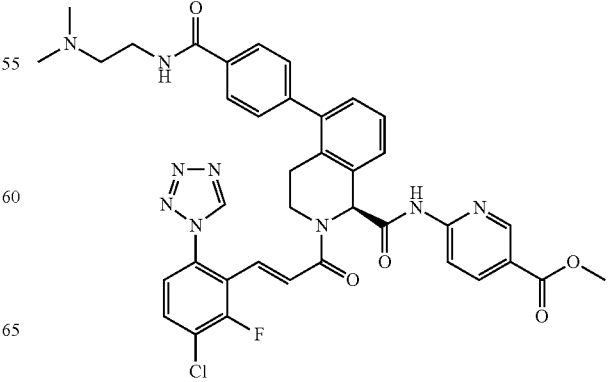

Example 162

Example 162 was obtained by Chiral HPLC resolution of Example 156 performed using a Chiralpak (AD-H, 250×21 mm ID, 5 µm) column and a mobile phase consisting of 45% (1:1 EtOH-IPAl-0.1% DEA)/55% $CO_2$ with a flow rate of 60 mL/min, 100 bar BP, 35° C. $^1$H NMR (500 MHz, DMSO-$d_6$) δ 11.47 (1H, s), 9.85 (1H, s), 8.88 (1H, d, J=2.48 Hz), 8.74 (1H, t, J=5.64 Hz), 8.24 (1H, dd, J=8.80, 2.48 Hz), 8.06 (1H, d, J=8.53 Hz), 7.92-7.98 (3H, m), 7.82 (1H, d, J=7.43 Hz), 7.65 (1H, dd, J=8.67, 1.24 Hz), 7.49 (2H, d, J=8.53 Hz), 7.38 (1H, t, J=7.70 Hz), 7.27 (1H, d, J=6.88 Hz), 6.92-7.04 (2H, m), 6.02 (1H, s), 4.02 (1H, dd, J=7.15, 4.95 Hz), 3.85 (3H, s), 3.63 (2H, q, J=5.87 Hz), 3.40-3.48 (1H, m), 3.29 (2H, q, J=5.78 Hz), 3.15 (1H, s), 2.83-2.89 (6H, m), 2.75-2.82 (1H, m) ppm. MS (ESI) m/z: 752.3 (M+H)$^+$. Analytical HPLC: RT=6.13 min.

Example 163

(R,E)-4-(2-(3-(3-chloro-2-fluoro-6-(1H-tetrazol-1-yl)phenyl)acryloyl)-5-(2-(piperidin-4-yl)ethoxy)-1,2,3,4-tetrahydroisoquinoline-1-carboxamido)benzoic acid, TFA salt

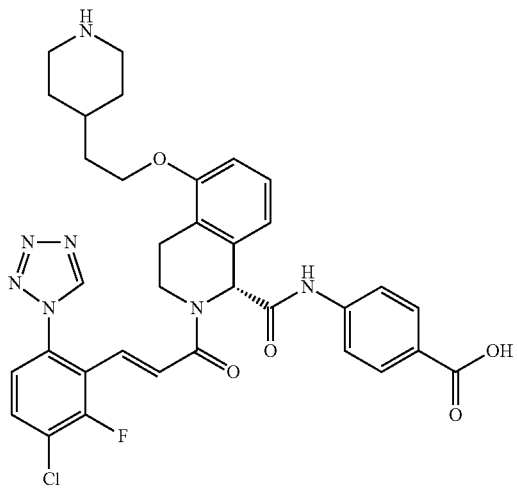 [SMILES: O=C(O)c1ccc(NC(=O)[C@H]2c3cccc(OCCC4CCNCC4)c3CCN2C(=O)/C=C/c2c(-n3cnnn3)ccc(Cl)c2F)cc1]

Example 163 was obtained by chiral resolution of Example 106 performed while the compound was a t-butyl ester. Chiral HPLC using a Chiralpak (IA-H, 250×30 mm ID, 5 µm) column and a mobile phase consisting of 50/50/0.1, $CO_2$/(1:1, EtOH/ACN)/DEA with a flow rate of 65 mL/min and 150 bar backpressure, 40° C. The desired intermediate was designated as peak 1 (>99.0% ee). The desired final compound was obtained by treatment with 50% TFA/DCM for 2 h and purification by reverse phase prep. HPLC. $^1$H NMR (500 MHz, DMSO-$d_6$) δ 12.71 (1H, br.s.), 10.82 (1H, s), 9.85-9.91 (1H, m), 7.83-8.00 (3H, m), 7.59-7.72 (3H, m), 7.12-7.25 (1H, m), 7.04-7.09 (1H, m), 6.88-7.00 (2H, m), 5.82 (1H, s), 4.00-4.11 (2H, m), 3.72 (1H, ddd, J=12.45, 7.08, 4.95 Hz), 3.23-3.30 (1H, m), 2.80-2.97 (4H, m), 1.77-1.96 (3H, m), 1.66-1.76 (2H, m), 1.28-1.42 (2H, m) ppm. MS (ESI) m/z: 674.5 (M+H)$^+$. Analytical HPLC: RT=5.55 min.

Example 164

(S,E)-4-(2-(3-(3-chloro-2-fluoro-6-(1H-tetrazol-1-yl)phenyl)acryloyl)-5-(2-(piperidin-4-yl)ethoxy)-1,2,3,4-tetrahydroisoquinoline-1-carboxamido)benzoic acid, TFA salt

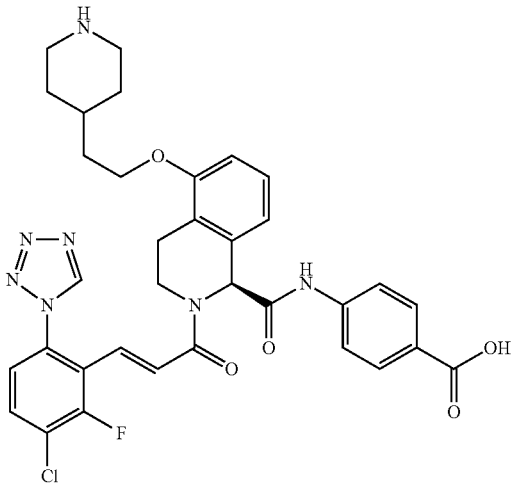 [SMILES: O=C(O)c1ccc(NC(=O)[C@@H]2c3cccc(OCCC4CCNCC4)c3CCN2C(=O)/C=C/c2c(-n3cnnn3)ccc(Cl)c2F)cc1]

Example 164 was obtained by chiral resolution of Example 106 performed while the compound was a t-butyl ester. Chiral HPLC using a Chiralcel (OD-H, 250×30 mm ID, 5 µm) column and a mobile phase consisting of 50/50/0.1, $CO_2$/(1:1, EtOH/ACN)/DEA with a flow rate of 70 mL/min and 150 bar back pressure. The desired intermediate was designated as peak 2 (>99.0% ee). The desired final compound was obtained by treatment with 50% TFA/DCM for 2 h and purification by reverse phase prep. HPLC. $^1$H NMR (500 MHz, DMSO-$d_6$) δ 12.74 (1H, br.s.), 10.82 (1H, s), 9.88 (1H, s), 7.85-8.00 (3H, m), 7.65-7.72 (3H, m), 7.17-7.25 (2H, m), 7.05-7.10 (1H, m), 6.90-7.01 (2H, m), 5.83 (1H, s), 4.01-4.12 (3H, m), 3.72 (1H, ddd, J=12.45, 7.08, 4.95 Hz), 3.24-3.31 (2H, m), 2.82-2.98 (4H, m), 1.70-1.93 (5H, m), 1.32-1.43 (2H, m) ppm. MS (ESI) m/z: 674.5 (M+H)$^+$. Analytical HPLC: RT=6.16 min.

Example 165

(E)-6-(2-(3-(3-Chloro-2-fluoro-6-(1H-tetrazol-1-yl)phenyl)acryloyl)-5-(4-(2-(dimethylamino)ethylcarbamoyl)phenyl)-1,2,3,4-tetrahydroisoquinoline-1-carboxamido)nicotinic acid, bis-TFA salt

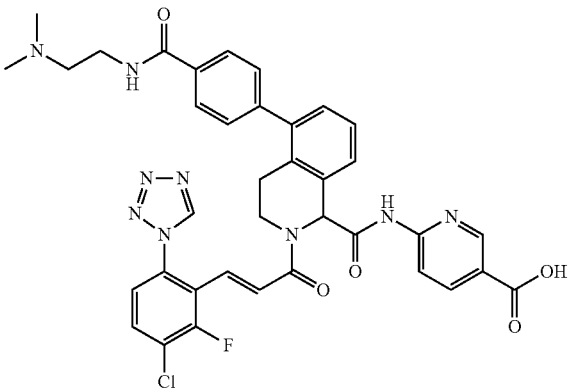 [SMILES: CN(C)CCNC(=O)c1ccc(-c2cccc3c2CCN(C(=O)/C=C/c2c(-n4cnnn4)ccc(Cl)c2F)C3C(=O)Nc2ccc(C(=O)O)cn2)cc1]

165A: tert-Butyl 6-aminonicotinate: To tert-butyl 6-bromonicotinate (2.0 g, 7.8 mmol), CuI (0.295 g, 1.6 mmol), L-proline (0.36 g, 3.1 mmol) and $K_2CO_3$ (3.21 g, 23.3 mmol) in degassed DMSO (15.5 ml) was added ammonium hydroxide (0.39 ml, 10.07 mmol) (28% aq.) and the reaction was heated at 85° C. After 3 h, additional CuI (0.295 g, 1.55 mmol) and ammonium hydroxide (0.392 ml, 10.07 mmol) were added. After 72 h, the cooled reaction was diluted with EtOAc, washed with $H_2O$, saturated $NaHCO_3$ solution, $H_2O$, brine, dried over $Na_2SO_4$, filtered and concentrated to give crude 165A (0.964 g) as a brown oil. MS (ESI) m/z: 195.1 $(M+H)^+$ 165B: tert-Butyl 5-bromo-1-(5-(tert-butoxycarbonyl)pyridin-2-ylcarbamoyl)-3,4-dihydroisoquinoline-2(1H)-carboxylate: $POCl_3$ (0.131 ml, 1.4 mmol) was added to a solution of 136C (0.50 g, 1.4 mmol) and 165A (0.545 g, 2.81 mmol) in pyridine (5.61 ml) at −15° C. The mixture was allowed to gradually come to rt and stirred for 14 h. The reaction mixture was diluted with EtOAc (40 mL), washed with 1.0 N HCl solution, $H_2O$, brine, dried over $Na_2SO_4$, filtered, and concentrated to give 165B. MS (ESI) m/z: 533.2 $(M+H)^+$.

Example 165: To a microwave vial was added 2.0 M $K_2CO_3$ (3 mL) and dioxane (10 mL)/EtOH (2 mL) were added 165B (0.15 g, 0.28 mmol) and N-(2-(dimethyl amino) ethyl)-4-(4,4,5,5-tetramethyl-1,3,2-dioxaborolan-2-yl)benzamide (0.18 g, 0.56 mmol). After degassing with $N_2$, tetrakis (triphenyl-phosphine)palladium (0) (0.016 g, 0.014 mmol) was added and the mixture irradiated in microwave at 130° C. for 15 min. The mixture was diluted with EtOAc (40 mL), washed with saturated $NaHCO_3$ solution, brine, dried over $Na_2SO_4$, filtered, and concentrated. The residue was treated with 50% TFA/DCM for 16 h before concentrating to give the amine TFA salt as a brown oil. In a separate round bottom flask, Intermediate 3A (0.076 g, 0.28 mmol) in DCM/THF (2:1, 15 mL) was treated with 1-chloro-N,N,2-trimethylprop-1-en-1-amine (0.041 g, 0.310 mmol). After 2 h, a solution of the amine TFA salt and pyridine (0.068 ml, 0.85 mmol) in DCM (15 mL) was added dropwise at 0° C. The reaction mixture was allowed to warm to rt. After 3 h, purification by reverse phase prep HPLC gave Example 165 as a white solid after lyophilization. $^1H$ NMR (400 MHz, DMSO-$d_6$) δ 11.45 (1H, s), 9.87 (1H, s), 8.86 (1H, d, J=2.20 Hz), 8.77 (1H, t, J=5.50 Hz), 8.22 (1H, dd, J=8.79, 2.75 Hz), 8.04 (1H, d, J=8.79 Hz), 7.92-8.00 (3H, m), 7.83 (1H, d, J=7.70 Hz), 7.63-7.69 (1H, m), 7.50 (2H, d, J=8.79 Hz), 7.39 (1H, t, J=7.70 Hz), 7.28 (1H, d, J=7.70 Hz), 6.93-7.06 (1H, m), 6.03 (1H, s), 4.04 (1H, dd, J=7.15, 4.95 Hz), 3.64 (2H, q, J=5.68 Hz), 3.45 (1H, d, J=2.75 Hz), 3.29 (2H, q, J=6.05 Hz), 3.10-3.21 (1H, m), 2.84-2.89 (6H, m), 2.75-2.83 (1H, m) ppm. MS (ESI) m/z: 738.3 $(M+H)^+$. Analytical HPLC: RT=5.41 min.

Example 166

(E)-6-(2-(3-(3-chloro-2-fluoro-6-(1H-tetrazol-1-yl) phenyl)acryloyl)-5-(4-(methylcarbamoyl)phenyl)-1,2,3,4-tetrahydroisoquinoline-1-carboxamido)nicotinic acid, TFA salt

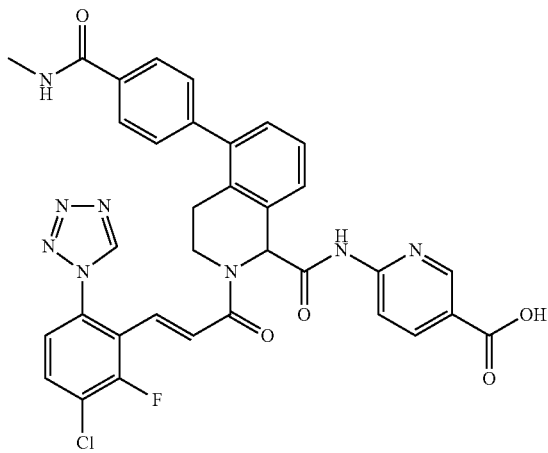 [SMILES: CNC(=O)c1ccc(-c2cccc3c2CCN(C(=O)/C=C/c2c(-n4cnnn4)ccc(Cl)c2F)C3C(=O)Nc2ccc(C(=O)O)cn2)cc1]

Example 166 (21.5 mg, 9.3%) was made in a similar manner as Example 165 substituting 4-(methylcarbamoyl)phenylboronic acid instead of N-(2-(dimethylamino)ethyl)-4-(4, 4,5,5-tetramethyl-1,3,2-dioxaborolan-2-yl)benzamide in the Suzuki reaction step. $^1H$ NMR (400 MHz, DMSO-$d_6$) δ 11.44 (1H, s), 9.87 (1H, s), 8.86 (1H, s), 8.52 (1H, q, J=4.40 Hz), 8.22 (1H, dd, J=8.79, 2.20 Hz), 8.05 (1H, d, J=8.79 Hz), 7.89-7.99 (3H, m), 7.82 (1H, d, J=7.70 Hz), 7.66 (1H, d, J=9.89 Hz), 7.45 (2H, d, J=8.25 Hz), 7.38 (1H, t, J=7.70 Hz), 7.28 (1H, d, J=6.60 Hz), 7.03-7.11 (1 H, m), 6.90-6.99 (1H, m), 6.03 (1H, s), 4.00-4.14 (1H, m), 3.42-3.55 (1H, m), 3.09-3.21 (1H, m), 2.76-2.87 (5H, m) ppm. MS (ESI) m/z: 681.2 $(M+H)^+$. Analytical HPLC: RT=7.66 min.

Example 167

(E)-4-(5-(3-Amino-3-oxopropyl)-2-(3-(3-chloro-2-fluoro-6-(1H-tetrazol-1-yl)phenyl)acryloyl)-1,2,3,4-tetrahydroisoquinoline-1-carboxamido)benzoic acid

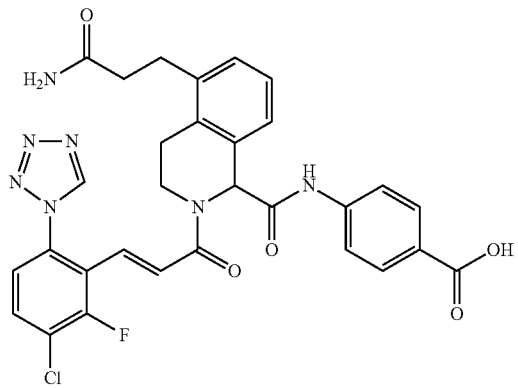 [SMILES: NC(=O)CCc1cccc2c1CCN(C(=O)/C=C/c1c(-n3cnnn3)ccc(Cl)c1F)C2C(=O)Nc1ccc(C(=O)O)cc1]

Example 167: 140A (0.090 g, 0.16 mmol) in EtOH (10 mL) was hydrogenated at 55 psi in the presence of $PtO_2$ (3.53 mg, 0.016 mmol) for 2h. The reaction was filtered through a plug of Celite® and the filtrate was concentrated. The residue was treated with 50% TFA/DCM for 2.5 h, concentrated, and the crude amine purified using reverse phase prep HPLC. DIEA (0.246 ml, 1.411 mmol) was added to the amine TFA salt and Intermediate 3 in DMF (8 mL) and heated at 50° C. overnight. Purification by reverse phase prep HPLC afforded the desired product (6 mg, 6%) as a white solid. $^1H$ NMR (500 MHz, DMSO-$d_6$) δ 12.71 (1H, br.s.), 10.75-10.81 (1H, m), 9.86 (1H, s), 7.83-7.99 (3H, m), 7.54-7.73 (4H, m), 7.49 (1H, dd, J=18.16, 7.43 Hz), 7.26-7.35 (1H, m), 7.08-7.21 (2H, m), 6.93-6.99 (1H, m), 6.50 (1H, d, J=15.68 Hz), 5.78-5.87 (1H, m), 4.07-4.21 (1H, m), 3.64-3.74 (1H, m), 2.76-3.21 (3H, m), 2.25-2.32 (1H, m) ppm. MS (ESI) m/z: 617.3 $(M+H)^+$. Analytical HPLC: RT=6.76 min.

Example 168

(R,E)-4-(2-(3-(3-Chloro-2-fluoro-6-(1H-tetrazol-1-yl)phenyl)acryloyl)-5-(1-methylpiperidin-4-yl)-1,2,3,4-tetrahydroisoquinoline-1-carboxamido)benzoic acid, TFA salt

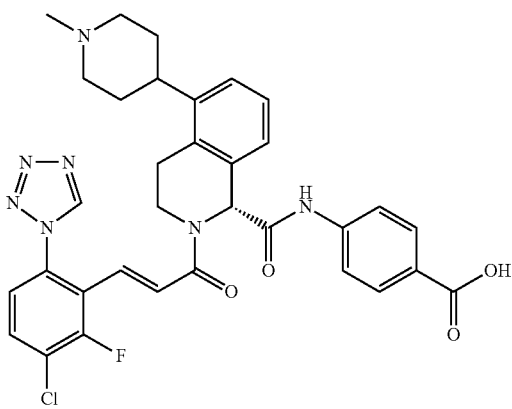 [SMILES: CN1CCC(c2cccc3c2CCN(C(=O)/C=C/c2c(-n4cnnn4)ccc(Cl)c2F)[C@H]3C(=O)Nc2ccc(C(=O)O)cc2)CC1]

Example 168: Chiral HPLC separation of Example 149 (164 mg 0.216 mmol) using Chiralpak AD-H, 25×3 cm, 5 μm, using 60/40 CO$_2$/1:1 EtOH-IPA-0.1% DEA-0.1% HCOOH-3% H$_2$O at 40.0 mL/min, 100 bar BP, 35° C., afforded 42 mg (25%) of Example 168 (first eluting enantiomer) as a white solid. 1H NMR (400 MHz, MeOD) δ 9.57 (1H, s), 7.97 (2H, d, J=8.59 Hz), 7.82 (1H, t, J=8.08 Hz), 7.59-7.71 (2H, m), 7.43-7.55 (2H, m), 7.30 (2H, d, J=17.43 Hz), 7.19 (1H, d, J=15.92 Hz), 6.97 (1H, d, J=16.17 Hz), 5.86 (1H, s), 4.10-4.28 (1H, m), 3.56-3.74 (4H, m), 3.15-3.26 (3H, m), 3.05-3.17 (1H, m), 2.97 (3H, s), 1.90-2.18 (4H, m) ppm. MS (ESI) m/z: 644.3 (M+H)$^+$. Analytical HPLC: RT=5.13 min.

Example 169

(S,E)-4-(2-(3-(3-Chloro-2-fluoro-6-(1H-tetrazol-1-yl)phenyl)acryloyl)-5-(1-methylpiperidin-4-yl)-1,2,3,4-tetrahydroisoquinoline-1-carboxamido)benzoic acid, TFA salt

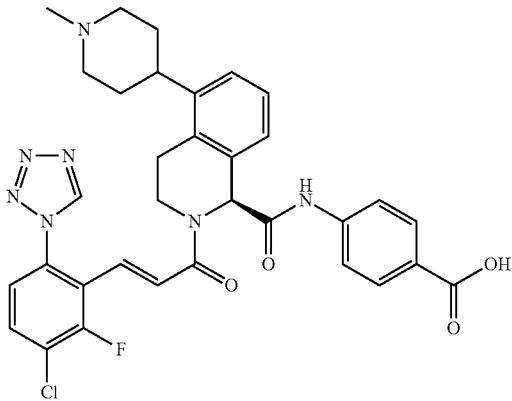 [SMILES: CN1CCC(c2cccc3c2CCN(C(=O)/C=C/c2c(-n4cnnn4)ccc(Cl)c2F)[C@@H]3C(=O)Nc2ccc(C(=O)O)cc2)CC1]

Example 169: Chiral HPLC separation of Example 149 (164 mg 0.216 mmol) using Chiralpak AD-H, 25×3 cm, 5 μm, using 60/40 CO$_2$/1:1 EtOH-IPA-0.1% DEA-0.1% HCOOH-3% H$_2$O at 40.0 mL/min, 100 bar BP, 35° C., afforded 37 mg (22%) of Example 169 second eluting enantiomer) as a white solid. 1H NMR (400 MHz, MeOD) δ 9.45 (1H, s), 7.85 (2H, d, J=8.84 Hz), 7.70 (1H, t, J=8.21 Hz), 7.53 (2H, d, J=8.84 Hz), 7.30-7.46 (2H, m), 7.14-7.28 (2H, m), 7.07 (1H, d, J=15.92 Hz), 6.85 (1H, d, J=15.92 Hz), 5.74 (1H, s), 4.05 (1H, d, J=12.38 Hz), 3.41-3.67 (4H, m), 3.06-3.19 (3H, m), 2.92-3.05 (1H, m), 2.85 (3H, s), 1.92-2.18 (4H, m) ppm. MS (ESI) m/z: 644.3 (M+H)$^+$. Analytical HPLC: RT=5.16 min.

Example 170

(E)-2-(3-(3-Chloro-2-fluoro-6-(1H-tetrazol-1-yl)phenyl)acryloyl)-N-(6-methoxypyridin-3-yl)-5-(4-(methylcarbamoyl)phenyl)-1,2,3,4 tetrahydroisoquinoline-1-carboxamide, TFA salt

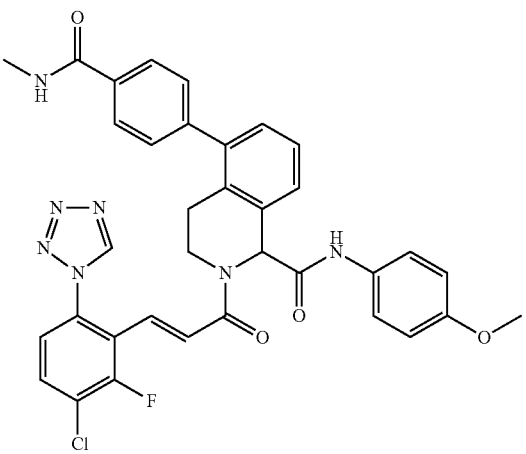

170A: 2-tert-Butyl 1-methyl 5-(4-(methylcarbamoyl)phenyl)-3,4-dihydroisoquinoline-1,2(1H)-dicarboxylate: To a flame-dried RBF was added 136D (2.0 g, 5.4 mmol), 4-(methylcarbamoyl)phenylboronic acid (1.93 g, 10.8 mmol), potassium phosphate, tribasic (2.29 g, 10.8 mmol) and PdCl$_2$ (dppf)-CH$_2$Cl$_2$ Adduct (0.44 g, 0.54 mmol). The flask was purged with argon for several minutes and then degassed DMSO (36.0 ml) was added. The reaction mixture was warmed to 90° C. to give a black solution. After 5 h, the reaction was partitioned between H$_2$O and DCM and the layers separated. The aqueous layer was extracted with DCM (1×). The combined organic layers were washed with H$_2$O, brine, dried over MgSO$_4$, filtered and concentrated. Purification by column chromatography on silica gel gave 170A as an off-white foam. MS (ESI) m/z: 425.2 (M+H)$^+$.

170B: 2-(tert-Butoxycarbonyl)-5-(4-(methylcarbamoyl)phenyl)-1,2,3,4-tetrahydroisoquinoline-1-carboxylic acid: 170A (1.56 g, 3.68 mmol) was dissolved in THF/MeOH (1:1, 50 mL) and treated with NaOH (18.38 ml, 18.38 mmol). After 20 h, the organics evaporated and pH of the remaining aqueous layer adjusted to 3 with 1 M HCl solution. This solution was extracted with EtOAc, washed with H$_2$O, brine, dried over Na$_2$SO$_4$, filtered, and concentrated to give 170B: (1.48 g, 98% yield) as a light tan solid. MS (ESI) m/z: 411.1 (M+H)$^+$.

Example 170: 170B (0.050 g, 0.122 mmol), EDC (0.023 g, 0.122 mmol), 1-hydroxybenzotriazole hydrate (0.019 g, 0.122 mmol) and DIEA (0.032 mL, 0.183 mmol) were added to DCM (5 mL). After 15 minutes, 5-amino-2-methoxypyridine (0.015 g, 0.122 mmol) was added. The reaction mixture was washed with 1.0 M HCl solution, brine, dried over Na$_2$SO$_4$, filtered, and concentrated. The residue was treated with 50% TFA/DCM. After 3 h, the reaction mixture was concentrated to dryness. The crude amine was purified by reverse phase prep HPLC. DIEA (0.032 mL, 0.183 mmol) was added to a solution of the amine TFA salt, Intermediate 3 (0.045 g, 0.122 mmol), and DMF (3 mL). The resulting mixture was heated 50° C. After 5 h, the reaction mixture was cooled to rt and purified directly by reverse phase prep HPLC to afford the title compound as a white solid. $^1$H NMR (400

MHz, DMSO-d$_6$) δ 10.52 (1H, s), 9.85 (1H, s), 7.85-8.00 (5H, m), 7.65 (2H, dd, J=7.96, 3.66 Hz), 7.44 (2H, d, J=8.08 Hz), 7.37 (1H, t, J=7.58 Hz), 7.26 (1H, d, J=7.58 Hz), 7.03-7.10 (1H, m), 6.92-6.99 (1H, m), 6.78 (1H, d, J=8.84 Hz), 5.87 (1H, s), 3.95-4.13 (1H, m), 3.80 (3H, s), 3.48-3.66 (1H, m), 2.97-3.15 (1H, m) ppm. MS (ESI) m/z: 667.2 (M+H)$^+$. Analytical HPLC: RT=8.25 min.

Example 171

(E)-4-(2-(3-(3-Chloro-2-fluoro-6-(1H-tetrazol-1-yl) phenyl)acryloyl)-5-(1-methyl-1H-pyrazol-4-yl)-1,2, 3,4-tetrahydroisoquinoline-1-carboxamido)benzoic acid

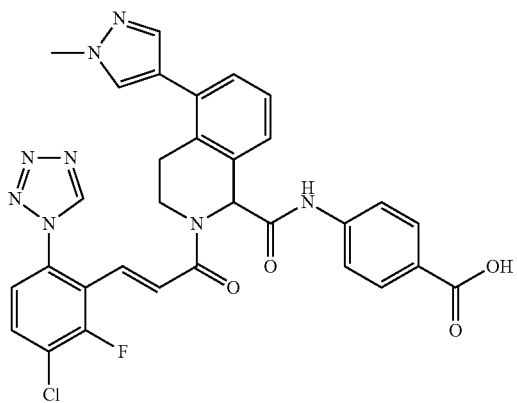 [SMILES: Cn1cc(-c2cccc3c2CCN(C(=O)/C=C/c2c(-n4cnnn4)ccc(Cl)c2F)C3C(=O)Nc2ccc(C(=O)O)cc2)cn1]

Example 171 was prepared in a similar manner as Example 73 (Table 7) substituting 1-methyl-4-(4,4,5,5-tetramethyl-1, 3,2-dioxaborolan-2-yl)-1H-pyrazole instead of 4-(2-(dimethyl amino)ethylcarbamoyl)phenylboronic acid, HCl salt in the Suzuki reaction and Intermediate 3 in the place of (E)-2, 5-dioxopyrrolidin-1-yl 3-(6-acetyl-3-chloro-2-fluorophenyl) acrylate in the amide formation step. $^1$H NMR (400 MHz, DMSO-d$_6$) δ 10.77 (1H, s), 9.86 (1H, s), 7.85-8.00 (4H, m), 7.61-7.73 (4H, m), 7.49-7.60 (1H, m), 7.23-7.36 (2H, m), 7.05-7.14 (1H, m), 6.91-7.00 (1H, m), 5.84 (1H, s), 4.04-4.14 (1H, m), 3.90 (3H, s), 3.53-3.65 (1H, m), 2.97-3.09 (1H, m) ppm. MS (ESI) m/z: 627.2 (M+H)$^+$. Analytical HPLC: RT=8.12 min.

Example 172

(E)-4-(2-(3-(3-Chloro-2-fluoro-6-(1H-tetrazol-1-yl) phenyl)acryloyl)-5-(1-(2-morpholinoethyl)-1H-pyrazol-4-yl)-1,2,3,4-tetrahydroisoquinoline-1-carboxamido)benzoic acid, TFA salt

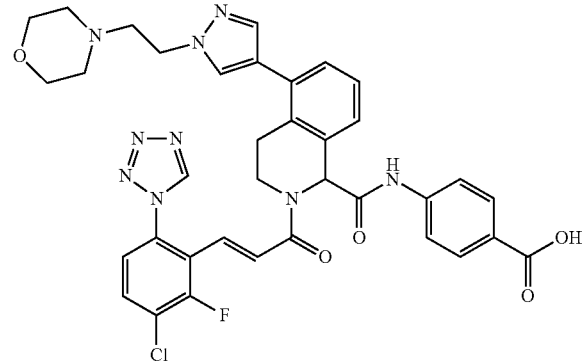 [SMILES: O=C(O)c1ccc(NC(=O)C2c3cccc(-c4cnn(CCN5CCOCC5)c4)c3CCN2C(=O)/C=C/c2c(-n3cnnn3)ccc(Cl)c2F)cc1]

Example 172 was prepared in a similar manner as Example 73 (Table 7) substituting 4-(2-(4-(4,4,5,5-tetramethyl-1,3,2-dioxaborolan-2-yl)-1H-pyrazol-1-yl)ethyl)morpholine instead of 4-(2-(dimethylamino)ethylcarbamoyl)phenylboronic acid, HCl salt in the Suzuki reaction and Intermediate 3 in the place of (E)-2,5-dioxopyrrolidin-1-yl 3-(6-acetyl-3-chloro-2-fluorophenyl)acrylate in the amide formation step. $^1$H NMR (400 MHz, DMSO-d$_6$) δ 10.82 (1H, s), 9.87 (1H, s), 8.09 (1H, s), 7.93-8.00 (2H, m), 7.87 (2H, d, J=8.79 Hz), 7.79 (1H, s), 7.65-7.71 (3H, m), 7.58 (1H, d, J=6.05 Hz), 7.27-7.37 (2H, m), 6.93-7.08 (2H, m), 5.84 (1H, s), 4.60 (2H, t, J=6.05 Hz), 3.89-4.13 (2H, m), 3.60-3.78 (3H, m), 3.49-3.59 (1H, m), 3.34-3.48 (1H, m), 3.10-3.27 (2H, m), 2.97-3.06 (1H, m), 2.88 (2H, s), 2.71-2.74 (2H, m) ppm. MS (ESI) m/z: 726.2 (M+H)$^+$. Analytical HPLC: RT=5.64 min.

Example 173

(E)-4-(2-(3-(3-Chloro-2-fluoro-6-(1H-tetrazol-1-yl) phenyl)acryloyl)-5-(1-methyl-1H-pyrazol-5-yl)-1,2, 3,4-tetrahydroisoquinoline-1-carboxamido)benzoic acid

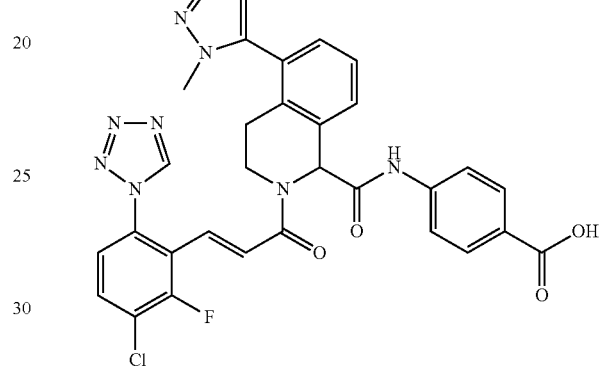

Example 173 was prepared in a similar manner as Example 53 substituting 1-methyl-5-(4,4,5,5-tetramethyl-[1,3,2]dioxaborolan-2-yl)-1H-pyrazole instead of 4-(2-(dimethylamino) ethylcarbamoyl)phenylboronic acid, HCl salt in the Suzuki reaction. $^1$H NMR (500 MHz, DMSO-d$_6$) δ 10.86 (1H, s), 9.86 (1H, s), 7.92-8.00 (1H, m), 7.89 (2H, d, J=8.80 Hz), 7.76 (1H, d, J=7.70 Hz), 7.71 (2H, d, J=8.80 Hz), 7.62-7.68 (1H, m), 7.50-7.56 (1H, m), 7.41 (1H, t, J=7.70 Hz), 7.26-7.35 (1H, m), 7.05-7.12 (1H, m), 6.94-7.00 (1H, m), 6.33 (1H, d, J=1.93 Hz), 5.91 (1H, s), 4.03-4.17 (1H, m), 3.57-3.67 (4H, m), 2.94-3.05 (1H, m), 2.64 (1H, dt, J=15.96, 4.81 Hz) ppm. MS (ESI) m/z: 627.2 (M+H)$^+$. Analytical HPLC: RT=7.97 min.

Example 174

(E)-4-(2-(3-(3-chloro-2-fluoro-6-(1H-tetrazol-1-yl) phenyl)acryloyl)-5-(1-(3-hydroxypropyl)-1H-pyrazol-4-yl)-1,2,3,4-tetrahydroisoquinoline-1-carboxamido)benzoic acid

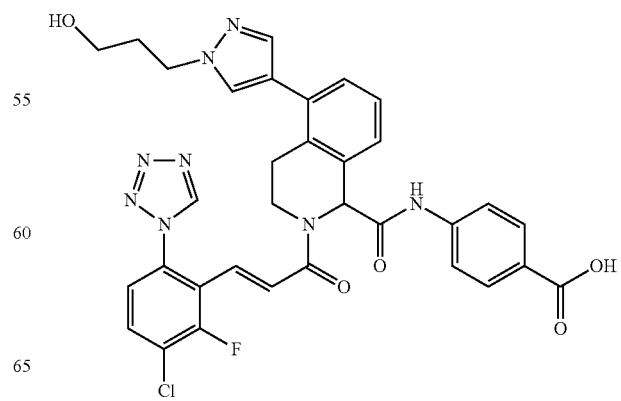

Example 174 was prepared in a similar manner as Example 53 using appropriate intermediates. ¹H NMR (500 MHz, DMSO-d₆) δ 10.79 (1H, s), 9.87 (1H, s), 7.85-7.99 (4H, m), 7.62-7.74 (4H, m), 7.51-7.59 (1H, m), 7.22-7.38 (2H, m), 7.08-7.16 (1H, m), 6.90-7.01 (1H, m), 5.84 (1H, s), 4.18-4.25 (2H, m), 4.05-4.14 (1H, m), 3.53-3.63 (1H, m), 3.38-3.47 (2H, m), 3.13-3.26 (1H, m), 3.03 (1H, ddd, J=16.02, 4.88, 4.68 Hz), 1.97 (2H, qd, J=6.65, 6.46 Hz) ppm. MS (ESI) m/z: 671.2 (M+H)⁺. Analytical HPLC: RT=7.44 min.

Example 175

(E)-4-(5-(3-amino-1H-indazol-6-yl)-2-(3-(3-chloro-2-fluoro-6-(1H-tetrazol-1-yl)phenyl)acryloyl)-1,2,3,4-tetrahydroisoquinoline-1-carboxamido)benzoic acid, TFA salt

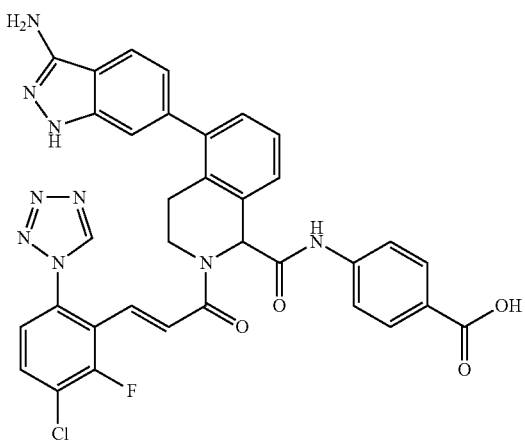 [SMILES: Nc1n[nH]c2cc(-c3cccc4c3CCN(C(=O)/C=C/c3c(-n5cnnn5)ccc(Cl)c3F)C4C(=O)Nc3ccc(C(=O)O)cc3)ccc12]

Example 175: To a large microwave vial containing 2.0M K₂CO₃ (2 mL) was added dioxane (10 mL)/EtOH (3 mL). To the above solution was then added tert-butyl 5-bromo-1-(4-(tert-butoxycarbonyl)phenylcarbamoyl)-3,4-dihydroisoquinoline-2(1H)-carboxylate (0.25 g, 0.47 mmol) and 4-cyano-3-fluorophenylboronic acid (0.155 g, 0.941 mmol) and degassed with N₂ for 10 mins. To the above mixture was then added, Tetrakis(triphenylphosphine)palladium (0) (0.027 g, 0.024 mmol) and the mixture was irradiated at 130° C. for 15 mins. The reaction mixture was then diluted with EtOAc (40 mL), washed with saturated NaHCO₃ solution, brine, dried over Na₂SO₄, filtered, and concentrated. To the above residue in EtOH (9.41 mL) was then added hydrazine monohydrate (0.343 mL, 7.06 mmol) and heated in a microwave vial at 160° C. for 40 mins. The reaction mixture was then concentrated to dryness and the residue was treated with 50% TFA/DCM for 1.5 h, concentrated, and purified by prep HPLC. Product fractions were concentrated under vacuum. DIEA (0.246 ml, 1.411 mmol) was added to the amine TFA salt followed by (E)-2,5-dioxopyrrolidin-1-yl 3-(3-chloro-2-fluoro-6-(1H-tetrazol-1-yl)phenyl)acrylate (0.172 g, 0.470 mmol) in DMF (8 mL) and heated at 55° C. The crude product was then purified by prep HPLC to yield the desired product. ¹H NMR (500 MHz, DMSO-d₆) δ 10.83 (1H, s), 9.85 (1H, s), 7.81-7.98 (4H, m), 7.61-7.75 (4H, m), 7.17-7.42 (3H, m), 6.89-7.10 (3H, m), 5.89 (1H, s), 3.97-4.13 (1H, m), 3.49-3.62 (1H, m), 3.07-3.18 (1H, m), 2.85 (1H, dd, J=11.00, 4.68 Hz) ppm. MS (ESI) m/z: 678.4 (M+H)⁺. Analytical HPLC: RT=7.38 min.

Example 176

(R,E)-4-(2-(3-(3-Chloro-2-fluoro-6-(1H-tetrazol-1-yl)phenyl)acryloyl)-3,3-dimethyl-5-(4-(methyl carbamoyl)phenyl)-1,2,3,4-tetrahydroisoquinoline-1-carboxamido)benzoic acid

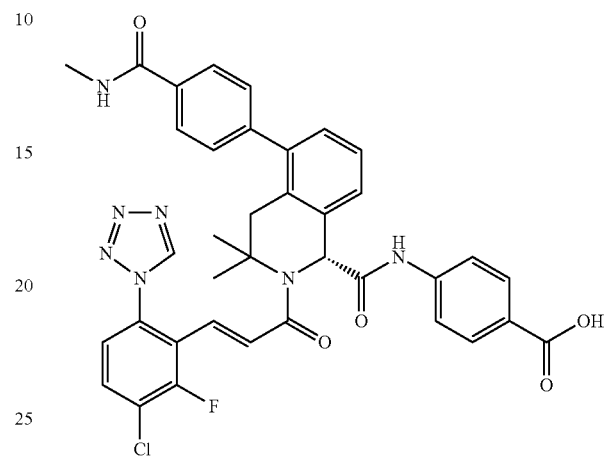

Example 176 was prepared from Example 135 tert-butyl ester intermediate by chiral HPLC separation using Chiralpak IA (250×4.6) mm eluting with hexane:EtOH (70:30) and 0.2% DEA at 1 mL/min. ¹H NMR (400 MHz, DMSO-d₆) δ 12.79 (1H, s), 10.53 (1H, s), 9.86 (1H, s), 8.49 (1H, q), 7.83-7.97 (6H, m), 7.72-7.64 (3H, m), 7.39-7.43 (3H, m), 7.32 (1H, d, J=7.2 Hz), 7.12 (1H, d, J=15.6 Hz), 6.86 (1H, bs), 5.87 (1H, bs), 3.37 (2H, bs), 2.81 (3H, d, J=4.4 Hz), 1.69 (3H, s), 1.08 (3H, s) ppm. MS (ESI) m/z: 708.0 (M+H)⁺. Analytical HPLC: RT=9.27 min.

Example 177

(S,E)-4-(2-(3-(3-Chloro-2-fluoro-6-(1H-tetrazol-1-yl)phenyl)acryloyl)-3,3-dimethyl-5-(4-(methyl carbamoyl)phenyl)-1,2,3,4-tetrahydroisoquinoline-1-carboxamido)benzoic acid

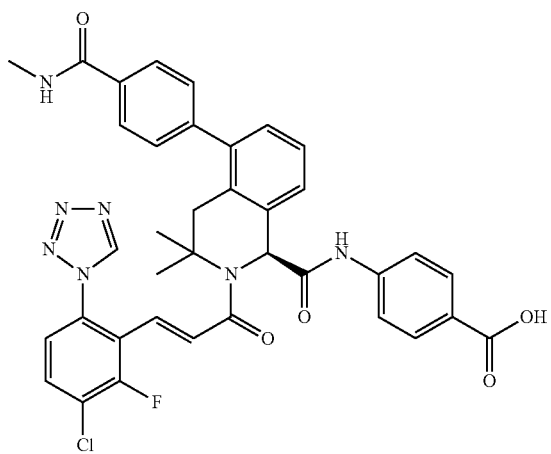 [SMILES: CNC(=O)c1ccc(-c2cccc3c2CC(C)(C)N(C(=O)/C=C/c2c(-n4cnnn4)ccc(Cl)c2F)[C@@H]3C(=O)Nc2ccc(C(=O)O)cc2)cc1]

Example 177 was prepared from Example 135 tert-butyl ester intermediate by chiral HPLC separation using Chiralpak IA (250×4.6) mm eluting with hexane:EtOH (70:30) and 0.2% DEA at 1 mL/min. $^1$H NMR (400 MHz, DMSO-$d_6$) δ 12.75 (1H, s), 10.53 (1H, s), 9.86 (1H, s), 8.50 (1H, q), 7.83-7.97 (6H, m), 7.64-7.72 (3H, m), 7.39-7.43 (3H, m), 7.32 (1H, d, J=7.2 Hz), 7.12 (1H, d, J=15.6 Hz), 6.95 (1H, bs), 5.87 (1H, bs), 3.37 (2H, bs), 2.81 (3H, d, J=4.4 Hz), 1.69 (3H, s), 1.08 (3H, s) ppm. MS (ESI) m/z: 708.0 (M+H)$^+$. Analytical HPLC: RT=9.27 min.

The following Examples in Table 11 were prepared according to methods analogous to that described for Example 123. Representative chiral compounds were obtained by chiral resolution of the appropriate late stage intermediate followed by purification,

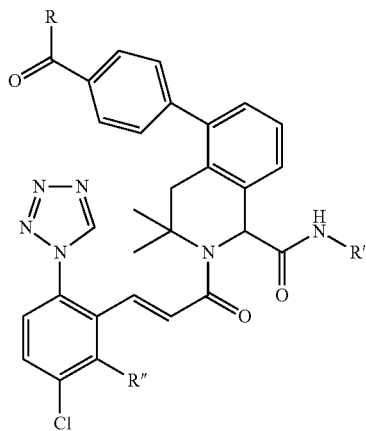

Example 181 (102 mg, 31%) was made in a similar manner as Example 137 substituting 1-[4-(4,4,5,5-tetramethyl-1,3,2-dioxaborolan-2-yl)phenyl]pyrrolidine instead of 4-(2-(dimethylamino)ethylcarbamoyl)phenylboronic acid, HCl salt in the Suzuki reaction and Intermediate 3A instead of Intermediate 12 in the final coupling step. 1H NMR (400 MHz, DMSO-$d_6$) δ 10.80 (1H, s), 9.87 (1H, s), 7.85-7.98 (3H, m), 7.61-7.75 (3H, m), 7.54-7.62 (1H, m), 7.26-7.34 (1H, m), 7.13-7.22 (3H, m), 7.03-7.09 (1H, m), 6.92-6.99 (1H, m), 6.62 (2H, d, J=8.79 Hz), 5.74-5.89 (1H, m), 3.99-4.11 (1H, m), 3.42-3.52 (1H, m), 3.23-3.35 (4H, m), 3.05-3.19 (1H, m), 2.83-2.96 (1H, m), 1.98 (4H, t, J=6.32 Hz) ppm. MS (ESI) m/z: 692.4 (M+H)$^+$. Analytical HPLC: RT=10.15 min.

The following Examples in Table 12 were prepared according to methods analogous to that described for Example 181. Representative chiral compounds were obtained by chiral resolution of the appropriate late stage intermediate followed by purification.

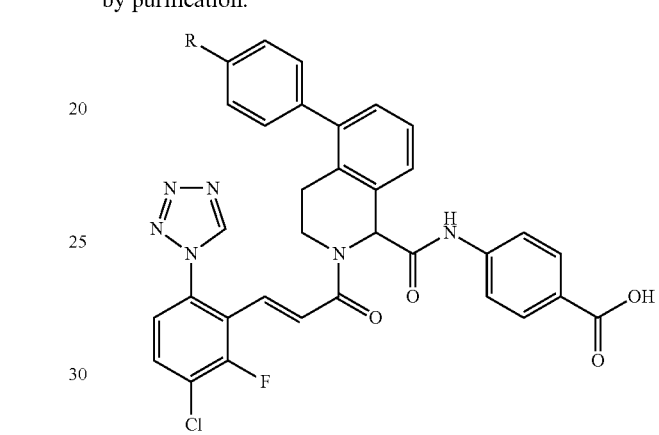

TABLE 11

| Example # | Stereochemistry | R | R' | R'' | M + H | RT |
|---|---|---|---|---|---|---|
| 178 | Racemic | —NHCH$_3$ | 4-PhCN | F | 689.2 | 2.012 |
| 179 | R-enantiomer | —NHCH$_3$ | 4-PhCN | F | 689.2 | 1.957 |
| 180 | R-enantiomer | —NHCH$_3$ | 4-PhCOOEt | F | 736.2 | 2.029 |

Example 181

(E)-4-(2-(3-(3-Chloro-2-fluoro-6-(1H-tetrazol-1-yl)phenyl)acryloyl)-5-(4-(pyrrolidin-1-yl)phenyl)-1,2,3,4-tetrahydroisoquinoline-1-carboxamido)benzoic acid, TFA salt

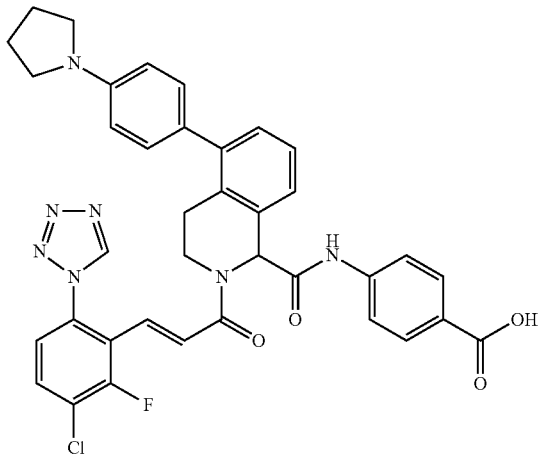 [SMILES: O=C(O)c1ccc(NC(=O)C2c3cccc(-c4ccc(N5CCCC5)cc4)c3CCN2C(=O)/C=C/c2c(-n3cnnn3)ccc(Cl)c2F)cc1]

TABLE 12

| Example # | Stereochemistry | R | M + H | RT |
|---|---|---|---|---|
| 182 | Racemic | ![pyrrolidinone] | 706.4 | 8.94 |
| 183 | Racemic | ![pyrazole] | 689.4 | 9.94 |

Example 184

(E)-4-(2-(3-(3-Chloro-2-fluoro-6-(1H-tetrazol-1-yl)phenyl)acryloyl)-5-(dimethylamino)-1,2,3,4-tetrahydroisoquinoline-1-carboxamido)benzoic acid, TFA salt

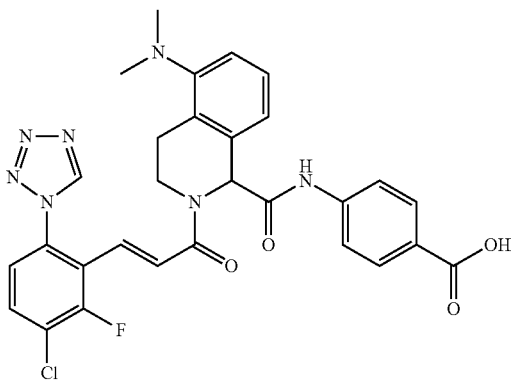 [SMILES: CN(C)c1cccc2c1CCN(C(=O)/C=C/c1c(-n3cnnn3)ccc(Cl)c1F)C2C(=O)Nc1ccc(C(=O)O)cc1]

Example 184 was prepared in a similar manner as Example 40, substituting Intermediate 3A for Intermediate 2 in the Ugi reaction. $^1$H NMR (400 MHz, MeOD) δ 9.56 (1H, s), 7.96 (2H, d, J=8.84 Hz), 7.81 (1H, t, J=8.08 Hz), 7.60-7.76 (4H, m), 7.47-7.60 (2H, m), 7.14-7.25 (1H, d, J=15.9 Hz), 6.95-7.07 (1H, d, J=15.9 Hz), 5.97 (1H, s), 4.14-4.31 (1H, m), 3.75 (1H, ddd, J=12.38, 8.72, 3.92 Hz), 3.29-3.38 (7H, m), 3.14-3.23 (1H, m) ppm. MS (ESI) m/z: 590.4 (M+H)$^+$. Analytical HPLC: RT=5.56 min.

Example 185

(E)-ethyl 4-(2-(3-(3-Chloro-2-fluoro-6-(1H-tetrazol-1-yl)phenyl)acryloyl)-5-(6-(methylcarbamoyl) pyridin-3-yl)-1,2,3,4-tetrahydroisoquinoline-1-carboxamido)benzoate, TFA salt

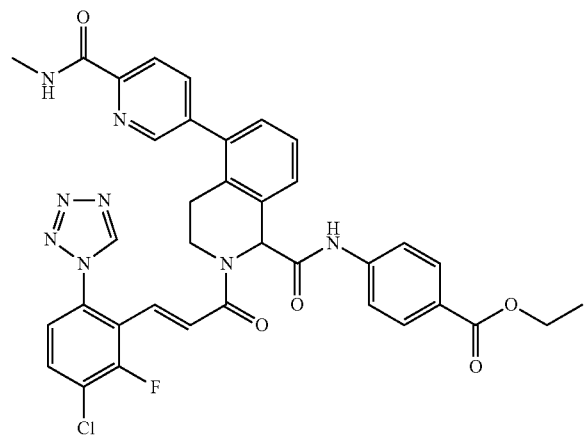 [SMILES: CCOC(=O)c1ccc(NC(=O)C2c3cccc(-c4ccc(C(=O)NC)nc4)c3CCN2C(=O)/C=C/c2c(-n3cnnn3)ccc(Cl)c2F)cc1]

Example 185: To 2.0 M K$_2$CO$_3$ (2 mL) and dioxane (10 mL)/EtOH (3 mL) were added 139A (0.500 g, 0.941 mmol) and N-methyl-5-(4,4,5,5-tetramethyl-1,3,2-dioxaborolan-2-yl)picolinamide (0.296 g, 1.129 mmol). After degassing, tetrakis(triphenylphosphine)palladium (0) (0.054 g, 0.047 mmol) was added and the mixture was irradiated in a microwave at 130° C. for 15 min. The reaction mixture was diluted with EtOAc (40 mL), washed with saturated NaHCO$_3$ solution, brine, dried over Na$_2$SO$_4$, filtered, and concentrated. Boc deprotection of the amine and transesterfication of the t-butyl ester to a ethyl ester was accomplished by dissolving the residue in EtOH (10 mL) and adding HCl (4.0 M in dioxane) (10 ml, 40.0 mmol). After 3 days, the reaction mixture was concentrated to dryness. The residue was taken up in EtOAc and neutralized with aq.NaHCO$_3$. The organic layer was washed with brine, dried over Na$_2$SO$_4$, filtered, and concentrated. The amine, Intermediate 3 (0.344 g, 0.94 mmol), and DIEA (0.49 ml, 2.82 mmol) were added to DMF (10 mL) and heated at 50° C. for 18 h. The crude mixture was purified by reverse phase HPLC to give the desired product (110 mg, 13%) as a white solid. $^1$H NMR (500 MHz, DMSO-d$_6$) δ 10.89 (1H, s), 9.85-9.88 (1H, m), 8.84 (1H, q, J=4.59 Hz), 8.63 (1H, d, J=1.65 Hz), 8.12 (1H, d, J=7.98 Hz), 8.02 (1H, dd, J=7.98, 2.20 Hz), 7.90-7.98 (3H, m), 7.72-7.78 (3H, m), 7.64-7.69 (1H, m), 7.41-7.47 (1H, m), 7.36 (1H, d, J=6.60 Hz), 7.07-7.12 (1H, m), 6.92-6.99 (1H, m), 5.92 (1H, s), 4.29 (2H, q, J=7.06 Hz), 4.04-4.14 (1H, m), 3.61 (1H, ddd, J=12.45, 8.87, 3.99 Hz), 3.05-3.15 (1H, m), 2.79-2.89 (4H, m), 1.32 (3H, t, J=7.01 Hz) ppm. MS (ESI) m/z: 709.5 (M+H)$^+$. Analytical HPLC: RT=10.04 min.

The following Examples in Table 13 were prepared according to methods analogous to that described for Example 185. Representative chiral compounds were obtained by chiral resolution of the appropriate late stage intermediate followed by purification.

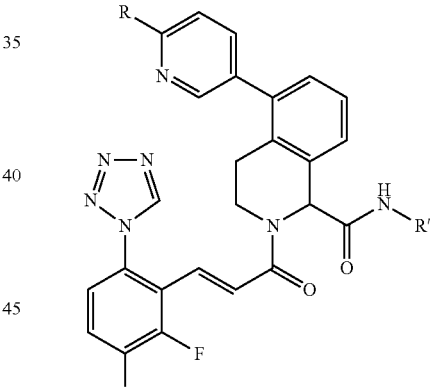

TABLE 13

| Example # | Stereochemistry | R | R' | M + H | RT |
|---|---|---|---|---|---|
| 186 | S-enantiomer$^a$ | | 4-PhCOOH | 681.5 | 8.75 |
| 187 | R-enantiomer$^a$ | | 4-PhCOOH | 681.4 | 8.75 |

TABLE 13-continued

| Example # | Stereo-chemistry | R | R' | M + H | RT |
|---|---|---|---|---|---|
| 188 | R-enantiomer[b] | 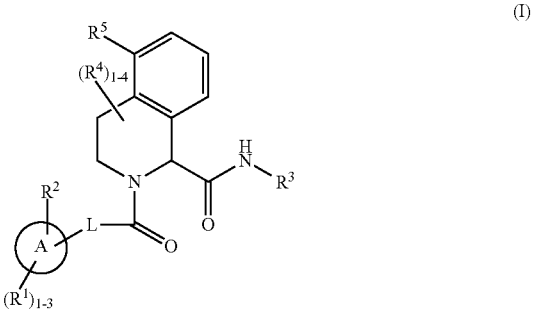 | 4-PhCOOEt | 709.5 | 10.57 |
| 189 | S-enantiomer[b] | 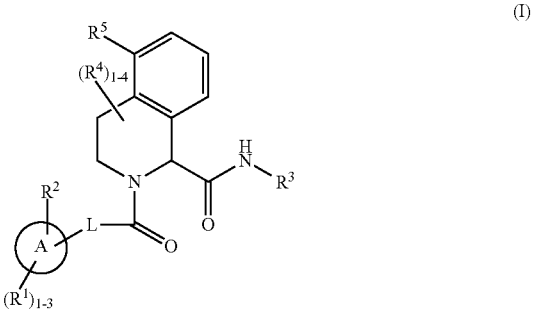 | 4-PhCOOEt | 709.5 | 10.59 |
| 190 | Racemic | —NH$_2$ | 4-PhCOOH | 639.2 | 5.18 |
| 191 | Racemic | —N(CH$_3$)$_2$ | 4-PhCOOH | 667.3 | 5.42 |

[a]Chiralpak AD-H 250 × 4.6 mm ID, 5 μm, using 55/45/0.1, CO$_2$/(1:1 EtOH-ACN)/DEA hold for 8 min. then gradient to 60/40, 3.0 mL/min, 150 bar BP, 35° C.
[b]Chiralpak AD-H SFC, 250 × 30 cm ID, 5 μm, using 50% 1:1 Isopropanol-MeOH-0.1% DEA/50% CO$_2$ at 65 mL/min, 150 Bar, 35° C.

The following Examples in Table 14 were made by Ugi reaction as described in Example 1 using appropriate nitrile intermediates. Deprotection with TFA/DCM was carried out where necessary. Single enantiomers were isolated by chiral HPLC at a protected late stage intermediate and then, deprotected where indicated.

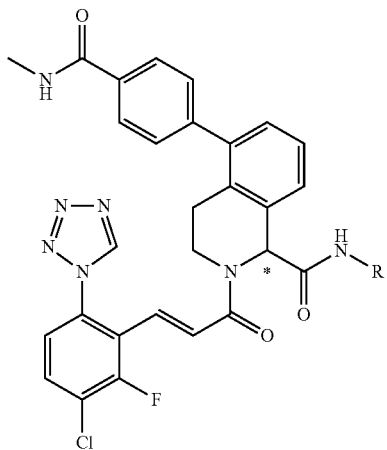

TABLE 14

| Example # | Stereochemistry | R | M + H | RT |
|---|---|---|---|---|
| 192 | Racemic | ![piperidine] | 643.4 | 5.25 |
| 193 | Racemic | ![cyclobutylmethyl] | 614.4 | 8.38 |

What is claimed is:
1. A compound according to formula (I):

(I)

or a stereoisomer, tautomer, pharmaceutically acceptable salt thereof, wherein:
ring A is $C_{3-10}$ carbocycle;
L is selected from the group consisting of: a bond, —CHR$^{10}$CHR$^{10}$—, —CR$^{10}$═CR$^{10}$—, and —C≡C—;
$R^1$, at each occurrence, is selected from the group consisting of: H, halo, $C_{1-2}$ alkyl, —O($C_{1-4}$ alkyl), CN, —CH$_2$NH$_2$, and —C(═NH)NH$_2$;
$R^2$ is selected from the group consisting of: H, halo, CN, OH, $C_{1-6}$ alkyl, $C_{1-4}$ alkoxy, $C_{1-6}$haloalkyl, $C_{1-6}$haloalkoxy, CO($C_{1-4}$ alkyl), CONH$_2$, CO$_2$H and a 5- to 7-membered heterocycle comprising carbon atoms and 1-4 heteroatoms selected from N, NH, N($C_{1-4}$ alkyl), O, and S(O)$_p$, wherein said heterocycle is substituted with 1-2 $R^{2a}$;
$R^{2a}$, at each occurrence, is selected from the group consisting of: H, halo, $C_{1-4}$ alkyl, CO$_2$H, —CO$_2$($C_{1-4}$ alkyl), —CONH$_2$, —CH$_2$OH, —CH$_2$OC$_{1-4}$alkyl, and —CH$_2$NH$_2$;
$R^3$ is selected from the group consisting of: $C_{1-6}$ alkyl substituted with 1-3 $R^{3a}$, $C_{3-10}$ carbocycle substituted with 1-3 $R^{3a}$, and 5-10 membered heterocycle containing carbon atoms and 1-4 heteroatoms selected from the group consisting of N, NR$^7$, O, and S(O)$_p$; wherein said heterocycle is substituted with 1-3 $R^{3a}$;
$R^{3a}$, at each occurrence, is selected from the group consisting of: H, halo, $C_{1-4}$ alkyl, —OH, $C_{1-4}$ alkoxy, —CN, —NH$_2$, —NH($C_{1-4}$ alkyl), —N($C_{1-4}$ alkyl)$_2$, —CO$_2$H, —CH$_2$CO$_2$H, —CO$_2$($C_{1-4}$ alkyl), —CO$_2$—$C_{1-4}$ alkylene-O($C_{1-4}$ alkyl), —CO$_2$—$C_{1-4}$ alkylene-N($C_{1-4}$ alkyl)$_2$, —CO$_2$—$C_{1-4}$ alkylene-O—$C_{1-4}$ alkylene-N($C_{1-4}$ alkyl)$_2$, —CO$_2$—$C_{1-4}$ alkylene-O—$C_{1-4}$ alkylene-O($C_{1-4}$ alkyl), —CONH$_2$, —CONH($C_{1-6}$ alkyl), —CON($C_{1-4}$ alkyl)$_2$, —CONH—$C_{1-4}$ alkylene-CO$_2$($C_{1-4}$ alkyl), —CONHCO$_2$C$_{1-4}$ alkyl, —CONH—$C_{1-4}$ alkylene-NHCO($C_{1-4}$ alkyl), —CONH—$C_{1-4}$ alkylene-CONH$_2$, —NHCOC$_{1-4}$ alkyl, —NHCO$_2$($C_{1-4}$ alkyl), $R^c$, —CONHR$^c$, and —CO$_2$R$^c$;
$R^4$, at each occurrence, is selected from the group consisting of: H, halo, and $C_{1-4}$ alkyl;
$R^5$ is selected from the group consisting of: halo, $C_{1-4}$ alkyl substituted with 0-2 $R^b$, $C_{2-4}$ alkenyl substituted with 0-2 $R^b$, —OH, —CN, —NH$_2$, —N($C_{1-4}$ alkyl)$_2$, —OCO($C_{1-4}$ alkyl), —O—$C_{1-4}$ alkylene-O($C_{1-4}$ alkyl), —O—$C_{1-4}$ alkylene-N($C_{1-4}$ alkyl)$_2$, —CO$_2$H, —CO$_2$($C_{1-4}$ alkyl), —CONH$_2$, —(CH$_2$)$_2$CONH$_2$, —CONR$^9$($C_{1-4}$ alkyl), —CON($C_{1-4}$ alkyl)$_2$, —CONR$^9$—$C_{1-4}$ alkylene-O($C_{1-4}$ alkyl), —CONR$^9$—$C_{1-4}$ alkylene-N($C_{1-4}$ alkyl)$_2$, —CONR$^9$—$C_{1-4}$ alkylene-CO$_2$($C_{1-4}$ alkyl), —NR$^9$COC$_{1-4}$ alkyl, —NR$^9$CO$_2$C$_{1-4}$ alkyl, —NR$^9$CONH($C_{1-4}$ alkyl), —NR$^9$CONR$^9$—$C_{1-4}$ alkylene-CO$_2$C$_{1-4}$ alkyl, —NR$^9$—$C_{1-4}$ alkylene-N($C_{1-4}$ alkyl)$_2$, —NR$^9$SO$_2$($C_{1-4}$ alkyl), —S($C_{1-4}$ alkyl), —SO$_2$($C_{1-4}$ alkyl), —SO$_2$NH$_2$, $R^8$, $C_{2-4}$ alkenylene-R$^8$, —OR⁸, —COR⁸, $C_{2-4}$ alkenylene-COR⁸, —CONR⁹R⁸, —NR⁹COR⁸, —NR⁹CO₂R⁸, and —NR⁹CONR⁹R⁸;

R⁷, at each occurrence, is selected from the group consisting of: H, $C_{1-4}$ alkyl, $COC_{1-4}$ alkyl, $CO_2(C_{1-4}$ alkyl), CO₂Bn, —CONH—$C_{1-4}$ alkylene-$CO_2C_{1-4}$ alkyl, phenyl, benzyl, and —CO₂—$C_{1-4}$ alkylene-aryl;

R⁸, at each occurrence, is selected from the group consisting of: —(CH₂)ₙ—$C_{3-10}$ carbocycle and —(CH₂)ₙ-5- to 10-membered heterocycle containing carbon atoms and 1-4 heteroatoms selected from the group consisting of: N, $NR^a$, O, and $S(O)_p$; wherein said carbocycle or heterocycle is substituted with 0-3 $R^b$;

R⁹, at each occurrence, is selected from the group consisting of: H and $C_{1-4}$alkyl;

R¹⁰, at each occurrence, is selected from the group consisting of: H, halo, OH, and $C_{1-4}$ alkyl;

$R^a$ is selected from the group consisting of: H, $C_{1-4}$ alkyl, —(CH₂)ₙ—OH, CO($C_{1-4}$ alkyl), COCF₃, $CO_2(C_{1-4}$ alkyl), —CONH₂, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$;

$R^b$ is selected from the group consisting of: =O, halo, $C_{1-4}$ alkyl, $C_{1-4}$ alkoxy, OCF₃, NH₂, NO₂, $N(C_{1-4}$ alkyl)₂, CO($C_{1-4}$ alkyl), CO($C_{1-4}$ haloalkyl), $CO_2(C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$ alkyl), —CONH—$C_{1-4}$ alkylene-N($C_{1-4}$ alkyl)₂, —CONH—$C_{1-4}$ alkylene-N'($C_{1-4}$ alkyl)₂-$C_{1-4}$ alkylene-O—P(O)(OH)₂, —NHCO₂($C_{1-4}$ alkyl), —$R^c$, $COR^c$, $CO_2R^c$, and $CONHR^c$;

$R^c$ is, independently at each occurrence, selected from the group consisting of: —(CH₂)ₙ—$C_{3-6}$ cycloalkyl, —(CH₂)ₙ-phenyl, and —(CH₂)ₙ-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$ is selected from the group consisting of: =O, halo, —OH, $C_{1-4}$ alkyl, NH₂, NH($C_{1-4}$ alkyl), N($C_{1-4}$ alkyl)₂, $C_{1-4}$ alkoxy, and —NHCO($C_{1-4}$ alkyl), and heterocycle containing carbon atoms and 1-4 heteroatoms selected from the group consisting of: N, NH, N($C_{1-4}$ alkyl), O, and $S(O)_p$;

n, at each occurrence, is selected from 0, 1, 2, 3, and 4;

p, at each occurrence, is selected from 0, 1, and 2;

provided when R⁵ is heterocycle, the point of attachment of the heterocycle to the fused phenyl ring is not on a nitrogen atom.

2. The compound of claim 1 having formula (II):

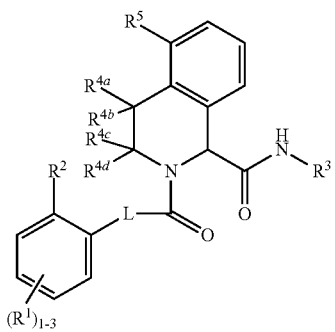

(II)

or a stereoisomer, tautomer, pharmaceutically acceptable salt thereof, wherein:

R¹, at each occurrence, is selected from the group consisting of: H, halo, $C_{1-2}$ alkyl, —O($C_{1-4}$ alkyl), and —C(=NH)NH₂;

$R^{4a}$, $R^{4b}$, $R^{4c}$, and $R^{4d}$ are independently selected from the group consisting of: H, F, and $C_{1-4}$ alkyl;

R⁵ is selected from the group consisting of: halo, $C_{1-4}$ alkyl substituted with 0-2 $R^b$, $C_{2-4}$ alkenyl substituted with 0-2 $R^b$, —OH, —CN, —N($C_{1-4}$ alkyl)₂, —O—$C_{1-4}$ alkylene-O($C_{1-4}$ alkyl), —O—$C_{1-4}$ alkylene-N($C_{1-4}$ alkyl)₂, —CO₂H, —CO₂($C_{1-4}$ alkyl), —CON($C_{1-4}$ alkyl)₂, —CONR⁹—$C_{1-4}$ alkylene-O($C_{1-4}$ alkyl), —CONR⁹—$C_{1-4}$ alkylene-CO₂($C_{1-4}$ alkyl), —NR⁹CO$C_{1-4}$ alkyl, NR⁹CO₂$C_{1-4}$ alkyl, —NR⁹CONR⁹—$C_{1-4}$ alkylene-CO₂$C_{1-4}$ alkyl, —NHSO₂($C_{1-4}$ alkyl), R⁸, $C_{2-4}$ alkenylene-R⁸, —OR⁸, —COR⁸, $C_{2-4}$ alkenylene-COR⁸, —CONR⁹R⁸, —NR⁹COR⁸, and —NR⁹CONR⁹R⁸.

3. The compound of claim 2 having formula (III):

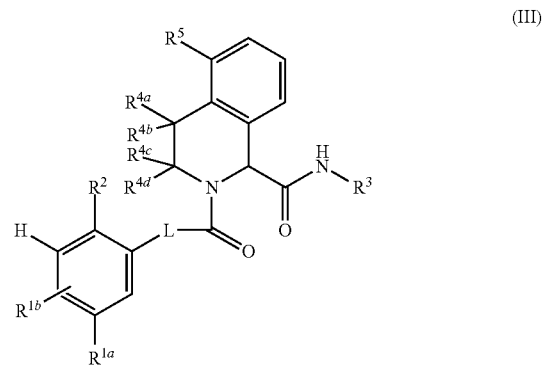

(III)

or a stereoisomer, tautomer, pharmaceutically acceptable salt thereof, wherein:

$R^{1a}$ is selected from the group consisting of: H, halo, $C_{1-2}$ alkyl, and methoxy;

$R^{1b}$ is selected from the group consisting of: H and halo;

R² is selected from the group consisting of: H, F, CN, OH, $C_{1-4}$ alkoxy, —CHF₂, —CF₃, —CH₂NH₂, —OCHF₂, —CO($C_{1-4}$ alkyl), —CONH₂, —COOH, triazole substituted with $R^{2a}$, and tetrazole substituted with $R^{2a}$;

R³ is selected from the group consisting of: phenyl substituted with 1-2 $R^{3a}$, $C_{3-6}$ cycloalkyl substituted with 1-2 $R^{3a}$, and heterocycle substituted with 1-2 $R^{3a}$; wherein said heterocycle is selected from the group consisting of: piperidinyl, pyridyl, indolyl, and indazolyl;

$R^{3a}$, at each occurrence, is selected from the group consisting of: H, halo, —OH, —O($C_{1-4}$ alkyl), —CN, —CO₂H, —CONH₂, —CO₂($C_{1-4}$ alkyl), —CO₂—$C_{1-4}$ alkylene-O($C_{1-4}$ alkyl), —CO₂—$C_{1-4}$ alkylene-N($C_{1-4}$ alkyl)₂, —CO₂—$C_{1-4}$ alkylene-O—$C_{1-4}$ alkylene-N($C_{1-4}$ alkyl)₂, —CO₂—$C_{1-4}$ alkylene-O—$C_{1-4}$ alkylene-O ($C_{1-4}$ alkyl), —NHCO₂($C_{1-4}$ alkyl), $R^c$, and —CO₂$R^c$;

R⁵ is selected from the group consisting of: R⁸, $C_{2-4}$ alkenylene-R⁸, —OR⁸, COR⁸, $C_{2-4}$ alkenylene-COR⁸, —CONHR⁸, and NHCONHR⁸;

R⁸, at each occurrence, is selected from the group consisting of: —(CH₂)ₙ—$C_{3-6}$ cycloalkyl, —(CH₂)ₙ-phenyl and —(CH₂)ₙ-5- to 10-membered heterocycle containing carbon atoms and 1-4 heteroatoms selected from the group consisting of: N, $NR^a$, O, and $S(O)_p$; wherein said cycloalkyl, phenyl and heterocycle are substituted with 0-3 $R^b$;

$R^a$, at each occurrence, is selected from the group consisting of: H, $C_{1-4}$ alkyl, —(CH₂)ₙ—OH, CO($C_{1-4}$ alkyl), COCF₃, $CO_2(C_{1-4}$ alkyl), —CONH—$C_{1-4}$ alkylene-$CO_2(C_{1-4}$ alkyl), $C_{1-4}$ alkylene-$CO_2(C_{1-4}$ alkyl), $R^c$, and $CO_2R^c$;

$R^b$, at each occurrence, is selected from the group consisting of: halo, $C_{1-4}$ alkyl, $C_{1-4}$ alkoxy, $OCF_3$, $NH_2$, $NO_2$, $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, —$CONH$—$C_{1-4}$ alkylene-$CO_2(C_{1-4}$ alkyl), —$CONH$—$C_{1-4}$ alkylene-$N^+(C_{1-4}$ alkyl)$_2$-$C_{1-4}$ alkylene-$O$—$P(O)(OH)_2$, —$NHCO_2(C_{1-4}$ alkyl), $R^c$, $COR^c$, and $CONHR^c$; and $R^c$, at each occurrence, is selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, O, and $S(O)_p$; wherein each ring moiety is substituted with 0-2 $R^d$.

4. The compound of claim 3, wherein:

$R^{1a}$ is Cl;

$R^{1b}$ is selected from the group consisting of: H and F;

$R^2$ is selected from the group consisting of: H, F, $CF_3$, $COC_{1-4}$ alkyl, and tetrazolyl;

$R^3$ is selected from the group consisting of: phenyl substituted with 1-2 $R^{3a}$, $C_{3-6}$ cycloalkyl substituted with 1-2 $R^{3a}$, and indazolyl substituted with 1-2 $R^{3a}$;

$R^{3a}$, at each occurrence, is selected from the group consisting of: H, halo, —OH, —$O(C_{1-4}$ alkyl), —CN, —$CO_2H$, —$CONH_2$, —$CO_2(C_{1-4}$ alkyl), —$CO_2$—$(CH_2)_{1-4}$—$O(C_{1-4}$ alkyl), —$CO_2$—$(CH_2)_{1-4}$—$N(C_{1-4}$ alkyl)$_2$, —$CO_2$—$(CH_2)_{1-4}$—$O$—$(CH_2)_{1-4}$—$N(C_{1-4}$ alkyl)$_2$, —$CO_2$—$(CH_2)_{1-4}$—$O$—$(CH_2)_{1-4}$—$O(C_{1-4}$ alkyl), —$NHCO_2(C_{1-4}$ alkyl), $R^c$, and —$CO_2R^c$; and $R^8$, at each occurrence, is selected from the group consisting of: phenyl, cyclopropyl, cyclobutyl, cyclopentyl, cyclohexyl, morpholine, thiamorpholine, —$(CH_2)_{0-2}$-piperidine, tetrahydroquinoline, piperazine, pyridine, benzodioxolyl, pyrazolyl, and indazolyl.

5. The compound of claim 4, wherein:

$R^2$ is selected from the group consisting of: H, F, $CF_3$, C(O)Me, and tetrazolyl;

$R^3$ is selected from the group consisting of: phenyl substituted with 1-2 $R^{3a}$, $C_{3-6}$ cycloalkyl substituted with 1-2 $R^{3a}$, pyridyl substituted with 1-2 $R^{3a}$,

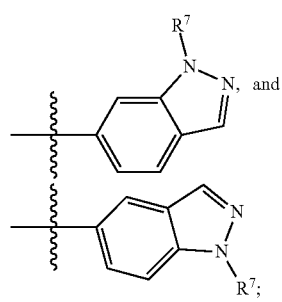

and $R^{3a}$, at each occurrence, is selected from the group consisting of: F, —OH, —OMe, —OEt, —CN, —$CO_2H$, —$CONH_2$, —$CO_2Me$, —$CO_2Et$, —$CO_2(t$-butyl), —$CO_2(CH_2)_2OMe$, —$CO_2(CH_2)_2N(C_{1-4}$ alkyl)$_2$, —$CO_2(CH_2)_2O(CH_2)_2N(C_{1-4}$ alkyl)$_2$, —$CO_2(CH_2)_2O(CH_2)_2OMe$, —$NHCO_2Me$, $R^c$, and —$CO_2R^c$;

$R^5$, at each occurrence, is selected from the group consisting of:

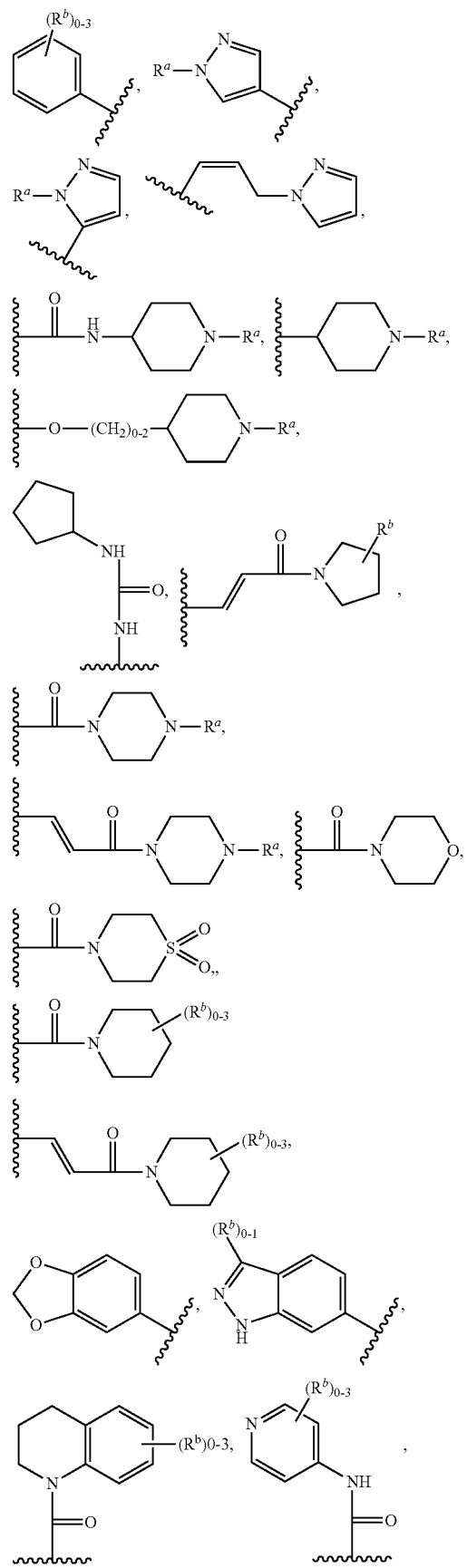

-continued

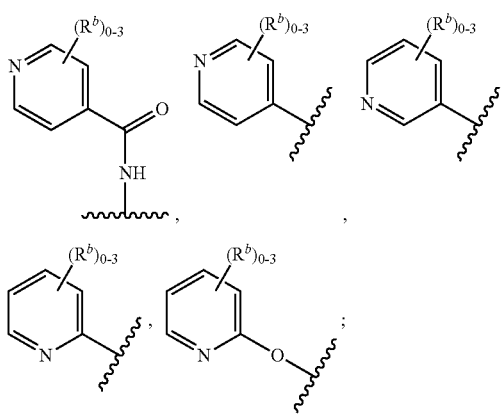

R$^a$ is selected from the group consisting of: H, Me, Et, —(CH$_2$)$_3$OH, COCF$_3$, COMe, CO$_2$Me, CO$_2$Et, CO$_2$(t-butyl), —CONH(CH$_2$)$_2$CO$_2$(C$_{1-4}$ alkyl), R$^c$, and CO$_2$R$^c$;

R$^b$ is, independently at each occurrence, selected from the group consisting of: Me, Et, Cl, OMe, OCF$_3$, NO$_2$, NH$_2$, N(Me)$_2$, CO$_2$Me, CO$_2$Et, CONH$_2$, —CONH(C$_{1-4}$ alkyl), —CON(C$_{1-4}$ alkyl)$_2$, —CONH(CH$_2$)$_{1-2}$O(C$_{1-4}$ alkyl), —CONH(CH$_2$)$_{1-2}$N(C$_{1-4}$ alkyl)$_2$, —CONH(CH$_2$)$_{1-2}$N$^+$(C$_{1-4}$ alkyl)$_2$(CH$_2$)$_{1-2}$—O—P(O)(OH)$_2$, —NHCO$_2$(C$_{1-4}$ alkyl), —R$^c$, COR$^c$, CONHR$^c$; and R$^c$ is, independently at each occurrence, selected from the group consisting of: —(CH$_2$)$_n$—C$_{3-6}$ cycloalkyl, —(CH$_2$)$_n$-phenyl, and —(CH$_2$)$_{0-2}$-morpholine, methylpiperazine, pyrrolidine optionally substituted with =O, and pyrazole.

6. The compound of claim 5 having formula (IV):

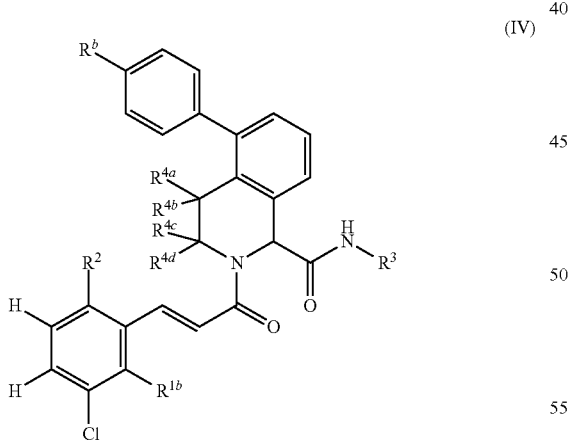

or a stereoisomer, tautomer, pharmaceutically acceptable salt thereof, wherein:

R$^{1b}$ is H and F;

R$^2$ is selected from the group consisting of: H, F, CF$_3$, C(O)Me, and tetrazole;

R$^3$ is independently selected from the group consisting of: phenyl substituted with 1-2 R$^{3a}$, cyclohexyl substituted with 1-3 R$^{3a}$,

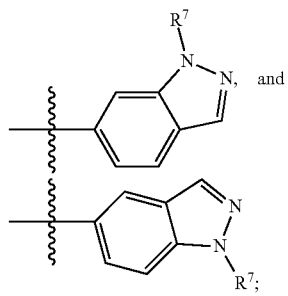

R$^{3a}$ is, independently at each occurrence, selected from the group consisting of: F and —CO$_2$H;

R$^7$ is selected from the group consisting of: H and C$_{1-4}$ alkyl;

R$^b$ is, independently at each occurrence, selected from the group consisting of: Cl, OMe, OCF$_3$, NO$_2$, CONH$_2$, —CONHMe, —CONHEt, —CON(Me)$_2$, —CON(Et)$_2$, —CONH(CH$_2$)$_{1-2}$O(C$_{1-4}$ alkyl), —CONH(CH$_2$)$_{1-2}$N(C$_{1-4}$ alkyl)$_2$, —CONH(CH$_2$)$_{1-2}$N$^+$(C$_{1-4}$ alkyl)$_2$(CH$_2$)$_{1-2}$—O—P(O)(OH)$_2$, NHCO$_2$Me, NHCO$_2$Et, and COR$^c$; and R$^c$ is, independently at each occurrence, selected from the group consisting of: —(CH$_2$)$_n$—C$_{3-6}$ cycloalkyl, —(CH$_2$)$_n$-phenyl, and —(CH$_2$)$_{0-2}$-morpholine, methylpiperazine, pyrrolidine optionally substituted with =O, and pyrazole.

7. The compound of claim 2, wherein:

R$^2$ is selected from the group consisting of: H, F, CF$_3$, C(O)Me, and tetrazolyl;

R$^3$ is selected from the group consisting of: phenyl substituted with 1-2 R$^{3a}$ and pyridyl substituted with 1-2 R$^{3a}$;

R$^5$ is selected from the group consisting of: halo, C$_{1-4}$ alkyl substituted with 0-2 R$^b$, C$_{2-4}$ alkenyl substituted with 0-2 R$^b$, —OH, —N(C$_{1-4}$ alkyl)$_2$, —O—C$_{1-4}$ alkylene-O(C$_{1-4}$ alkyl), —O—C$_{1-4}$ alkylene-N(C$_{1-4}$ alkyl)$_2$, and —NHSO$_2$(C$_{1-4}$ alkyl);

R$^{3a}$, at each occurrence, is selected from the group consisting of: F and —CO$_2$H;

R$^b$, at each occurrence, is selected from the group consisting of: CONH$_2$, CO$_2$(C$_{1-4}$ alkyl), R$^c$, and COR$^c$;

R$^c$, at each occurrence, is selected from the group consisting of: imidazole, methylpiperazine, pyrrolidine substituted with 0-2 R$^d$, and piperidine substituted with 0-2 R$^d$; and R$^d$, at each occurrence, is selected from the group consisting of: NH$_2$ and pyrrolidine.

8. The compound of claim 2 having formula (V):

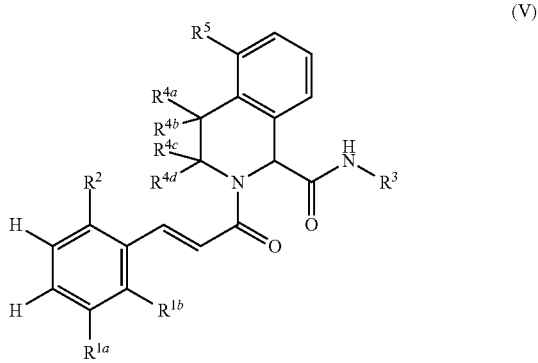

or a stereoisomer, tautomer, pharmaceutically acceptable salt thereof, wherein:

R$^{1b}$ is selected from the group consisting of: H and F;
R$^3$ is selected from the group consisting of: phenyl substituted with 1-2 R$^{3a}$,

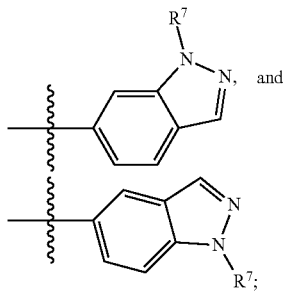

and

R$^{3a}$, at each occurrence, is selected from the group consisting of: H, halo, CN, CO$_2$H, —CO$_2$(C$_{1-4}$ alkyl), —CO$_2$(CH$_2$)$_{1-2}$O(C$_{1-4}$ alkyl), —CO$_2$(CH$_2$)$_{1-2}$CON(C$_{1-4}$ alkyl)$_2$, —CONH$_2$, —CONH(C$_{1-4}$ alkyl), —NHCO$_2$(C$_{1-4}$ alkyl), —CO$_2$(C$_{3-6}$ cycloalkyl), —CO$_2$(CH$_2$)$_{1-2}$Ph, and —CO$_2$(CH$_2$)$_{1-2}$triazole;

R$^{4a}$, R$^{4b}$, R$^{4c}$, and R$^{4d}$ are independently selected from the group consisting of: H and methyl;

R$^5$ is selected from the group consisting of: halo, C$_{1-4}$ alkyl substituted with 0-2 R$^b$, C$_{2-4}$ alkenyl substituted with 0-2 R$^b$, —OH, —CN, —N(C$_{1-4}$ alkyl)$_2$, —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$ alkyl), —CONR$^9$(C$_{1-4}$ alkyl)$_2$, —CONR$^9$—C$_{1-4}$ alkylene-O(C$_{1-4}$ alkyl), —CONR$^9$—C$_{1-4}$ alkylene-N(C$_{1-4}$ alkyl)$_2$, —CON(C$_{1-4}$ alkyl)$_2$, —CONR$^9$—C$_{1-4}$ alkylene-CO$_2$(C$_{1-4}$ alkyl), —NR$^9$COC$_{1-4}$ alkyl, NR$^9$CO$_2$C$_{1-4}$ alkyl, —NR$^9$CONR$^9$—C$_{1-4}$ alkylene-CO$_2$C$_{1-4}$ alkyl, —NR$^9$SO$_2$(C$_{1-4}$ alkyl), R$^8$, C$_{2-4}$ alkenylene-R$^8$, —OR$^8$, —COR$^8$, —CO$_2$R$^8$, C$_{2-4}$ alkenylene-COR$^8$, —CONR$^9$R$^8$, —NR$^9$COR$^8$, and —NR$^9$CONR$^9$R$^8$;

R$^7$, at each occurrence, is selected from the group consisting of: H and methyl;

R$^8$, at each occurrence, is selected from the group consisting of: C$_{3-6}$ cycloalkyl, phenyl and 5- to 10-membered heterocycle containing carbon atoms and 1-4 heteroatoms selected from the group consisting of: N, NR$^a$, O, and S(O)$_p$; wherein said cycloalkyl, phenyl and heterocycle are substituted with 0-3 R$^b$;

R$^a$, at each occurrence, is selected from the group consisting of: H, C$_{1-4}$ alkyl, —(CH$_2$)—OH, CO(C$_{1-4}$ alkyl), COCF$_3$, CO$_2$(C$_{1-4}$ alkyl), —CONH—C$_{1-4}$ alkylene-CO$_2$(C$_{1-4}$ alkyl), R$^c$, and CO$_2$R$^c$;

R$^b$, at each occurrence, is selected from the group consisting of: halo, C$_{1-4}$ alkoxy, OCF$_3$, NH$_2$, NO$_2$, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-CO$_2$(C$_{1-4}$ alkyl), —CONH—C$_{1-4}$ alkylene-N$^+$(C$_{1-4}$ alkyl)$_2$-C$_{1-4}$ alkylene-O—P(O)(OH)$_2$, —NHCO$_2$(C$_{1-4}$ alkyl), R$^c$, COR$^c$, and CONHR$^c$;

R$^c$, at each occurrence, is selected from the group consisting of: —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NR$^c$, O, and S; wherein each ring moiety is substituted with 0-2 R$^d$; and R$^d$, at each occurrence, is selected from the group consisting of: =O, N(C$_{1-4}$ alkyl)$_2$, heterocycle containing carbon atoms and 1-4 heteroatoms selected from the group consisting of: N, NH, N(C$_{1-4}$ alkyl), O, and S.

9. The compound of claim 8, wherein:

R$^5$ is selected from the group consisting of: C$_{1-4}$ alkyl substituted with 0-2 R$^b$, C$_{2-4}$ alkenyl substituted with 0-2 R$^b$, —N(Me)$_2$, —O(CH$_2$)$_2$N(Me)$_2$, O(CH$_2$)$_2$OMe, CONH(CH$_2$)$_2$N(Me)$_2$, —NHSO$_2$Me,

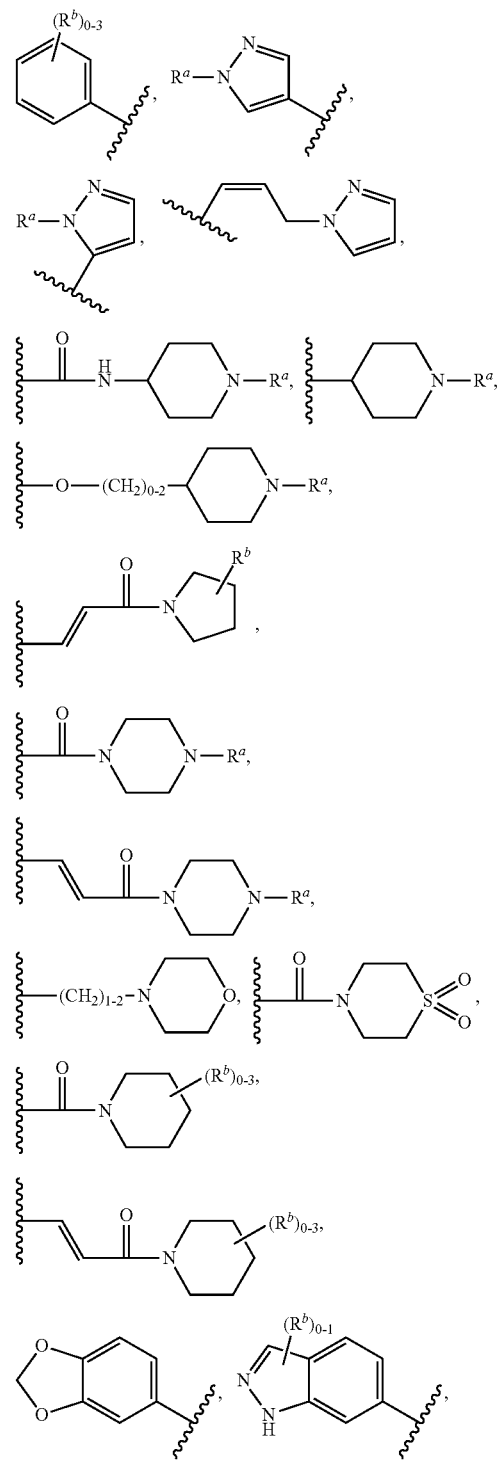

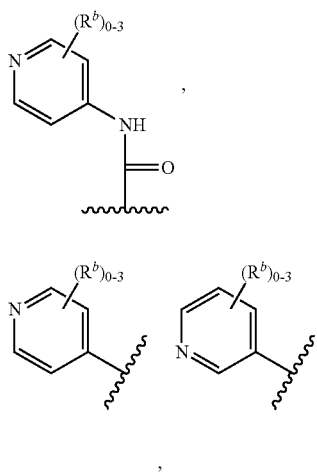

wherein said ring moieties are substituted with 0-3 $R^b$;

$R^{3a}$, at each occurrence, is selected from the group consisting of: F, CN, $CO_2H$, $CO_2Me$, $CO_2Et$, $CO_2$(i-Bu), and $NHCO_2Me$;

$R^a$, at each occurrence, is selected from the group consisting of: H, methyl, $-(CH_2)_{0-3}OH$, COMe, $COCF_3$, $CO_2Me$, $R^c$, and $CO_2R^c$;

$R^b$, at each occurrence, is selected from the group consisting of: H Cl, OMe, $OCF_3$, $NO_2$, $NH_2$, $-N(Me)_2$, $-CO_2Me$, $-CO_2Et$, $CONH_2$, $-CONHMe$, $-CONHEt$, $-CON(Me)_2$, $-CONH(CH_2)_2OMe$, $-CONH(CH_2)_2N(Me)_2$, $-CONH(CH_2)_2N^+(Me)_2CH_2-OP(O)(OH)_2$, $-NHCO_2Et$, $-NHCO_2Me$, $R^c$, $COR^c$, and $CONHR^c$;

$R^c$, at each occurrence, is selected from the group consisting of: $-(CH_2)_{0-1}$phenyl, pyrrolidine substituted with 0-2 $R^d$, pyrazole, imidazole, $-(CH_2)_{0-2}$morpholine, piperidine substituted with 0-2 $R^d$, methylpiperidine, and methylpiperazine; and $R^d$, at each occurrence, is selected from the group consisting of: $=O$, pyrrolidine, and $N(Me)_2$.

10. A pharmaceutical composition, comprising: a pharmaceutically acceptable carrier and a therapeutically effective amount of a compound of claim 1.

11. A compound of claim 1 selected from the group consisting of

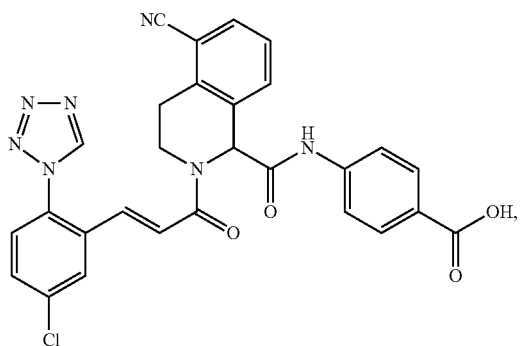

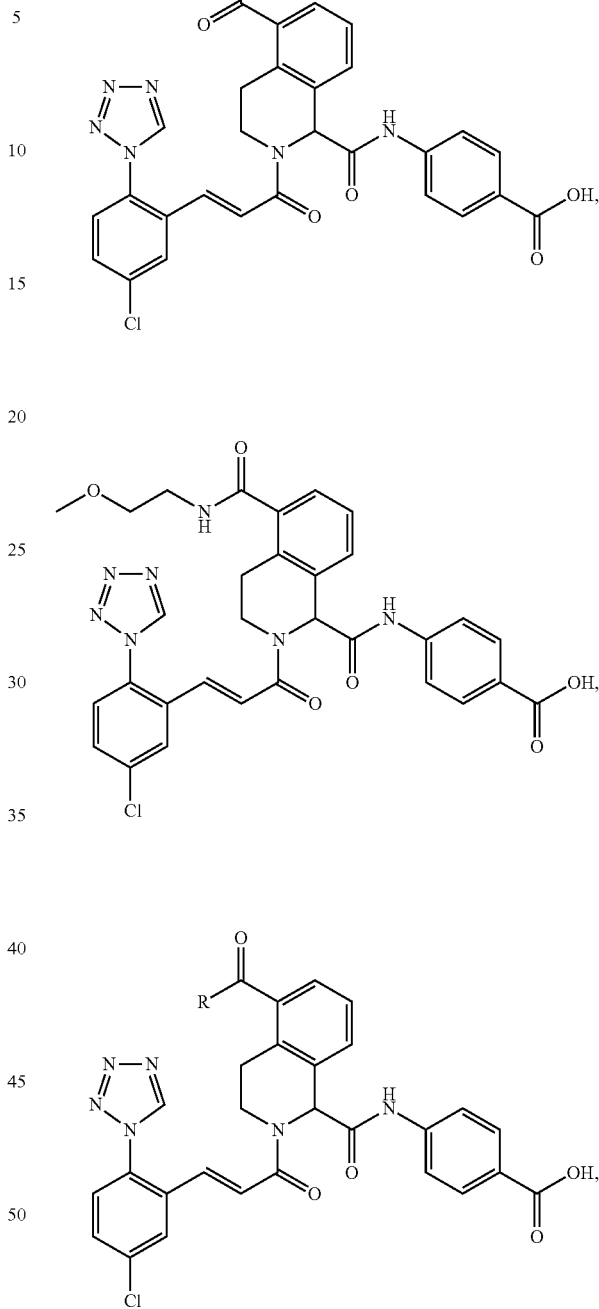

wherein R is as follows:

| R |
|---|
| 2-methoxy-N-methylethanamine |
| Morpholine |
| Piperidine |
| Dimethylamine |

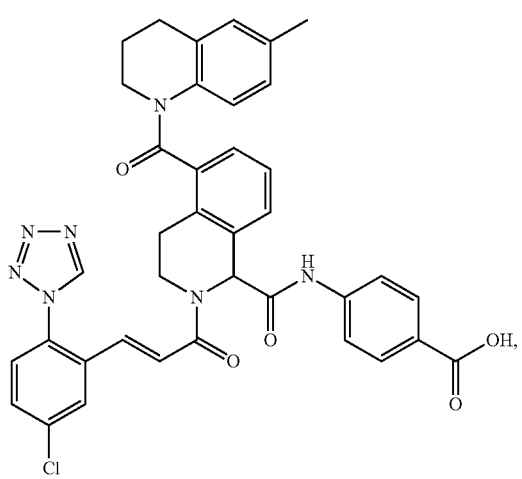
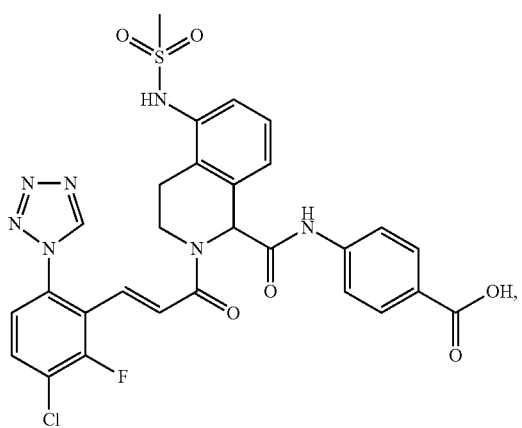
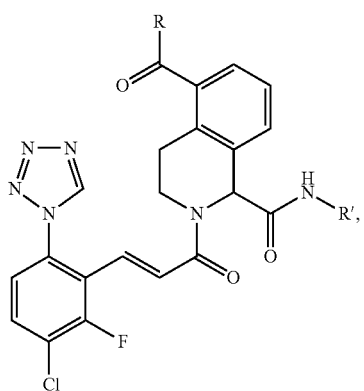
wherein R, R' and R" are as follows:
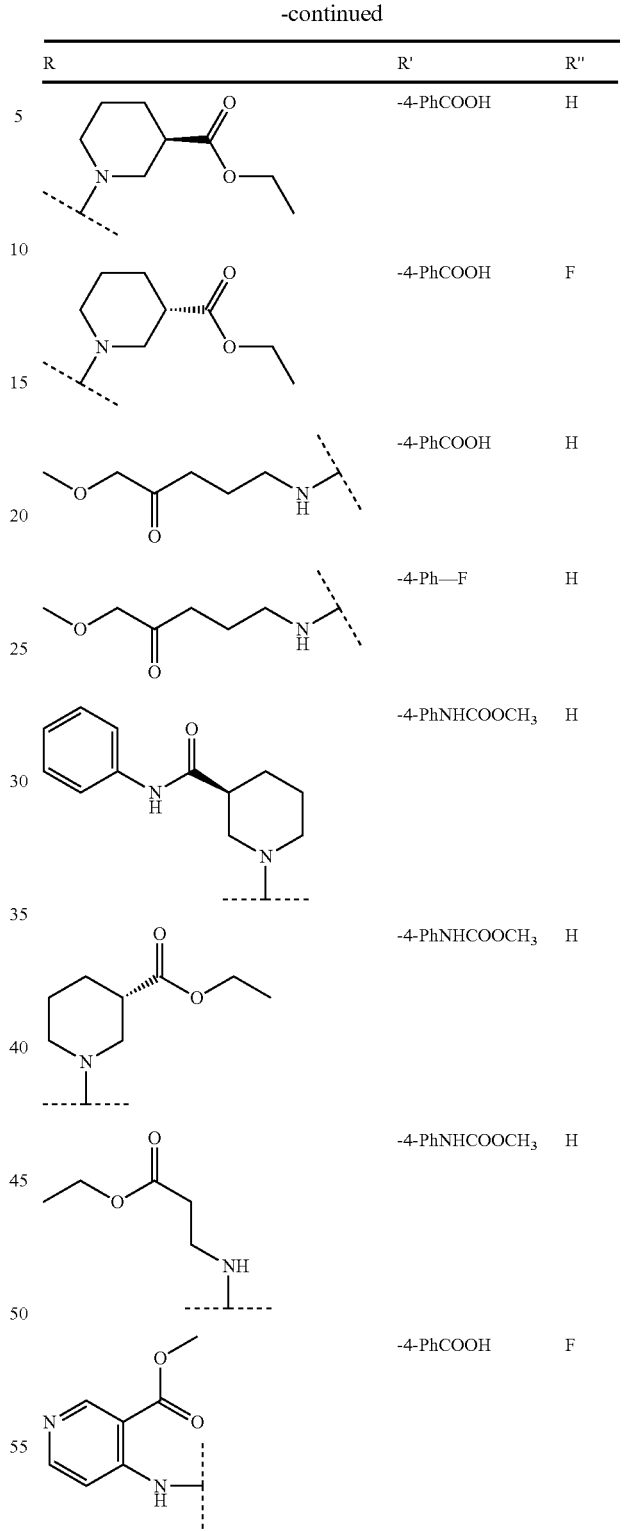

-continued

| R | R' | R'' |
|---|----|-----|
| ethyl piperidin-4-ylcarbamate (OEt-NH-piperidine) | -4-PhCOOH | F |
| 4-aminopyridine | -6-indazole | F |
| 4-aminopyridine | -4-PhCOOH | F |
| tert-butyl piperazine-1-carboxylate | -4-PhCOOtBu | F |
| Piperazine | -4-PhCOOH | F |
| 1-methylpiperidin-4-amine | -4-PhCOOH | F |
| 4-aminopiperidine | -4-PhCOOH | F |
| 1-methylpiperidin-4-amine | -6-indazole | F, | wherein R is as follows:

| R |
|---|
| piperazine |
| piperazine |
| thiomorpholine 1,1-dioxide |
| 4-(pyrrolidin-1-yl)piperidine ; |

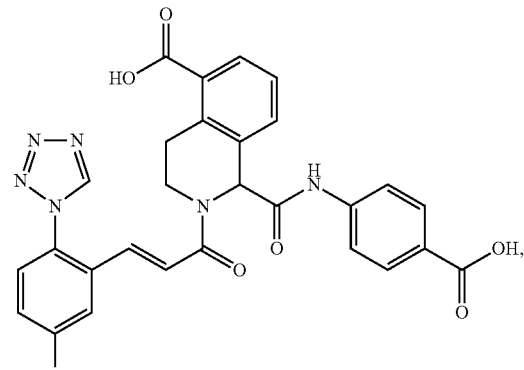

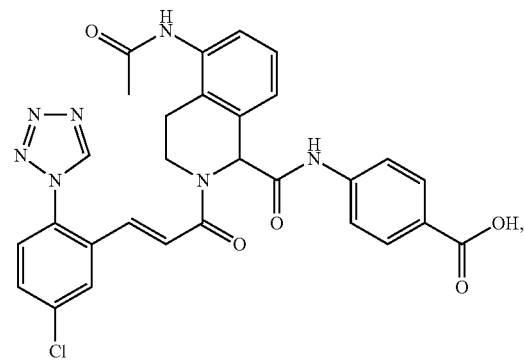

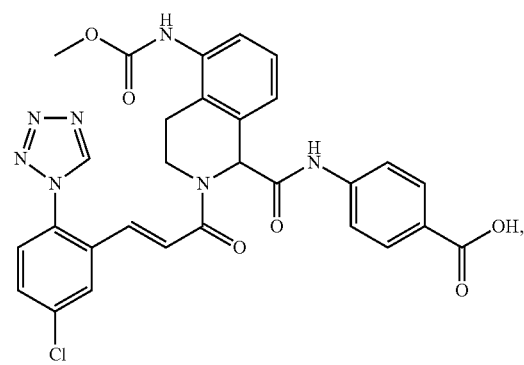

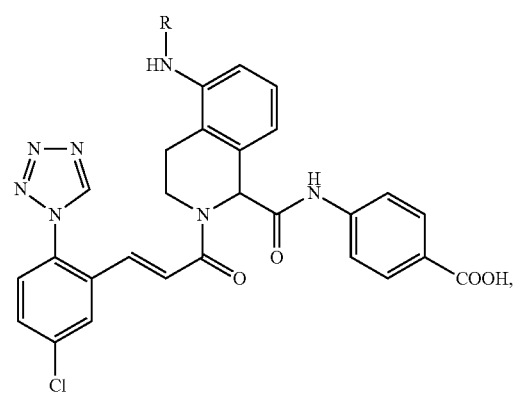

wherein R is as follows:
| R |
|---|
| 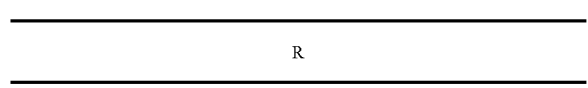 |
| 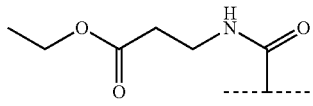 |
| 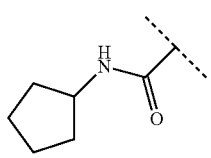 |
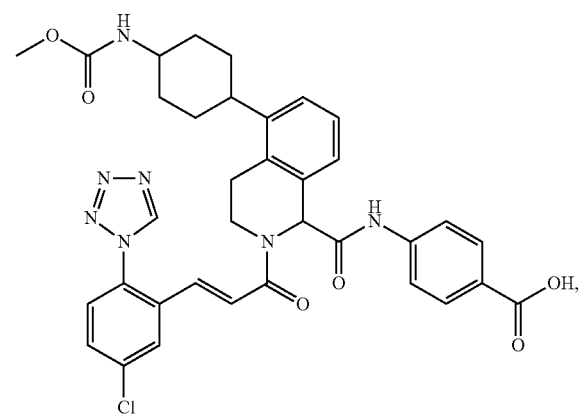
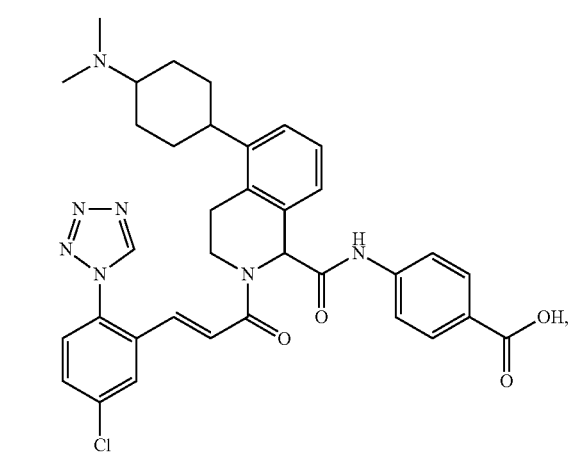
-continued
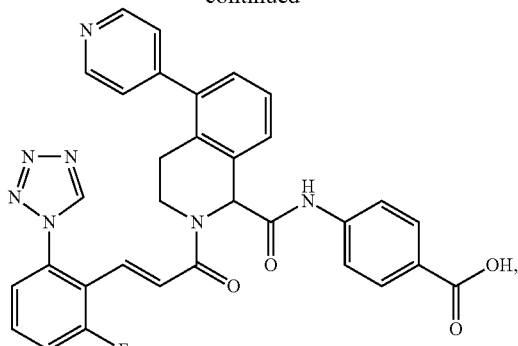
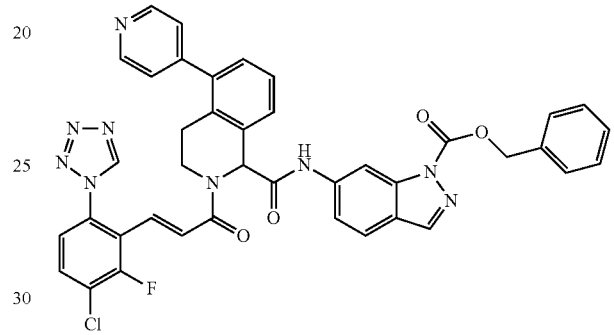
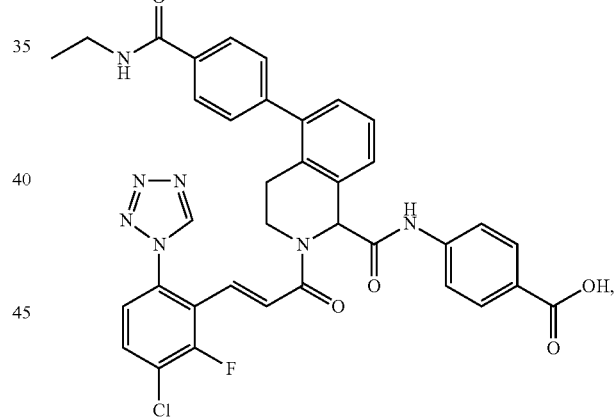
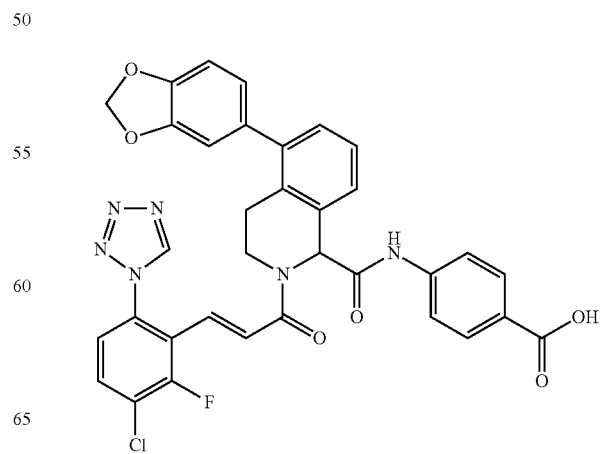

165
-continued
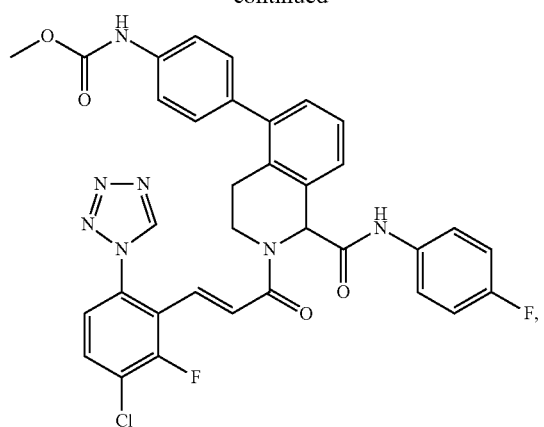
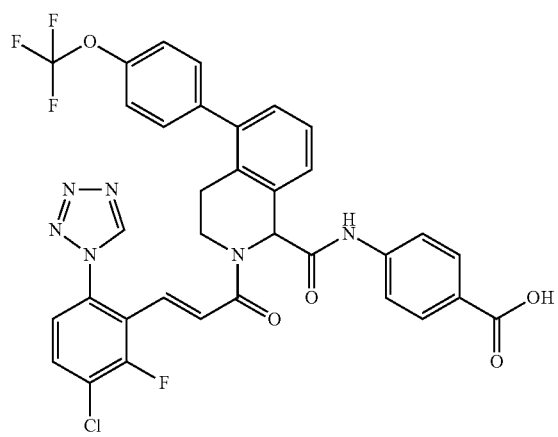
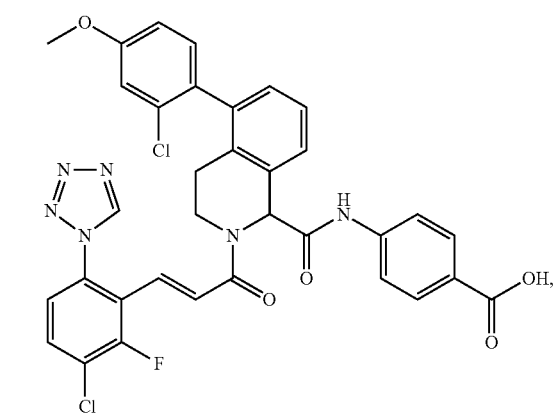
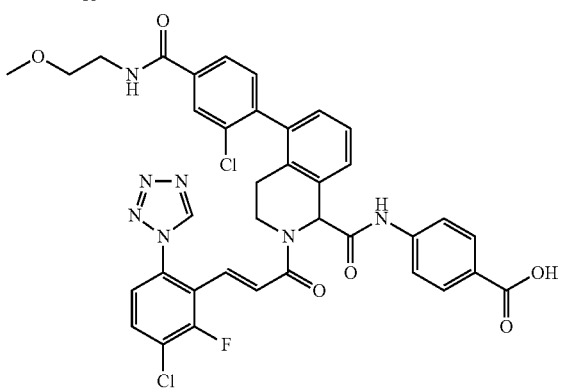
166
-continued
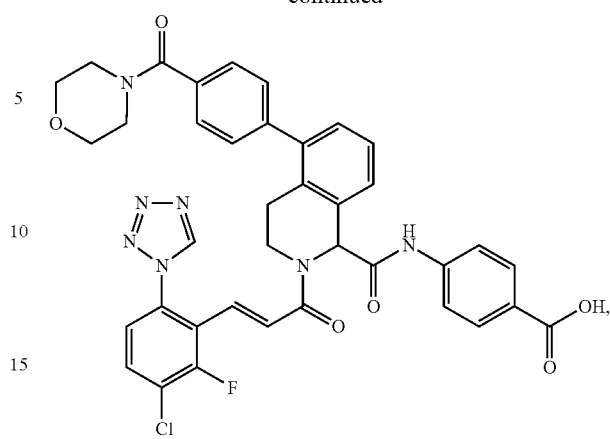
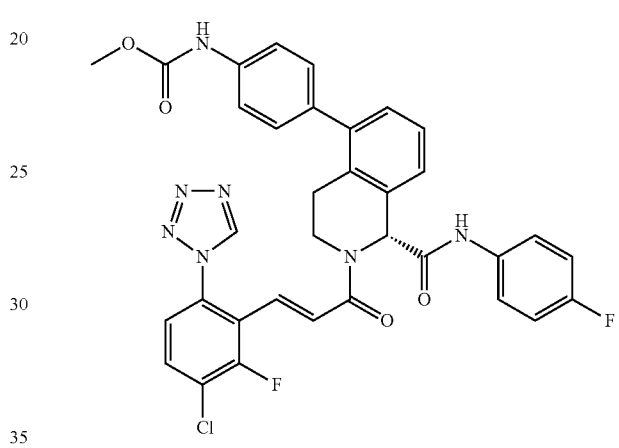
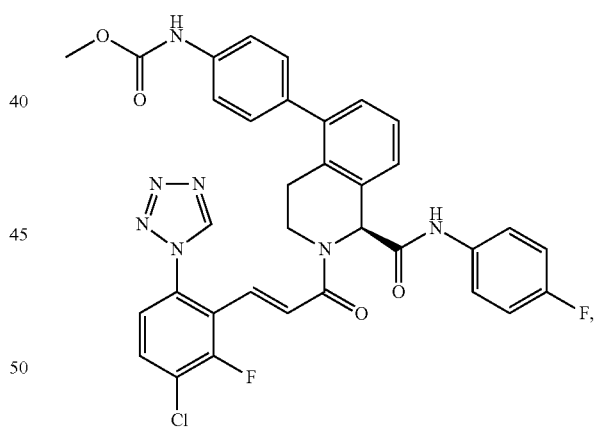
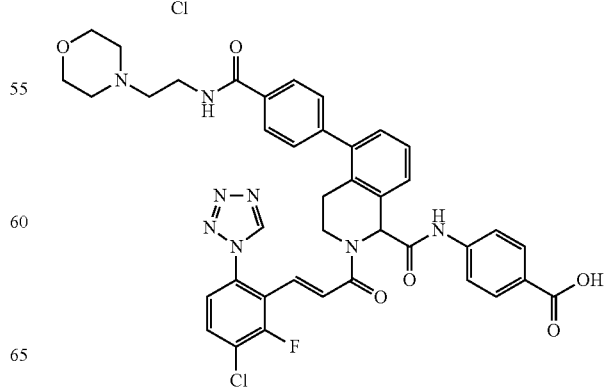

167
-continued
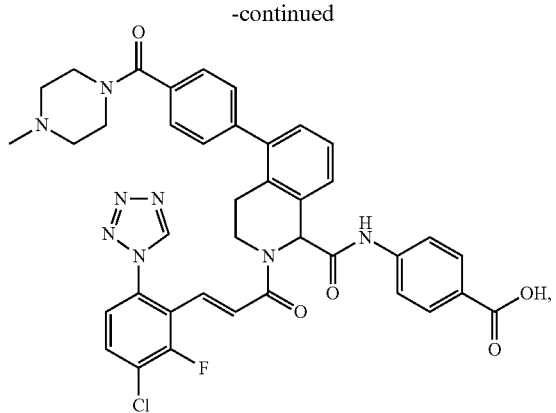
168
-continued
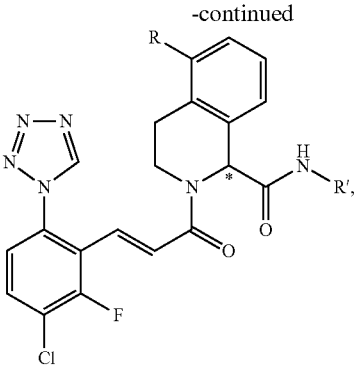
wherein R and R' are as follows
| R | R' |
|---|---|
| —NH—C(O)—C6H4— | 4-PhCO2H |
| —NH—C(O)—C6H4— | trans-4-hydroxycyclohexyl |
| —NH—C(O)—C6H4— | cyclohexyl |
| —NH—C(O)—C6H4— | tert-butyl |
| —NH—C(O)—C6H4— | isopropyl |
| —NH—C(O)—C6H4— | n-propyl |
| —NH—C(O)—C6H4— | isobutyl |
| —NH—C(O)—C6H4— | —CH2C(O)OCH3 |
| —NH—C(O)—C6H4— | (S)-sec-butyl-methyl |

-continued
| R | R' |
|---|---|
| 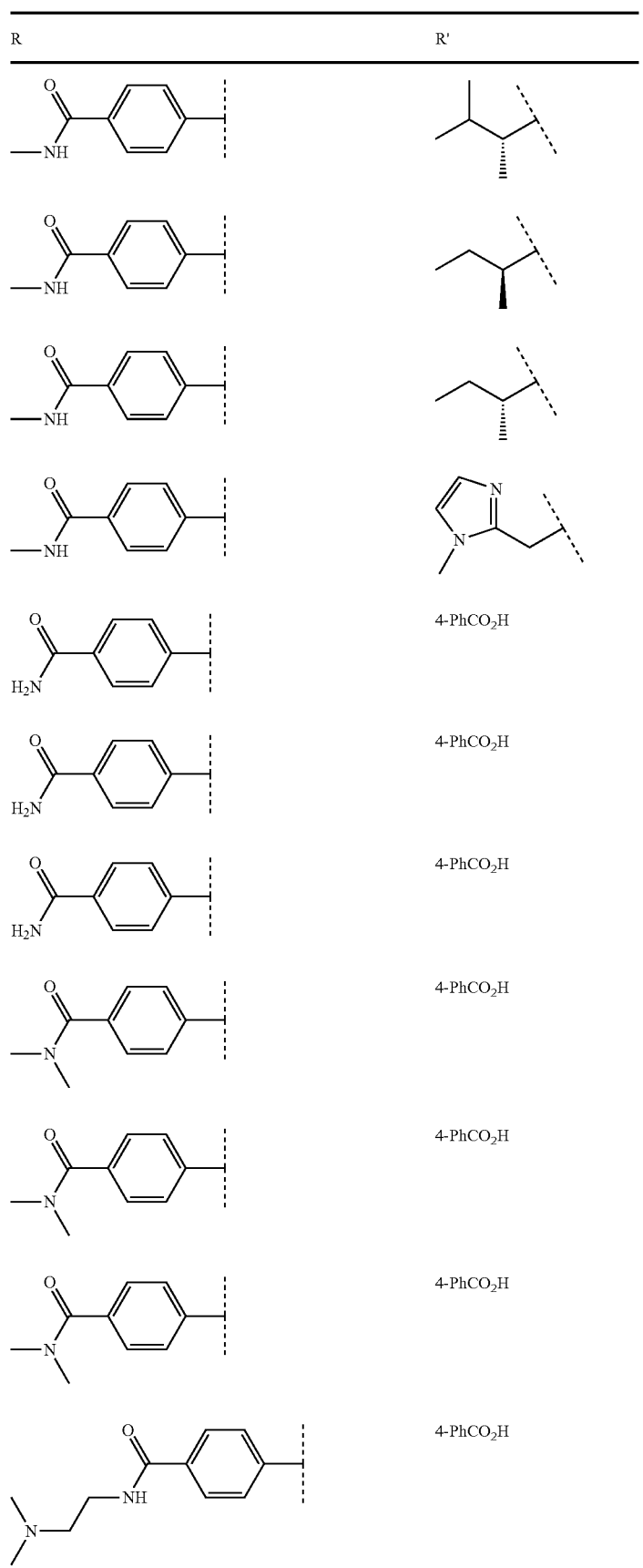 | |

-continued
| R | R' |
|---|---|
| 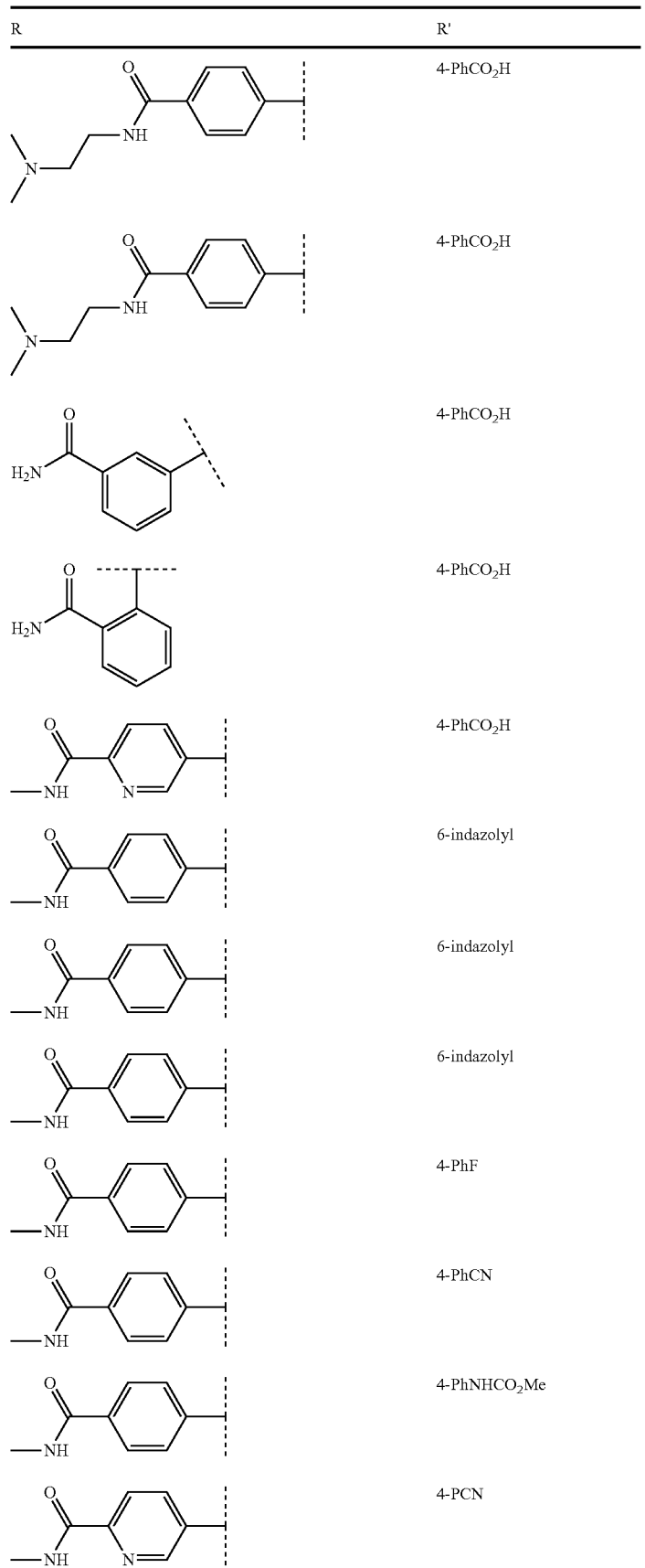 | 4-PhCO$_2$H |
| | 4-PhCO$_2$H |
| | 4-PhCO$_2$H |
| | 4-PhCO$_2$H |
| | 4-PhCO$_2$H |
| | 6-indazolyl |
| | 6-indazolyl |
| | 6-indazolyl |
| | 4-PhF |
| | 4-PhCN |
| | 4-PhNHCO$_2$Me |
| | 4-PCN |

-continued
| R | R' |
|---|---|
| 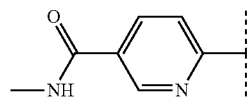 | 4-PhCN |
| 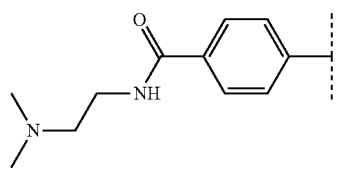 | 4-PhCO$_2$tBu |
| 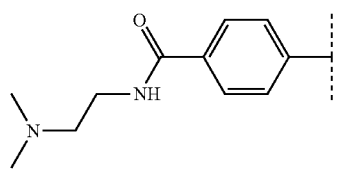 | 4-PhCO$_2$tBu |
| 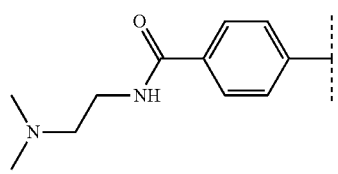 | 4-PhCO$_2$tBu |
| 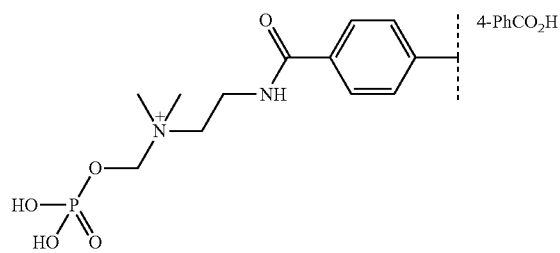 | 4-PhCO$_2$H |
| 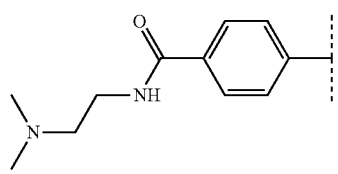 | 4-PhF |
| 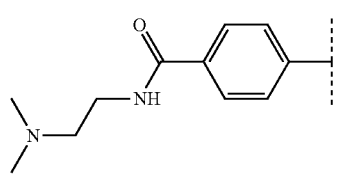 | 4-PhNHCO$_2$Me, |

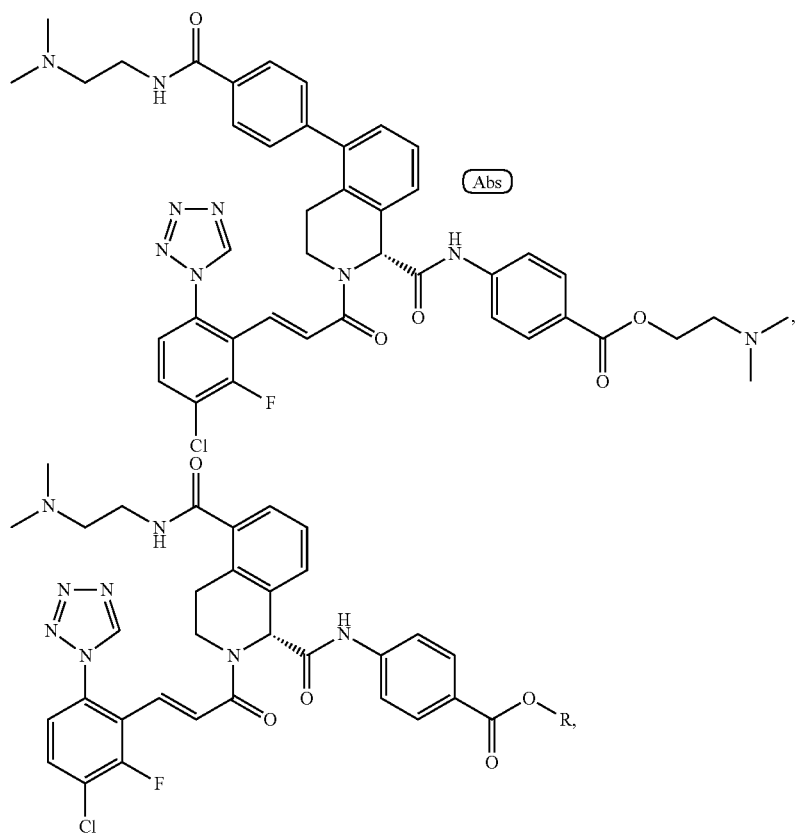
wherein R is as follows:
| R |
|---|
| (methoxyethyl) |
| (dimethylaminoethoxyethyl) |
| (methoxyethoxyethyl) |
| (3-pyridylmethyl) |
| (2-pyridylmethyl) |
| (1,2,4-triazol-1-yl-ethyl), |
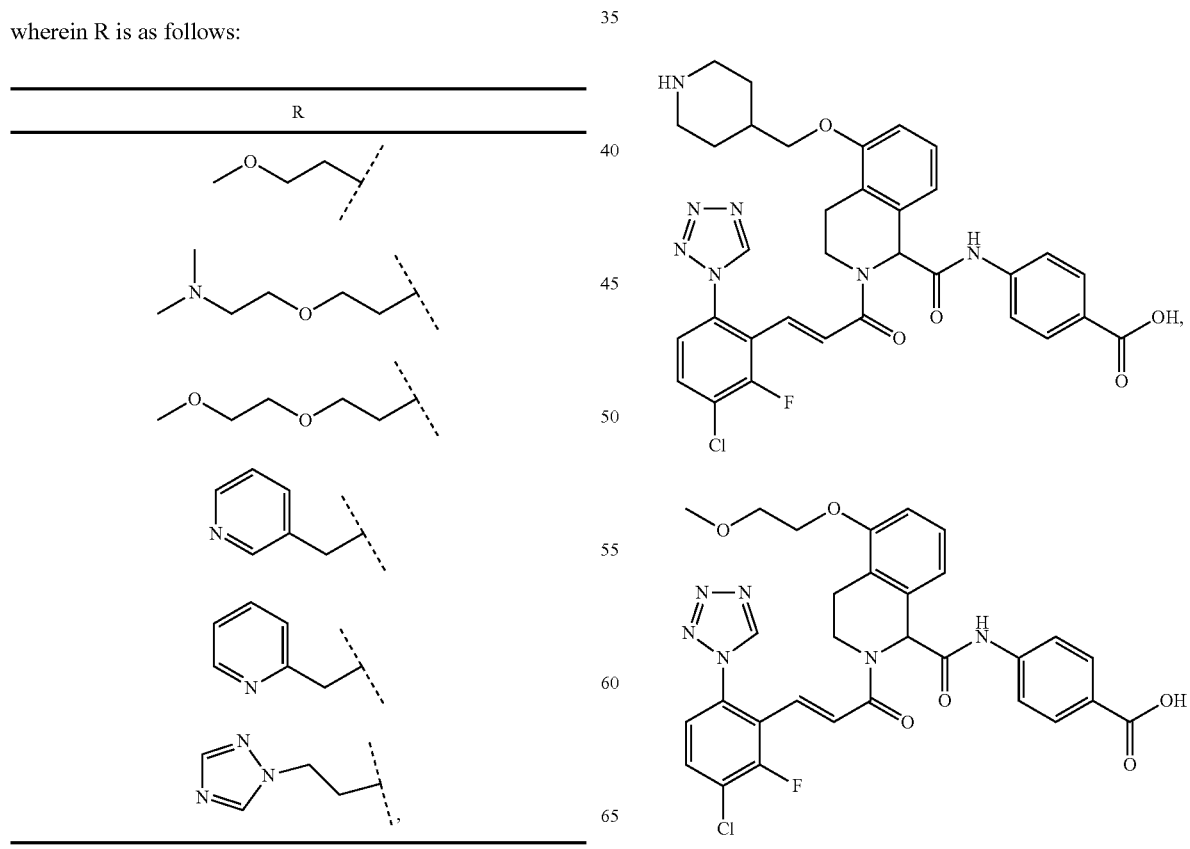

177
-continued
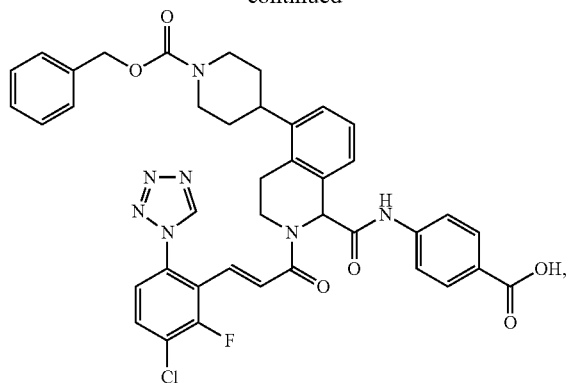
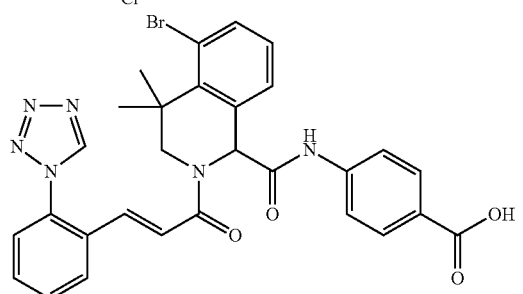
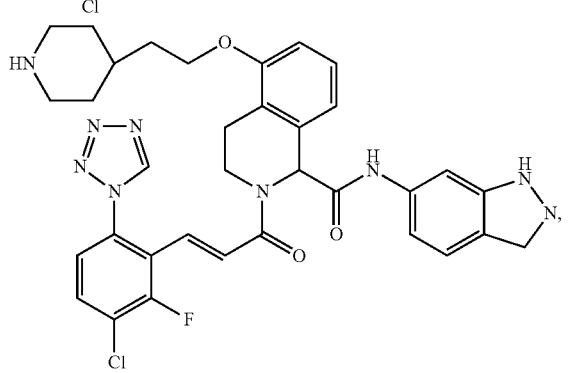
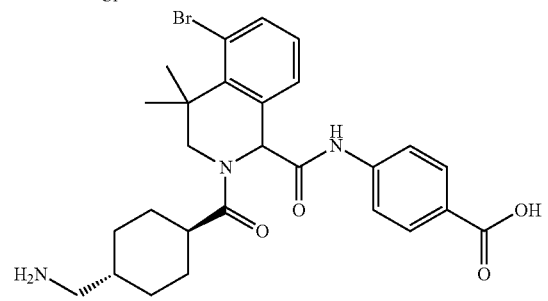
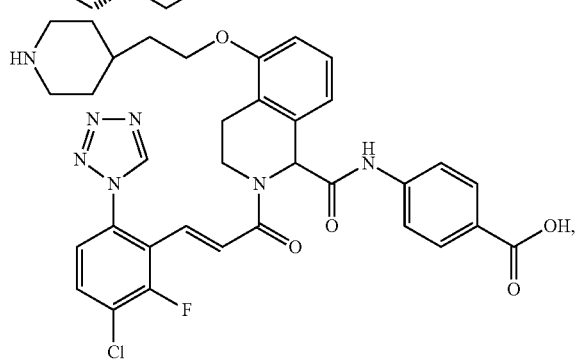
178
-continued
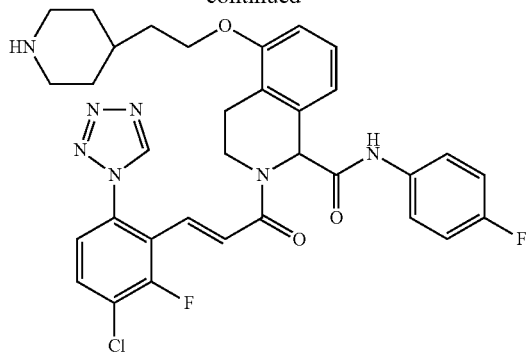
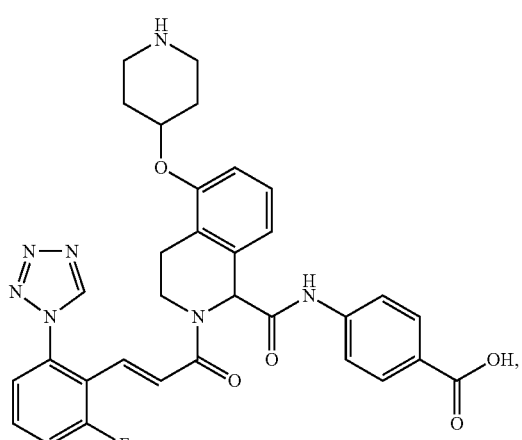
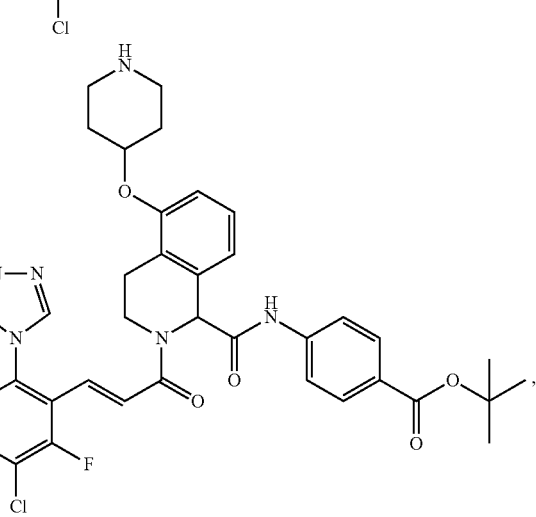
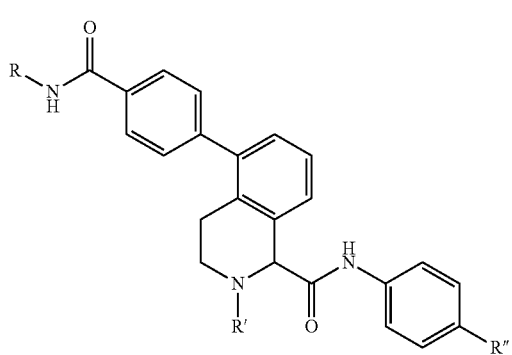

wherein R, R' and R" are as follows:
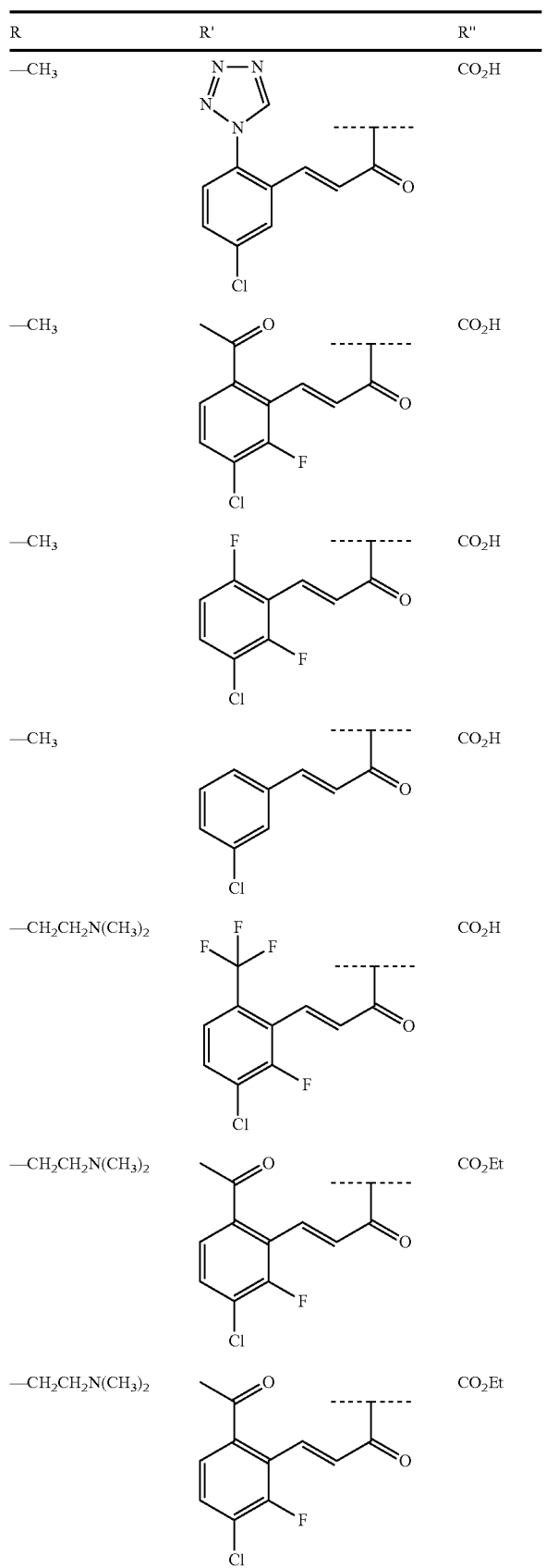
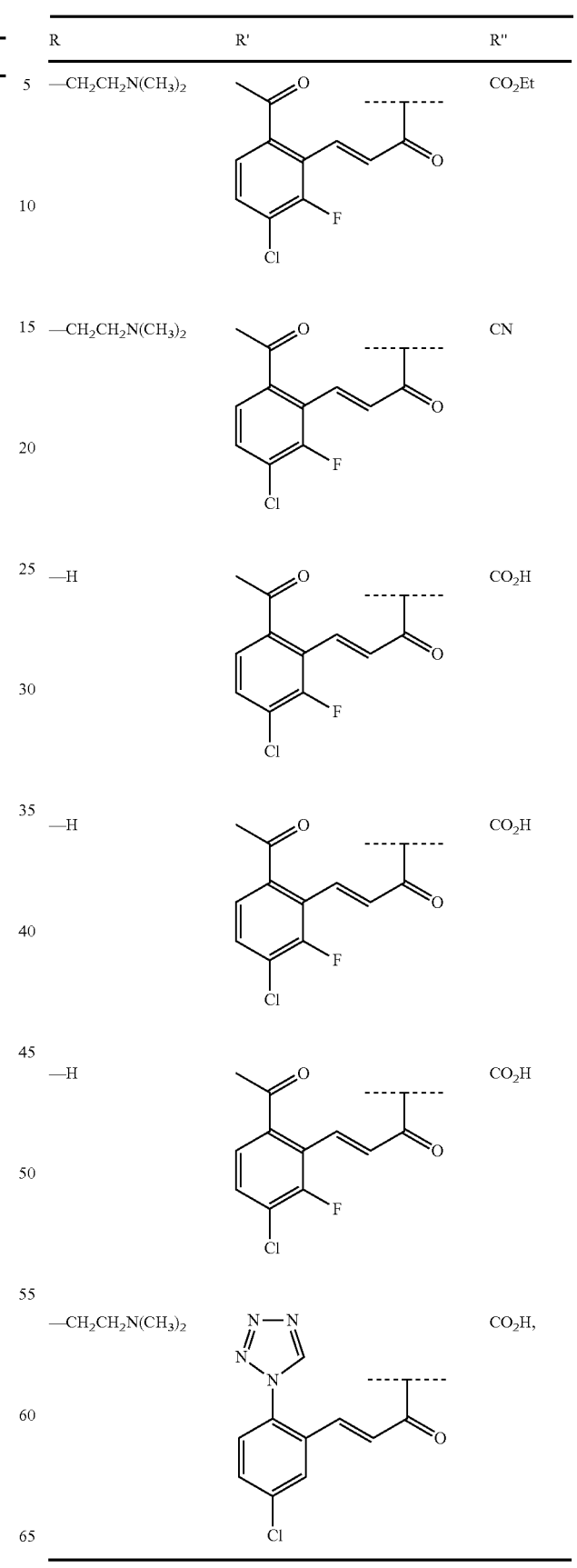

181
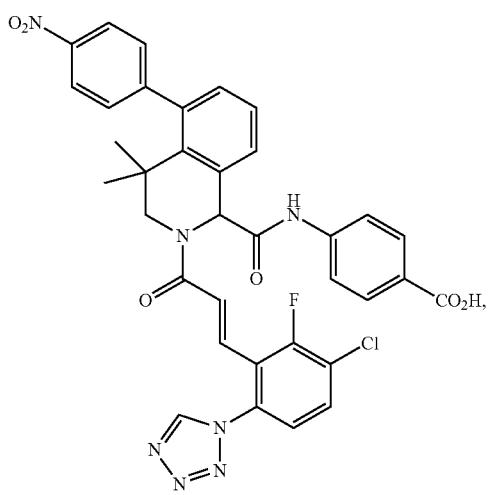
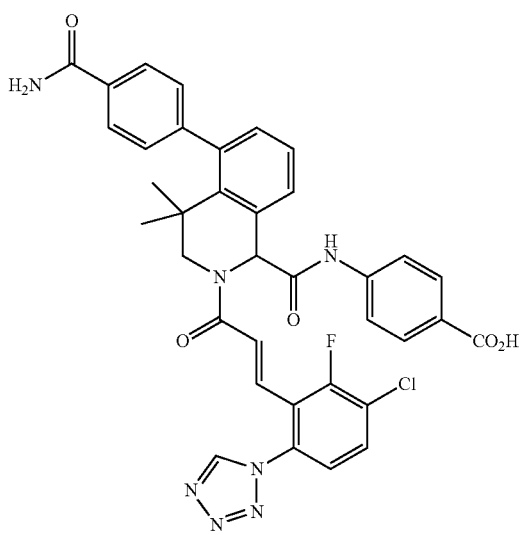
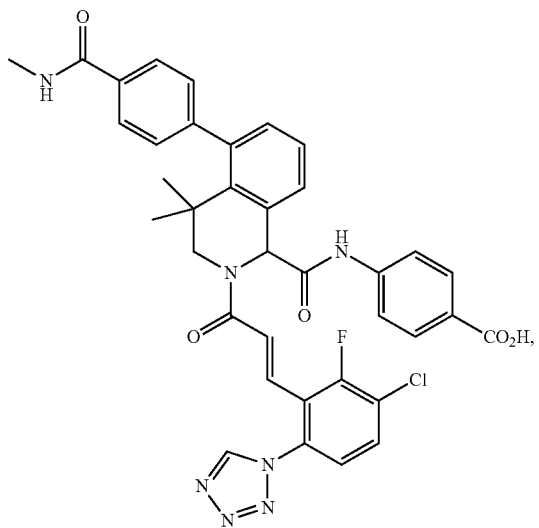
182
-continued
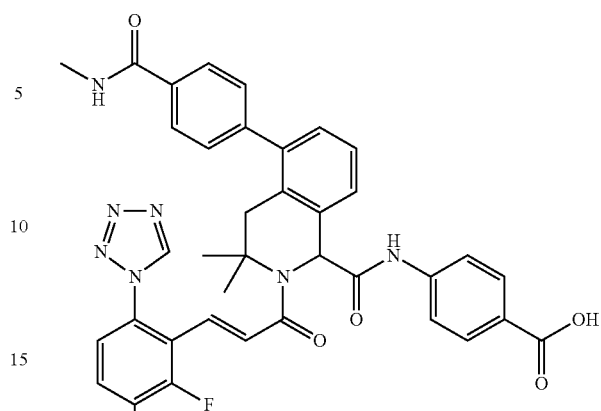
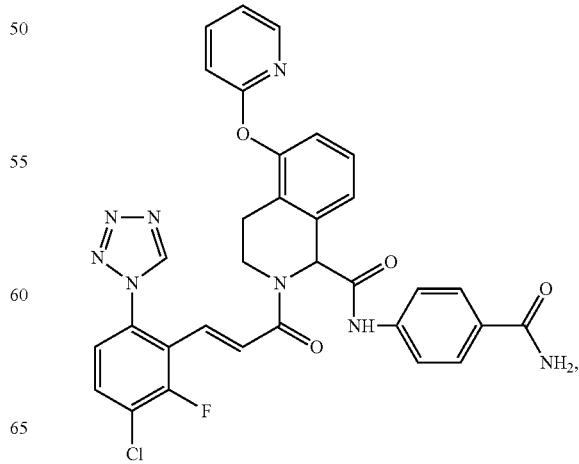
wherein R is as follows:
| R |
|---|
| 4-COOH |
| 4-CN |
| 4-F |
| 4-NHCOOMe |

183
-continued
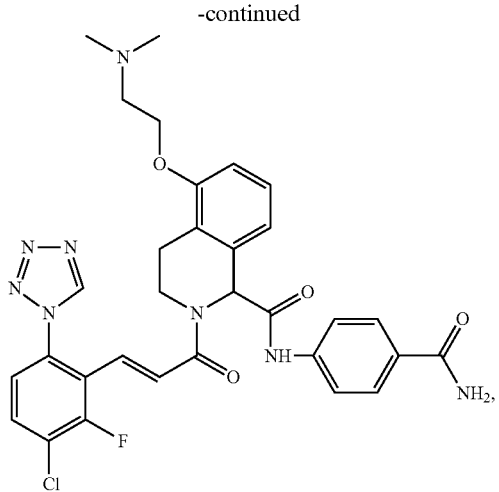
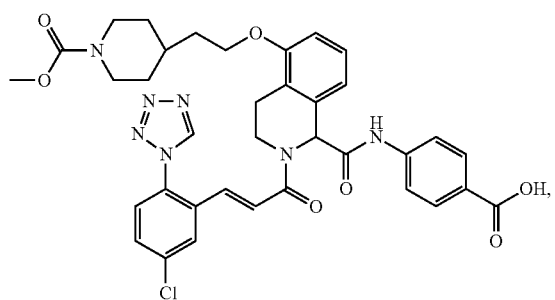
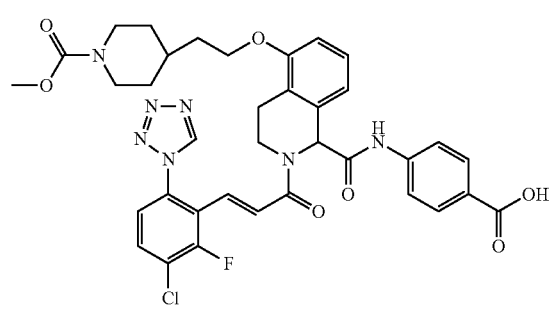
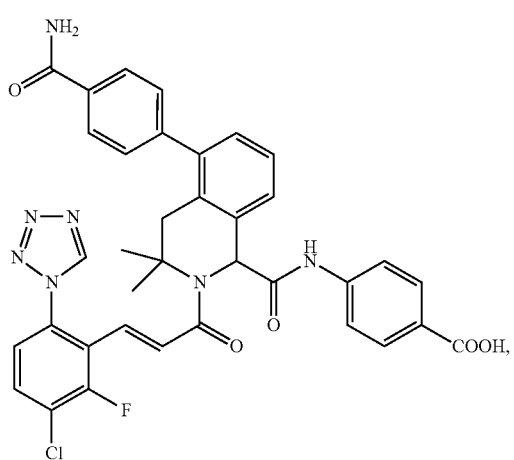
184
-continued
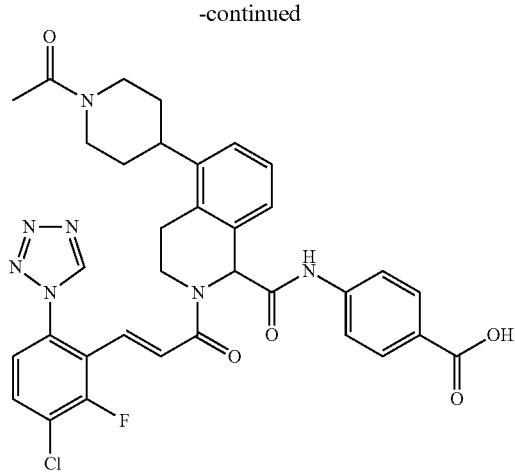
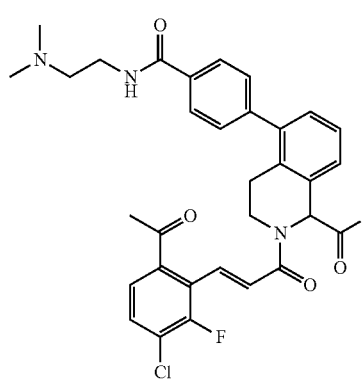
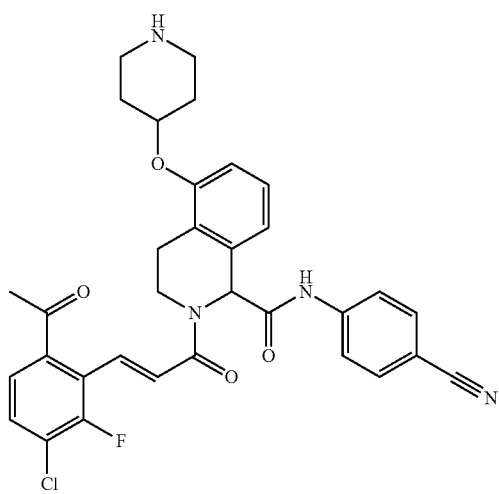

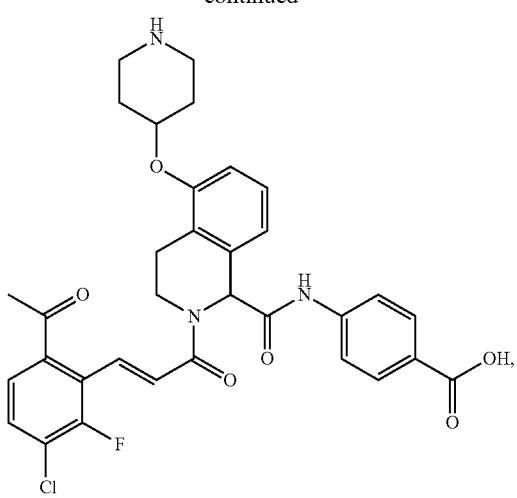
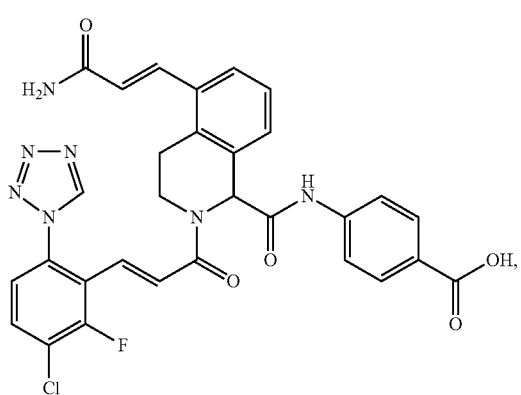
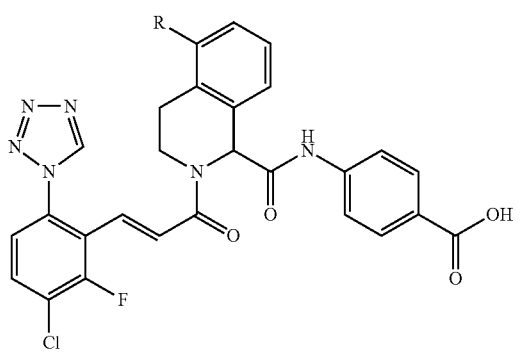
wherein R is as follows:
| R |
|---|
| 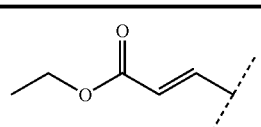 |
| 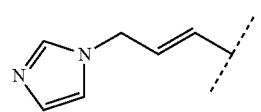 |
| R |
|---|
| 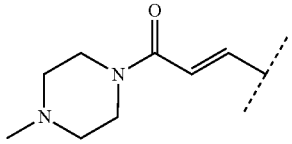 |
| 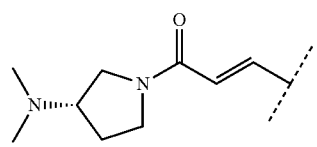 |
| 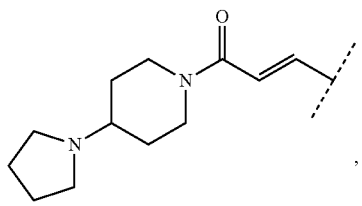 |
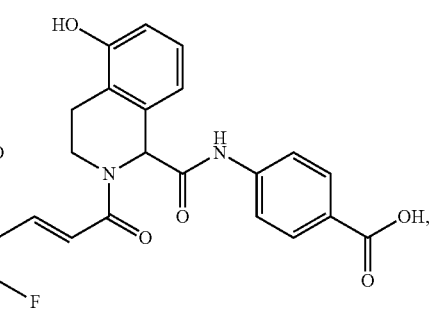
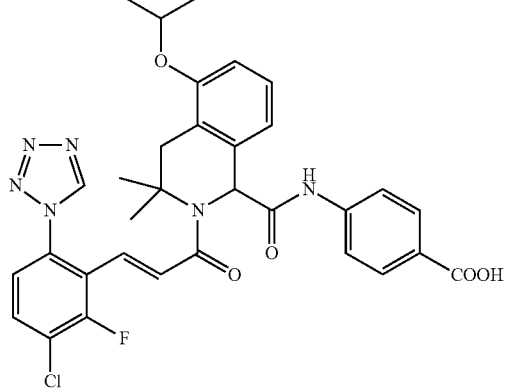

187
-continued
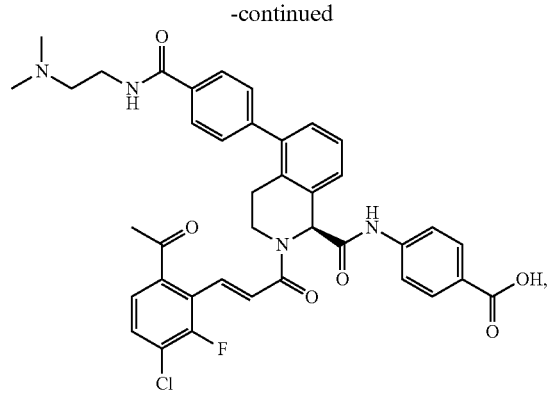
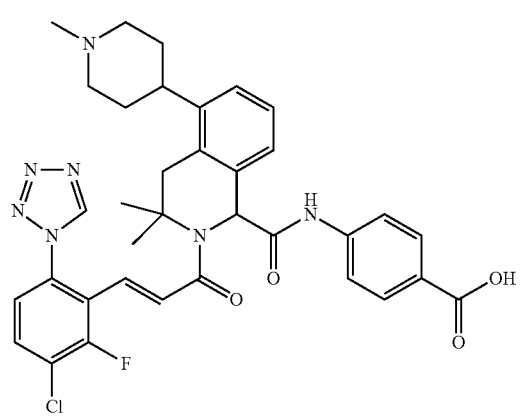
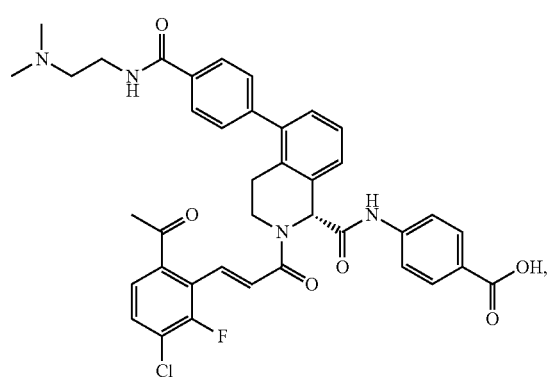
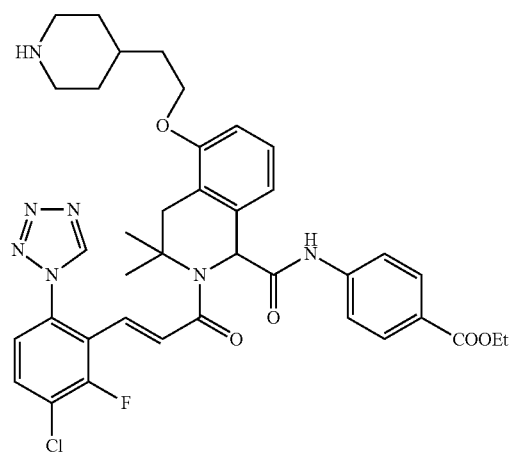
188
-continued
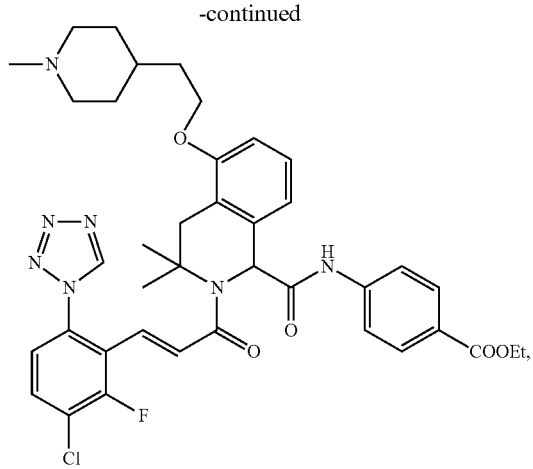
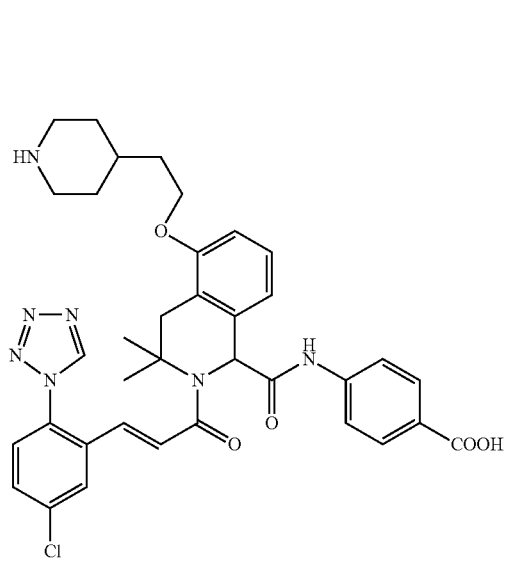
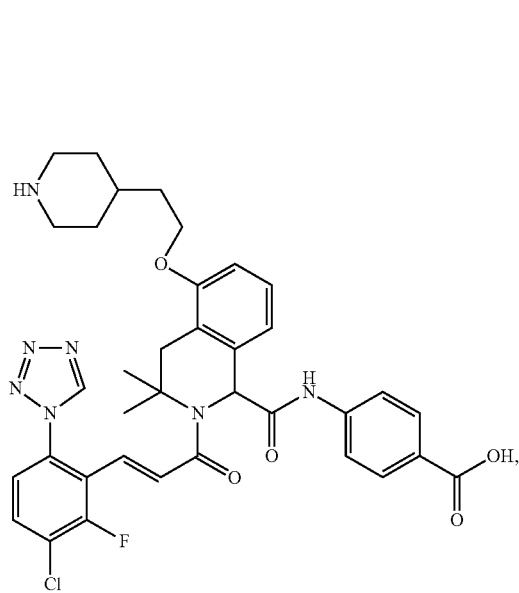

189
-continued
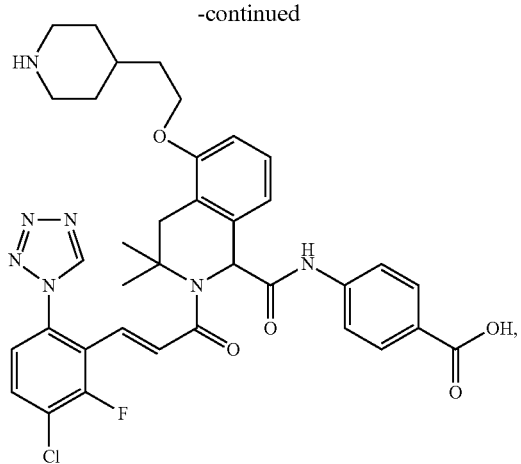
190
-continued
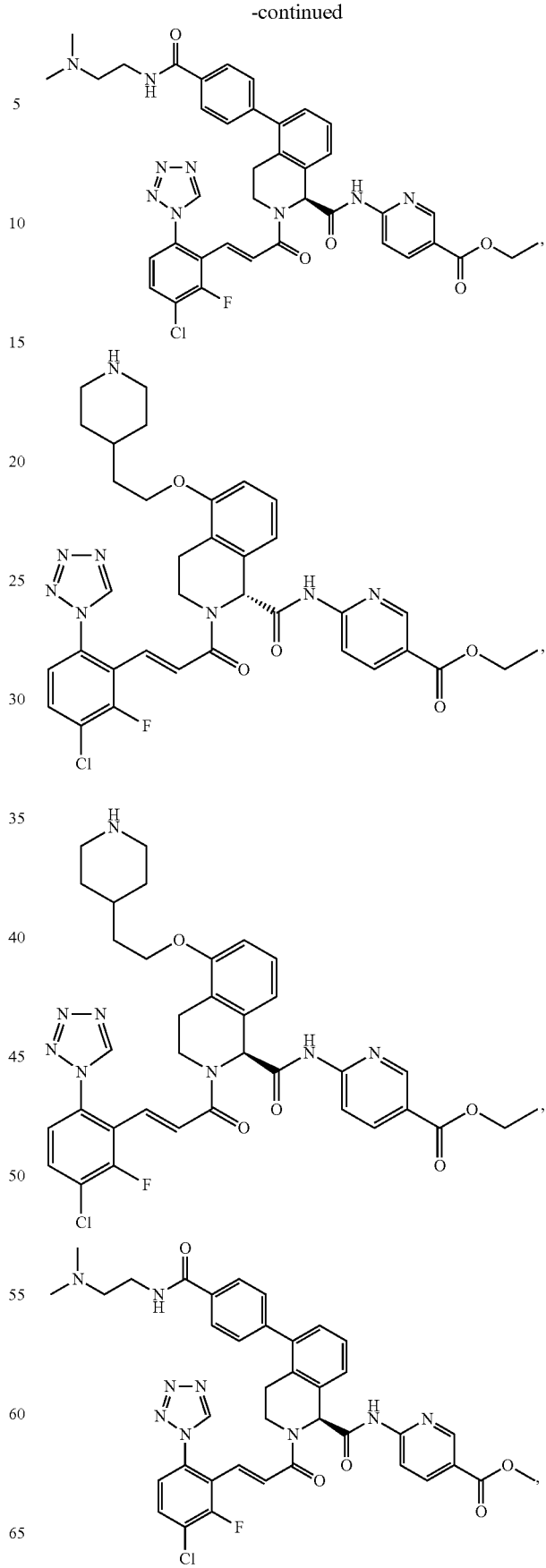

191 -continued
192 -continued
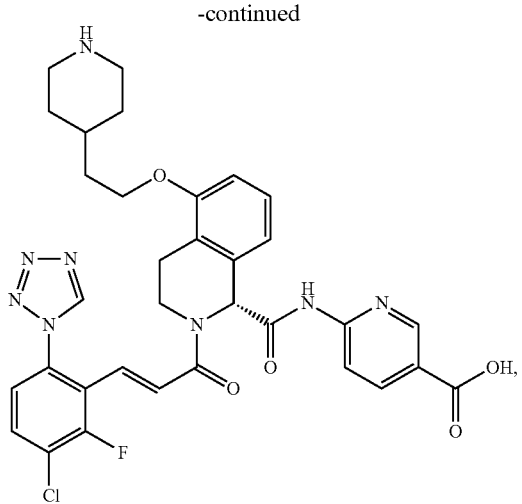
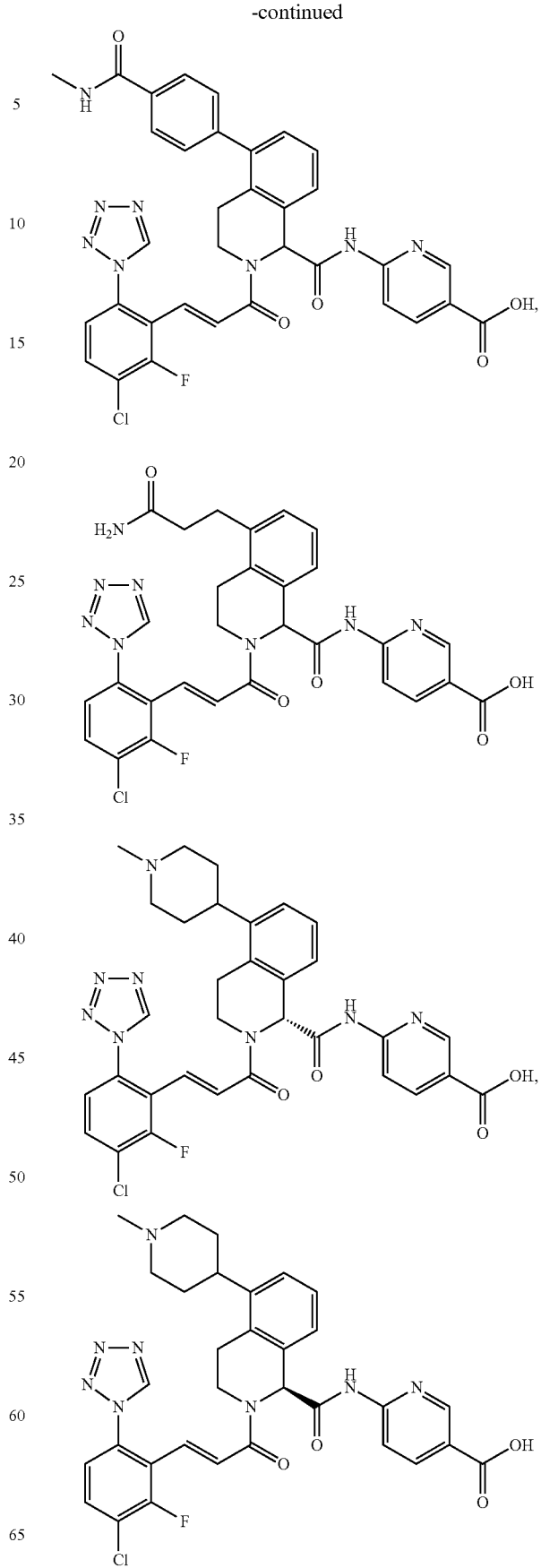

193
-continued
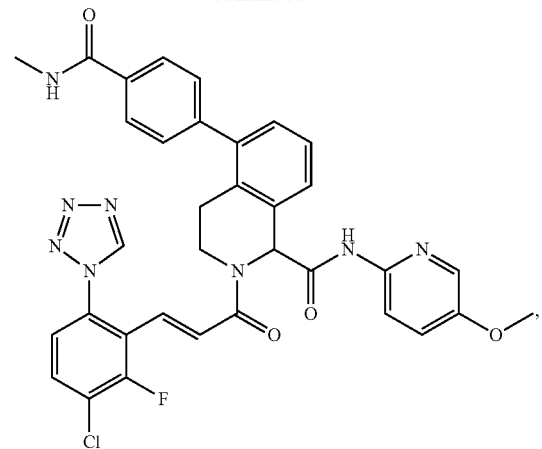
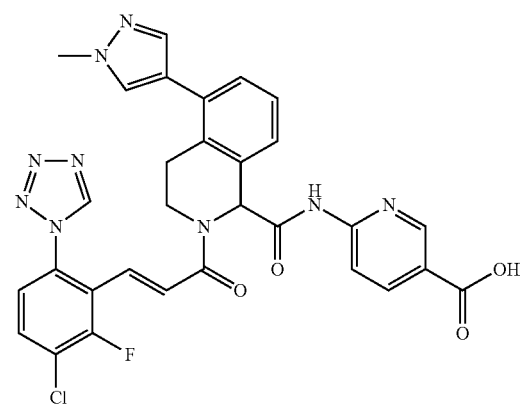
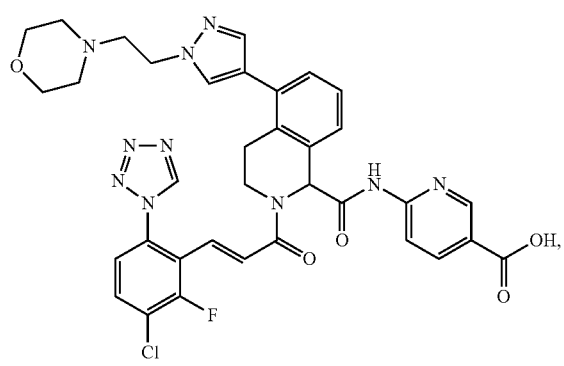
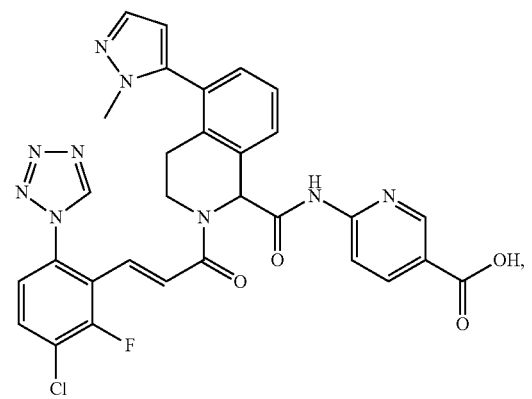
194
-continued
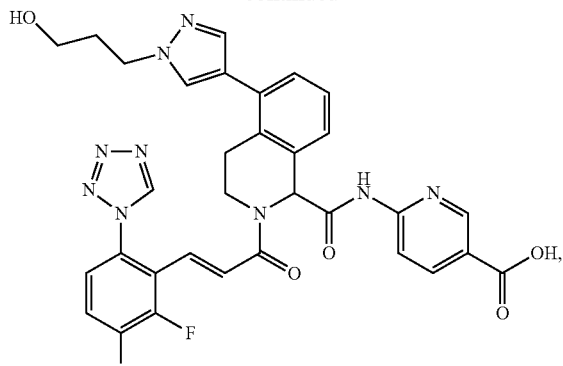
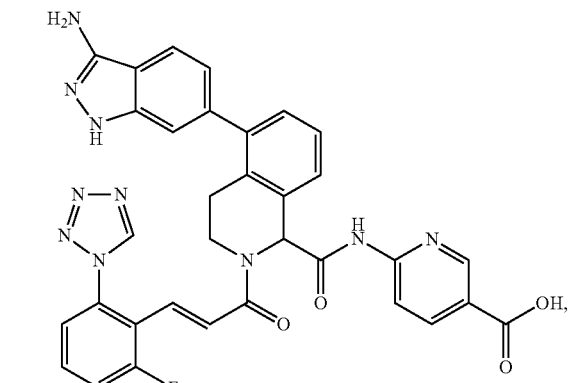
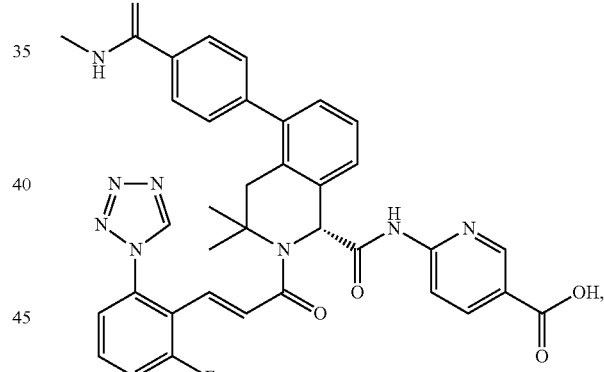
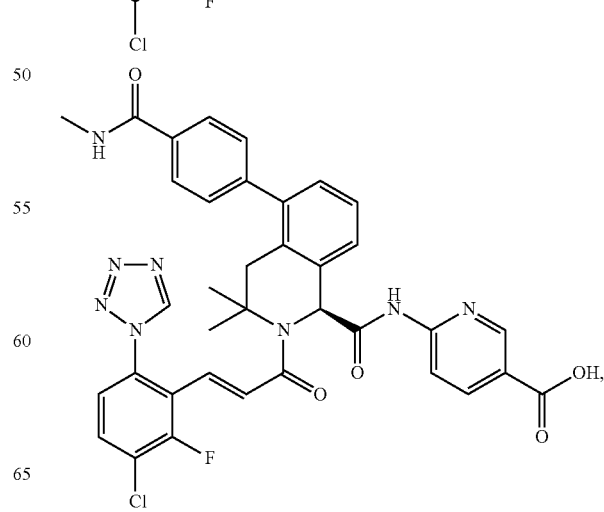

195
-continued
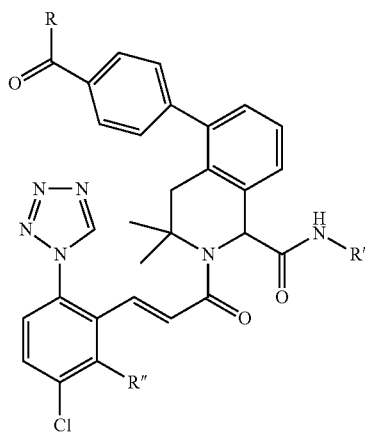
wherein R, R' and R" are as follows:
| R | R' | R" |
|---|---|---|
| —NHCH₃ | 4-PhCN | F |
| —NHCH₃ | 4-PhCN | F |
| —NHCH₃ | 4-PhCOOEt | F |
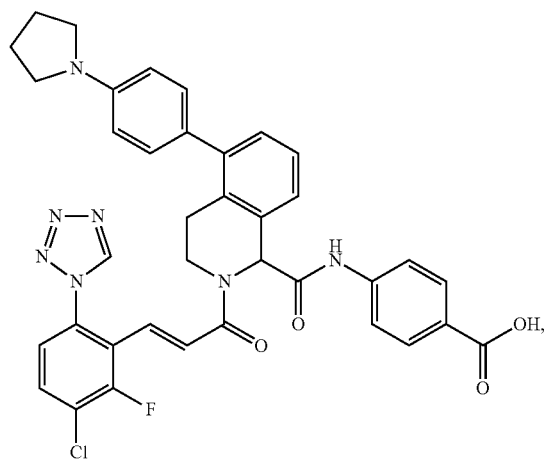
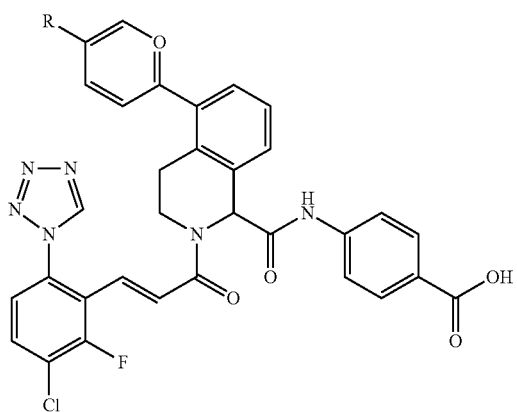
196
wherein R is as follows:
| R |
|---|
| 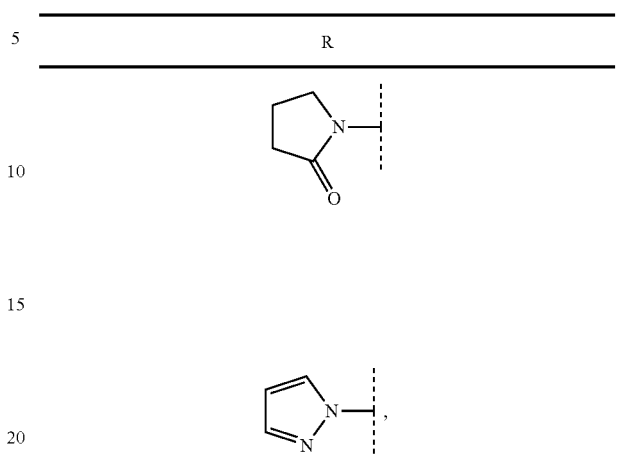 |
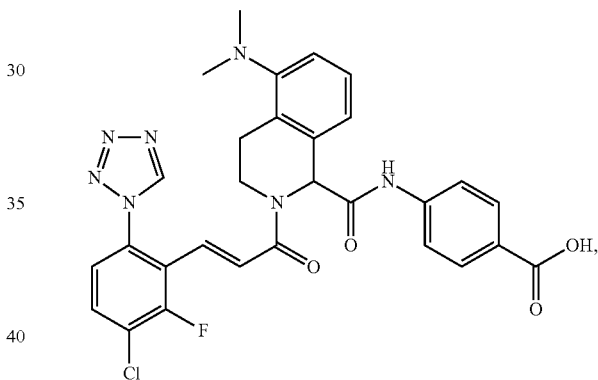
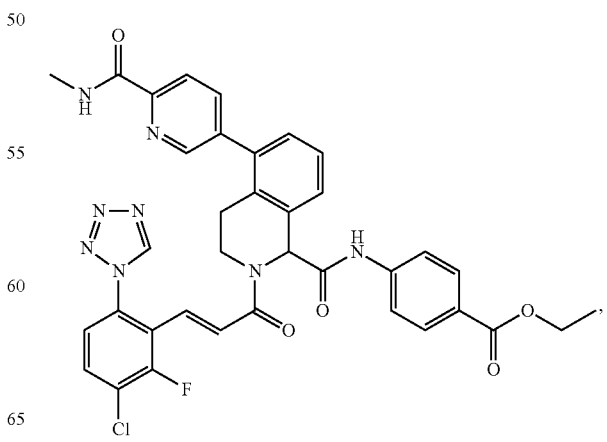

wherein R and R' are as follows:
| R | R' |
|---|---|
| *N*-methylacetamide (CH₃NHC(O)CH(–)–) | 4-PhCOOH |
| *N*-methylacetamide (CH₃NHC(O)CH(–)–) | 4-PhCOOH |
| *N*-methylacetamide (CH₃NHC(O)CH(–)–) | 4-PhCOOEt |
| *N*-methylacetamide (CH₃NHC(O)CH(–)–) | 4-PhCOOEt |
| —NH₂ | 4-PhCOOH |
| —N(CH₃)₂ | 4-PhCOOH, |
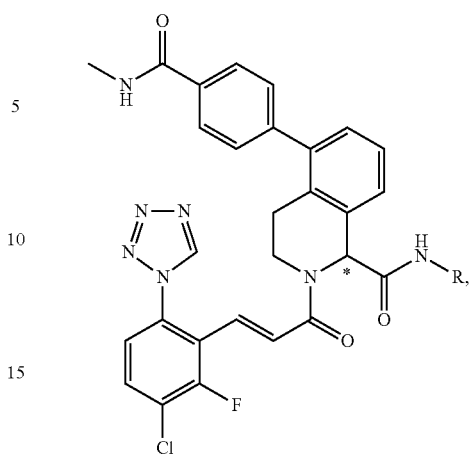
wherein R is as follows:
| R |
|---|
| (3)-piperidinyl |
| cyclobutylmethyl, |
or a pharmaceutically acceptable salt thereof.
* * * * *